US011926648B2

(12) United States Patent
Rey et al.

(10) Patent No.: US 11,926,648 B2
(45) Date of Patent: Mar. 12, 2024

(54) NEUTRALISING ANTIBODY AGAINST DENGUE FOR USE IN A METHOD OF PREVENTION AND/OR TREATMENT OF ZIKA INFECTION

(71) Applicants: IMPERIAL COLLEGE INNOVATIONS LIMITED, London (GB); INSTITUT PASTEUR, Paris (FR)

(72) Inventors: Felix Rey, Paris (FR); Giovanna Barba Spaeth, Paris (FR); Marie-Christine Vaney, Paris (FR); Alexander Rouvinski, Jerusalem (IL); Gavin Screaton, London (GB); Juthathip Mongkolsapaya, London (GB)

(73) Assignees: INSTITUT PASTEUR, Paris (FR); IMPERIAL COLLEGE INNOVATIONS LIMITED, London (GB)

( * ) Notice: Subject to any disclaimer, the term of this patent is extended or adjusted under 35 U.S.C. 154(b) by 163 days.

(21) Appl. No.: 17/241,884

(22) Filed: Apr. 27, 2021

(65) Prior Publication Data

US 2021/0355167 A1 Nov. 18, 2021

Related U.S. Application Data

(63) Continuation of application No. 16/308,745, filed as application No. PCT/GB2017/051692 on Jun. 9, 2017, now Pat. No. 11,111,274.

(30) Foreign Application Priority Data

Jun. 10, 2016 (GB) .................... 1610162

(51) Int. Cl.
| | |
|---|---|
| C07K 16/10 | (2006.01) |
| A61K 39/00 | (2006.01) |
| A61K 39/12 | (2006.01) |
| A61P 31/14 | (2006.01) |
| C07K 14/005 | (2006.01) |
| C07K 14/18 | (2006.01) |
| C07K 14/705 | (2006.01) |
| G01N 33/569 | (2006.01) |

(52) U.S. Cl.
CPC ............ *C07K 14/005* (2013.01); *A61K 39/12* (2013.01); *A61P 31/14* (2018.01); *C07K 14/1825* (2013.01); *C07K 16/1081* (2013.01); *G01N 33/56983* (2013.01); *C07K 2317/21* (2013.01); *C07K 2317/33* (2013.01); *C07K 2317/34* (2013.01); *C07K 2317/565* (2013.01); *C07K 2317/76* (2013.01); *C12N 2770/24122* (2013.01); *C12N 2770/24134* (2013.01); *C12N 2770/24171* (2013.01); *Y02A 50/30* (2018.01)

(58) Field of Classification Search
CPC ...... A61P 31/14; A61P 31/12; C07K 16/1081; C07K 2317/76; C07K 14/1825
See application file for complete search history.

(56) References Cited

U.S. PATENT DOCUMENTS

2009/0312190 A1 12/2009 Chinea Santiago

FOREIGN PATENT DOCUMENTS

| EP | 1360287 | 11/2003 |
|---|---|---|
| EP | 2264163 | 12/2010 |
| WO | 2006025990 | 3/2006 |
| WO | 2016012800 | 1/2016 |

OTHER PUBLICATIONS

Backovic, et al., "Efficient method for production of high yields of Fab fragments in Drosophila S2 cells", Protein Eng Des Sel, 23:169-174 (2010).
Balsitis, et al., "Lethal Antibody Enhancement of Dengue Disease in Mice Is Prevented by Fc Modification", PLoS Pathog, 6:e1000790 (2010).
Barba-Spaeth, et al., "Structural basis of Zika and Dengue virus potent antibody cross2 neutralization", Nature, 536(7614):48-53 (2016).
Bearcroft, et al., , "Zika virus infection experimentally induced in a human volunteer", Trans R Soc Trop Med Hyg, 50:442-448 (1956).
Beltramello, et al., Cell Host Microbe "The Human Immune Response to Dengue Virus Is Dominated by Highly Cross-Reactive Antibodies Endowed with Neutralizing and Enhancing Activity", 8: 271-283 (2010).
Bhamarapravatii, et al., "Live attenuated tetravalent dengue vaccine", Vaccine, 18 Suppl 2: 44-47 (2000).
Bhatt, et al., "The global distribution and burden of dengue", Nature, 496:504-507 (2013).
Biasini, et al., "Swiss-Model: modelling protein tertiary and quaternary structure using evolutionary information", Nucleic Acids Res, 42:W252-258 (2014).

(Continued)

*Primary Examiner* — Barry A Chestnut
(74) *Attorney, Agent, or Firm* — PABST PATENT GROUP LLP

(57) ABSTRACT

A flavivirus Envelope Dimer Epitope (EDE) and isolated neutralizing antibody or antigen binding fragment thereof directed against the EDE for use in vaccinating an individual against one or more flaviviruses wherein the EDE is a stabilized recombinant flavivirus are provided. The dimer is: covalently stabilized with at least one disulphide inter-chain bond or one sulfhydryl-reactive crosslinker between the two sE monomers, and/or by being formed as a single polypeptide chain, and/or by linking the two sE monomers through modified sugar, and/or non-covalently stabilized by substituting at least one amino acid residue in the amino acid sequence of at least one sE monomer with at least one bulky side chain amino acid, at the dimer interface or in domain 1 (D1)/domain 3 (D3) linker of each monomer. The dimer is a homodimer or heterodimer of native and/or mutant envelope polypeptides, from DENV-1, DENV-2, DENV-3, DENV-4, Zika and/or other flavivirus.

19 Claims, 41 Drawing Sheets

Figure 1A:
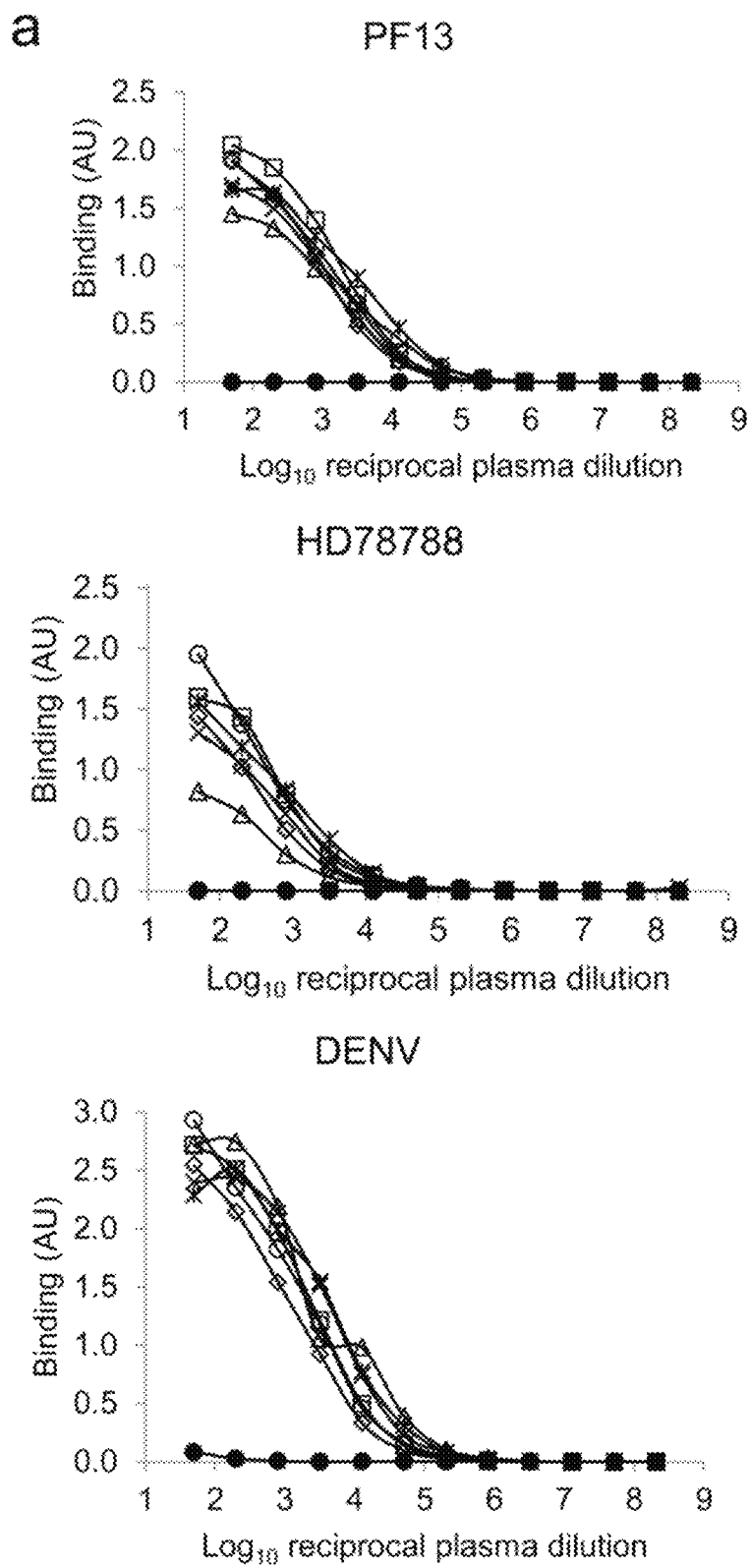

Specification includes a Sequence Listing.

(56) References Cited

OTHER PUBLICATIONS

Blanc, et al., "Refinement of severely incomplete structures with maximum likelihood in Buster-TNT", Acta Crystallogr D Biol Crystallogr, 60:2210-2221 (2004).
Braga, et al., "Seroprevalence and risk factors for dengue infection in socioeconomically distinct areas of Recife, Brazil", Acta Trop, 113:234-240 (2010).
Brasil, et al., "Zika Virus Infection in Pregnant Women in Rio de Janeiro", N Engl J Med, 375:2321-2334 (2016).
Brathwaite, et al., "Review: The History of Dengue Outbreaks in the Americas", Am J Trop Med Hyg, 87:584-593 (2012).
Broutet et al., "Zika Virus as a Cause of Neurologic Disorders", N Engl J Med, 374:1506-1509 (2016).
Buathong, et al., "Detection of Zika Virus Infection in Thailand, 2012-2014", Am J Trop Med Hyg, 93:380-383 (2015).
Calisher et al., "Antigenic Relationships between Flaviviruses as Determined by Cross-neutralization Tests with Polyclonal Antisera", J Gen Virol, 70(Pt1):37-43 (1989).
Calvet, et al., "Detection and sequencing of Zika virus from amniotic fluid of fetuses with microcephaly in Brazil: a case study", Lancet Infect Dis, 16(6):653-660 (2016).
Campos, et al., "Zika Virus Outbreak, Bahia, Brazil", Emerg Infect Dis, 21:1885-1886 (2015).
Cao-Lormeau, et al., "Guillain-Barré Syndrome outbreak associated with Zika virus infection in French Polynesia: a case-control study", Lancet, 387(10027):1531-153 (2016).
Cao-Lormeau, et al., "Zika Virus, French Polynesia, South Pacific, 2013", Emerg Infect Dis, 20:1085-1086 (2014).
Capeding, et al., "Antibody-enhanced dengue virus infection in primate leukocytes", Lancet, (2014).
Cardoso, et al., "Outbreak of Exanthematous Illness Associated with Zika, Chikungunya, and Dengue Viruses, Salvador, Brazil", Emerg Infect Dis, 21:2274-2276 (2015).
Carteaux, et al., "Zika Virus Associated with Meningoencephalitis", N Engl J Med., 374:1595-1596 (2016).
Castanha, et al., "Force of infection of dengue serotypes in a population-based study in the northeast of Brazil", Epidemiol Infect, 141:1080-1088 (2013).
Cauchemez, et al., "Association between Zika virus and microcephaly in French Polynesia, 2013-2015: a retrospective study", Lancet, 387:2125-2132 (2016).
Chakraborty, et al., "Computational analysis of perturbations in the post-fusion Dengue virus envelope protein highlights known epitopes and conserved residues in the Zika virus", F1000Research, 5:1150:1-21 (2016).
Chapman et al., "Scratching the Surface: Resurfacing Proteins to Endow New Properties and Function", Cell Chem Biol, 23:543-553 (2016).
Cherrier, et al., "Structural basis for the preferential recognition of immature flaviviruses by a fusion-loop antibody", EMBO J, 28: 3269-3276 (2009).
Correia, et al., , "Computational Protein Design Using Flexible Backbone Remodeling and Resurfacing: Case Studies in Structure-Based Antigen Design", J Mol Biol, 405:284-297 (2011).
Correia, et al., "Proof of principle for epitope-focused vaccine design", Nature, 507:201-206 (2014).
Cugola, et al., "The Brazilian Zika virus strain causes birth defects in experimental models", Nature, 534:267-271 (2016).
D'Ortenzio, et al., "Evidence of Sexual Transmission of Zika Virus", N Engl J Med, 374(22):2195-2198 (2016).
Dai et al., "Structures of the Zika Virus Envelope Protein and Its Complex with a Flavivirus Broadly Protective Antibody", Cell Host Microbe, 19(5):696-704 (2016).
Dang et al., "Zika Virus Depletes Neural Progenitors in Human Cerebral Organoids through Activation of the Innate Immune Receptor TLR3", Cell Stem Cell, 19(2):258-265 (2016).
De Alwis, et al., "Identification of human neutralizing antibodies that bind to complex epitopes on dengue virions", Proc Natl Acad Sci, 109(19):7439-7444 (2012).

De Alwis, et al., "In-Depth Analysis of the Antibody Response of Individuals Exposed to Primary Dengue Virus Infection", PLoS Negl Trop Disl, 5:e1188 (2011).
Dejnirattisai, et al., "A new class of highly potent, broadly neutralizing antibodies isolated from viremic patients infected with dengue virus", Nat Immunol., 16:170-177 (2015).
Dejnirattisai, et al., "Cross-reacting antibodies enhance dengue virus infection in humans", Science, 328:745-748, (2010).
Dejnirattisai, et al., "Dengue virus sero-cross-reactivity drives antibody-dependent enhancement of infection with zika virus", Nat Immunol., 17(9):1102-1108, (2016).
Dick, et al., "Zika virus (II). Pathogenicity and physical properties", Trans R Soc Trop Med Hyg, 46:521-534 (1952b).
Dick, et al., "Zika virus. I. Isolations and serological specificity", Trans R Soc Trop Med Hyg, 46:509-520 (1952a).
Dowd, et al., "Combined Effects of the Structural Heterogeneity and Dynamics of Flaviviruses on Antibody Recognition", J Virol, 88:11726-11737 (2014).
Dubois, et al., "Functional and evolutionary insight from the crystal structure of rubella virus protein E1", Nature, 493:552-556 (2013).
Duffy, et al., "Zika Virus Outbreak on Yap Island, Federated States of Micronesia", N Engl J Med, 360:2536-2543 (2009).
Emsley, et al., "Features and development of Coot", Acta Crystallogr D Biol Crystallogr, 66:486-501 (2010).
European Centre for Disease Prevention and Control (2015: http://ecdc.europa.eu/en/ publications/Publications/zika-virus-americas-association-with-microcephaly-rapid-risk-assessment.pdf).
Evans, et al., "How good are my data and what is the resolution?", Acta Crystallogr D Biol Crystallogr, 69:1204-1214 (2013).
Fagbami, "Zika virus infections in Nigeria: virological and seroepidemiological investigations in Oyo State", J Hyg Lond, 83:213-219 (1979).
Faria, et al., "Zika virus in the Americas: Early epidemiological and genetic findings", Science, 352:345-349 (2016).
Fibriansah, et al., "Cryo-EM structure of an antibody that neutralizes dengue virus type 2 by locking E protein dimers", Science, 349:88-91 (2015).
Fibriansah, et al., "Structural Changes in Dengue Virus When Exposed to a Temperature of 37o C", J Virol, 87:7585-7592 (2013).
Foy, et al., "Probable Non-Vector-borne Transmission of Zika Virus, Colorado, USA", Emerg Infect Dis., 17:880-882 (2011).
Frei, et al., "Comprehensive Mapping of Functional Epitopes on Dengue Virus Glycoprotein E DIII for Binding to Broadly Neutralizing Antibodies 4E11 and 4E5A by Phage Display", Virology, 485:371-382 (2015).
Garcez, et al., , "Zika virus impairs growth in human neurospheres and brain organoids", Science, 352:816-818 (2016).
Gilmartin, et al., , "High-level secretion of recombinant monomeric murine and human single-chain Fv antibodies from *Drosophila* S2 cells", Protein Eng Des Sel, 25:59-66 (2012).
Goncalvez, et al., "Monoclonal antibody-mediated enhancement of dengue virus infection in vitro and in vivo and strategies for prevention", Proc Natl Acad Sci, 104:9422-9427 (2007).
Gouet et al., "ESPript: analysis of multiple sequence alignments in PostScript", Bioinformatics, 15:305-308 (1999).
Goujon, et al., "A new bioinformatics analysis tools framework at EMBL-EBI", Nucleic Acids Res, 38:W695-699 (2010).
Guindon, et al., "New algorithms and methods to estimate maximum-likelihood phylogenies: assessing the performance of PhyML 3.0", Syst Bio., 59:307-321 (2010).
Guy, et al., ,"From research to phase III: Preclinical, industrial and clinical development of the Sanofi Pasteur tetravalent dengue vaccine", Vaccine, 29:7229-7241 (2011).
Guzman, et al., , "Dengue: a continuing global threat", Nat Rev Microbiol, 8, S7-16 (2010).
Guzman, et al., "Dengue", Lancet, 385:453-465 (2015).
Guzman, et al., "Epidemiologic studies on Dengue in Santiago de Cuba, 1997", Am J Epidemiol, 152:793-799 (2000).
Guzman, et al., "Neutralizing Antibodies after Infection with Dengue 1 Virus", Emerg Infect Dis Nat Immunol, 13:282-286 (2007).
Haddow, et al., "Genetic Characterization of Zika Virus Strains: Geographic Expansion of the Asian Lineage", PLoS Negl Trop Dis, 6:e1477 (2012).

(56) References Cited

OTHER PUBLICATIONS

Hadinegoro, et al., "Efficacy and Long-Term Safety of a Dengue Vaccine in Regions of Endemic Disease", N Engl J Med, (2015).
Halstead, "In vivo enhancement of dengue virus infection in rhesus monkeys by passively transferred antibody", J Infect Dis, 140:527-533 (1979).
Halstead, et al., "Antibody-enhanced dengue virus infection in primate leukocytes", Nature, 265:739-741 (1977a).
Halstead, et al., "Dengue Viruses And Mononuclear Phagocytes I. Infection Enhancement by Non-Neutralizing Antibody", J Exp Med, 146:201-217 (1977b).
Halstead, et al., "Intrinsic antibody-dependent enhancement of microbial infection in macrophages: disease regulation by immune complexes", Lancet Infect Dis, 10:712-722 (2010).
Halstead, et al., "Observations Related to Pathogenesis of Dengue Hemorrhagic Fever. 1. Experience With Classification of Dengue Viruses", Yale J Biol Med, 42:261-275 (1970).
Harrison et al., "Immunogenic cross-talk between dengue and Zika viruses", Nat Immunol, 17(9):1010-1012 (2016).
Hayes, "Zika Virus Outside Africa", Emerg Infect Dis, 15:1347-1350 (2009).
Hessell et al., "Fc receptor but not complement binding is important in antibody protection against HIV", Nature, 449:101-104 (2007).
Impagliazzo, et al., "A stable trimeric influenza hemagglutinin stem as a broadly protective immunogen", Science, (2015).
Jardine, et al., "Priming a broadly neutralizing antibody response to HIV-1 using a germline-targeting immunogen", Science, 349:156-161 (2015).
Jardine, et al., "Rational HIV immunogen design to target specific germline B cell receptors", Science, 340:711-716 (2013).
Jarmer, et al., "Variation of the Specificity of the Human Antibody Responses after Tick-Borne Encephalitis Virus Infection and Vaccination", J Virol, 88:13845-13857 (2014).
Johnson, et al., "New Mouse Model for Dengue Virus Vaccine Testing" J Virol , 73:783-786 (1999).
Junjhon, et al., "Influence of pr-M Cleavage on the Heterogeneity of Extracellular Dengue Virus Particles", J Virol, 84:8353-8358 (2010).
Kabsch, "XDS", Acta Crystallogr D Biol Crystallogr, 66:125-132 (2010).
Kanekiyo et al., "Self-assembling influenza nanoparticle vaccines elicit broadly neutralizing H1N1 antibodies", Nature, 499(7456):102-106 (2013).
Khakshoor, et al., "Use of Disulfide "Staples" to Stabilize β-Sheet Quaternary Structure", Org Lett, 11(14):3000-3003 (2009).
Kostyuchenko et al., "Structure of the thermally stable Zika virus", Nature, 533:425-428 (2016).
Krissinel, et al., "Inference of Macromolecular Assemblies from Crystalline State", J Mol Biol, 372:774-797 (2007).
Kuhn, et al., "Shake, rattle, and roll: Impact of the dynamics of flavivirus particles on their interactions with the host", Virology, 479-480:508-517 (2015).
Kuhn, et al., "Structure of Dengue Virus: Implications for Flavivirus Organization, Maturation, and Fusion", Cell, 108:717-725 (2002).
Lanciotti, et al., "Genetic and Serologic Properties of Zika Virus Associated with an Epidemic, Yap State, Micronesia, 2007", Emerg Infect Dis, 14:1232-1239 (2008).
Larkin, et al., "Clustal W and Clustal X version 2.0", Bioinformatics, 23:2947-2948 (2007).
Lazear, et al., "Zika Virus: New Clinical Syndromes and Its Emergence in the Western Hemisphere", J Virol, 90:4864-4875 (2016).
Lee, et al., "Complete humanization of the mouse immunoglobulin loci enables efficient therapeutic antibody discovery", Nat Biotech, 32(4):356-363 (2014).
Lee, et al., "The Fc Region of an Antibody Impacts the Neutralization of West Nile Viruses in Different Maturation States", J Virol, 87:13729-13740 (2013).
Li, et al., "Zika Virus Disrupts Neural Progenitor Develpment and Leads to Microcephaly in Mice", Cell Stem Cell, 19:120-126 (2016).
Li, et al., "The Flavivirus Precursor Membrane-Envelope Protein Complex: Structure and Maturation", 319:1830-1834 (2008).
Lindenbach, et al., "Flaviviridae: the viruses and their replication", Fields Virology 5th Edition, 1:1101-1152 (2007).
Liu, et al., "RosettaDesign server for protein deisgn", Nucleic acids research 34: W235-238 (2006).
Lok, et al., "Binding of a neutralizing antibody to dengue virus alters the arrangement of surface glycoproteins", Nat Struct Mol Biol, 15:312-317 (2008).
Mackenzie, et al., "Emerging flaviviruses: the spread and resurgence of Japanese encephalitis, West Nile and dengue viruses", Nat Med, 10:S98B (2004).
Macnamara, "Zika virus: a report on three cases of human infection during an epidemic of jaundice in Nigeria", Trans R Soc Trop Med Hyg, 48:139-145 (1954).
Mallajosyula, et al., "Hemagglutinin sequence conservation guided stem immunogen design from influenza A H3 subtype", Frontiers in immunology, 6:329 (2015).
Martines, et al., "Evidence of Zika Virus Infection in Brain and Placental Tissues from Two Congenitally Infected Newborns and Two Fetal Losses—Brazil, 2015", MMWR Morb Mortal Wkly Rep, 65:159-160 (2016).
McCoy, et al., "Phaser crystallographic software", Journal of applied crystallography, 40:658-674 (2007).
McLellan, et al., "Structure of RSV Fusion Glycoprotein Trimer Bound to a Prefusion-Specific Neutralizing Antibody", Science, 340:1113-1117 (2013).
McLellan, et al., "Structure-Based Design of a Fusion Glycoprotein Vaccine for Respiratory Syncytial Virus", Science, 342:592-598 (2013).
Meaney-Delman, et al., "Zika Virus Infection Among U.S. Pregnant Travelers—Aug. 2015-Feb. 2016", MMWR Morb Mortal Wkly Rep, 65:211-214 (2016).
Midgely, et al., "Structural analysis of a dengue cross-reactive antibody complexed with envelope domain III reveals the molecular basis of cross-reactivity", J Immunol, 188(10):4971-4979 (2012).
Milligan, et al., "A Dengue Virus Type 4 Model of Disseminated Lethal Infection in AG129 Mice", PLoS One, 10:e0125476 (2015).
Miner, et al., "Zika Virus Infection during Pregnancy in Mice Causes Placental Damage and Fetal Demise", Cell, 165:1-11 (2016).
Mlakar, et al., "Zika Virus Associated with Microcephaly", N Engl J Med, 374:951-958 (2016).
Modis, et al., "Structure of the dengue virus envelope protein after membrane fusion", Nature, 427:313-319 (2004).
Morrison, "Reemergence of Chikungunya Virus", J Virol, 88:11644-11647 (2014).
Mukherjee, et al., "Mechanism and Significance of Cell Type-Dependent Neutralization of Flaviviruses", J Virol, 88:7210-7220 (2014).
Mukhopadhyay, et al., "A structural perspective of the flavivirus life cycle", Nat Rev Microbiol, 3:13-22 (2005).
Mukhopadhyay, et al., "Structure of West Nile Virus", Science, 302:248 (2003).
Musso, et al., "Zika virus: following the path of dengue and chikungunya", Lancet, 386:243-244 (2015).
Musso, et al., "Zika Virus", Clin Microbiol Rev, 29:487-524 (2016).
Paixao, et al., "History, Epidemiology, and Clinical Manifestations of Zika: A Systematic Review", Am J Public Health, 106:606-612 (2016).
Plevka, et al., "Maturation of flaviviruses starts from one or more icosahedrally independent nucleation centres", EMBO Rep, 12:602-606 (2011).
Rey, "Dengue virus: Two hosts, two structures", Nature, 497:443-444 (2013).
Rodenhuis-Zybert, et al., "Immature Dengue Virus: A Veiled Pathogen?" PLoS Pathog, 6:e1000718 (2010).
Rouvinski, et al., "Covalently linked dengue virus envelope glycoprotein dimers reduce exposure of the immunodominant fusion loop epitope", Nat Comm, 8:15411 (2017).
Rouvinski, et al., "Recognition determinants of broadly neutralizing human antibodies against dengue viruses", Nature, 520:109-113 (2015).

(56) References Cited

OTHER PUBLICATIONS

Sabchareon et al., "Efficacy of tetravalent dengue vaccine in Thai schoolchildren", Lancet, 381:1094-1095 (2013).
Sabchareon, et al., "Protective efficacy of the recombinant, live-attenuated, CYD tetravalent dengue vaccine in Thai schoolchildren: a randomised, controlled phase 2b trial", The Lancetl, 380:1559-1567 (2012).
Sabin, "Research On Dengue During World War II", Am J Trop Med Hyg, 1:30-50 (1952).
Salam, et al., "Structure-based approach to the prediction of disulfide bonds in proteins", Protein Eng Des Sel ,27:365-374 (2014).
Sanders, et al., "HIV Neutralizing Antibodies Induced by Native-like Envelope Trimers", Science, 349:aac4223 (2015).
Sangkawibha, et al., , Risk factors in dengue shock syndrome: a prospective epidemiologic study in Rayong, Thailand. I. The 1980 outbreak, Am J Epidermiol, 120:653-669 (1984).
Sarathy, et al., "A Lethal Murine Infection Model for Dengue Virus 3 in AG129 Mice Deficient in Type I and II Interferon Receptors Leads to Systemic Disease", J Virol, 89:1254-1266 (2015).
Sarno, et al., "Zika Virus Infection and Stillbirths: A Case of Hydrops Fetalis, Hydranencephaly and Fetal Demise", PLoS Negl Trop Dis, 10:e0004517 (2016).
Sasaki, et al., "Dengue virus neutralization and antibody-dependent enhancement activities of human monoclonal antibodies derived from dengue patients at acute phase of secondary infection", Antiviral Research, 98(3):423-431 (2013).
Schoggins, et al., "Dengue reporter viruses reveal viral dynamics in interferon receptor-deficient mice and sensitivity to interferon effectors in vitro", Proc Natl Acad Sci U S A, 109:14610-14615 (2012).
Screaton et al., "New insights into the immunopathology and control of dengue virus infection", Nat Rev Immunol, 15:745-759 (2015).
Shresta, et al., , "Murine Model for Dengue Virus-Induced Lethal Disease with Increased Vascular Permeability", J Virol, 80:10208-10217 (2006).
Simmons, et al., , "Dengue", N Engl J Med., 366:1423-32 (2012).
Sirohi, et al., , "Zika Virus Is Not Uniquely Stable at Physiological Temperatures Compared to Other Flaviviruses", Science, 352:467-470 (2016).
Smith, et al., "Human Monoclonal Antibodies Derived From Memory B Cells Following Live Attenuated Dengue Virus Vaccination or Natural Infection Exhibit Similar Characteristics", J Infect Dis, 207:1898-1908 (2013).
Smith, et al., "Persistence of Circulating Memory B Cell Clones with Potential for Dengue Virus Disease Enhancement for Decades following Infection", J Virol, 86;2665-2675 (2010).
Stadler, et al., , "Proteolytic activation of tick-borne encephalitis virus by furin", J Virol, 71:8475-8481 (1997).
Stiasny et al., "Cryptic Properties of a Cluster of Dominant Flavivirus Cross-Reactive Antigenic Sites", J Virol, 80:9557-9568 (2006).
Swanstrom, et al., "Dengue Virus Envelope Dimer Epitope Monoclonal Antibodies Isolated from Dengue Patients Are Protective against Zika Virus", mBio, 7(4)-e01123-16 (2016).
Tan, et al., "Subcutaneous Infection with Non-mouse Adapted Dengue Virus D2Y98P Strain Induces Systemic Vascular Leakage in AG129 Mice", Ann Acad Med Singapore, 40:523-532 (2011).
Teixeira, et al., "East/Central/South African Genotype Chikungunya Virus, Brazil, 2014", Emerg Infect Dis, 21(5):906-907 (2015).
Teixeira, et al., "The Epidemic of Zika Virus-Related Microcephaly in Brazil: Detection, Control, Etiology, and Future Scenarios", Am J Public Health, 106:601-605 (2016).
Vannice, et al., "Status of vaccine research and development of vaccines for dengue", Vaccine, 34(26):2934-2938 (2016).
Villar, et al., "Efficacy of a Tetravalent Dengue Vaccine in Children in Latin America", N Engl J Med, 372:113-123 (2015).
Vogt, et al., "Poorly Neutralizing Cross-Reactive Antibodies against the Fusion Loop of West Nile Virus Envelope Protein Protect In Vivo via Fc Receptor and Complement-Dependent Effector Mechanisms", J Virol, 85:11567-11580 (2011).
Vratskikh, et al., "Dissection of Antibody Specificities Induced by Yellow Fever Vaccination", PLoS Pathog, 9:e1003458 (2013).
Weaver, et al., "Chikungunya Virus and the Global Spread of a Mosquito-Borne Disease", N Engl J Med, 372:1231-1239 (2015).
Wengler, et al., "Cell-associated West Nile flavivirus is covered with E+pre-M protein heterodimers which are destroyed and reorganized by proteolytic cleavage during virus release", J Virol, 63:2521-2526 (1989).
Winn, et al., "Overview of the CCP4 suite and current developments", Acta Crystallogr D Biol Crystallogr, 67:235-242 (2011).
World Health Organization (2016: Director-General summarizes the outcome of the Emergency Committee regarding clusters of microcephaly and Guillain-Barré syndrome).
World Health Organization (Situation Report 2016: Zika virus microcephaly Guillain-Barré syndrome).
World Health Organization (Zika emergency 2016: http://www.who.int/mediacentre/news/statements/2016/1 st-emergency-committee-zika/en/).
World Health Organization (Zika Virus Fact sheet 2016: http://www.who.int/mediacentre /factsheets/zika/en/).
World Health Organization http://www.who.int/mediacentre/factsheets/fs117/en/ (2015).
World Health Organization Strategic Advisory Group of Experts (Dengue vaccine 2016: http://www.who.int/immunization/sage/ meetings/2016/april/SAGE_April_2016_Meeting_Web_summary.pdf?ua=1).
Yassine, et al., "Hemagglutinin-stem nanoparticles generate heterosubtypic influenza protection", Nat Med, 21:1065-1070 (2015).
Yu, et al., "Structure of the Immature Dengue Virus at Low pH Primes Proteolytic Maturation", Science, 319:1834-1837 (2008).
Zanluca, et al., "First report of autochthonous transmission of Zika virus in Brazil", Mem Inst Oswaldo Cruz, 110:569-572 (2015).
Zellweger, et al., "Antibodies enhance infection of LSECs in a model of ADE-induced severe dengue disease", Cell Host Microbe, 7:128-139 (2010).
Zhang, et al., "CryoEM structure of the mature dengue virus at 3.5-Å resolution", Nat Struct Mol Biol, 20:105-110 (2013c).
Zhang, et al., "Dengue structure differs at the temperatures of its human and mosquito hosts", Proc Natl Acad Sci U S A, 110:6795-6799 (2013a).
Zhang, et al., "Membrane Curvature in Flaviviruses", J Struct Biol, 183:86-94 (2013b).
Zhang, et al., "Structures of immature flavivirus particles", EMBO J, 22:2604-2613 (2003).
Zompi, et al., "Animal Models of Dengue Virus Infection", Viruses, 4:62-82 (2012).
Zust, et al., "Type I Interferon Signals in Macrophages and Dendritic Cells Control Dengue Virus Infection: Implications for a New Mouse Model To Test Dengue Vaccines", J. Virol, 88:7276-7285 (2014).

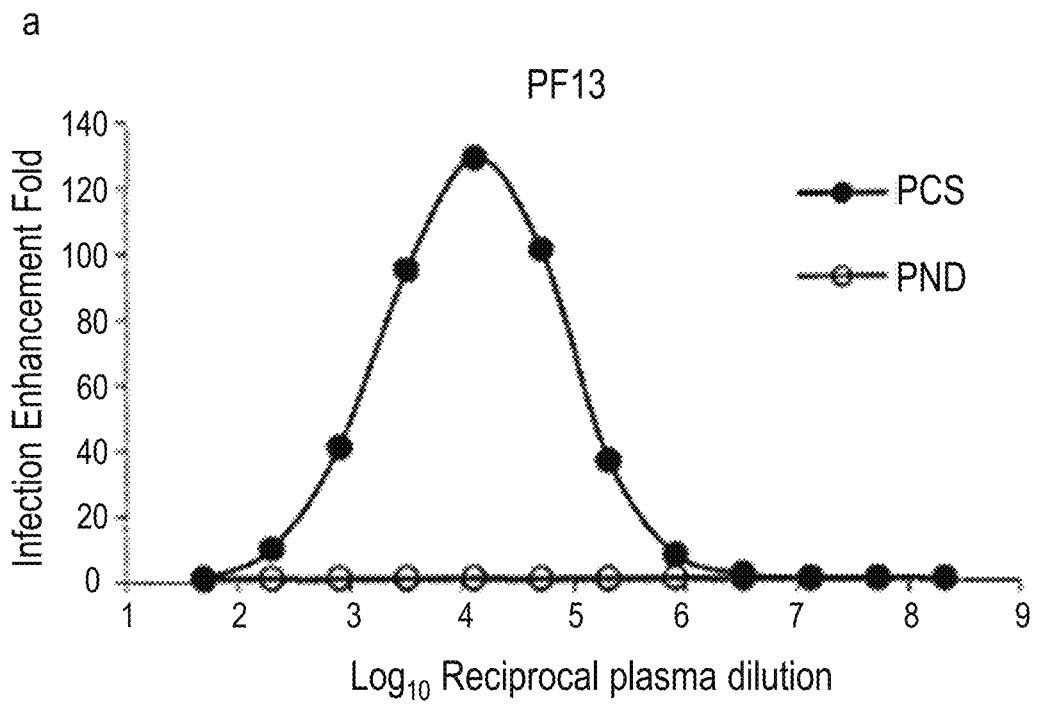
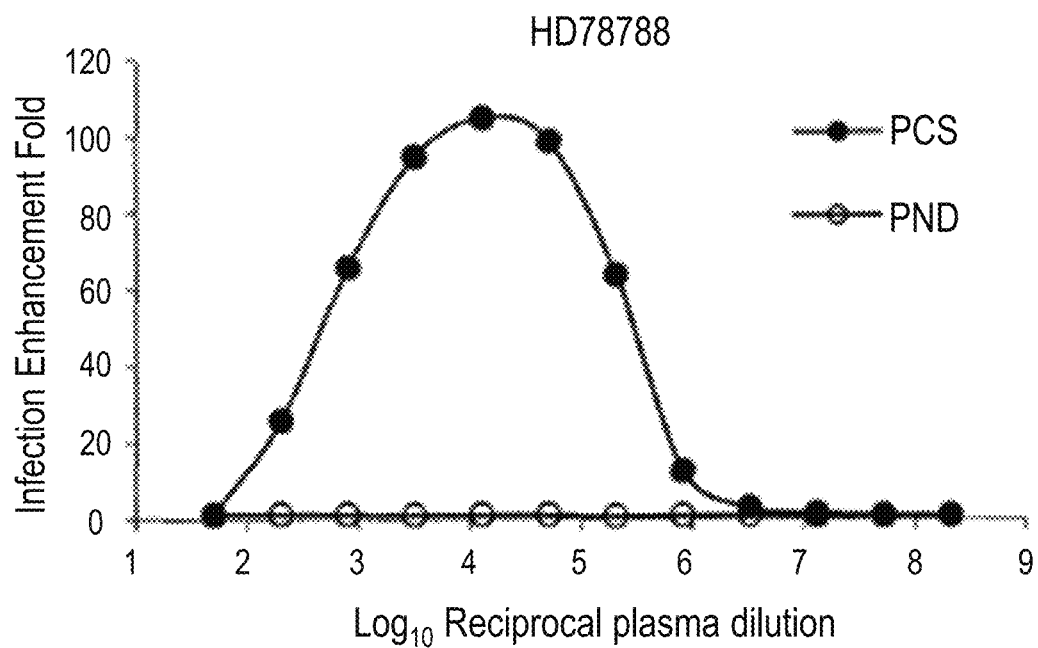
FIG. 3A

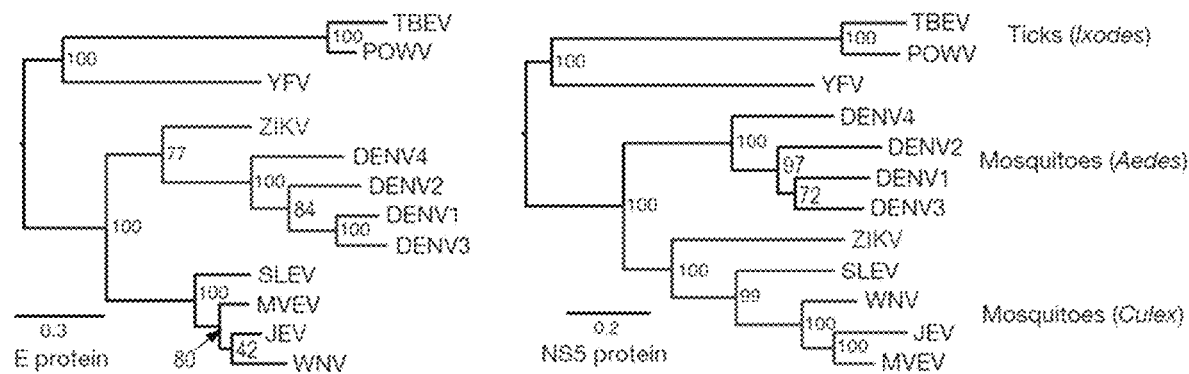
FIG. 8A
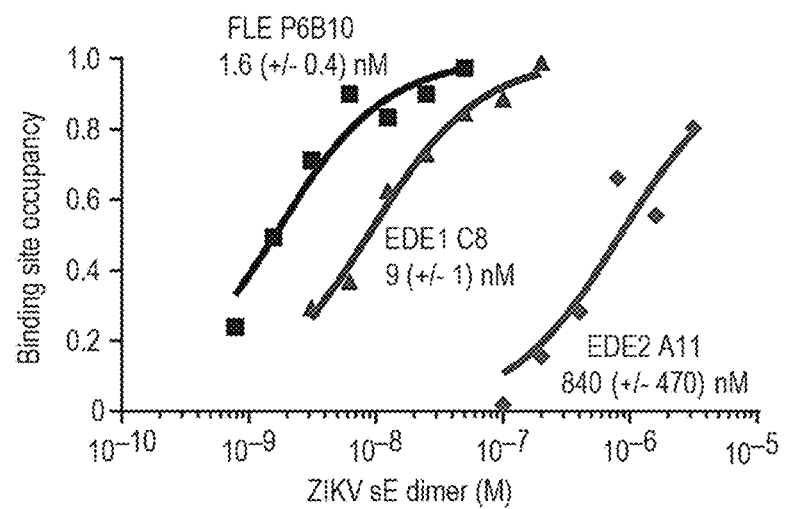
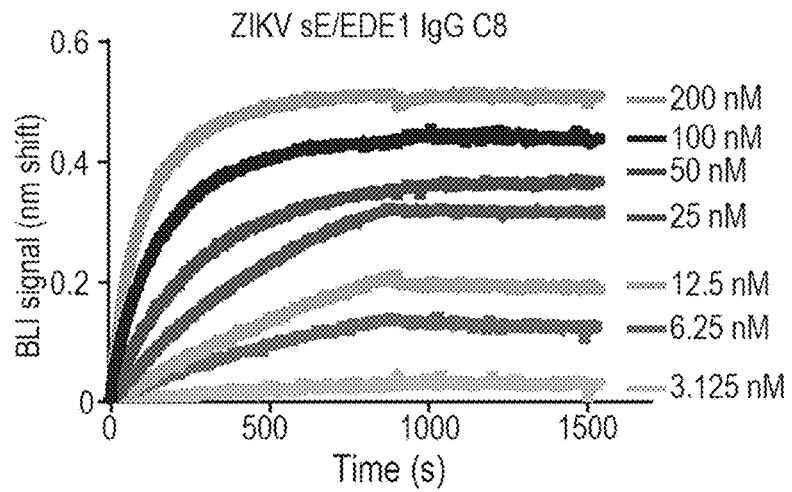
FIG. 8B

FIG. 10D     FIG. 10E     FIG. 10F

Structure of ZIKV sE / EDE2 A11 Fab Complex
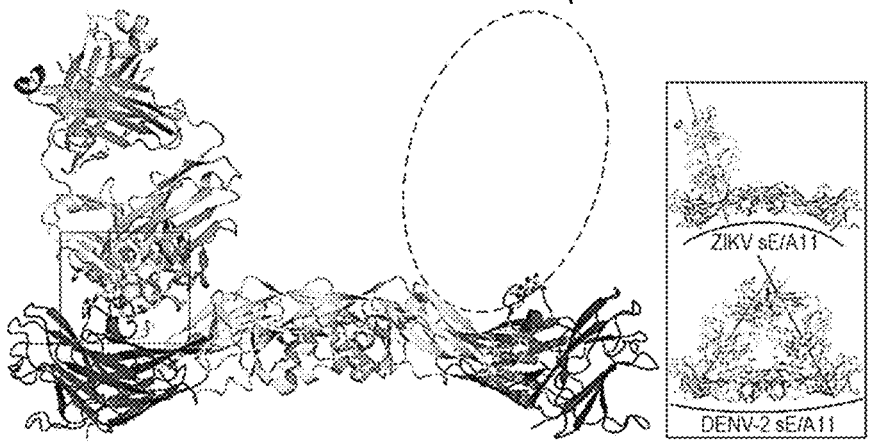
FIG. 11A
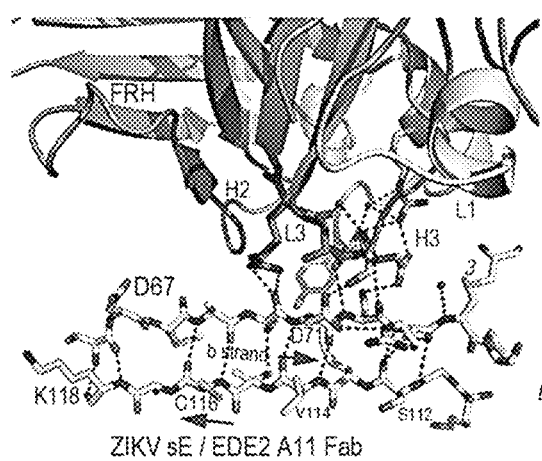
ZIKV sE / EDE2 A11 Fab
FIG. 11B
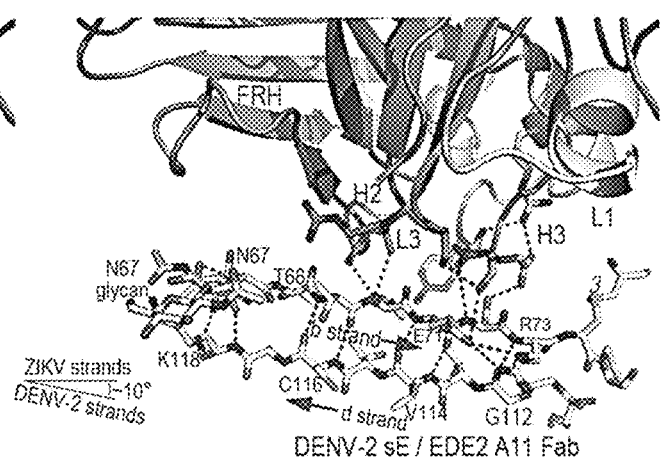
DENV-2 sE / EDE2 A11 Fab
FIG. 11C
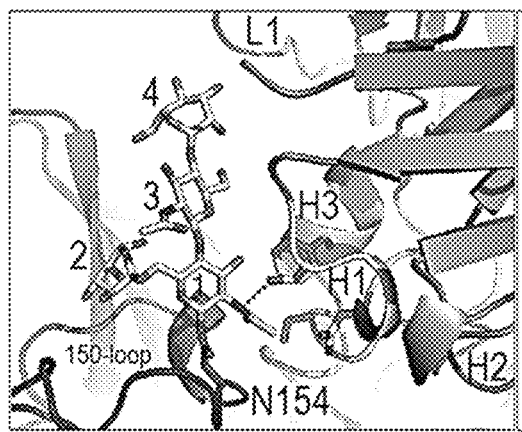
ZIKV sE / EDE2 A11 Fab
FIG. 11D
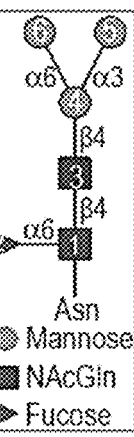
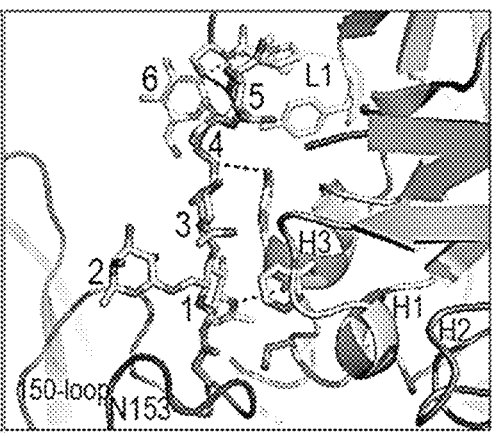
DENV-2 sE / EDE2 A11 Fab
FIG. 11E

Table 1: 50% FRNT values of EDE1, EDE2, and FLE antibodies Tested against ZIKV and DENV 1-4

| | | ZIKV | |
|---|---|---|---|
| | | 50% FRNT (nM) | |
| | Epitope | PF13 | HD78788 |
| 752-2-C8 | EDE1 | 0.095 (±0.026) | 0.015 (±0.003) |
| 753(3) C10 | EDE1 | 0.063 (±0.016) | 0.013 (±0.025) |
| 752-2 B2 | EDE1 | 1.062 (±0.362) | 0.021 (±0.004) |
| 747(4) A11 | EDE2 | 0.904 (±0.191) | 0.506 (±0.102) |
| 747(4) B7 | EDE2 | 4.31 (±1.47) | 1.17 (±0.180) |
| 747 C4 | EDE2 | 102 (±25.6) | 11.6 (±2.6) |
| 758 P6B10 | FLE | No neut. | No neut. |
| 749 B12 | FLE | No neut. | No neut. |
| 750-2 C5 | FLE | No neut. | No neut. |

| DENV | | | |
|---|---|---|---|
| 50% FRNT (nM) | | | |
| DENV1 | DENV2 | DENV3 | DENV4 |
| 0.39 (±0.21) | 0.24 (±0.06) | 0.64 (±0.08) | 1.13 (±0.14) |
| 0.54 (±0.04) | 0.18 (±0.02) | 1.89 (±0.79) | 0.08 (±0.03) |
| 0.32 (±0.05) | 0.23 (±0.02) | 0.22 (±0.09) | 0.44 (±0.14) |
| 0.11 (±0.01) | 0.07 (±0.03) | 0.11 (±0.02) | 7.79 (±3.19) |
| 0.10 (±0.01) | 0.11 (±0.02) | 0.12 (±0.03) | 93.19 (±19.15) |
| 0.23 (±0.02) | 0.08 (±0.01) | 0.11 (±0.01) | 0.12 (±0.05) |
| 1.85 (±0.44) | 4.97 (±0.28) | 9.40 (±2.83) | 7.47 (±1.65) |
| 0.43 (±0.12) | 0.73 (±0.20) | 1.04 (±0.31) | 1.80 (±0.64) |
| 1.08 (±0.21) | 0.76 (±0.46) | 1.40 (±0.25) | 2.30 (±0.02) |

FIG. 12

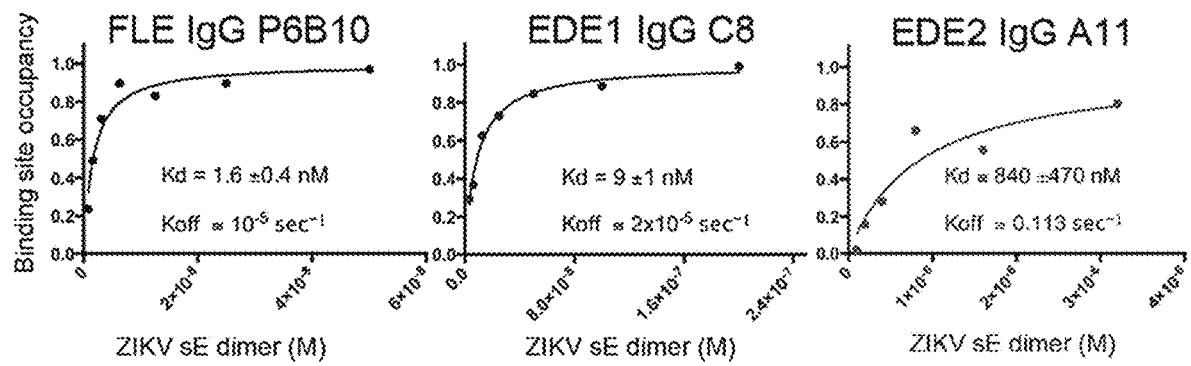
FIG. 13A
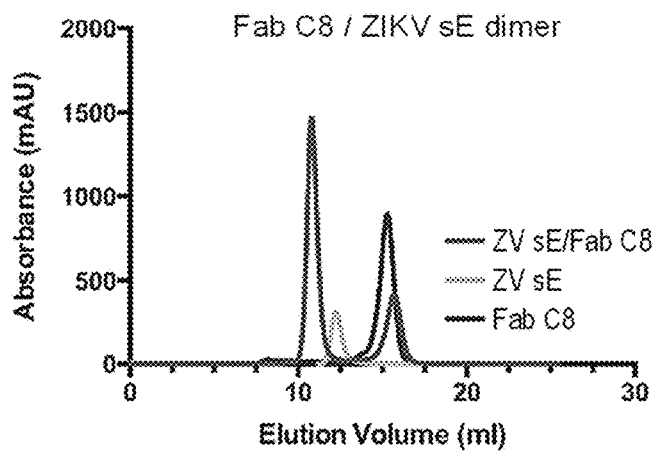
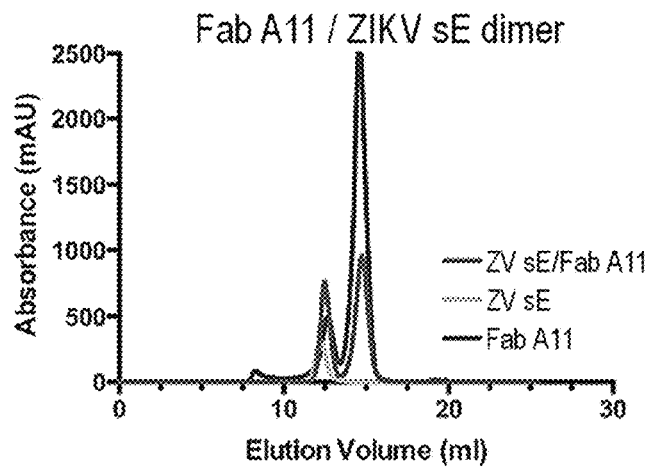
FIG. 13B

Detailed interactions between ZIKA sE / EDE1 C8 ScFv and DENV-2 sE / EDE1 C8 Fab ZIKV sE / EDE1 C8 ScFv DENV2 sE / EDE1 C8 Fab

FIG. 17

Zoom view of the glycans in ZIKV and DENV-2 complexes with EDE2 A11 Fab and in the ZIKV mature virion ZIKV sE / EDE2 A11 Fab
ZIKV sE mature virion (5IRE) coloured in white ZIKV sE / EDE2 A11 Fab; DENV-2 sE / EDE2
A11 Fab (4UT7) colored in white ZIKV sE / EDE2 A11 Fab
ZIKV sE / EDE1 C8 ScFv coloured in pink Extended Data Table 1 | Crystallization conditions, data collection and refinement statistics

| | ZIKV sE – EDE1 C8 scFv | ZIKV sE – EDE2 A11 Fab | ZIKV sE |
|---|---|---|---|
| Protein Data Bank code | 5LBS | 5LCV | 5LBV |
| Crystallization conditions | | | |
| Protein conc. (mg/ml)* | 1.3 (complex) | 1.5 (ZIKV sE) / 3 (EDE2 A11 Fab) | 1.4 |
| Crystallization buffer | 1.26 M (NH4)2SO4, 0.1 M CHES pH 9.5, 0.2 M NaCl | 3.5 M Na Formate, 0.1 M Tris pH 8.5 | 28.8% PEG 8K, 0.1 M Bicine pH 9.3 |
| Crystallization method | sitting drop at 18°C | sitting drop at 18°C | hanging drop at 18°C |
| Cryo-protectant | 20% ethylene glycol in 67% of crystallization solution | 16% glycerol in 67% of crystallization solution | oil mixture paraffin:paratone (1:1) |
| Data Collection†‡ | | | |
| Beamline | SOLEIL, Proxima 1 | SOLEIL, Proxima 2 | SOLEIL, Proxima 1 |
| Detector | Pilatus 6M | Eiger 9M | Pilatus 6M |
| Space group | P 2₁ 2 2₁ | C 2 2 2₁ | C 2 2 2₁ |
| Unit cell: a, b, c (Å) | 69.8, 121.3, 257.8 | 204.3, 207.3, 124.6 | 64.6, 213.6, 124.0 |
| α, β, γ (°) | 90, 90, 90 | 90, 90, 90 | 90, 90, 90 |
| Resolution (Å) | 40.0-2.41 (2.46-2.41) | 40.0-2.64 (2.69-2.64) | 38.5-2.2 (2.25-2.20) |
| Anisotropy direction† | | | |
| Resolution where CC₁/₂ > 0.50 | | | |
| overall (Å) | 2.69 | 2.87 | 2.2 |
| along h axis (Å) | 3.24 | 4.23 | 3.28 |
| along k axis (Å) | 2.95 | 2.64 | 2.3 |
| along l axis (Å) | 2.41 | 2.9 | 2.2 |
| Measured reflections | 560,284 (35,314) | 760,128 (38,978) | 318,556 (18,018) |
| Unique reflections | 74,842 (4,571) | 77,483 (4,547) | 44,168 (3,026) |
| Completeness (%) | 100 (100) | 99.8 (99.4) | 99.5 (93.4) |
| Mn(I) half-set correlation | 0.99 (0.15) | 0.98 (0.17) | 0.99 (0.33) |
| Mean I/σ(I) | 6.7 (1.4) | 5.1 (0.4) | 9.4 (0.5) |
| Multiplicity | 7.5 (7.7) | 9.8 (8.6) | 7.2 (6.0) |
| B wilson (Å²) | 41.2 | 47.4 | 60.1 |
| Rmerge | 0.33 (3.1) | 0.50 (6.6) | 0.10 (3.3) |
| Rmeas | 0.36 (2.9) | 0.53 (7.1) | 0.11 (3.7) |
| Rpim | 0.13 (1.2) | 0.17 (2.4) | 0.04 (1.5) |
| Structure Determination | | | |
| MR search models | ZIKV sE from ZIKV sE – EDE2 A11 Fab complex (5LCV); EDE1 C8 Fab variable domain (4UTA) | ZIKV model sE from DENV-2 sE (4UTA); EDE2 A11 scFv (4UT7); EDE2 A11 Fab constant domain (4UTB) | ZIKV sE from ZIKV sE – EDE1 C8 scFv complex (5LBS) |
| NCS restraint | 2 | 2 applied only on sE dimer | 2 |
| Targeting | NA | EDE2 A11 scFv (4UT7) | NA |
| Number of TLS groups | 12 | 12 | 12 |
| Refinement§ | | | |
| Resolution cut-off (Å) | 40.0-2.41 | 40.0-2.64 | 40.0-2.2 |
| Rwork (%) / Rfree (%) | 19.5 / 22.1 | 22.3 / 23.7 | 20.8 / 23.6 |
| N° of Work / Free reflections | 74,785 / 3,719 | 76,253 / 3,840 | 44,038 / 2,219 |
| <B> atomic factors (Å²) | 72.6 | 89.3 | 64.1 |
| N° of protein atoms | 9,595 | 9,495 | 5,978 |
| N° of heteroatoms | 212 | 43 | 43 |
| R.m.s.d. from ideal | | | |
| Bond lengths (Å) | 0.01 | 0.01 | 0.01 |
| Bond angles (°) | 1.22 | 1.26 | 1.24 |
| Ramachandran‖ | | | |
| Favoured (%) | 96.5 | 95.7 | 97.3 |
| Allowed (%) | 3.26 | 3.65 | 1.96 |
| Outliers (%) | 0.24 | 0.65 | 0.64 |

The ZIKV sE buffer used for all crystallization experiments was: 150 mM NaCl, 15 mM Tris, pH 8.
*The protein concentration was estimated using theoretical extinction coefficients of the complexes (ZIKV sE + Fab or scFv). Absorbance at 280 nm (A280 nm) of the protein solution was measured before crystallization. The theoretical extinction coefficients for individual component are: ZIKV sE: 1.345; bnAb EDE2 A11 Fab: 1.68 (see Methods for more details); bnAb EDE1 C8 scFv: 1.9. Extinction coefficients were calculated without taking carbohydrate moieties into account. One crystal was used to collect a diffraction data set for each complex to determine the structure.
†The anisotropy statistics were computed with AIMLESS.
‡Highest resolution shell is shown in parentheses.
§Low-resolution for data processing and refinements was truncated to 40 Å.
‖Ramachandran statistics were calculated with MolProbity.
CC1/2, correlation coefficient; h, k and l: indices that define the lattice planes; I/σ(I), empirical signal-to-noise ratio; MR, molecular replacement; NCS, non-crystallographic symetry; Rmeas, multiplicity-corrected R; Rpim, expected precision; TLS, parameterization describing translation, liberation and screw-motion to model anisotropic displacements.

FIG. 18D

Extended Data Table 2. Root mean square deviations between sE dimers in the various structures of ZIKV and DENV-2

| ZIKV* | PDB code | ZIKV sE (this work) SL8V | ZIKV sE-EDE2 A11 Fab (this work) SLCV | ZIKV sE-EDE1 C8 scFv† (this work) SL8S | ZIKV sE (Dai et al, 2016) 5JHM | ZIKV mature virion sE dimer from au 5IRE | ZIKV mature virion icosahedral sE dimer 5IRE | ZIKV thermally stable mature virion sE dimer from au 5IZ7 | ZIKV thermally stable mature virion icosahedral sE dimer 5IZ7 |
|---|---|---|---|---|---|---|---|---|---|
| ZIKV sE (this work) | SL8V | / | | | | | | | |
| ZIKV sE-EDE2 A11 Fab | SLCV | 3.33 (758) | / | | | | | | |
| ZIKV sE-EDE1 C8 scFv† | SL8S | 2.31 (778) 2.29 (764) | 3.41 (773) 2.39 (761) | 0.57 (764)‡ | | | | | |
| ZIKV sE (Dai et al, 2016) | 5JHM | 1.8 (769) | 4.1 (768) | 3.06 (771) 2.93 (761) | / | | | | |
| ZIKV mature virion sE dimer from au | 5IRE | 3.22 (800) | 1.72 (789) | 1.67 (778) 1.69 (764) | 3.72 (775) | / | | | |
| ZIKV mature virion icosahedral sE dimer | 5IRE | 2.88 (800) | 1.76 (789) | 1.60 (778) 1.71 (764) | 3.74 (775) | 0.46 (808)§ 0.45 (1002)§ | / | | |
| ZIKV thermally stable mature virion sE dimer from au | 5IZ7 | 3.03 (800) | 1.85 (789) | 1.75 (778) 1.88 (764) | 3.89 (775) | 1.36 (808)§ 1.57 (1002)§ | 1.36 (808)§ 1.56 (1002)§ | / | |
| ZIKV thermally stable mature virion icosahedral sE dimer | 5IZ7 | 2.94 (800) | 1.84 (789) | 1.67 (778) 1.80 (764) | 3.79 (775) | 1.36 (808)§ 1.58 (1002)§ | 1.36 (808)§ 1.54 (1002)§ | 1.41 (808)§ 1.43 (1008)§ | / |

| ZIKV/DENV-2* | PDB code | ZIKV sE (this work) SL8V | ZIKV sE-EDE2 A11 Fab (this work) SLCV | ZIKV sE-EDE1 C8 scFv† (this work) SL8S | ZIKV sE (Dai et al, 2016) 5JHM | ZIKV sE mature virion sE dimer from au 5IRE | ZIKV sE mature virion icosahedral sE dimer 5IRE | ZIKV thermally stable mature virion sE dimer from au 5IZ7 | ZIKV thermally stable mature virion icosahedral sE dimer 5IZ7 |
|---|---|---|---|---|---|---|---|---|---|
| DENV-2 sE | 4UTC | 4.57 (766) | 6.47 (768) | 5.49 (756) 5.55 (742) | 4.76 (753) | 5.94 (772) | 5.94 (772) | 6.23 (757) | 6.18 (757) |
| DENV-2 sE-EDE2 A11 Fab | 4UT6 | 4.45 (773) | 7.98 (774) 0.29/0.28 (241)¶ | 5.81 (763) 5.57 (744) | 4.2 (754) | 6.29 (773) | 6.28 (773) | 7.38 (763) | 7.31 (763) |
| DENV-2 sE-EDE1 C8 Fab | 4UTA | 6.04 (749) | 8.17 (744) | 6.88 (748) 6.78 (736) | 5.71 (747) | 7.52 (751) | 7.49 (751) | 7.66 (738) | 7.57 (738) |
| DENV-2 mature virion sE dimer from au | 3J27 | 3.69 (779) | 2.28 (776) | 2.36 (768) 3.81 (755) | 4.82 (766) | 2.01 (789)§ 2.09 (979)§ | 2.04 (789)§ 2.13 (979)§ | 4.33 (770)§ 2.15 (988)§ | 4.38 (770)§ 2.29 (988)§ |
| DENV-2 mature virion icosahedral sE dimer | 3J27 | 3.58 (779) | 2.45 (776) | 2.25 (768) 3.68 (755) | 4.49 (766) | 1.99 (789)§ 2.07 (979)§ | 1.99 (789)§ 2.07 (979)§ | 4.31 (770)§ 2.14 (988)§ | 4.33 (770)§ 2.15 (988)§ |

| DENV-2* | PDB code | DENV-2 sE 4UTC | DENV-2 sE-EDE2 A11 Fab 4UT6 | DENV-2 sE-EDE1 C8 Fab 4UTA | DENV-2 mature virion sE dimer from au 3J27 | DENV-2 mature virion icosahedral sE dimer 3J27 |
|---|---|---|---|---|---|---|
| DENV-2 sE | 4UTC | / | | | | |
| DENV-2 sE-EDE2 A11 Fab | 4UT6 | 2.34 (775) | / | | | |
| DENV-2 sE-EDE1 C8 Fab | 4UTA | 2.93 (747) | 1.53 (741) | / | | |
| DENV-2 mature virion sE dimer from au | 3J27 | 5.26 (779) | 6.76 (775) | 6.99 (754) | / | |
| DENV-2 mature virion icosahedral sE dimer | 3J27 | 4.92 (779) | 6.37 (775) | 6.56 (754) | 0.89 (789)§ 0.88 (980)§ | / | r.m.s.d. (in Å) computed with PyMOL software using the Cα atoms of the sE dimers. In parentheses, the number of Cα atoms used for the calculation. au, asymmetric unit.
* The r.m.s.d. is computed using residues 1 to 403 for ZIKV sE, or residues 1 to 395 for DENV-2 sE, except where indicated§,‖.
† There are two independent half dimers (ZIKV sE-EDE1 C8 scFv) in the asymmetric unit. The r.m.s.d. is computed between the two dimers of sE generated by crystallographic symmetry for each sE in the asymmetric unit.
‡ The r.m.s.d. is computed between the two independent half dimers of sE in the asymmetric unit.
§ This r.m.s.d. is computed between the sE dimers excluding stem and transmembrane regions of ZIKV (residues 1 to 403) and DENV-2 (residues 1 to 395).
‖ This r.m.s.d. is computed between the sE dimers including stem and transmembrane regions of ZIKV and DENV-2 (residues 1 to C-terminus).
¶ The two r.m.s.d. values refer to the superposition of the variable domains of Fab A11 in ZIKV sE-EDE2 A11 Fab complex on each Fab A11 in DENV-2 sE-EDE2 A11 Fab complex.

FIG. 18E

| | BSA BNA Fab or scFv | | | BSA sE dimer | | | | | Complex | |
|---|---|---|---|---|---|---|---|---|---|---|
| | vH | vL | Total | Reference subunit (glycans*) | Opposite subunit (glycans*) | Total | Main chain atoms‡ | Total glycan BSA | BSA/molecule | SC |
| ZIKV sE - EDE1 C8 scFv fragment§ | | | | | | | | | | |
| ZIKV sE dimer Epitope dimer-1 | 426.1 | 494.8 | 920.9 | 653.0 (NA) | 237.2 (NA) | 890.2 | 346.9 (39%) | NA | 905.5 | 0.683 |
| ZIKV sE dimer Epitope dimer-2 | 438.4 | 492.4 | 930.8 | 678.1 (NA) | 223.2 (NA) | 901.3 | 343.9 (38%) | NA | 916.0 | 0.738 |
| DENV-2 sE - EDE1 C8 Fab fragment (4UTA) | | | | | | | | | | |
| DENV-2 sE dimer Epitope A | 718.9 (516.8)† | 471.0 (471.0)† | 1189.9 | 919.1 (192.9) | 222.2 | 1141.3 | 357.8 (31%) | 192.9 (17%) | 1165.6 | 0.693 |
| DENV-2 sE dimer Epitope B | 831.9 (570.3)† | 528.3 (528.3)† | 1360.2 | 945.5 (230.9) | 340.0 | 1285.5 | 359.0 (28%) | 230.9 (18%) | 1322.8 | 0.687 |
| ZIKV sE - EDE2 A11 Fab fragment‖ | | | | | | | | | | |
| ZIKV sE dimer Epitope | 718.5 | 75.7 | 793.4 | 570.0 (0.0) | 217.4 (134.6) | 787.4 | 253.7 (32.2%) | 134.6 (17%) | 790.4 | 0.674 |
| DENV-2 sE - EDE2 A11 Fab fragment (4UTB) | | | | | | | | | | |
| DENV-2 sE dimer Epitope A | 923.8 (251.3)† | 189.2 (148.8)† | 1113.0 | 531.8 (14.2) | 472.6 (342.4) | 1004.4 | 221.5 (22%) | 356.6 (35%) | 1058.7 | 0.706 |
| DENV-2 sE dimer Epitope B | 954.1 (302.2)† | 185.1 (136.7)† | 1139.8 | 460.3 (58.5) | 571.3 (341.4) | 1031.6 | 219.3 (21.2%) | 400.0 (39%) | 1085.2 | 0.668 |

BSA, buried surface area (in Å²) of sE protein by the Fabs or scFv (calculated with the program 'areaimol' in CCP4). BSA/molecule, average buried surface area between one Fab or one scFv and the sE dimer. SC, shape complementarity coefficient (calculated with the program 'sc' in CCP4). The dots density used to compute both BSA and SC was set to 15 dots per Å². The van der Waals probe radius was set to 1.4 Å. NA, non applicable.

*In parentheses, contribution of glycan chains to buried surface area: N154 (for ZIKV sE) and N67 and/or N153 (for DENV-2 sE).

†In parentheses, the BSA was computed removing the glycan chains N67 for DENV-2 sE, to compare with the BSA of ZIKV sE, which does not carry the N67 glycan.

‡Contribution of main-chain atoms to BSA, in parentheses, contribution indicated as percentages.

§There are two independent half dimers (ZIKV sE—EDE1 C8 scFv) in the asymmetric unit. Two dimers of ZIKV sE (dimer-1 and dimer-2) are generated by applying crystallographic symmetry for each sE in the asymmetric unit.

‖Only one Fab A11 binds to the sE dimer in the ZIKV sE—EDE2 A11 Fab complex.

FIG. 18F

Extended Data Table 4. Polar and salt bridges interactions for ZIKV sE/EDE1 C8 ScFv, ZIKV sE/EDE2 A11 Fab, DENV-2 sE/EDE1 C8 Fab and DENV-2 sE/EDE2 A11 Fab The polar contacts were computed with PISA server (REF). In bold red: main chain atoms involved in contacts; in bold black: salt bridges. In bold blue: glycan interactions. Hydrogen bonds distances cut-off: 3.5A; Salt bridges distances cut-off: ≤ 4A

FIG. 19

Extended Data Table 5 Polar and salt bridges interactions for ZIKV sE/EDE1 C8 ScFv, ZIKV sE/EDE2 A11 Fab, DENV-2 sE/EDE1 C8 Fab and DENV-2 sE/EDE2 A11 Fab

FIG. 20

E PROTEIN AMINO ACIDS IDENTITY

FIG. 22A

FIG. 22B

Immature particle

Mature particle

FIG. 23A  FIG. 23B

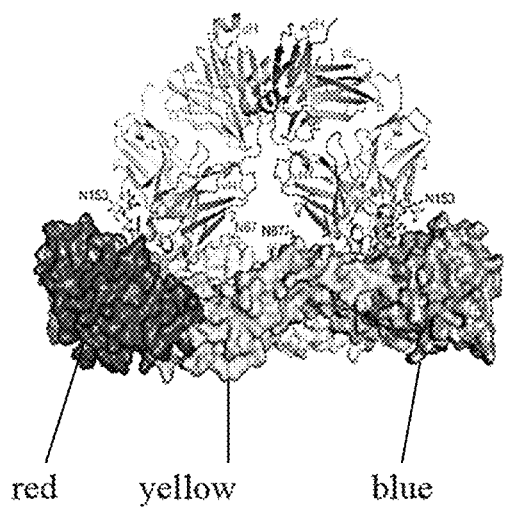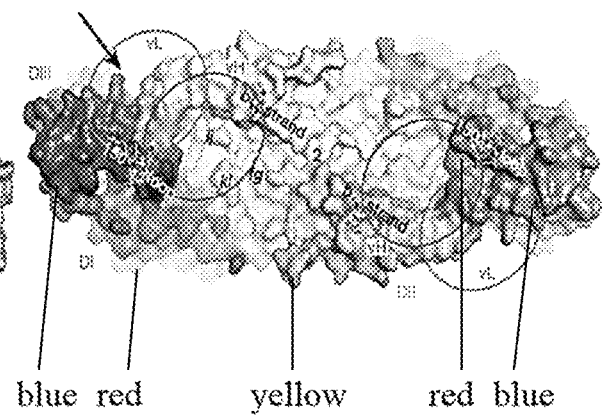
FIG. 24A  FIG. 24B
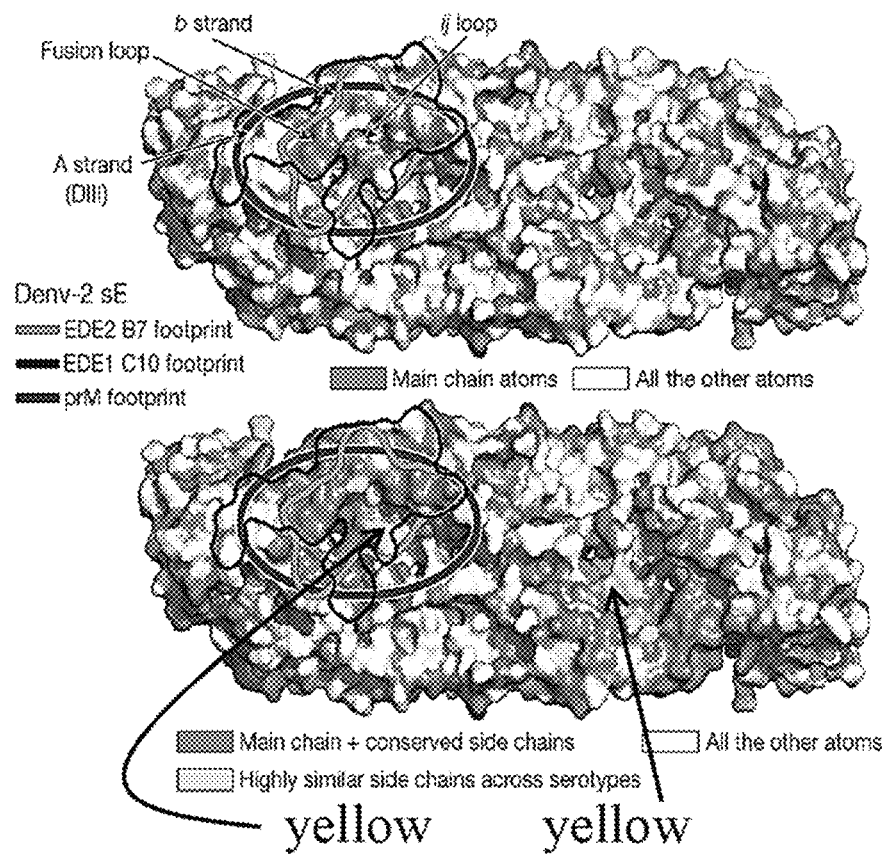
FIG. 24C

FLOW CHART FOR RE-SURFACING STRATEGY

ANALYSIS OF EXPOSED RESIDUES ON THE E DIMER OUTER SURFACE
↓
EXCLUDE RESIDUES INVOLVED IN CONTACT WITH EDE1/EDE2 Ab BY ANALYSIS OF STRUCTURES AND DATA FROM ALANINE SCANNING MUTAGENESIS
↓
46 RESIDUES FOUND ON THE SURFACE OF THE E DIMER NOT ENGAGED IN EDE
ALLOCATE SUBSET OF RESIDUES CONSERVED AMONG 4 DENGUE SEROTYPES (17 RESIDUES)
↓
RE-DESIGN → DESIGN MULTIPLE SUBSTITUTIONS AT THOSE POSITIONS
TWO POSSIBLE AMINO ACID SUBSTITUTIONS PER POSITION

INFORMATION FROM STRUCTURAL/SEQUENCE COMPARISON WITH ALL 4 DENGUE SEROTYPES

ROSETTA SCORING FOR STABILITY AND FOLDING
↓
MANUAL ANALYSIS OF THE ROSETTA BEST CANDIDATE

INFORMATION FROM STRUCTURAL/SEQUENCE COMPARISON WITH OTHER FLAVIVIRUSES

INTRODUCE N-LINKED GLYCOSYLATION SITES TO MASK THE HYPERVARIABLE REGIONS OUTSIDE EDE EPITOPE

SELECTION OF 192 BEST SCORED CANDIDATES FOR EXPERIMENTAL TESTING
↓
EXPRESSION AND IMMUNOREACTIVITY TESTS WITH PANEL OF EDE Abs VERSUS SEROTYPE SPECIFIC AND ENHANCING Abs

FIG. 27

FIG. 28

SEQUENCE LISTING

<160> NUMBER OF SEQ ID NOS: 151

<210> SEQ ID NO 1
<211> LENGTH: 404
<212> TYPE: PRT
<213> ORGANISM: Zika virus
<220> FEATURE:
<223> OTHER INFORMATION: Zika virus (ZIKV, KJ776791, strain
      H-PF-2013_French_Polynesia) Envelope portion of polyprotein
      sequence

<400> SEQUENCE: 1

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95
```

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly

<210> SEQ ID NO 2
<211> LENGTH: 395
<212> TYPE: PRT
<213> ORGANISM: Dengue virus 1
<220> FEATURE:
<223> OTHER INFORMATION: dengue virus serotype 1 (DENV-1, NC_001477)
      Envelope portion of polyprotein sequence

<400> SEQUENCE: 2

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

```
Glu Val Thr Asn Pro Ala Val Leu Arg Lys Leu Cys Ile Glu Ala Lys
 50                  55                  60

Ile Ser Asn Thr Thr Thr Asp Ser Arg Cys Pro Thr Gln Gly Glu Ala
 65                  70                  75                  80

Thr Leu Val Glu Glu Gln Asp Thr Asn Phe Val Cys Arg Arg Thr Phe
                 85                  90                  95

Val Asp Arg Gly Trp Gly Asn Gly Cys Gly Leu Phe Gly Lys Gly Ser
                100                 105                 110

Leu Ile Thr Cys Ala Lys Phe Lys Cys Val Thr Lys Leu Glu Gly Lys
            115                 120                 125

Ile Val Gln Tyr Glu Asn Leu Lys Tyr Ser Val Ile Val Thr Val His
        130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Lys Ser Trp Leu Val
        195                 200                 205

His Lys Gln Trp Phe Leu Asp Leu Pro Leu Pro Trp Thr Ser Gly Ala
210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Ile Leu Lys Gly Met Ser Tyr Val Met Cys Thr Gly
290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
370                 375                 380

Lys Ala Leu Lys Leu Ser Trp Phe Lys Lys Gly
385                 390                 395

<210> SEQ ID NO 3
<211> LENGTH: 395
<212> TYPE: PRT
<213> ORGANISM: Dengue virus 2
<220> FEATURE:
<223> OTHER INFORMATION: dengue virus serotype 2 (DENV-2, NC_001474)
      Envelope portion of polyprotein sequence

<400> SEQUENCE: 3

Met Arg Cys Ile Gly Met Ser Asn Arg Asp Phe Val Glu Gly Val Ser
```

```
                1               5                   10                  15
        Gly Gly Ser Trp Val Asp Ile Val Leu Glu His Gly Ser Cys Val Thr
                        20                  25                  30
        Thr Met Ala Lys Asn Lys Pro Thr Leu Asp Phe Glu Leu Ile Lys Thr
                        35                  40                  45
        Glu Ala Lys Gln Pro Ala Thr Leu Arg Lys Tyr Cys Ile Glu Ala Lys
                        50                  55                  60
        Leu Thr Asn Thr Thr Thr Glu Ser Arg Cys Pro Thr Gln Gly Glu Pro
        65                      70                  75                  80
        Ser Leu Asn Glu Glu Gln Asp Lys Arg Phe Val Cys Lys His Ser Met
                        85                  90                  95
        Val Asp Arg Gly Trp Gly Asn Gly Cys Gly Leu Phe Gly Lys Gly Gly
                        100                 105                 110
        Ile Val Thr Cys Ala Met Phe Arg Cys Lys Lys Asn Met Glu Gly Lys
                        115                 120                 125
        Val Val Gln Pro Glu Asn Leu Glu Tyr Thr Ile Val Ile Thr Pro His
                        130                 135                 140
        Ser Gly Glu Glu His Ala Val Gly Asn Asp Thr Gly Lys His Gly Lys
        145                     150                 155                 160
        Glu Ile Lys Ile Thr Pro Gln Ser Ser Ile Thr Glu Ala Glu Leu Thr
                        165                 170                 175
        Gly Tyr Gly Thr Val Thr Met Glu Cys Ser Pro Arg Thr Gly Leu Asp
                        180                 185                 190
        Phe Asn Glu Met Val Leu Leu Gln Met Glu Asn Lys Ala Trp Leu Val
                        195                 200                 205
        His Arg Gln Trp Phe Leu Asp Leu Pro Leu Pro Trp Leu Pro Gly Ala
                        210                 215                 220
        Asp Thr Gln Gly Ser Asn Trp Ile Gln Lys Glu Thr Leu Val Thr Phe
        225                     230                 235                 240
        Lys Asn Pro His Ala Lys Lys Gln Asp Val Val Val Leu Gly Ser Gln
                        245                 250                 255
        Glu Gly Ala Met His Thr Ala Leu Thr Gly Ala Thr Glu Ile Gln Met
                        260                 265                 270
        Ser Ser Gly Asn Leu Leu Phe Thr Gly His Leu Lys Cys Arg Leu Arg
                        275                 280                 285
        Met Asp Lys Leu Gln Leu Lys Gly Met Ser Tyr Ser Met Cys Thr Gly
                        290                 295                 300
        Lys Phe Lys Val Val Lys Glu Ile Ala Glu Thr Gln His Gly Thr Ile
        305                     310                 315                 320
        Val Ile Arg Val Gln Tyr Glu Gly Asp Gly Ser Pro Cys Lys Ile Pro
                        325                 330                 335
        Phe Glu Ile Met Asp Leu Glu Lys Arg His Val Leu Gly Arg Leu Ile
                        340                 345                 350
        Thr Val Asn Pro Ile Val Thr Glu Lys Asp Ser Pro Val Asn Ile Glu
                        355                 360                 365
        Ala Glu Pro Pro Phe Gly Asp Ser Tyr Ile Ile Ile Gly Val Glu Pro
                        370                 375                 380
        Gly Gln Leu Lys Leu Asn Trp Phe Lys Lys Gly
        385                     390                 395

<210> SEQ ID NO 4
<211> LENGTH: 393
<212> TYPE: PRT
<213> ORGANISM: Dengue virus 3
```

<220> FEATURE:
<223> OTHER INFORMATION: dengue virus serotype 3 (DENV-3, NC_001475)
      Envelope port 385          390

<210> SEQ ID NO 5
<211> LENGTH: 395
<212> TYPE: PRT
<213> ORGANISM: Dengue virus 4
<220> FEATURE:
<223> OTHER INFORMATION: dengue virus serotype 4 (DENV-4, NC_002640)
      Envelope portion of polyprotein sequence

<400> SEQUENCE: 5

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Val Thr Val His
    130                 135                 140

Asn Gly Asp Thr His Ala Val Gly Asn Asp Thr Ser Asn His Gly Val
145                 150                 155                 160

Thr Ala Met Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

```
Ser Ser Thr Pro Leu Ala Glu Asn Thr Asn Ser Val Thr Asn Ile Glu
            355                 360                 365

Leu Glu Pro Pro Phe Gly Asp Ser Tyr Ile Val Ile Gly Val Gly Asn
            370                 375                 380

Ser Ala Leu Thr Leu His Trp Phe Arg Lys Gly
385                 390                 395

<210> SEQ ID NO 6
<211> LENGTH: 401
<212> TYPE: PRT
<213> ORGANISM: St. Louis encephalitis virus
<220> FEATURE:
<223> OTHER INFORMATION: Saint Louis encephalitis virus (SLEV,
      NC_007580) Envelope portion of polyprotein sequence

<400> SEQUENCE: 6

Phe Asn Cys Leu Gly Thr Ser Asn Arg Asp Phe Val Glu Gly Ala Ser
1               5                   10                  15

Gly Ala Thr Trp Ile Asp Leu Val Leu Glu Gly Gly Ser Cys Val Thr
            20                  25                  30

Val Met Ala Pro Glu Lys Pro Thr Leu Asp Phe Lys Val Met Lys Met
            35                  40                  45

Glu Ala Thr Glu Leu Ala Thr Val Arg Glu Tyr Cys Tyr Glu Ala Thr
    50                  55                  60

Leu Asp Thr Leu Ser Thr Val Ala Arg Cys Pro Thr Thr Gly Glu Ala
65                  70                  75                  80

His Asn Thr Lys Arg Ser Asp Pro Thr Phe Val Cys Lys Arg Asp Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Thr Cys Lys Asn Lys Ala Thr Gly Lys
            115                 120                 125

Thr Ile Leu Arg Glu Asn Ile Lys Tyr Glu Val Ala Ile Phe Val His
    130                 135                 140

Gly Ser Thr Asp Ser Thr Ser His Gly Asn Tyr Ser Glu Gln Ile Gly
145                 150                 155                 160

Lys Asn Gln Ala Ala Arg Phe Thr Ile Ser Pro Gln Ala Pro Ser Phe
                165                 170                 175

Thr Ala Asn Met Gly Glu Tyr Gly Thr Val Thr Ile Asp Cys Glu Ala
            180                 185                 190

Arg Ser Gly Ile Asn Thr Glu Asp Tyr Tyr Val Phe Thr Val Lys Glu
            195                 200                 205

Lys Ser Trp Leu Val Asn Arg Asp Trp Phe His Asp Leu Asn Leu Pro
    210                 215                 220

Trp Thr Ser Pro Ala Thr Thr Asp Trp Arg Asn Arg Glu Thr Leu Val
225                 230                 235                 240

Glu Phe Glu Glu Pro His Ala Thr Lys Gln Thr Val Val Ala Leu Gly
                245                 250                 255

Ser Gln Glu Gly Ala Leu His Thr Ala Leu Ala Gly Ala Ile Pro Ala
            260                 265                 270

Thr Val Ser Ser Ser Thr Leu Thr Leu Gln Ser Gly His Leu Lys Cys
            275                 280                 285

Arg Ala Lys Leu Asp Lys Val Lys Ile Lys Gly Thr Thr Tyr Gly Met
    290                 295                 300

Cys Asp Ser Ala Phe Thr Phe Ser Lys Asn Pro Thr Asp Thr Gly His
305                 310                 315                 320
```

-continued

Gly Thr Val Ile Val Glu Leu Gln Tyr Thr Gly Ser Asn Gly Pro Cys
                325                 330                 335

Arg Val Pro Ile Ser Val Thr Ala Asn Leu Met Asp Leu Thr Pro Val
            340                 345                 350

Gly Arg Leu Val Thr Val Asn Pro Phe Ile Ser Thr Gly Gly Ala Asn
        355                 360                 365

Asn Lys Val Met Ile Glu Val Glu Pro Pro Phe Gly Asp Ser Tyr Ile
370                 375                 380

Val Val Gly Arg Gly Thr Thr Gln Ile Asn Tyr His Trp His Lys Glu
385                 390                 395                 400

Gly

<210> SEQ ID NO 7
<211> LENGTH: 400
<212> TYPE: PRT
<213> ORGANISM: Japanese encephalitis virus
<220> FEATURE:
<223> OTHER INFORMATION: Japanese encephalitis virus (JEV, NC_001437)
      Envelope portion of polyprotein sequence

<400> SEQUENCE: 7

Phe Asn Cys Leu Gly Met Gly Asn Arg Asp Phe Ile Glu Gly Ala Ser
1               5                   10                  15

Gly Ala Thr Trp Val Asp Leu Val Leu Glu Gly Asp Ser Cys Leu Thr
            20                  25                  30

Ile Met Ala Asn Asp Lys Pro Thr Leu Asp Val Arg Met Ile Asn Ile
        35                  40                  45

Glu Ala Ser Gln Leu Ala Glu Val Arg Ser Tyr Cys Tyr His Ala Ser
    50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Pro Glu Asn Ile Lys Tyr Glu Val Gly Ile Phe Val His
    130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Ile Thr Pro Asn Ala Pro Ser Ile
                165                 170                 175

Thr Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Ser Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
            260                 265                 270

```
Glu Tyr Ser Ser Ser Val Lys Leu Thr Ser Gly His Leu Lys Cys Arg
            275                 280                 285

Leu Lys Met Asp Lys Leu Ala Leu Lys Gly Thr Thr Tyr Gly Met Cys
        290                 295                 300

Thr Glu Lys Phe Ser Phe Ala Lys Asn Pro Ala Asp Thr Gly His Gly
305                 310                 315                 320

Thr Val Val Ile Glu Leu Ser Tyr Ser Gly Ser Asp Gly Pro Cys Lys
                325                 330                 335

Ile Pro Ile Val Ser Val Ala Ser Leu Asn Asp Met Thr Pro Val Gly
            340                 345                 350

Arg Leu Val Thr Val Asn Pro Phe Val Ala Thr Ser Ser Ala Asn Ser
        355                 360                 365

Lys Val Leu Val Glu Met Glu Pro Pro Phe Gly Asp Ser Tyr Ile Val
    370                 375                 380

Val Gly Arg Gly Asp Lys Gln Ile Asn His His Trp His Lys Ala Gly
385                 390                 395                 400
```

<210> SEQ ID NO 8
<211> LENGTH: 401
<212> TYPE: PRT
<213> ORGANISM: Murray Valley encephalitis virus
<220> FEATURE:
<223> OTHER INFORMATION: Murray Valley encephalitis virus (MVEV, NC_000943) Envelope portion of polyprotein sequence

<400> SEQUENCE: 8

```
Phe Asn Cys Leu Gly Met Ser Ser Arg Asp Phe Ile Glu Gly Ala Ser
1               5                   10                  15

Gly Ala Thr Trp Val Asp Leu Val Leu Glu Gly Asp Ser Cys Ile Thr
            20                  25                  30

Ile Met Ala Ala Asp Lys Pro Thr Leu Asp Ile Arg Met Met Asn Ile
        35                  40                  45

Glu Ala Thr Asn Leu Ala Leu Val Arg Asn Tyr Cys Tyr Ala Ala Thr
    50                  55                  60

Val Ser Asp Val Ser Thr Val Ser Asn Cys Pro Thr Thr Gly Glu Ser
65                  70                  75                  80

His Asn Thr Lys Arg Ala Asp His Asn Tyr Leu Cys Lys Arg Gly Val
                85                  90                  95

Thr Asp Arg Gly Trp Gly Asn Gly Cys Gly Leu Phe Gly Lys Gly Ser
            100                 105                 110

Ile Asp Thr Cys Ala Lys Phe Thr Cys Ser Asn Ser Ala Ala Gly Arg
        115                 120                 125

Leu Ile Leu Pro Glu Asp Ile Lys Tyr Glu Val Gly Val Phe Val His
    130                 135                 140

Gly Ser Thr Asp Ser Thr Ser His Gly Asn Tyr Ser Thr Gln Ile Gly
145                 150                 155                 160

Ala Asn Gln Ala Val Arg Phe Thr Ile Ser Pro Asn Ala Pro Ala Ile
                165                 170                 175

Thr Ala Lys Met Gly Asp Tyr Gly Glu Val Thr Val Glu Cys Glu Pro
            180                 185                 190

Arg Ser Gly Leu Asn Thr Glu Ala Tyr Tyr Val Met Thr Ile Gly Thr
        195                 200                 205

Lys His Phe Leu Val His Arg Glu Trp Phe Asn Asp Leu Leu Leu Pro
    210                 215                 220

Trp Thr Ser Pro Ala Ser Thr Glu Trp Arg Asn Arg Glu Ile Leu Val
```

-continued

```
                225                 230                 235                 240
Glu Phe Glu Glu Pro His Ala Thr Lys Gln Ser Val Val Ala Leu Gly
                245                 250                 255

Ser Gln Glu Gly Ala Leu His Gln Ala Leu Ala Gly Ala Ile Pro Val
                260                 265                 270

Glu Phe Ser Ser Thr Leu Lys Leu Thr Ser Gly His Leu Lys Cys
                275                 280                 285

Arg Val Lys Met Glu Lys Leu Lys Leu Lys Gly Thr Thr Tyr Gly Met
                290                 295                 300

Cys Thr Glu Lys Phe Thr Phe Ser Lys Asn Pro Ala Asp Thr Gly His
305                 310                 315                 320

Gly Thr Val Val Leu Glu Leu Gln Tyr Thr Gly Ser Asp Gly Pro Cys
                325                 330                 335

Lys Ile Pro Ile Ser Ser Val Ala Ser Leu Asn Asp Met Thr Pro Val
                340                 345                 350

Gly Arg Met Val Thr Ala Asn Pro Tyr Val Ala Ser Ser Thr Ala Asn
                355                 360                 365

Ala Lys Val Leu Val Glu Ile Glu Pro Pro Phe Gly Asp Ser Tyr Ile
                370                 375                 380

Val Val Gly Arg Gly Asp Lys Gln Ile Asn His His Trp His Lys Glu
385                 390                 395                 400

Gly

<210> SEQ ID NO 9
<211> LENGTH: 397
<212> TYPE: PRT
<213> ORGANISM: West Nile virus
<220> FEATURE:
<223> OTHER INFORMATION: West Nile virus (WNV, NC_001563) Envelope
      portion of polyprotein sequence

<400> SEQUENCE: 9

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
                20                  25                  30

Ile Met Ser Lys Asp Lys Pro Thr Ile Asp Val Lys Met Met Asn Met
                35                  40                  45

Glu Ala Ala Asn Leu Ala Asp Val Arg Ser Tyr Cys Tyr Leu Ala Ser
                50                  55                  60

Val Ser Asp Leu Ser Thr Arg Ala Ala Cys Pro Thr Met Gly Glu Ala
65                  70                  75                  80

His Asn Glu Lys Arg Ala Asp Pro Ala Phe Val Cys Lys Gln Gly Val
                85                  90                  95

Val Asp Arg Gly Trp Gly Asn Gly Cys Gly Leu Phe Gly Lys Gly Ser
                100                 105                 110

Ile Asp Thr Cys Ala Lys Phe Ala Cys Thr Thr Lys Ala Thr Gly Trp
                115                 120                 125

Ile Ile Gln Lys Glu Asn Ile Lys Tyr Glu Val Ala Ile Phe Val His
                130                 135                 140

Gly Pro Thr Thr Val Glu Ser His Gly Lys Ile Gly Ala Thr Gln Ala
145                 150                 155                 160

Gly Arg Phe Ser Ile Thr Pro Ser Ala Pro Ser Tyr Thr Leu Lys Leu
                165                 170                 175

Gly Glu Tyr Gly Glu Val Thr Val Asp Cys Glu Pro Arg Ser Gly Ile
```

```
                180                 185                 190
Asp Thr Ser Ala Tyr Tyr Val Met Ser Val Gly Glu Lys Ser Phe Leu
            195                 200                 205

Val His Arg Glu Trp Phe Met Asp Leu Asn Leu Pro Trp Ser Ser Ala
210                 215                 220

Gly Ser Thr Thr Trp Arg Asn Arg Glu Thr Leu Met Glu Phe Glu Glu
225                 230                 235                 240

Pro His Ala Thr Lys Gln Ser Val Val Ala Leu Gly Ser Gln Glu Gly
            245                 250                 255

Ala Leu His Gln Ala Leu Ala Gly Ala Ile Pro Val Glu Phe Ser Ser
            260                 265                 270

Asn Thr Val Lys Leu Thr Ser Gly His Leu Lys Cys Arg Val Lys Met
            275                 280                 285

Glu Lys Leu Gln Leu Lys Gly Thr Thr Tyr Gly Val Cys Ser Lys Ala
            290                 295                 300

Phe Lys Phe Ala Arg Thr Pro Ala Asp Thr Gly His Gly Thr Val Val
305                 310                 315                 320

Leu Glu Leu Gln Tyr Thr Gly Thr Asp Gly Pro Cys Lys Val Pro Ile
            325                 330                 335

Ser Ser Val Ala Ser Leu Asn Asp Leu Thr Pro Val Gly Arg Leu Val
            340                 345                 350

Thr Val Asn Pro Phe Val Ser Val Ala Thr Ala Asn Ser Lys Val Leu
            355                 360                 365

Ile Glu Leu Glu Pro Pro Phe Gly Asp Ser Tyr Ile Val Val Gly Arg
            370                 375                 380

Gly Glu Gln Gln Ile Asn His His Trp His Lys Ser Gly
385                 390                 395

<210> SEQ ID NO 10
<211> LENGTH: 395
<212> TYPE: PRT
<213> ORGANISM: Dengue virus 2
<220> FEATURE:
<223> OTHER INFORMATION: Envelope ectodomain of the DENV-2 strain used
      in the structural studies described in Example 2, shown in
      Example 2 ED Figure 7

<400> SEQUENCE: 10

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Ile Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Lys Phe Thr Cys Lys Lys Asn Met Glu Gly Lys
        115                 120                 125

Ile Val Gln Pro Glu Asn Leu Glu Tyr Thr Ile Val Ile Thr Pro His
    130                 135                 140
```

```
Ser Gly Glu Glu His Ala Val Gly Asn Asp Thr Gly Lys His Gly Lys
145                 150                 155                 160

Glu Ile Lys Ile Thr Pro Gln Ser Ser Thr Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asp Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Met
                260                 265                 270

Ser Ser Gly Asn Leu Leu Phe Thr Gly His Leu Lys Cys Arg Leu Arg
            275                 280                 285

Met Asp Lys Leu Gln Leu Lys Gly Met Ser Tyr Ser Met Cys Thr Gly
    290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Thr Asp Leu Glu Lys Arg His Val Leu Gly Arg Leu Ile
                340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Val Gly Val Glu Pro
        370                 375                 380

Gly Gln Leu Lys Leu Asn Trp Phe Lys Lys Gly
385                 390                 395

<210> SEQ ID NO 11
<211> LENGTH: 120
<212> TYPE: PRT
<213> ORGANISM: Artificial Sequence
<220> FEATURE:
<223> OTHER INFORMATION: Antibody EDE1 752-2 C8 H chain

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
                20                  25                  30

Ser Met His Trp Val Arg Gln Ala Pro Gly Lys Gly Leu Glu Tyr Val
            35                  40                  45

Ser Ala Ile Thr Gly Glu Gly Asp Ser Ala Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Phe Glu Met Asn Ser Leu Arg Pro Glu Asp Thr Ala Val Tyr Tyr Cys
                85                  90                  95

Val Gly Gly Tyr Ser Asn Phe Tyr Tyr Tyr Thr Met Asp Val Trp
                100                 105                 110
```

Gly Gln Gly Thr Thr Val Thr Val
        115                 120

<210> SEQ ID NO 12
<211> LENGTH: 126
<212> TYPE: PRT
<213> ORGANISM: Artificial Sequence
<220> FEATURE:
<223> OTHER INFORMATION: Antibody EDE1 753(3) C10 H chain

<400> SEQUENCE: 12

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Lys Val Asp Asp Tyr Gly Asp Tyr Trp Phe Pro Thr Leu
            100                 105                 110

Trp Tyr Phe Asp Tyr Trp Gly Gln Gly Thr Leu Val Thr Val
        115                 120                 125

<210> SEQ ID NO 13
<211> LENGTH: 108
<212> TYPE: PRT
<213> ORGANISM: Artificial Sequence
<220> FEATURE:
<223> OTHER INFORMATION: Antibody EDE1 752-2 C8 L chain

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Phe
            20                  25                  30

Leu Ala Trp Tyr Gln His Lys Pro Gly Gln Ala Pro Arg Leu Leu Ile
        35                  40                  45

Tyr Asp Ala Ser Thr Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln Gln Arg Tyr Asn Trp Pro Pro
                85                  90                  95

Tyr Thr Phe Gly Gln Gly Thr Lys Val Glu Ile Lys
            100                 105

<210> SEQ ID NO 14
<211> LENGTH: 110
<212> TYPE: PRT
<213> ORGANISM: Artificial Sequence
<220> FEATURE:
<223> OTHER INFORMATION: Antibody EDE1 753(3) C10 L chain

<400> SEQUENCE: 14

-continued

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Phe
            20                  25                  30

Asn Tyr Val Ser Trp Phe Gln Gln His Pro Gly Lys Ala Pro Lys Leu
        35                  40                  45

Met Leu Tyr Asp Val Thr Ser Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser His Thr Ser Arg
                85                  90                  95

Gly Thr Trp Val Phe Gly Gly Gly Thr Lys Leu Thr Val Leu
            100                 105                 110

<210> SEQ ID NO 15
<211> LENGTH: 5
<212> TYPE: PRT
<213> ORGANISM: Artificial Sequence
<220> FEATURE:
<223> OTHER INFORMATION: C8 CDR H1

<400> SEQUENCE: 15

Thr Tyr Ser Met His
1               5

<210> SEQ ID NO 16
<211> LENGTH: 17
<212> TYPE: PRT
<213> ORGANISM: Artificial Sequence
<220> FEATURE:
<223> OTHER INFORMATION: C8 CDR H2

<400> SEQUENCE: 16

Ala Ile Thr Gly Glu Gly Asp Ser Ala Phe Tyr Ala Asp Ser Val Lys
1               5                   10                  15

Gly

<210> SEQ ID NO 17
<211> LENGTH: 8
<212> TYPE: PRT
<213> ORGANISM: Artificial Sequence
<220> FEATURE:
<223> OTHER INFORMATION: C8 CDR H3

<400> SEQUENCE: 17

Gly Tyr Ser Asn Phe Tyr Tyr Tyr
1               5

<210> SEQ ID NO 18
<211> LENGTH: 5
<212> TYPE: PRT
<213> ORGANISM: Artificial Sequence
<220> FEATURE:
<223> OTHER INFORMATION: C10 CDR H1

<400> SEQUENCE: 18

Ser Tyr Ala Met His
1               5

<210> SEQ ID NO 19
<211> LENGTH: 17
<212> TYPE: PRT

```
<213> ORGANISM: Artificial Sequence
<220> FEATURE:
<223> OTHER INFORMATION: C10 CDR H2

<400> SEQUENCE: 19

Trp Ile Asn Ala Gly Asn Gly Asn Thr Lys Tyr Ser Gln Lys Phe Gln
1               5                   10                  15

Asp

<210> SEQ ID NO 20
<211> LENGTH: 15
<212> TYPE: PRT
<213> ORGANISM: Artificial Sequence
<220> FEATURE:
<223> OTHER INFORMATION: C10 CDR H3

<400> SEQUENCE: 20

Asp Lys Val Asp Asp Tyr Gly Asp Tyr Trp Phe Pro Thr Leu Trp
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: C8-CDR L1

<400> SEQUENCE: 21

Arg Ala Ser Gln Ser Ile Ser Thr Phe Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: C8 CDR L2

<400> SEQUENCE: 22

Asp Ala Ser Thr Arg Ala Thr
1               5

<210> SEQ ID NO 23
<211> LENGTH: 10
<212> TYPE: PRT
<213> ORGANISM: Artificial Sequence
<220> FEATURE:
<223> OTHER INFORMATION: C8 CDR L3

<400> SEQUENCE: 23

Gln Gln Arg Tyr Asn Trp Pro Pro Tyr Thr
1               5                   10

<210> SEQ ID NO 24
<211> LENGTH: 14
<212> TYPE: PRT
<213> ORGANISM: Artificial Sequence
<220> FEATURE:
<223> OTHER INFORMATION: C10 CDR L1

<400> SEQUENCE: 24

Thr Gly Thr Ser Ser Asp Val Gly Gly Phe Asn Tyr Val Ser
1               5                   10

<210> SEQ ID NO 25
<211> LENGTH: 7
```

```
<212> TYPE: PRT
<213> ORGANISM: Artificial Sequence
<220> FEATURE:
<223> OTHER INFORMATION: C10 CDR L2

<400> SEQUENCE: 25

Asp Val Thr Ser Arg Pro Ser
1               5

<210> SEQ ID NO 26
<211> LENGTH: 11
<212> TYPE: PRT
<213> ORGANISM: Artificial Sequence
<220> FEATURE:
<223> OTHER INFORMATION: C10 CDR L3

<400> SEQUENCE: 26

Ser Ser His Thr Ser Arg Gly Thr Trp Val Phe
1               5                   10

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000
```

<210> SEQ ID NO 35

<400> SEQUENCE: 35

000

<210> SEQ ID NO 36

<400> SEQUENCE: 36

000

<210> SEQ ID NO 37
<211> LENGTH: 108
<212> TYPE: PRT
<213> ORGANISM: Artificial Sequence
<220> FEATURE:
<223> OTHER INFORMATION: Antibody EDE1 752-2 C8 L chain

<400> SEQUENCE: 37

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Phe
            20                  25                  30

Leu Ala Trp Tyr Gln His Lys Pro Gly Gln Ala Pro Arg Leu Leu Ile
        35                  40                  45

Tyr Asp Ala Ser Thr Arg Ala Thr Gly Val Pro Ala Arg Phe Ser Gly
50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln Gln Arg Tyr Asn Trp Pro Pro
                85                  90                  95

Tyr Thr Phe Gly Gln Gly Thr Lys Val Glu Ile Lys
            100                 105
```

<210> SEQ ID NO 38
<211> LENGTH: 110
<212> TYPE: PRT
<213> ORGANISM: Artificial Sequence
<220> FEATURE:
<223> OTHER INFORMATION: Antibody EDE1 753(3) C10 L chain

<400> SEQUENCE: 38

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Phe
            20                  25                  30

Asn Tyr Val Ser Trp Phe Gln Gln His Pro Gly Lys Ala Pro Lys Leu
        35                  40                  45

Met Leu Tyr Asp Val Thr Ser Arg Pro Ser Gly Val Ser Ser Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser His Thr Ser Arg
                85                  90                  95

Gly Thr Trp Val Phe Gly Gly Gly Thr Lys Leu Thr Val Leu
            100                 105                 110
```

<210> SEQ ID NO 39

```
<400> SEQUENCE: 39

000

<210> SEQ ID NO 40

<400> SEQUENCE: 40

000

<210> SEQ ID NO 41

<400> SEQUENCE: 41

000

<210> SEQ ID NO 42
<211> LENGTH: 122
<212> TYPE: PRT
<213> ORGANISM: Artificial Sequence
<220> FEATURE:
<223> OTHER INFORMATION: Antibody EDE1 752 B10 H chain

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Thr Asp Gly Asn Ser Ala Phe Tyr Ala Asp Ser Val
    50                  55                  60

Lys Gly Arg Phe Thr Ile Ser Arg Asp Asn Ser Lys Asn Thr Met Tyr
65                  70                  75                  80

Phe His Met Asn Ser Leu Arg Pro Glu Asp Thr Ala Val Tyr Tyr Cys
                85                  90                  95

Val Gly Gly Tyr Ser Ser Phe Tyr Tyr Tyr Thr Met Asp Val Trp
            100                 105                 110

Gly Gln Gly Thr Thr Val Thr Val Ser Ser
        115                 120

<210> SEQ ID NO 43
<211> LENGTH: 122
<212> TYPE: PRT
<213> ORGANISM: Artificial Sequence
<220> FEATURE:
<223> OTHER INFORMATION: Antibody EDE1 752 B11 H chain

<400> SEQUENCE: 43

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Thr Asp Gly Asp Ser Ala Phe Tyr Ala Asp Ser Val
    50                  55                  60

Lys Gly Arg Phe Thr Ile Ser Arg Asp Asn Ser Lys Asn Thr Met Phe
65                  70                  75                  80

Phe His Met Ser Asn Leu Arg Pro Glu Asp Thr Ala Val Tyr Tyr Cys
                85                  90                  95
```

```
Val Gly Gly Tyr Ser Ser Phe Tyr Tyr Tyr Thr Leu Asp Val Trp
            100                 105                 110

Gly Gln Gly Thr Thr Val Thr Val Ser Ser
        115                 120

<210> SEQ ID NO 44
<211> LENGTH: 122
<212> TYPE: PRT
<213> ORGANISM: Artificial Sequence
<220> FEATURE:
<223> OTHER INFORMATION: Antibody EDE1 752 C9 H chain

<400> SEQUENCE: 44

Glu Val Gln Leu Val Glu Ser Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
            35                  40                  45

Ser Ala Ile Thr Thr Asn Gly Asp Ser Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Phe Gln Met Ser Ser Leu Arg Ala Glu Asp Thr Gly Val Tyr Tyr Cys
                85                  90                  95

Val Gly Gly Tyr Ser Ser Phe Tyr Tyr Tyr Thr Met Asp Val Trp
            100                 105                 110

Gly Gln Gly Thr Thr Val Thr Val Ser Ser
        115                 120

<210> SEQ ID NO 45

<400> SEQUENCE: 45

000

<210> SEQ ID NO 46

<400> SEQUENCE: 46

000

<210> SEQ ID NO 47
<211> LENGTH: 124
<212> TYPE: PRT
<213> ORGANISM: Artificial Sequence
<220> FEATURE:
<223> OTHER INFORMATION: Antibody EDE1 752(2) A7 H chain

<400> SEQUENCE: 47

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Ser Ser Asn
            20                  25                  30

Asn Tyr Gln Trp Asn Trp Ile Arg Gln Pro Ala Gly Lys Gly Leu Glu
            35                  40                  45

Trp Leu Gly Arg Ile Asp Thr Thr Gly Ser Thr Asn Tyr Asn Pro Ser
        50                  55                  60

Leu Lys Ser Arg Ile Ser Ile Ser Ile Asp Thr Ser Lys Lys Gln Phe
65                  70                  75                  80
```

Ser Leu Arg Leu Asn Ser Val Thr Ala Ala Asp Thr Ala Val Tyr Tyr
            85                  90                  95

Cys Ala Arg Ser Leu Trp Ser Gly Glu Leu Trp Gly Gly Pro Leu Gly
            100                 105                 110

Tyr Trp Gly Gln Gly Thr Leu Val Thr Val Ser Ser
            115                 120

<210> SEQ ID NO 48
<211> LENGTH: 125
<212> TYPE: PRT
<213> ORGANISM: Artificial Sequence
<220> FEATURE:
<223> OTHER INFORMATION: Antibody EDE1 752(2) A8 H chain

<400> SEQUENCE: 48

Glu Val Gln Leu Val Glu Ser Gly Ala Glu Val Lys Asn Pro Gly Ala
1               5                   10                  15

Ser Val Lys Val Ser Cys Lys Ala Ser Gly Tyr Thr Phe Ile Gly Tyr
            20                  25                  30

Tyr Ile His Trp Val Arg Gln Ala Pro Gly Gln Gly Leu Glu Trp Met
            35                  40                  45

Gly Trp Ile Asn Pro Asn Ser Gly Ala Thr Tyr Ser Ala Gln Lys Phe
50                  55                  60

Gln Gly Arg Val Thr Leu Thr Gly Asp Ala Ser Pro Ser Thr Val Tyr
65                  70                  75                  80

Met Glu Leu Ser Ser Leu Arg Ser Asp Asp Thr Ala Ile Tyr Tyr Cys
            85                  90                  95

Ala Gly Arg Ser Tyr Asn Trp Asn Asp Val Phe Tyr Tyr Tyr Tyr Met
            100                 105                 110

Asp Val Trp Gly Gln Gly Thr Thr Val Thr Val Ser Ser
            115                 120                 125

<210> SEQ ID NO 49
<211> LENGTH: 125
<212> TYPE: PRT
<213> ORGANISM: Artificial Sequence
<220> FEATURE:
<223> OTHER INFORMATION: Antibody EDE1 752(2) B10 H chain

<400> SEQUENCE: 49

Glu Val Gln Leu Val Glu Ser Gly Pro Gly Leu Val Lys Pro Ser Glu
1               5                   10                  15

Thr Leu Ser Leu Thr Cys Thr Ile Ser Gly Val Ser Ile Ser Asp Tyr
            20                  25                  30

Tyr Trp Thr Trp Ile Arg Gln Pro Pro Gly Lys Gly Leu Glu Trp Ile
            35                  40                  45

Gly Asn Ile Tyr Asn Thr Gly Ser Thr Asn Tyr Asn Pro Ser Leu Lys
50                  55                  60

Ser Arg Val Ala Ile Trp Met Asp Thr Ser Lys Asn Lys Phe Ser Leu
65                  70                  75                  80

Arg Leu Thr Ser Val Thr Ser Ala Asp Thr Ala Val Tyr Tyr Cys Ala
            85                  90                  95

Arg Val Glu Gly Gly Pro Lys Tyr Tyr Phe Gly Ser Gly Asp Phe Tyr
            100                 105                 110

Asn Leu Trp Gly Arg Gly Ser Leu Val Thr Val Ser Ser
            115                 120                 125

```
<210> SEQ ID NO 50
<211> LENGTH: 125
<212> TYPE: PRT
<213> ORGANISM: Artificial Sequence
<220> FEATURE:
<223> OTHER INFORMATION: Antibody EDE1 752(2) C2 H chain

<400> SEQUENCE: 50

Ser Gln Val Gln Leu Val Gln Ser Gly Ala Glu Leu Lys Lys Pro Gly
1               5                   10                  15

Ala Ser Val Lys Val Ser Cys Lys Thr Ser Gly Tyr Thr Phe Ser Tyr
            20                  25                  30

Tyr Ile His Trp Val Arg Gln Ala Pro Gly Gln Gly Leu Glu Trp Met
        35                  40                  45

Ala Met Ile Asn Pro Thr Ser Gly Ser Thr Ser Tyr Ala Gln Arg Phe
    50                  55                  60

Gln Gly Arg Val Thr Met Thr Arg Asp Thr Pro Thr Asn Thr Val Tyr
65                  70                  75                  80

Met Glu Val Arg Ser Leu Arg Ser Asp Asp Thr Ala Val Tyr Phe Cys
                85                  90                  95

Ala Ser Arg Gly Tyr Asn Trp Asn Asp Val Gln Tyr Tyr Tyr Thr Met
            100                 105                 110

Asp Val Trp Gly Gln Gly Thr Thr Val Thr Val Ser Ser
        115                 120                 125

<210> SEQ ID NO 51
<211> LENGTH: 125
<212> TYPE: PRT
<213> ORGANISM: Artificial Sequence
<220> FEATURE:
<223> OTHER INFORMATION: Antibody EDE1 752(2) D4 H chain

<400> SEQUENCE: 51

Ser Glu Val Gln Leu Val Gln Ser Gly Ala Glu Leu Lys Lys Pro Gly
1               5                   10                  15

Ala Ser Val Lys Val Ser Cys Lys Ala Ser Gly Tyr Thr Phe Ser Tyr
            20                  25                  30

Tyr Ile His Trp Val Arg Gln Ala Pro Gly Gln Gly Leu Glu Trp Met
        35                  40                  45

Ala Ile Ile Asn Pro Thr Ser Gly Ser Thr Ser Tyr Ala Gln Arg Phe
    50                  55                  60

Gln Gly Arg Val Thr Met Thr Arg Asp Thr Ser Thr Asn Thr Val Tyr
65                  70                  75                  80

Met Glu Leu Ser Ser Leu Ile Ser Glu Asp Thr Ala Val Tyr Tyr Cys
                85                  90                  95

Ala Ser Arg Gly Tyr Asn Trp Asn Asp Val His Tyr Tyr Tyr Thr Met
            100                 105                 110

Asp Val Trp Gly Gln Gly Thr Thr Val Thr Val Ser Ser
        115                 120                 125

<210> SEQ ID NO 52

<400> SEQUENCE: 52

000

<210> SEQ ID NO 53
<211> LENGTH: 122
<212> TYPE: PRT
<213> ORGANISM: Artificial Sequence
```

```
<220> FEATURE:
<223> OTHER INFORMATION: Antibody EDE1 752-2 A2 H chain

<400> SEQUENCE: 53

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Ile
        35                  40                  45

Ser Ala Ile Thr Thr Asp Gly Asp Ser Ala Phe Tyr Ala Asp Ser Val
    50                  55                  60

Lys Gly Arg Phe Thr Ile Ser Arg Asp Asn Ser Lys Asn Thr Met Tyr
65                  70                  75                  80

Phe His Met Asn Ser Leu Arg Pro Glu Asp Thr Ala Val Tyr Tyr Cys
                85                  90                  95

Val Gly Gly Tyr Ser Ser Phe Tyr Tyr Tyr Tyr Thr Met Asp Val Trp
            100                 105                 110

Gly Gln Gly Thr Thr Val Thr Val Ser Ser
        115                 120

<210> SEQ ID NO 54

<400> SEQUENCE: 54

000

<210> SEQ ID NO 55

<400> SEQUENCE: 55

000

<210> SEQ ID NO 56
<211> LENGTH: 122
<212> TYPE: PRT
<213> ORGANISM: Artificial Sequence
<220> FEATURE:
<223> OTHER INFORMATION: Antibody EDE1 752-2 A9 H chain

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Thr Asp Gly Asp Ser Ala Phe Tyr Ala Asp Ser Val
    50                  55                  60

Lys Gly Arg Phe Thr Ile Ser Arg Asp Asn Ser Lys Asn Thr Met Tyr
65                  70                  75                  80

Phe His Met Asn Ser Val Arg Pro Glu Asp Thr Ala Val Tyr Tyr Cys
                85                  90                  95

Val Gly Gly Tyr Ser Ser Phe Tyr Tyr Tyr Tyr Thr Met Asp Val Trp
            100                 105                 110

Gly Gln Gly Thr Thr Val Thr Val Ser Ser
        115                 120

<210> SEQ ID NO 57
```

```
<211> LENGTH: 122
<212> TYPE: PRT
<213> ORGANISM: Artificial Sequence
<220> FEATURE:
<223> OTHER INFORMATION: Antibody EDE1 752-2 B2 H chain

<400> SEQUENCE: 57
```

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Thr Asp Gly Asp Ser Ala Phe Tyr Ala Asp Ser Val
    50                  55                  60

Lys Gly Arg Phe Thr Ile Ser Arg Asp Asn Ser Lys Asn Thr Met Tyr
65                  70                  75                  80

Phe His Met Asn Ser Leu Arg Pro Glu Asp Thr Ala Val Tyr Tyr Cys
                85                  90                  95

Val Gly Gly Tyr Ser Ser Phe Tyr Tyr Tyr Thr Met Asp Val Trp
            100                 105                 110

Gly Gln Gly Thr Thr Val Thr Val Ser Ser
        115                 120

```
<210> SEQ ID NO 58
<211> LENGTH: 122
<212> TYPE: PRT
<213> ORGANISM: Artificial Sequence
<220> FEATURE:
<223> OTHER INFORMATION: Antibody EDE1 752-2 B3 H chain

<400> SEQUENCE: 58
```

Glu Val Gln Leu Leu Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Ser Thr Asp Gly Asp Ser Ala Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Phe His Met Ser Ser Leu Arg Ala Glu Asp Thr Ala Val Tyr Tyr Cys
                85                  90                  95

Leu Gly Gly Tyr Ser Thr Phe Tyr Tyr Tyr Thr Met Asp Val Trp
            100                 105                 110

Gly Gln Gly Thr Thr Val Thr Val Ser Ser
        115                 120

```
<210> SEQ ID NO 59
<211> LENGTH: 112
<212> TYPE: PRT
<213> ORGANISM: Artificial Sequence
<220> FEATURE:
<223> OTHER INFORMATION: Antibody EDE1 752-2 B4 H chain

<400> SEQUENCE: 59
```

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Pro Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Thr Asn Gly Asp Ser Thr Tyr Ala Asp Ser Val
50                  55                  60

Lys Gly Arg Phe Thr Ile Ser Arg Asp Asn Ser Lys Asn Thr Val Tyr
65                  70                  75                  80

Phe Gln Leu Ser Ser Leu Arg Ala Glu Asp Thr Ala Val Tyr Tyr Cys
                85                  90                  95

Val Gly Gly Tyr Ser Ser Phe Tyr Phe Tyr Tyr Thr Met Asp Val Trp
            100                 105                 110

<210> SEQ ID NO 60

<400> SEQUENCE: 60

000

<210> SEQ ID NO 61
<211> LENGTH: 122
<212> TYPE: PRT
<213> ORGANISM: Artificial Sequence
<220> FEATURE:
<223> OTHER INFORMATION: Antibody EDE1 752-2 B11 H chain

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Thr Thr Tyr
            20                  25                  30

Ser Leu His Trp Val Arg Gln Thr Pro Gly Lys Gly Leu Glu Tyr Val
        35                  40                  45

Ser Ala Ile Thr Thr Asp Gly Asp Ser Ala Phe Tyr Ala Asp Ser Val
50                  55                  60

Lys Gly Arg Phe Thr Ile Ser Arg Asp Asn Ser Lys Asn Thr Met Tyr
65                  70                  75                  80

Phe His Met Ser Ser Leu Arg Pro Glu Asp Thr Ala Val Tyr Tyr Cys
                85                  90                  95

Val Gly Gly Tyr Ser Ser Phe Tyr Tyr Phe Tyr Thr Val Asp Val Trp
            100                 105                 110

Gly Gln Gly Thr Thr Val Thr Val Ser Phe
        115                 120

<210> SEQ ID NO 62
<211> LENGTH: 125
<212> TYPE: PRT
<213> ORGANISM: Artificial Sequence
<220> FEATURE:
<223> OTHER INFORMATION: Antibody EDE1 752-2 C4 H chain

<400> SEQUENCE: 62

Ser Gln Val Gln Leu Val Glu Ser Gly Ala Glu Leu Lys Lys Pro Gly
1               5                   10                  15

Ala Ser Val Lys Val Ser Cys Lys Ala Ser Gly Tyr Thr Phe Ser Tyr
            20                  25                  30

Tyr Met His Trp Val Arg Gln Ala Pro Gly Gln Gly Leu Glu Trp Met
        35                  40                  45

Ala Ile Ile Asn Pro Thr Ser Gly Ser Thr Thr Tyr Ala Gln Arg Phe

```
                    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Arg Gly Tyr Asn Trp Asn Asp Val His Tyr Tyr Tyr Thr Met
            100                 105                 110

Asp Val Trp Gly Gln Gly Thr Thr Val Thr Val Ser Ser
        115                 120                 125

<210> SEQ ID NO 63
<211> LENGTH: 131
<212> TYPE: PRT
<213> ORGANISM: Artificial Sequence
<220> FEATURE:
<223> OTHER INFORMATION: Antibody EDE1 753(3) B10 H chain

<400> SEQUENCE: 63

Glu Val Gln Leu Val Glu Ser Gly Pro Glu Val Lys Lys Pro Gly Ala
1               5                   10                  15

Ser Val Lys Val Ser Cys Lys Thr Ser Gly Tyr Thr Phe Ile Asn Tyr
                20                  25                  30

Tyr Ile His Trp Val Arg Gln Ala Pro Gly Gln Gly Leu Glu Trp Leu
            35                  40                  45

Gly Leu Ile Asn Pro Arg Gly Gly Asn Thr Asn Tyr Ala Glu Lys Phe
        50                  55                  60

Glu Asp Arg Val Thr Met Thr Arg Asp Thr Ser Thr Ser Thr Val Asn
65                  70                  75                  80

Met Glu Leu Ser Ser Leu Thr Ser Glu Asp Thr Ala Val Tyr Tyr Cys
                85                  90                  95

Ala Arg Pro Leu Ala His Thr Tyr Asp Phe Trp Ser Gly Tyr His Arg
            100                 105                 110

Ala Thr Gly Tyr Gly Met Asp Val Trp Gly Gln Gly Thr Thr Val Thr
        115                 120                 125

Val Ser Ser
    130

<210> SEQ ID NO 64
<211> LENGTH: 126
<212> TYPE: PRT
<213> ORGANISM: Artificial Sequence
<220> FEATURE:
<223> OTHER INFORMATION: Antibody EDE1 758 P6A1 H chain

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Phe Gly Phe Thr Phe Val Asn Tyr
                20                  25                  30

Ala Met Asn Trp Val Arg Gln Ala Pro Gly Lys Gly Pro Glu Trp Val
            35                  40                  45

Ala Val Ile Tyr Ala Ala Gly Asp Gly Ala Asn Tyr Gly Asp Ser Val
        50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Ile Tyr Tyr Cys
                85                  90                  95
```

```
Ala Lys Pro Ala His Tyr Asp Asp Ser Gly Tyr Pro Tyr Met Ala Tyr
            100                 105                 110

Phe Asp Ser Trp Gly Gln Gly Thr Leu Val Thr Val Ser Ser
        115                 120                 125

<210> SEQ ID NO 65
<211> LENGTH: 126
<212> TYPE: PRT
<213> ORGANISM: Artificial Sequence
<220> FEATURE:
<223> OTHER INFORMATION: Antibody EDE1 758 P6A3 H chain

<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Phe Ser Ser Tyr
            20                  25                  30

Ala Ile Thr Trp Val Arg Gln Ala Pro Gly Gln Gly Leu Glu Trp Met
        35                  40                  45

Gly Gly Ile Ile Pro Asp Tyr Asp Ser Ala Lys Tyr Ala Gln Lys Phe
    50                  55                  60

Gln Gly Arg Val Thr Ile Thr Ala Asp Glu Ser Thr Ser Thr Ala Tyr
65                  70                  75                  80

Leu Glu Leu Arg Ser Leu Arg Ser Glu Asp Thr Ala Val Tyr Tyr Cys
                85                  90                  95

Ala Arg Arg His Cys Ser Ser Thr Ser Cys Ser Asp Pro Trp Thr Phe
            100                 105                 110

Phe Pro Ser Trp Gly Gln Gly Thr Leu Val Thr Ser Pro Gln
        115                 120                 125

<210> SEQ ID NO 66

<400> SEQUENCE: 66

000

<210> SEQ ID NO 67
<211> LENGTH: 130
<212> TYPE: PRT
<213> ORGANISM: Artificial Sequence
<220> FEATURE:
<223> OTHER INFORMATION: Antibody EDE1 758 P6B4 H chain

<400> SEQUENCE: 67

Glu Val Gln Leu Val Gln Ser Gly Ala Thr Val Arg Lys Pro Gly Ala
1               5                   10                  15

Ser Val Thr Ile Ser Cys Lys Thr Ser Gly Tyr Thr Phe Thr Asp Tyr
            20                  25                  30

Ala Leu His Trp Val Arg Gln Ala Pro Gly Gln Arg Leu Glu Trp Met
        35                  40                  45

Gly Trp Leu Ile Pro Gly Ser Gly Tyr Thr Lys Phe Ala Glu Asn Phe
    50                  55                  60

Gln Gly Arg Val Thr Ile Thr Arg Ala Thr Ser Ala His Thr Ala Tyr
65                  70                  75                  80

Met Glu Leu Ser Asn Leu Arg Ser Glu Asp Thr Ala Val Tyr Tyr Cys
                85                  90                  95

Ala Arg Trp Gly Gly Asp Cys Asn Ala Gly Ser Cys Tyr Gly Pro Tyr
            100                 105                 110

Gln Tyr Arg Gly Leu Asp Ala Trp Gly Gln Gly Thr Thr Val Thr Val
```

```
                115                 120                 125

Ser Ser
    130

<210> SEQ ID NO 68
<211> LENGTH: 125
<212> TYPE: PRT
<213> ORGANISM: Artificial Sequence
<220> FEATURE:
<223> OTHER INFORMATION: Antibody EDE1 758 P6B5 H chain

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ile Gly Tyr
            20                  25                  30

Tyr Leu His Trp Val Arg Gln Ala Pro Gly Gln Gly Leu Glu Trp Met
        35                  40                  45

Gly Arg Ile Asn Pro Asn Ser Gly Gly Ile Asp Tyr Gly Gln Thr Phe
    50                  55                  60

Gln Gly Arg Val Thr Met Thr Arg Asp Met Ser Ser Thr Val Tyr
65                  70                  75                  80

Leu Glu Leu Thr Arg Leu Arg Ser Asp Thr Ala Arg Tyr Tyr Cys
                85                  90                  95

Ala Gly Arg Ser Asp Asn Trp Asn Asp Val Tyr Tyr Asn Tyr Ala Leu
            100                 105                 110

Asp Val Trp Gly Gln Gly Thr Thr Val Thr Val Ser Ser
        115                 120                 125

<210> SEQ ID NO 69

<400> SEQUENCE: 69

000

<210> SEQ ID NO 70
<211> LENGTH: 128
<212> TYPE: PRT
<213> ORGANISM: Artificial Sequence
<220> FEATURE:
<223> OTHER INFORMATION: Antibody EDE1 758 P6C4 H chain

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Ile His Trp Val Arg Gln Ala Pro Gly Gln Gly Leu Glu Trp Met
        35                  40                  45

Gly Ser Ile Asn Pro Asn Asn Gly Gly Thr Asn Tyr Ala Gln Gly Phe
    50                  55                  60

Gln Gly Arg Val Thr Met Thr Arg Asp Thr Ser Ile Arg Thr Val Tyr
65                  70                  75                  80

Met Glu Leu Ser Lys Leu Arg Ser Asp Asp Thr Ala Leu Tyr Tyr Cys
                85                  90                  95

Ala Arg Asp Leu Gly Ala Met Gly Tyr Tyr Leu Cys Ser Ala Gly Asn
            100                 105                 110

Cys Pro Phe Asp Tyr Trp Gly Gln Gly Thr Leu Val Thr Val Ser Ser
        115                 120                 125
```

<210> SEQ ID NO 71
<211> LENGTH: 122
<212> TYPE: PRT
<213> ORGANISM: Artificial Sequence
<220> FEATURE:
<223> OTHER INFORMATION: Antibody EDE1 752-2 C8 H chain (page 90)

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Ala Ile Thr Gly Glu Gly Asp Ser Ala Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Phe Glu Met Asn Ser Leu Arg Pro Glu Asp Thr Ala Val Tyr Tyr Cys
                85                  90                  95

Val Gly Gly Tyr Ser Asn Phe Tyr Tyr Tyr Thr Met Asp Val Trp
            100                 105                 110

Gly Gln Gly Thr Thr Val Thr Val Ser Ser
        115                 120
```

<210> SEQ ID NO 72
<211> LENGTH: 128
<212> TYPE: PRT
<213> ORGANISM: Artificial Sequence
<220> FEATURE:
<223> OTHER INFORMATION: Antibody EDE1 753(3) C10 H chain (page 90)

<400> SEQUENCE: 72

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Lys Val Asp Asp Tyr Gly Asp Tyr Trp Phe Pro Thr Leu
            100                 105                 110

Trp Tyr Phe Asp Tyr Trp Gly Gln Gly Thr Leu Val Thr Val Ser Ser
        115                 120                 125
```

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

```
000

<210> SEQ ID NO 86

<400> SEQUENCE: 86

000

<210> SEQ ID NO 87

<400> SEQUENCE: 87

000

<210> SEQ ID NO 88
<211> LENGTH: 108
<212> TYPE: PRT
<213> ORGANISM: Artificial Sequence
<220> FEATURE:
<223> OTHER INFORMATION: Antibody EDE1 752 B10 L chain

<400> SEQUENCE: 88

Glu Ile Val Leu Thr Gln Ser Pro Ala Thr Leu Ser Leu Ser Ala Gly
1               5                   10                  15

Asp Arg Ala Thr Leu Ser Cys Arg Ala Ser Gln Asp Ile Ser Ser Phe
            20                  25                  30

Leu Ala Trp Tyr Gln Gln Lys Pro Gly Gln Ala Pro Arg Leu Leu Met
        35                  40                  45

Tyr Asp Thr Ser Asn Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Val Ala Val Tyr Tyr Cys Gln His Arg Tyr Asn Trp Pro Pro
                85                  90                  95

Tyr Thr Phe Gly Gln Gly Thr Lys Val Glu Ile Lys
            100                 105

<210> SEQ ID NO 89
<211> LENGTH: 108
<212> TYPE: PRT
<213> ORGANISM: Artificial Sequence
<220> FEATURE:
<223> OTHER INFORMATION: Antibody EDE1 752 B11 L chain

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Val Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln His Arg Tyr Asn Trp Pro Pro
                85                  90                  95

Tyr Thr Phe Gly Gln Gly Thr Lys Val Glu Ile Lys
            100                 105
```

```
<210> SEQ ID NO 90
<211> LENGTH: 108
<212> TYPE: PRT
<213> ORGANISM: Artificial Sequence
<220> FEATURE:
<223> OTHER INFORMATION: Antibody EDE1 752 C9 L chain

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Val Pro Ala Arg Phe Ser Gly
50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln Gln Arg Tyr Asn Trp Pro Pro
                85                  90                  95

Tyr Thr Phe Gly Gln Gly Thr Lys Val Glu Ile Lys
            100                 105

<210> SEQ ID NO 91

<400> SEQUENCE: 91

000

<210> SEQ ID NO 92

<400> SEQUENCE: 92

000

<210> SEQ ID NO 93
<211> LENGTH: 108
<212> TYPE: PRT
<213> ORGANISM: Artificial Sequence
<220> FEATURE:
<223> OTHER INFORMATION: Antibody EDE1 752(2) A7 L chain

<400> SEQUENCE: 93

Glu Ile Val Met Thr Gln Ser Pro Ala Thr Leu Ser Ala Ser Pro Gly
1               5                   10                  15

Glu Arg Ala Thr Leu Ser Cys Arg Ala Ser Gln Asp Val Ser Thr Phe
            20                  25                  30

Val Ala Trp Phe Gln Gln Asn Pro Gly Gln Ala Pro Arg Leu Leu Ile
        35                  40                  45

Tyr Asp Ala Ser Thr Arg Ala Pro Gly Ile Pro Ala Arg Phe Ser Gly
50                  55                  60

Ser Arg Ser Gly Thr Glu Phe Thr Leu Thr Ile Asn Ser Leu Gln Ser
65                  70                  75                  80

Glu Asp Phe Ala Val Tyr Tyr Cys Gln Gln Tyr Tyr Asn Trp Pro Pro
                85                  90                  95

Trp Thr Phe Gly Gln Gly Thr Lys Val Glu Ile Lys
            100                 105

<210> SEQ ID NO 94
<211> LENGTH: 107
<212> TYPE: PRT
```

<213> ORGANISM: Artificial Sequence
<220> FEATURE:
<223> OTHER INFORMATION: Antibody EDE1 752(2) A8 L chain

<400> SEQUENCE: 94

Asp Ile Gln Met Thr Gln Ser Pro Ser Ser Val Ser Ala Ser Val Gly
1               5                   10                  15

Asp Arg Val Thr Ile Ser Cys Arg Ala Ser Gln Asp Ile Ser Ala Ser
            20                  25                  30

Leu Gly Trp Tyr Gln Gln Lys Pro Gly Lys Ala Pro Lys Leu Leu Ile
        35                  40                  45

Tyr Arg Ala Ser Asn Leu Glu Gly Gly Val Pro Ser Arg Phe Arg Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Asn Ser Phe Pro Leu
                85                  90                  95

Thr Phe Gly Gly Gly Thr Lys Val Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: Antibody EDE1 752(2) B10 L chain

<400> SEQUENCE: 95

Asp Ile Gln Met Thr Gln Ser Pro Ser Ser Leu Ser Ala Ser Val Gly
1               5                   10                  15

Asp Ser Val Thr Val Ala Cys Arg Ala Ser Gln Pro Ile Tyr Arg Asn
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Ser Gly Val Pro Ala Arg Phe Ser Gly
50                  55                  60

Ser Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Ser Pro Arg
                85                  90                  95

Thr Phe Gly Gln Gly Thr Lys Val Glu Ile Lys
            100                 105

<210> SEQ ID NO 96
<211> LENGTH: 109
<212> TYPE: PRT
<213> ORGANISM: Artificial Sequence
<220> FEATURE:
<223> OTHER INFORMATION: Antibody EDE1 752(2) C2 L chain

<400> SEQUENCE: 96

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ile Gly Val Pro Ser Arg Phe Ser Gly
50                  55                  60

```
Ser Gly Ser Gly Thr Glu Phe Thr Leu Thr Ile Ser Ser Leu Gln Pro
65                  70                  75                  80

Asp Asp Phe Ala Ile Tyr Tyr Cys Gln Gln Tyr Asn Asn Tyr Ser Pro
                85                  90                  95

Pro Val Thr Phe Gly Gly Gly Thr Lys Val Glu Ile Lys
                100                 105

<210> SEQ ID NO 97
<211> LENGTH: 109
<212> TYPE: PRT
<213> ORGANISM: Artificial Sequence
<220> FEATURE:
<223> OTHER INFORMATION: Antibody EDE1 752(2) D4 L chain

<400> SEQUENCE: 97

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Tyr
                20                  25                  30

Leu Ala Trp Tyr Gln Gln Lys Pro Gly Lys Ala Pro Lys Leu Leu Ile
            35                  40                  45

Tyr Lys Ala Ser Thr Leu Glu Ser Gly Val Pro Leu Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Ile Tyr Tyr Cys Gln Gln Tyr Asn Asn Tyr Ser Pro
                85                  90                  95

Pro Val Thr Phe Gly Gly Gly Thr Lys Val Glu Ile Lys
                100                 105

<210> SEQ ID NO 98

<400> SEQUENCE: 98

000

<210> SEQ ID NO 99
<211> LENGTH: 108
<212> TYPE: PRT
<213> ORGANISM: Artificial Sequence
<220> FEATURE:
<223> OTHER INFORMATION: Antibody EDE1 752-2 A2 L chain

<400> SEQUENCE: 99

Glu Ile Val Leu Thr Gln Ser Pro Ala Thr Leu Ser Leu Ser Ala Gly
1               5                   10                  15

Glu Arg Ala Thr Leu Ser Cys Arg Ala Ser Gln Ser Ile Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Val Pro Ala Arg Phe Ser Gly
        50                  55                  60

Ser Gln Ser Gly Thr Asp Phe Thr Leu Thr Ile Ser Thr Leu Glu Pro
65                  70                  75                  80

Glu Asp Phe Ala Val Tyr Tyr Cys Gln Leu Arg Tyr Asn Trp Pro Pro
                85                  90                  95

Tyr Thr Phe Gly Gln Gly Thr Lys Val Glu Ile Lys
                100                 105
```

<210> SEQ ID NO 100

<400> SEQUENCE: 100

000

<210> SEQ ID NO 101

<400> SEQUENCE: 101

000

<210> SEQ ID NO 102
<211> LENGTH: 108
<212> TYPE: PRT
<213> ORGANISM: Artificial Sequence
<220> FEATURE:
<223> OTHER INFORMATION: Antibody EDE1 752-2 A9 L chain

<400> SEQUENCE: 102

Glu Ile Val Leu Thr Gln Ser Pro Ala Thr Leu Ser Leu Ser Ala Gly
1               5                   10                  15

Glu Arg Ala Thr Leu Ser Cys Arg Ala Ser Gln Asp Ile Ser Thr Phe
            20                  25                  30

Leu Ala Trp Tyr Gln Gln Lys Pro Gly Gln Ala Pro Arg Leu Leu Ile
        35                  40                  45

Tyr Asp Thr Ser Thr Arg Ala Thr Gly Val Pro Ala Arg Phe Ser Gly
    50                  55                  60

Ser Arg Ser Gly Thr Asp Phe Thr Leu Thr Ile Thr Thr Leu Glu Pro
65                  70                  75                  80

Glu Asp Phe Ala Val Tyr Tyr Cys Gln His Arg Tyr Asn Trp Pro Pro
                85                  90                  95

Tyr Thr Phe Gly Gln Gly Thr Lys Val Glu Ile Lys
            100                 105

<210> SEQ ID NO 103
<211> LENGTH: 108
<212> TYPE: PRT
<213> ORGANISM: Artificial Sequence
<220> FEATURE:
<223> OTHER INFORMATION: Antibody EDE1 752-2 B2 L chain

<400> SEQUENCE: 103

Glu Ile Val Leu Thr Gln Ser Pro Ala Thr Leu Ser Leu Ser Ala Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln His Arg Tyr Asn Trp Pro Pro
                85                  90                  95

Tyr Thr Phe Gly Gln Gly Thr Lys Val Glu Ile Lys
            100                 105

<210> SEQ ID NO 104
<211> LENGTH: 108

```
<212> TYPE: PRT
<213> ORGANISM: Artificial Sequence
<220> FEATURE:
<223> OTHER INFORMATION: Antibody EDE1 752-2 B3 L chain

<400> SEQUENCE: 104

Glu Ile Val Leu Thr Gln Ser Pro Ala Thr Leu Ser Leu Ser Pro Gly
1               5                   10                  15

Glu Arg Ala Thr Leu Ser Cys Arg Ala Ser His Ser Ile Ser Thr Phe
            20                  25                  30

Leu Ala Trp Tyr Gln Gln Lys Pro Gly Gln Ala Pro Arg Leu Leu Ile
        35                  40                  45

Tyr Asp Thr Ser Thr Arg Ala Thr Gly Val Pro Ala Arg Phe Ser Gly
    50                  55                  60

Ser Arg Ser Gly Thr Asp Phe Thr Leu Thr Ile Asn Thr Leu Glu Pro
65                  70                  75                  80

Glu Asp Phe Ala Val Tyr Tyr Cys Gln Gln Arg Tyr Asn Trp Pro Pro
                85                  90                  95

Tyr Thr Phe Gly Gln Gly Thr Lys Val Glu Ile Lys
            100                 105

<210> SEQ ID NO 105
<211> LENGTH: 108
<212> TYPE: PRT
<213> ORGANISM: Artificial Sequence
<220> FEATURE:
<223> OTHER INFORMATION: Antibody EDE1 752-2 B4 L chain

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Phe
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Ile Tyr Tyr Cys Gln His Arg Tyr Asn Trp Pro Pro
                85                  90                  95

Tyr Thr Phe Gly Gln Gly Thr Lys Val Glu Ile Lys
            100                 105

<210> SEQ ID NO 106

<400> SEQUENCE: 106

000

<210> SEQ ID NO 107
<211> LENGTH: 108
<212> TYPE: PRT
<213> ORGANISM: Artificial Sequence
<220> FEATURE:
<223> OTHER INFORMATION: Antibody EDE1 752-2 B11 L chain

<400> SEQUENCE: 107

Glu Ile Val Leu Thr Gln Ser Pro Ala Thr Leu Ser Leu Ser Pro Gly
1               5                   10                  15
```

Glu Arg Ala Thr Leu Ser Cys Arg Ala Ser Gln Ser Ile Ser Thr Tyr
            20                  25                  30

Leu Val Trp Tyr Gln Gln Lys Pro Gly Gln Ala Pro Arg Leu Leu Ile
        35                  40                  45

Tyr Asp Ala Ser Thr Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln His Arg Tyr Asn Trp Pro Pro
                85                  90                  95

Tyr Thr Phe Gly Arg Gly Thr Lys Val Glu Ile Lys
            100                 105

<210> SEQ ID NO 108
<211> LENGTH: 109
<212> TYPE: PRT
<213> ORGANISM: Artificial Sequence
<220> FEATURE:
<223> OTHER INFORMATION: Antibody EDE1 752-2 C4 L chain

<400> SEQUENCE: 108

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Ala Trp Tyr Gln Gln Lys Val Gly Lys Ala Pro Lys Leu Leu Ile
        35                  40                  45

Tyr Lys Ala Ser Thr Leu Glu Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ile Tyr Tyr Cys Gln Gln Tyr Asn Asn Tyr Ser Pro
                85                  90                  95

Pro Val Thr Phe Gly Gly Gly Thr Lys Val Glu Ile Lys
            100                 105

<210> SEQ ID NO 109
<211> LENGTH: 112
<212> TYPE: PRT
<213> ORGANISM: Artificial Sequence
<220> FEATURE:
<223> OTHER INFORMATION: Antibody EDE1 753(3) B10 L chain

<400> SEQUENCE: 109

Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Val Tyr Ser
            20                  25                  30

Asp Gly Asn Lys Tyr Leu Asp Trp Tyr Val Gln Lys Pro Gly Gln Ser
        35                  40                  45

Pro Gln Leu Leu Ile Tyr Leu Thr Ser Thr Arg Ala Ser Gly Val Pro
    50                  55                  60

Asp Arg Phe Ser Gly Ser Ala Ser Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 110
<211> LENGTH: 108
<212> TYPE: PRT
<213> ORGANISM: Artificial Sequence
<220> FEATURE:
<223> OTHER INFORMATION: Antibody EDE1 758 P6A1 L chain

<400> SEQUENCE: 110

Glu Ile Val Met Thr Gln Ser Pro Ala Thr Leu Ser Val Ser Pro Gly
1               5                   10                  15

Glu Arg Ala Thr Leu Thr Cys Arg Ala Ser Gln Thr Ile Ser Thr Phe
            20                  25                  30

Leu Ala Trp Tyr Gln Gln Lys Pro Gly Gln Pro Pro Arg Leu Leu Ile
        35                  40                  45

Tyr Asp Thr Ser Thr Arg Ala Thr Gly Ile Pro Gly Arg Phe Ser Gly
    50                  55                  60

Ser Arg Ser Gly Thr Glu Phe Thr Leu Thr Ile Ser Ser Leu Gln Ser
65                  70                  75                  80

Glu Asp Val Ala Val Tyr Tyr Cys Gln His Tyr Tyr Asn Trp Pro Pro
                85                  90                  95

Trp Thr Phe Gly Gln Gly Thr Lys Val Glu Ile Lys
            100                 105

<210> SEQ ID NO 111
<211> LENGTH: 109
<212> TYPE: PRT
<213> ORGANISM: Artificial Sequence
<220> FEATURE:
<223> OTHER INFORMATION: Antibody EDE1 758 P6A3 L chain

<400> SEQUENCE: 111

Gln Ser Ala Leu Thr Gln Pro Pro Ser Ala Ser Gly Ser Pro Gly Gln
1               5                   10                  15

Ser Val Thr Ile Ser Cys Thr Gly Ser Ser Ser Asp Ile Gly Gly Asn
            20                  25                  30

Glu Tyr Val Ser Trp Tyr Gln Leu Gln Pro Gly Lys Ala Pro Lys Leu
        35                  40                  45

Met Ile Tyr Glu Val Thr Lys Arg Pro Ser Gly Val Pro Asn Arg Phe
    50                  55                  60

Ser Gly Ser Lys Ser Gly Asn Thr Ala Ser Leu Thr Val Ser Gly Leu
65                  70                  75                  80

Gln Ser Glu Asp Glu Gly Asp Tyr Tyr Cys Ser Ser Tyr Ala Asp Asn
                85                  90                  95

Ser Val Leu Phe Gly Gly Gly Thr Thr Leu Thr Val Leu
            100                 105

<210> SEQ ID NO 112

<400> SEQUENCE: 112

000

<210> SEQ ID NO 113
<211> LENGTH: 108
<212> TYPE: PRT
<213> ORGANISM: Artificial Sequence
<220> FEATURE:
<223> OTHER INFORMATION: Antibody EDE1 758 P6B4 L chain

<400> SEQUENCE: 113

```
Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Thr Val Asp Ser Thr
            20                  25                  30

Tyr Leu Ala Trp Tyr Gln Gln Lys Pro Gly Arg Ala Pro Arg Leu Leu
        35                  40                  45

Ile Tyr Gly Ala Ser Asn Arg Ala Ile Gly Val Pro Ser Arg Phe Thr
50                  55                  60

Gly Ser Gly Ser Gly Thr Asp Phe Thr Leu Thr Ile Ser Arg Leu Glu
65                  70                  75                  80

Pro Glu Asp Phe Ala Leu Tyr Tyr Cys Gln Gln Ser Asp Gly Ser Leu
                85                  90                  95

Phe Thr Phe Gly Pro Gly Thr Lys Val Asp Ile Lys
            100                 105
```

<210> SEQ ID NO 114
<211> LENGTH: 107
<212> TYPE: PRT
<213> ORGANISM: Artificial Sequence
<220> FEATURE:
<223> OTHER INFORMATION: Antibody EDE1 758 P6B5 L chain

<400> SEQUENCE: 114

```
Asp Ile Gln Met Thr Gln Ser Pro Ala Ser Val Ser Ala Ser Val Gly
1               5                   10                  15

Asp Arg Val Thr Ile Ser Cys Arg Ala Ser Gln Gly Ile Ala Ser Trp
            20                  25                  30

Leu Ala Trp Tyr Gln Gln Lys Pro Gly Lys Ala Pro Arg Leu Leu Ile
        35                  40                  45

Tyr Gly Ala Ser Ser Leu Gln Ser Gly Val Pro Ser Arg Phe Arg Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105
```

<210> SEQ ID NO 115

<400> SEQUENCE: 115

000

<210> SEQ ID NO 116
<211> LENGTH: 110
<212> TYPE: PRT
<213> ORGANISM: Artificial Sequence
<220> FEATURE:
<223> OTHER INFORMATION: Antibody EDE1 758 P6C4 L chain

<400> SEQUENCE: 116

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45
```

Ile Ile Tyr Glu Val Ser Lys Arg Pro Ser Gly Val Pro His Arg Phe
     50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Ala Gly Ser
                 85                  90                  95

Asn Thr Phe Thr Phe Gly Gly Gly Thr Lys Leu Thr Val Leu
                100                 105                 110

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120
<211> LENGTH: 131
<212> TYPE: PRT
<213> ORGANISM: Artificial Sequence
<220> FEATURE:
<223> OTHER INFORMATION: Antibody EDE2 A11 vH (Example 2 ED Figure 3)

<400> SEQUENCE: 120

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Ser Tyr Ser Asn His
                20                  25                  30

Trp Met His Trp Val Arg Gln Ala Pro Gly Lys Gly Leu Val Trp Val
            35                  40                  45

Ser Arg Ile Asn Ser Asp Gly Ser Thr Arg Asn Tyr Ala Asp Phe Val
    50                  55                  60

Lys Gly Arg Phe Thr Ile Ser Arg Asp Asn Ala Glu Asn Thr Leu Tyr
65                  70                  75                  80

Leu Glu Met Asn Ser Leu Thr Ala Asp Thr Ala Val Tyr Tyr Cys
                85                  90                  95

Val Arg Asp Gly Val Arg Phe Tyr Tyr Asp Ser Thr Gly Tyr Tyr Pro
                100                 105                 110

Asp Ser Phe Phe Lys Tyr Gly Met Asp Val Trp Gly Gln Gly Thr Thr
            115                 120                 125

Val Thr Val
    130

<210> SEQ ID NO 121
<211> LENGTH: 110
<212> TYPE: PRT
<213> ORGANISM: Artificial Sequence
<220> FEATURE:
<223> OTHER INFORMATION: Antibody EDE2 A11 vL (Example 2 ED Figure 3)

<400> SEQUENCE: 121

```
Gln Ser Val Leu Thr Gln Pro Val Ser Val Ser Gly Ser Pro Gly Gln
1               5                   10                  15

Ser Ile Thr Ile Ser Cys Thr Gly Thr Ser Ser Asn Ala Asp Thr Tyr
            20                  25                  30

Asn Leu Val Ser Trp Tyr Gln Gln Arg Pro Gly Lys Ala Pro Lys Leu
        35                  40                  45

Met Ile Tyr Glu Gly Thr Lys Arg Pro Ser Gly Val Ser Asn Arg Phe
    50                  55                  60

Ser Ala Ser Lys Ser Ala Thr Ala Ala Ser Leu Thr Ile Ser Gly Leu
65                  70                  75                  80

Gln Pro Glu Asp Glu Ala Asp Tyr Tyr Cys Ser Tyr Ala Thr Ser
                85                  90                  95

Arg Thr Leu Val Phe Gly Gly Gly Thr Lys Leu Thr Val Val
            100                 105                 110
```

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

```
<210> SEQ ID NO 130
<400> SEQUENCE: 130
000

<210> SEQ ID NO 131
<400> SEQUENCE: 131
000

<210> SEQ ID NO 132
<400> SEQUENCE: 132
000

<210> SEQ ID NO 133
<400> SEQUENCE: 133
000

<210> SEQ ID NO 134
<400> SEQUENCE: 134
000

<210> SEQ ID NO 135
<400> SEQUENCE: 135
000

<210> SEQ ID NO 136
<400> SEQUENCE: 136
000

<210> SEQ ID NO 137
<400> SEQUENCE: 137
000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
```

```
<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148
<211> LENGTH: 12
<212> TYPE: PRT
<213> ORGANISM: Dengue virus 1
<220> FEATURE:
<223> OTHER INFORMATION: 150 loop of Denv-1

<400> SEQUENCE: 148

Gln His Gln Val Gly Asn Glu Thr Thr Glu His Gly
1               5                   10

<210> SEQ ID NO 149
<211> LENGTH: 12
<212> TYPE: PRT
<213> ORGANISM: Dengue virus 2
<220> FEATURE:
<223> OTHER INFORMATION: 150 loop of Denv 2

<400> SEQUENCE: 149

Glu His Ala Val Gly Asn Asp Thr Gly Lys His Gly
1               5                   10

<210> SEQ ID NO 150
<211> LENGTH: 10
<212> TYPE: PRT
<213> ORGANISM: Dengue virus 3
<220> FEATURE:
<223> OTHER INFORMATION: 150 loop of Denv 3
```

```
<400> SEQUENCE: 150

Gln His Gln Val Gly Asn Glu Thr Gln Gly
1               5                   10

<210> SEQ ID NO 151
<211> LENGTH: 12
<212> TYPE: PRT
<213> ORGANISM: Dengue virus 4
<220> FEATURE:
<223> OTHER INFORMATION: 150 loop of Denv 4

<400> SEQUENCE: 151

Thr His Ala Val Gly Asn Asp Ile Pro Asn His Gly
1               5                   10
```

NEUTRALISING ANTIBODY AGAINST DENGUE FOR USE IN A METHOD OF PREVENTION AND/OR TREATMENT OF ZIKA INFECTION

CROSS-REFERENCE TO RELATED APPLICATIONS

This application is a continuation of U.S. Ser. No. 16/308,745, filed Dec. 10, 2018, as a National Phase application under 35 U.S.C. 371 of PCT/GB2017/051692, filed Jun. 9, 2017, and claims the benefit of and priority to G.B. Provisional Patent Application No. 1610162.8 filed Jun. 10, 2016, the disclosures of which are hereby incorporated herein by reference in their entirety.

REFERENCE TO SEQUENCE LISTING

The Sequence Listing submitted Aug. 9, 2021, as a text file named "GB2017_051692ST25.txt," created on Dec. 6, 2018, and having a size of 94,300 bytes is hereby incorporated by reference.

A new abstract page on a separate sheet in accordance with 37 CFR 1.72 is attached hereto.

FIELD OF THE INVENTION

The invention relates to the field of treatment and prevention of flavivirus infection and related compounds and methods.

The Flavivirus Burden

Viruses in the Flavivirus genus are the most important arthropod borne human pathogens, causing increasingly serious epidemics such as the current Zika explosion in South America, for which neither preventive nor curative treatments are available. Besides the current media impact of ZikaV, the flaviviral disease that imposes the highest toll on society is dengue, which is caused by four different viruses termed serotypes DENV1-4, which differ in amino acid sequence by 30-35%. It is estimated that the annual global incidence is 390 million cases, of which 96 million are clinically apparent[1], with around 25 thousand deaths. Several factors drive the pandemic, including globalization, spread of the *Aedes* mosquito vector, inadequately planned urbanization, and absence until recently of a licensed vaccine or anti-dengue therapeutics[2]. ZikaV is also spread by *Aedes* mosquitos, and among the flaviviruses, its envelope protein is closest in amino acid sequence to that of the DENVs (42-46% divergence, FIG. 1A) than to other flaviviruses.

The hallmark of severe dengue disease is increased capillary permeability, causing plasma leakage and bleeding, leading to haemodynamic compromise and dengue shock syndrome. Untreated, severe disease can lead to a mortality of up to 20%, but with expert management, primarily fluid replacement, this can be reduced to below 1%[2]. Dengue has caused explosive epidemics, which put huge stress on healthcare systems in endemic countries and although several dengue control strategies are being evaluated, it is generally agreed that an effective vaccine available to all age groups is required to make serious inroads into the burden of disease. In the case of Zika virus, although discovered almost 70 years ago, it is only recently that severe neurological sequelae including micocephaly and Guillain-Barré syndrome have been described[3-6].

The Flavivirus Virion

Flaviviruses are relatively simple positive-sense single stranded RNA viruses, 50 nm in diameter with three structural proteins; Capsid (C) Precursor membrane protein (prM) and Envelope (E), and seven non-structural proteins (NS1, NS2A, NS2B, NS3, NS4A, NS4B and NS5)(FIG. 1B). E and prM form the glycoprotein shell of the virus, with E responsible for host cell binding and entry[7]. Assembly and maturation of the virus particle has been most thoroughly studied for DENV. During particle morphogenesis in the endoplasmic reticulum, 180 copies of E associate in a 1:1 fashion with 180 copies of prM to form 60 trimeric (heterohexameric) spikes, which gives "immature virions" their characteristic spiky appearance[7-9] (FIG. 2A). In the trans-Golgi network prM is cleaved by host encoded furin protease, generating a membrane-anchored M stump and pr, which remains associated with the virion until it is secreted[8,10,11]. On secretion from the host cell, pr falls away to leave the "mature virion", a smooth structure containing 180 copies of E, arranged into 90 head to tail dimers with icosahedral symmetry around 2, 3 and 5-fold axes (FIG. 2B).

In DENV prM cleavage is not complete in all virions, leaving a proportion of intermediate forms where viral particles contain a varying amount of cleaved and uncleaved prM[12-15]. prM cleavage is more efficient in certain cell types, particularly primary human cells such as dendritic cells compared to virus produced in insect cells or tumour cell lines such as Vero[16,17].

Immune Enhancement

Infection with one serotype of dengue results in the generation of lifelong immunity to reinfection with that serotype but not to the others[18-20]. As all four dengue serotypes frequently co-circulate, or cyclically replace each other, multiple infections are the norm in endemic countries. Well-controlled epidemiological studies demonstrate that most severe dengue infections occur in individuals who are experiencing a secondary or sequential dengue infection[21-23].

The theory of antibody dependent enhancement (ADE) posits that pre-existing heterologous antibodies generated to a primary infection may not be of sufficient avidity or concentration to neutralize a secondarily encountered virus, in which the amino acid sequence of the envelope proteins may vary by 30-35%. Instead, the virus may be opsonized and targeted for uptake into Fc-receptor (FcR)-bearing cells such as monocytes and macrophages, which are major sites of DENV replication in vivo, and therefore lead to an increase in viral production[24-27]

Dengue Vaccines

The exponential rise in dengue infections over the past few decades has made the search for a dengue vaccine an imperative, but achieving this goal has proved enormously challenging. Any successful vaccine will need to induce a protective and durable immune response to all four dengue serotypes, preferably with one or two doses, in individuals who have either been unexposed to dengue or had a previous dengue infection. At the same time a vaccine would need to avoid eliciting enhancing or pathogenic immune responses described above.

As primary dengue infection does not give long-term protection to re-infection with the other three viral serotypes[18,19,] it has been generally held that a vaccine will need to induce protective type specific responses against all four serotypes mandating a tetravalent formulation. Efforts to develop vaccines have been pursued for almost 50 years beginning in Thailand with work to produce live attenuated dengue vaccines (LATVs) by serial passage of viral strains representative of the four serotypes[28]. A particular challenge has been to develop attenuated forms of the virus that are not too virulent to induce overt dengue disease whilst not too over attenuated to be able to incite a protective immune response. Another challenge has been to produce a tetravalent formulation in which all four viruses are delivered together, replicate equally and induce a balanced response against all four serotypes rather than competition between serotypes leading to good responses to some serotypes but poor responses to one or more serotypes.

The most advanced dengue vaccine is the Sanofi Pasteur-vaccine CYD-TDV. This is a chimera using the yellow fever 17D vaccine strain as a backbone, with dengue prM and E genes replacing those from yellow fever. The vaccine contains a mixture of four recombinant viruses representing each serotype (CYD1-4)[29-32]. Initial clinical trials demonstrated good serological responses to the vaccine, with seropositivity ranging between 66.5 to 100%. Phase III trials of this vaccine in Asia and Latin America showed suboptimal efficacy ranging between 35 and 78% with efficacies against dengue 2 being the lowest[30,32].

Further analysis revealed that the vaccine gave better protection to vaccinees that were already immune to one or more serotypes prior to vaccination. Recently, interim results of the first 2-3 years of long term follow up have been published, substantiating the efficacy but revealing a concerning signal for increased hospitalized dengue illness in the <9 years of age vaccinated group compared to placebo[33]. There is a strong suspicion that this may represent immune enhancement by vaccine priming giving incomplete protection, which is probably occurring in younger vaccinees who were dengue naïve at the time of immunization. The vaccine has however been licensed in several dengue endemic countries but is restricted to ages 9-45 meaning a substantial proportion of at risk individuals will not be eligible. Two more LATV's from Takeda and NIH are close to Phase III evaluation and whether these will achieve superior efficacy will be determined.

It is currently unclear as to what the Dengue epitope is that most human neutralising antibodies target, for example de Alwis (de Alwis et al 2012 Identification of human neutralizing antibodies that bind to complex epitopes on dengue virions. Proc Natl Acad Sci USA 109: 7439-7444) suggests the epitope requires virus assembly for formation, whilst Rey (Rey 2013 Nature 497: 443-444) suggests that the envelope dimer itself is the target.

Earlier work involving the present inventors identifies human neutralising antibodies targeting part of the Dengue envelope dimer. See, for example, WO 2016/012800; Rouvinski et al (2015) Nature 520, 109-113; Dejnirattisai et al (2015) Nature Immunol 16, 170-177, which relate to the isolation and structural characterization of potently cross-neutralizing human antibodies against the four serotypes of dengue virus (DENY). These antibodies bind to a highly conserved epitope termed the E-dimer-epitope (EDE).

Dai et al (2016) Cell Host & Microbe 19, 1-9 reports a structure of the Zika virus envelope protein and its complex with an antibody that is described as a flavivirus broadly protective antibody that recognises a fusion loop epitope. Dai et al (2016) notes on page 5, second column that "Structural studies of EDE-specific neturalizing antibodies have revealed that the recognition determinants are found at a serotype-invariant site at the E-dimer interface, including the exposed main chain of the fusion loop and the two conserved glycan chains (N67- and N153-linked glycans) (Rouvinski et al., 2015). Theese two glycosylation sites are not highly conserved in other flaviviruses. Moreover, ZIKV does not possess the N67-linked gluycosylation site, and the N154-linked glycosylation site (equivalent to the N153-linked glycosylation site in DENV) is absent in some of the isolated ZIKV strains (Table S2). Further more, several residues in b strand, 150 loop, ij loop, and A strand, which are critical for DENV EDE mAb binding, are not conserved in ZIKV and other flaviviruses (Figure S2). Importantly, as ZIKV sE structure displays a uniques positively charged patch at the binding regions of EDE antibodies (Figure S1), the EDE-specific antibiodies may not be effective against ZIKV infection. However, may other known flavivirus FLE-specific antibodies, which target the highly conserved fusion loop, may be able to neutralize ZIKV, as confirmed by our neutralizing profile of 2A1-G6.".

In contrast to the conclusion expressed in Dai et al (2016), the present inventors have now determined that the EDE is also conserved beyond dengue viruses, for example in Zika virus (ZikaV), leading also to potent neutralization of flaviviruses beyond dengue viruses, for example potent neutralization of ZikaV, for example much more potent neutralisation than reported in Dai et al (2016). The conservation of the EDE epitope has wide ranging implications for the treatment and prevention of diseases caused by flaviviruses, for example Zika virus.

The invention, as described below, provides methods, uses, vaccines, compounds, and compositions, in relation to the newly identified conservation of the EDE beyond dengue viruses.

The invention will be described below with reference to various embodiments of different aspects of the invention. It is appreciated that certain features of the invention, which are, for clarity, described in the context of separate embodiments, may also be provided in combination in one or more embodiments or in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

Thus, a first aspect of the invention provides a compound that neutralises more than one serotype of flavivirus, for example more than one serotype of dengue virus and/or zika virus, for use in a method for prevention and/or treatment of infection by one or more flaviviruses, wherein the one or more flaviviruses is selected from zika virus; zika virus and dengue virus; zika virus and other flaviviruses; flaviviruses other than dengue.

The compound may be an antibody or antigen binding fragment thereof, as discussed further below. Thus, in an embodiment, the invention provides, for example, an isolated neutralizing antibody or antigen binding fragment thereof directed against the EDE as defined below, optionally wherein said antibody or fragment thereof binds the five polypeptide segments of the dengue virus glycoprotein E ectodomain (sE) consisting of the residues 67-74, residues 97-106, residues 307-314, residues 148-159 and residues 243-251, or corresponding residues of the flavivirus or Zika virus glycoprotein E ectodomain, or consisting of Zika PF13 residues 67-77, residues 97-106, residues 313-315, residues 243-253, residue K373 or corresponding residues of the flavivirus glycoprotein E ectodomain, optionally wherein binding is unaffected by presence or absence of dengue N153 (Zika N154) glycan or corresponding residue, for use in a method for prevention and/or treatment of infection by one or more flaviviruses, wherein the one or more flaviviruses is selected from zika virus; zika virus and dengue virus; zika virus and other flaviviruses; flaviviruses other than dengue.

The individual may be, for example, a pregnant woman, optionally a pregnant woman considered at risk of contacting Zika infection, for example through being known or suspected to have been infected with Dengue virus; being in close contact with one or more individuals known to be infected with Zika virus or Dengue virus; being in a location considered to have a high rate or risk of Zika virus or Dengue virus infection; or a woman of childbearing age, optionally a woman of childbearing age considered at risk of contacting Zika infection, for example through being known or suspected to have been infected with Dengue virus; being in close contact with one or more individuals known to be infected with Zika virus or Dengue virus; being in a location considered to have a high rate or risk of Zika virus or Dengue virus infection.

It is considered that the compound, for example antibody or antigen binding fragment thereof, may be particularly useful in reducing the likelihood, viral load or severity/impact of Zika infection in pregnant women, where the consequences may be particularly serious.

Figure 10A:
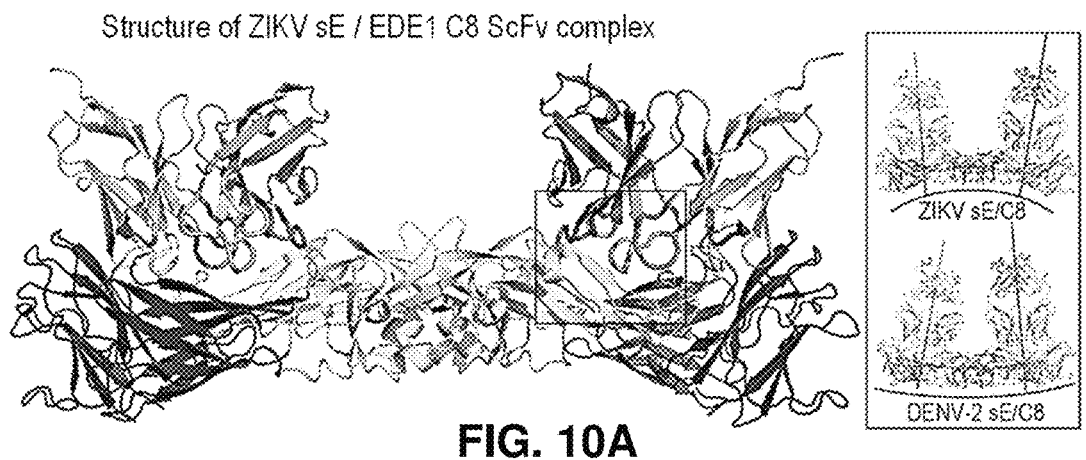
Figure 10B:
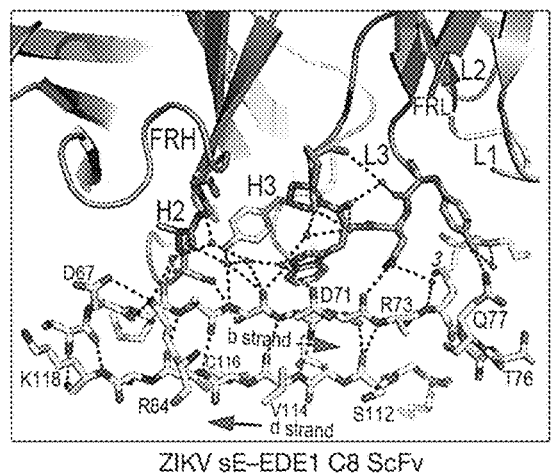
Figure 10C:
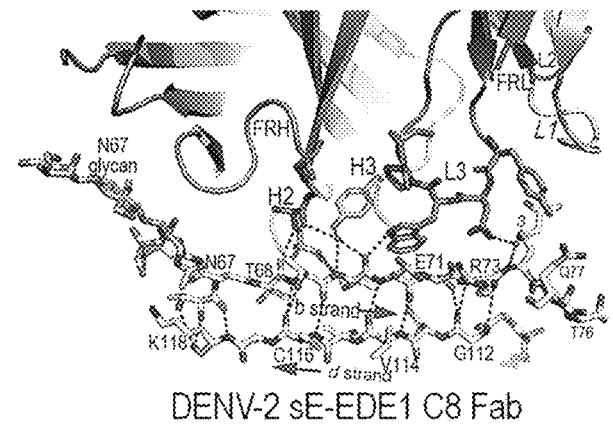

For Zika virus glycoprotein E ectodomain (sE) the binding segments may be as indicated in Example 2, for example in the section headed "EDE1 C8 complex" and with reference to FIGS. 10A-10F and 11A-11C. Interactions of antibody with Zika sE may include beta-strand b of domain II, with side chains from CDRs (for example H2, H3 and L3 recognizing hydrogen bond donors (NH groups) and acceptors (main chain carbonyls) of the bdc beta-sheet edge (FIGS. 10B and 10C). The fusion loop main chain (which contains several glycine residues) and the disulphide bond between Cys 74 and Cys 105 may be framed by aromatic side chains of residues in CDRs L1 and L3 (FIGs. 13A and 13B). Residues from these two CDRs for example may also recognise conserved side chains of the fusion loop eg Arg 99 or nearby eg Gln 77. Across the dimer interface, beta-strand E eg Lys 373 may interact with CDrs L1 and L2 for example, for example with a network of direct or water-mediated hydrogen bods (see for example FIGS. 16B and 16C). Charged residues in domain I and from the nearby kl loop of domain II may contribute to binding to the heavy chain, for example, for example CDRs H2 and H3 (FIGS. 16E and 16F). FIGS. 19 and 20 indicate polar interactions between EDE1 C8 and ZIKV sE, for example. Thus, contacts with the b strand and the fusion loop in domain II may be the main binding determinants, with other contributions, for example from across the dimer interface or with the N67 glycan in DENV stabilising the interaction.

Preferably the compound neutralises zika virus and the dengue virus of one or two serotypes of dengue virus, more preferably three types of dengue virus and most preferably four serotypes of dengue virus ie all serotypes of dengue virus, for example neutralises zika virus and one, two or more serotypes of dengue virus from the list comprising DENV-1, DENV-2, DENV-3 and DENV-4.

By a compound we mean any compound that can neutralise more than one serotype of flavivirus, for example zika and Dengue virus. The compound may, for example, be a small molecule, a polypeptide or protein (which terms are used interchangeably herein), including a glycoprotein, a nucleic acid, a carbohydrate, a fat, an element, for example a metal. In a preferred embodiment the compound is a polypeptide, preferably an antibody or antigen binding portion thereof. The antigen binding portion may be a Fv fragment; a Fab-like fragment (e.g. a Fab fragment, a Fab' fragment, a F(ab)₂ fragment, Fv or scFv fragments); or a domain antibody. The antibody binding portion may be derived from the linear amino acid sequence present in an intact antibody, or may comprise a set of non-consecutive amino acids, optionally interspersed with other amino acids, for example may comprise particular amino acids that are required for contact with an epitope, but may for example not comprise the amino acids required for the framework of a native antibody, which, in some cases, may be replaced by a heterologous scaffold protein, for example. An antibody for use according to the present invention is obtainable by, for example, a method comprising a step of immunizing a mammal, such as a human, a monkey, a rabbit or a mouse; and/or by an in vitro method, for example comprising a phage display selection step, as will be well known to those skilled in the art.

By antibody we include the meaning of a substantially intact antibody molecule, as well as a chimeric antibody, humanised antibody (wherein at least one amino acid is mutated relative to a non-human antibody, for example a naturally occurring non-human antibody or antibody assembled from non-human antibody sequences), single chain antibody, bi-specific antibody, antibody heavy chain, antibody light chain, homo-dimer or heterodimer of antibody heavy and/or light chains, and antigen binding portions and derivatives of the same.

When the compound is a protein, for example an antibody or fragment thereof, and is administered to a human subject and if the antibody is not a human antibody or fragment thereof, then it can be humanized in order to reduce immunogenicity in human. Methods for producing humanized antibodies or fragments thereof are known in the art (Vinckle et al., 2009).

Further, the bioavailability of the antibody or fragment thereof for use according to the present invention can be improved by conjugating the neutralizing antibody or fragment thereof to inert carriers like albumin (Coppieters et al, 2006) or immunoglobulins (Harmsen et al., 2005).

The term antibody also includes all classes of antibodies, including IgG, IgA, IgM, IdD and IgE. The term antibody also includes variants, fusions and derivatives of any defined antibodies and antigen binding portions thereof.

The compound may alternatively be a cyclic peptide, for example a polycyclic peptide, for example a bicyclic peptide, for example as described in MILLWARD STEVEN W ET AL: "Design of cyclic peptides that bind protein surfaces with antibody-like affinity", ACS CHEMICAL BIOLOGY, vol. 2, no. 9, 1 Jan. 2007 (2007 Jan. 1), pages 625-634, XP002616292, AMERICAN CHEMICAL SOCIETY, WASHINGTON, DC, US ISSN: 1554-8929, DOI: 10.1021/CB7001126; HEINIS CHRISTIAN ET AL: "Phage-encoded combinatorial chemical libraries based on bicyclic peptides" NATURE CHEMICAL BIOLOGY, vol. 5, no. 7, July 2009 (2009 July), pages 502-507, XP007913181. See also, for example WO2009098450. Bicyclic peptides with required binding properties can be selected by, for example, phage display techniques.

By neutralise we mean reduce the ability of the virus to infect previously uninfected cells.

The person skilled in the art will be well aware of suitable techniques to monitor the viral neutralising ability of a compound. One example of such a method is detailed in Example 3 of WO 2016/012800 and involves allowing one or more serotypes of dengue virus to infect a population of potential host cells, wherein the compound under assay is mixed with the virus, and then the mixture is incubated with the potential host cells. The number of cells infected is assayed which gives a measure of the neutralising ability of the compound, i.e. the ability of the compound to prevent infection In one particular example the neutralising potential of a compound, for example an antibody or antigen binding portion thereof can be determined using the Focus Reduction Neutralization Test (FRNT), where the reduction in the number of the infected foci is compared to control (no compound) (Dejnirattisai et al 2010 Cross-reacting antibodies enhance dengue virus infection in humans. Science 328: 745-748). Briefly, the compound is mixed with the virus and incubated for 1 hr at 37° C. The mixtures are then transferred to Vero cells (kidney epithelial cell line from the African Green Monkey) and incubated for 3 days. The focus-forming assay can be performed using anti-E mAb (4G2) followed by rabbit anti-mouse IgG, conjugated with HRP. The reaction can be visualized by the addition of DAB substrate. The percentage focus reduction is calculated for each compound. 50% FRNT values can be determined from graphs of percentage reduction versus concentration of compound using the probit program from the SPSS package. Typically the assay may be performed so that there are approximately 100 foci in the absence of the test compound, for example in a 96 well plate well with confluent cells, for example just-confluent cells.

Other such examples will be known to those skilled in the art, for example foci reduction neutralisation testing (FRNT); plaque reduction neutralisation testing (PRNT; see WHO document whqlibdoc.who.int/hq/2007/who_ivb_07.07_eng.pdf; FRNT; techniques using flow cytometry and in vivo such as mice and monkeys. See, for example, FIG. 30 of WO 2016/012800 for examples of FRNT and flow cytometry methods. See also the Examples of the present specification.

In one embodiment, the compound neutralises the virus to at least 80%, preferably 90%, more preferably 95% and most preferably 100%. In a more preferred embodiment, the compound neutralises all serotypes of Dengue virus and Zika virus, optionally neutralises all serotypes of Dengue virus and Zika virus to 80% or 90% or 98% or 100%, optionally neutralises all serotypes of Dengue virus and Zika virus to 100%, optionally neutralises all serotypes of Dengue virus to 100% at the same concentration of antibody or fragment.

The virus may be produced by insect cells or in human cancer cell lines (typically considered to produce high pr-M containing virus, as discussed further below); or alternatively in human primary cells, for example primary human dendritic cells, or in cell lines over-expressing furin (which are considered to make low-pr-M containing virus).

The compound may neutralise one or more serotypes of Dengue virus and/or Zika virus to 80, 90, 98 or 100% at a concentration of 0.5-0.01 µg/ml. The compound may neutralise all serotypes of Dengue virus and Zika virus to 80, 90, 98 or 100% at a concentration of 0.5-0.01 µg/ml.

Dai et al (2016) Cell Host & Microbe 19, 1-9, noted supra, reports a 50% plaque reduction neutralization titer (PRNT50) of 249 µg/ml in a plaque reduction assay (FIG. 3A and passage spanning pages 3 and 4) for fusion loop epitope-directed mAb 2A10G6.

By neutralise to a particular level, we include the meaning of neutralise to a particular level for a given concentration of compound. It will be appreciated that an appropriate concentration of a given compound may depend on the actual compound. For example, the concentration of the given compound, for example as used in the assay above, may be no more than 100 mM, 10 mM, 1 mM, 100 µM, 10 µM, 1 µM, 100 nM, 10 nM or 1 nM; or no more than 0.01 µg/ml, 0.02 µg/ml, 0.04 µg/ml, 0.05 µg/ml, 0.06 µg/ml, 0.075 µg/ml, 0.1 µg/ml, 0.25 µg/ml, 0.5 µg/ml, 0.75 µg/ml, 1.25 µg/ml, 1.5 µg/ml, 1.75 µg/ml, 2 µg/ml, 2.25 µg/ml, 2.5 µg/ml, 2.75 µg/ml, 3 µg/ml, 3.25 µg/ml, 3.5 µg/ml, 3.75 µg/ml, 4 µg/ml, 4.25 µg/ml, 4.5 µg/ml, 4.75 µg/ml, 5 µg/ml, 5.25 µg/ml, 5.5 µg/ml, 5.75 µg/ml, 6 µg/ml, 6.5 µg/ml, 7 µg/ml, 7.5 µg/ml, 8 µg/ml, 8.5 µg/ml, 9 µg/ml, 9.5 µg/ml or 10 µg/ml, or less than 0.01 µg/ml. Typically the concentration of the compound, for example an antibody, may be less than 1 µg/ml, for example.

For example, a compound (for example an antibody) may neutralise the one or more serotypes of the virus to 80% at a compound concentration of 0.1 µg/ml, and may neutralise one or more serotypes of the virus to at least 98%, for example 100%, at a compound concentration of 1 µg/ml. Preferably the compound (for example an antibody) neutralises one or more serotypes of the virus to 80% at a concentration of 0.05 µg/ml, or neutralises one or more serotypes of the virus to at least 98%, for example 100%, at a concentration of 0.5 µg/ml.

It will also be appreciated that the level of neutralisation observed for a given concentration of a compound may depend on the number of viral particles in the assay. For example, it may be expected that for a given concentration of compound, if the number of viral particles in the assay is doubled, then the level of neutralisation may reduce (for a given population of host cells). The number of viral particles in the assay will typically be such as to provide around 100 foci in the absence of the test compound, for example in a 96 well microtire plate well, for example with confluent cells, for example just-confluent cells.

For example, in one embodiment, the compound neutralises the one or more serotypes of the virus at a concentration of 1 µg/ml or 0.05 ug/ml or less to a level of at least 80%, or to a level of 100% when the viral concentration is sufficient to produce around 100 foci in the absence of the test compound for example in a 96 well microtire plate well, for example with confluent cells, for example just-confluent cells.

The number of cells in the assay which may be infected by the virus may also influence the apparent level of neutralisation. For example, a small number of cells may exhibit a larger infection rate, expressed per cell, than a large population of cells. Therefore the ratio of compound, virus and host cell number may also be important. The cells used in the assay may be confluent. The assay may be carried out in a microtitre well plate, for example in a 96-well microtitre plate. The cells may be confluent, for example, just-confluent in the container, for example a microtitre plate well, for example a well of a 96-well microtitre plate.

Preferably, the compound is able to neutralise virus made in both insect cells, for example C6/36 insect cells, or human tumour cell lines (which may typically produce high pr-M containing virus) and human cells, for example primary human cells, for example primary human dendritic cells, or cells which overexpress furin (which are considered to make low-pr-M containing virus). The production of a virus particle, sub-viral particle or a virus-like particle in different cell types will be well known to the person skilled in the art. For example the ability of the compound to neutralise the virus can be tested as detailed above and in the examples. In one embodiment the compound is able to neutralise the virus made in primary human cells, for example primary human dendritic cells, or in insect cells. In another embodiment the compound is able to neutralise the virus made in primary human and insect cells to the same level. By to the same level we include the meaning that for a given concentration of compound and/or given concentration of virus and/or given number of potential host cells, the level of neutralisation caused by the compound is not significantly different for virus made in both insect and primary human cells, or that the level of neutralisation caused by the compound is over a particular threshold for example over 80%, 90%, 95% or 98% neutralisation in virus from both insect and primary human cells. For example, for a given concentration of viral particles, and a given number of potential host cells, the 50% FRNT is the same (not significantly different) for virus made in insect and primary human cells, for example is 0.05 µg/ml or lower, or 0.5 µg/ml or lower or 1 µg/ml or lower or 5 µg/ml or lower. In a preferred embodiment, the compound is able to neutralise more than one serotype of zika and dengue virus made in primary human and insect cells, preferably two serotypes, preferably three serotypes, more preferably four serotypes or all serotypes. In a most preferred embodiment the compound is able to fully neutralise (i.e. to 100%) all serotypes of zika and dengue virus made in both insect and primary human cells. For example, the compound can neutralise virus made in both primary human and insect cells to 100%, at a viral concentration sufficient to yield around 100 foci, as discussed above at a compound concentration of 0.05 µg/ml. By made in both primary human and insect cells we include the meaning of virus made independently in primary human cells (for example), and virus made independently in insect cells rather than a particular population of viral particles that have been produced using both primary human and insect cells in the same procedure.

The cross-reactive, highly neutralising compounds for use in the present invention were found to bind to a specific epitope which can be found on both the intact virus and a dimer of envelope protein, independently of virus formation. Thus, the compounds for use of the present invention can be defined in terms of their ability to bind to this specific epitope.

By a compound that binds to an Envelope Dimer Epitope (EDE) we mean any compound that can bind to the EDE of a flavivirus, for example a zika or Dengue virus, of one or more serotypes. The compound may be a small molecule, a polypeptide, a nucleic acid, a carbohydrate, a fat, an element, for example a metal. In a preferred embodiment the compound is a polypeptide, preferably an antibody or antigen binding portion thereof. Preferences for the compound are as detailed earlier.

There are four serotypes of dengue virus as well as other flaviviruses, for example Zika virus and others as well known to those skilled in the art or as indicated in Examples 1, 2 and 3. Thus it will be appreciated that the compound may bind to the EDE of one serotype of flavivirus, for example zika virus or dengue virus. In a preferred embodiment, the compound will bind to the EDE of more than one serotype of flavivirus, for example more than one serotype of dengue virus or zika virus, and will bind to zika virus and/or one, two serotypes of dengue virus, or three serotypes of dengue virus, or four serotypes of dengue virus, ie considered to be all serotypes of dengue virus, as discussed above.

By "bind" we include the meaning of any form of non-covalent bonding between a compound for use of the invention and an epitope or molecule or macromolecule or compound, and we include the meaning of any significant degree of binding to the EDE as assessed by methods usual in the art. In a preferred embodiment the compound selectively binds the EDE. By selectively binds the EDE we include the meaning that the compound does not, or does not significantly, bind a flavivirus, for example the zika or dengue virus or envelope protein other than on the EDE. We also include the meaning that the compound does not bind to, or does not significantly bind to, another compound or molecule or macromolecule other than one displaying the EDE. Determining whether or not the compound binds the EDE will be well within the skill remit of a person skilled in the art. For example, an ELISA-type assay may be used, as well known to those skilled in the art. One non-limiting example of a method to determine whether the compound binds the EDE is as follows: Intact virus, of one or more, preferably of all serotypes of flavivirus, for example zika or dengue virus, and/or the envelope dimer of one or more, preferably of all serotypes flavivirus, for example zika or dengue virus, and/or the EDE according to any of the definitions described herein, for example a stabilised envelope dimer, or an EDE comprising residues from the envelope protein held within a heterologous scaffold; and mock uninfected supernatant are captured separately onto a solid support, for example a MAXISORP immunoplate (NUNC) coated anti-E Abs (4G2). The captured wells are then incubated with the compound, for example an antibody or antigen binding portion thereof, for example a human monoclonal antibody, for example 1 ug/ml of a human mAb, followed by incubation with a secondary antibody (that binds to the compound) conjugated to a reporter, for example ALP-conjugated anti-human IgG. The reaction is visualized by, for example the addition of a suitable substrate, for example PNPP substrate, and stopped with NaOH. For ALP/PNPP the absorbance is measured at 405 nm.

By a compound that binds to the EDE we include the meaning of any compound which binds to the wells containing the virus or EDE, for example stabilised soluble protein E dimer, to any degree above the level of background binding to the wells containing uninfected supernatant. Preferably the level of binding obtained to the virus or EDE, for example stabilised soluble protein E dimer, is 2 times the level of background binding to the uninfected supernatant wells, preferably 4 times, preferably 6 times, more preferably ten times. To determine if the compound binds to the virus or envelope protein at a site other than the EDE, the ability of the compound to bind to the denatured or monomeric or recombinant envelope protein may be assessed. If the compound binds to the denatured or monomeric or recombinant envelope protein to a significant level, it is deemed to bind to the virus or envelope protein at a site other than the EDE. To determine whether the compound selectively binds the EDE rather than any other molecule or macromolecule or compound, the ability of the compound to bind the EDE can be compared to the ability of the compound to bind to a molecule or macromolecule or compound using the above detailed method. A compound selectively binds the EDE if it binds the EDE to a significantly greater extent than it binds to another molecule or macromolecule or compound, for example denatured or monomeric envelope protein, for example if the compound binds to the EDE with at least 2 times, 4 times, 6 times, 8 times or 10 times greater affinity than it binds to another molecule, macromolecule or compound, for example denatured or monomeric or recombinant envelope protein.

The EDE is an epitope which is considered to be formed on an intact viral particle spanning a dimer of envelope proteins, or on a free dimer of envelope proteins, for example on a free dimer of soluble envelope proteins, spanning the two polypeptides. The envelope protein sequence for dengue virus is detailed in FIG. 29 and SEQ ID No: 29, 31, 33 and 35 of WO 2016/012800 and also discussed in the "Sequence" section below, for example.

In a preferred embodiment, the compound of the invention binds the EDE, either on the intact virus or on the free envelope dimer (ie having a molecular weight of twice that of an envelope polypeptide monomer), or other structure providing the EDE, as indicated above and discussed further below, and does not bind to the monomeric envelope protein, or denatured envelope protein. In one embodiment, if the compound binds to the monomeric envelope protein or denatured envelope protein, it is not considered a useful compound and is not a compound for use of the invention. Accordingly, one non-limiting method of identifying whether a compound is a compound for use of this embodiment of the invention is, for example, by assaying a compound, for example an antibody or antigen binding portion thereof, for its ability to bind to denatured envelope protein, for example on a western blot, and/or recombinant (monomeric) envelope protein, for example in an ELISA, and intact virus particles, and/or a dimer of envelope protein (for example a dimer of soluble envelope protein), for example in an ELISA. Preferred compounds for use of the invention are considered to bind to the intact virus or non-denatured dimer, but not (or to a significantly lesser extent) to denatured or monomeric envelope protein. The degree of binding can be assessed as described above.

A compound which binds to the fusion loop, and not to the EDE is not considered to be a compound for use of the invention. The fusion loop is a restricted set of residues in and around (dengue) 101W defining the previously described or classical fusion loop epitope (FL). In the fusion loop, residues 101-WGNG-104 make a distorted α-helical turn that projects the W101 side chain towards domain III across the dimer interface. If a compound binds to the envelope monomer or to denatured envelope protein (for example determined as described above), it may be considered to bind to the fusion loop, though it is possible that the antibody may instead bind to a different part of the envelope polypeptide (which could be checked by binding to envelope polypeptide mutated in the fusion loop region).

In another embodiment, a compound which binds the fusion loop is one which is unaffected (or not significantly affected) by mutation at any one or more of the following residues in the envelope protein, particularly DENV-1: E49, Q77, I161, T200, W391 or F392 (or corresponding residues in other flavivirus envelope proteins).

In an embodiment, a compound which binds to the fusion loop may be one which binds to the E protein fusion loop epitope as described in Dai et al (2016) supra, for example one which binds to the tip of the finger-like domain II at a perpendicular angle via the fusion loop and bc loop as described in Dai et al (2016) supra, for example on page 4 in the section entitled "Complex structure of E protein with 2A10G6 Antibody" with reference to FIG. 4. A compound for use of the present invention, in some embodiments, does not bind to the denatured EDE, or denatured envelope protein.

In one embodiment the EDE is considered to span the polypeptides of a flavivirus, for example zika and/or dengue virus, envelope polypeptide dimer, for example a soluble envelope polypeptide dimer. In a particular embodiment the EDE comprises areas of domains I, II and III of an envelope polypeptide dimer. It will be appreciated that the EDE comprises a quaternary structure dependent epitope at the dimer interface of the envelope proteins of one or more serotypes of flavivirus, for example one or more serotypes of zika and/or Dengue virus.

It will be appreciated that envelope proteins from different flavivirus, for example zika and/or dengue serotypes can dimerise, forming a hybrid dimer. The EDE that the compound binds to in one embodiment is made from envelope monomers derived from different flavivirus, for example zika and/or dengue serotypes and as such the EDE may comprise a homodimer or heterodimer.

It will also be appreciated that the EDE could be presented to the compound as part of a virion or a sub-viral particle or a virus-like particle, as the dimer of envelope protein is found on the intact virion or virus like particle. Where the EDE is presented as part of a virion or a sub-viral particle or a virus-like particle, the compound of the present invention is one that binds the intact virion or sub-viral particle or virus-like particle, but does not bind monomeric or denatured envelope protein.

Alternatively, the EDE could be presented to the compound not as part of a virion, for example the EDE which is formed from a dimer of two envelope proteins could be presented to the compound as a free dimer; or in the form of a nanoparticle, for example a self-assembling nanoparticle, for example as discussed further in Example 3. Thus, in one embodiment, the compound of the invention is a compound which binds to the EDE, when the EDE is a free dimer of envelope or soluble envelope (sE) protein or in the form of a nanoparticle, for example a self-assembling nanoparticle, for example as discussed further in Example 3. In another embodiment, the compound of the invention is a compound which binds to the EDE when the EDE is a stabilised dimer of envelope or sE protein, which may also be in the form of a nanoparticle, for example a self-assembling nanoparticle, for example as discussed further in Example 3.

In less preferred embodiments, the free dimer may be presented as part of a composition comprising elements that stabilise the dimerization of the proteins. For example, particular buffer components considered to promote protein association may be used. Alternatively, the envelope protein may be presented at high concentrations which promote dimer formation (see Example 7 of WO 2016/012800).

In more preferred embodiments the envelope protein may be engineered to have increased stability in the dimer configuration. For example, the dimer may be:
  covalently stabilized with at least one, optionally 2, 3, 4, 5, 6, 7, 8, 9, or 10 or more disulphide inter-chain bond between the two envelope or sE monomers and/or,
  covalently stabilized with at least one, optionally 2, 3, 4, 5, 6, 7, 8, 9, or 10 or more sulfhydryl-reactive cross-linker between the two sE monomers and/or,
  non-covalently stabilized by substituting at least one amino acid residue in the amino acid sequence of at least one envelope or sE monomer with at least one bulky side chain amino acid, at the dimer interface or in domain 1 (D1)/domain 3 (D3) linker of each monomer; and/or
  covalently stabilized by linking the two envelope or sE monomers through modified sugars.

A flavivirus, for example zika or dengue virus, envelope glycoprotein E ectodomain (sE; soluble envelope polypeptide/glycoprotein) refers to the 1-395 amino acid fragment of the envelope glycoprotein E of the flavivirus, for example zika or dengue virus serotypes 1, 2 and 4, the 1-393 amino acid fragment of the envelope glycoprotein E of the dengue virus serotype 3 and the 1-404 amino acid fragment of the envelope glycoprotein E of the Zika virus, for example as shown in SEQ ID NO: 10.

In an embodiment, the compound binds to the EDE wherein the EDE is a stabilised dimer of sE, wherein the recombinant flavivirus, for example zika or dengue virus envelope glycoprotein E ectodomain (recombinant sE) monomer is selected from the group consisting of: the DENV-1 sE of SEQ ID NO: 132, the DENV-2 sE of SEQ ID NO: 133 the DENV-3 sE of SEQ ID NO: 134, the DENV-4 sE of SEQ ID NO: 135 of WO 2016/012800 and a mutant sE thereof having at least one mutation (substitution) selected among residues corresponding to H27F, H27W, L107C, F108C, H244F, H244W, S255C, A259C, T/S262C, T/A265C, L278F, L292F, L294N, A313C (S313C in DENV-3) and T315C. These mutations are considered to contribute to increased stability in the dimer configuration, as detailed below.

It will be appreciated that the concept of a residue corresponding to a particular residue will be well known to the person skilled in the art and can readily be determined by consideration of sequence alignments, for example, as will also be well known to those skilled in the art.

Optionally, said mutant sE thereof has further at least one mutation (substitution) selected among Q227N, E174N and D329N, preferably the three mutations Q227N, E174N and D329N. These mutations are considered to allow masking non appropriate immunogenic regions and allow the stabilized recombinant sE dimer of the invention to preferentially elicit in a subject neutralizing antibodies directed to multiple flavivirus serotypes, for example zika virus and one or more for example all four dengue virus serotypes.

Mutations considered to be useful, for example noting Zika sE numbering, and their rationale, are discussed further in the Mutation section below.

In further embodiments, the compound binds to the EDE wherein the EDE is as set out in the claims directed to the EDE for use as set out in the claims.

Thus, for example, the recombinant sE monomer may be selected from the group consisting of
Zika virus (ZIKV, KJ776791, strain H-PF-2013_French-_Polynesia) SEQ ID No: 1;
dengue virus serotype 1 (DENV-1, NC_001477) SEQ ID No: 2;
dengue virus serotype 2 (DENV-2, NC_001474) SEQ ID No: 3;
dengue virus serotype 3 (DENV-3, NC_001475) SEQ ID No: 4;
dengue virus serotype 4 (DENV-4, NC_002640) SEQ ID No: 5;
Other Flavivirus:
Saint Louis encephalitis virus (SLEV, NC_007580) SEQ ID No: 6;
Japanese encephalitis virus (JEV, NC_001437 SEQ ID No: 7;
Murray Valley encephalitis virus (MVEV, NC_000943) SEQ ID No: 8;
West Nile virus (WNV, NC_001563) SEQ ID No: 9;
SEQ ID NO: 132, SEQ ID NO: 133, SEQ ID NO: 134, SEQ ID NO: 135 of WO 2016/012800;
and a mutant sE thereof having at least one mutation selected among mutations #1 to #13 as set out in the Mutation section below including Table M;
and also optionally at least one mutation selected among mutations #14 to #18 as set out in the Mutation section below including Table M.

The above-described mutagenesis of the sE dimer introduces mutations that do not interfere with its immunogenicity but provide a higher dimer affinity, including cysteine mutations at the dimer contacts to provide stabilization by cross-links, and/or introduces new glycosylation sites to allow chemical cross-linking between adjacent sugars on the dimer by click chemistry, and/or substitution of at least one amino acid residue in the amino acid sequence of at least one sE monomer with at least one bulky side chain amino acid to fill cavities at the dimer interface or in domain 1 (D1)/domain 3 (D3) linker of each monomer, in order to stabilise the dimer.

Figure 15:
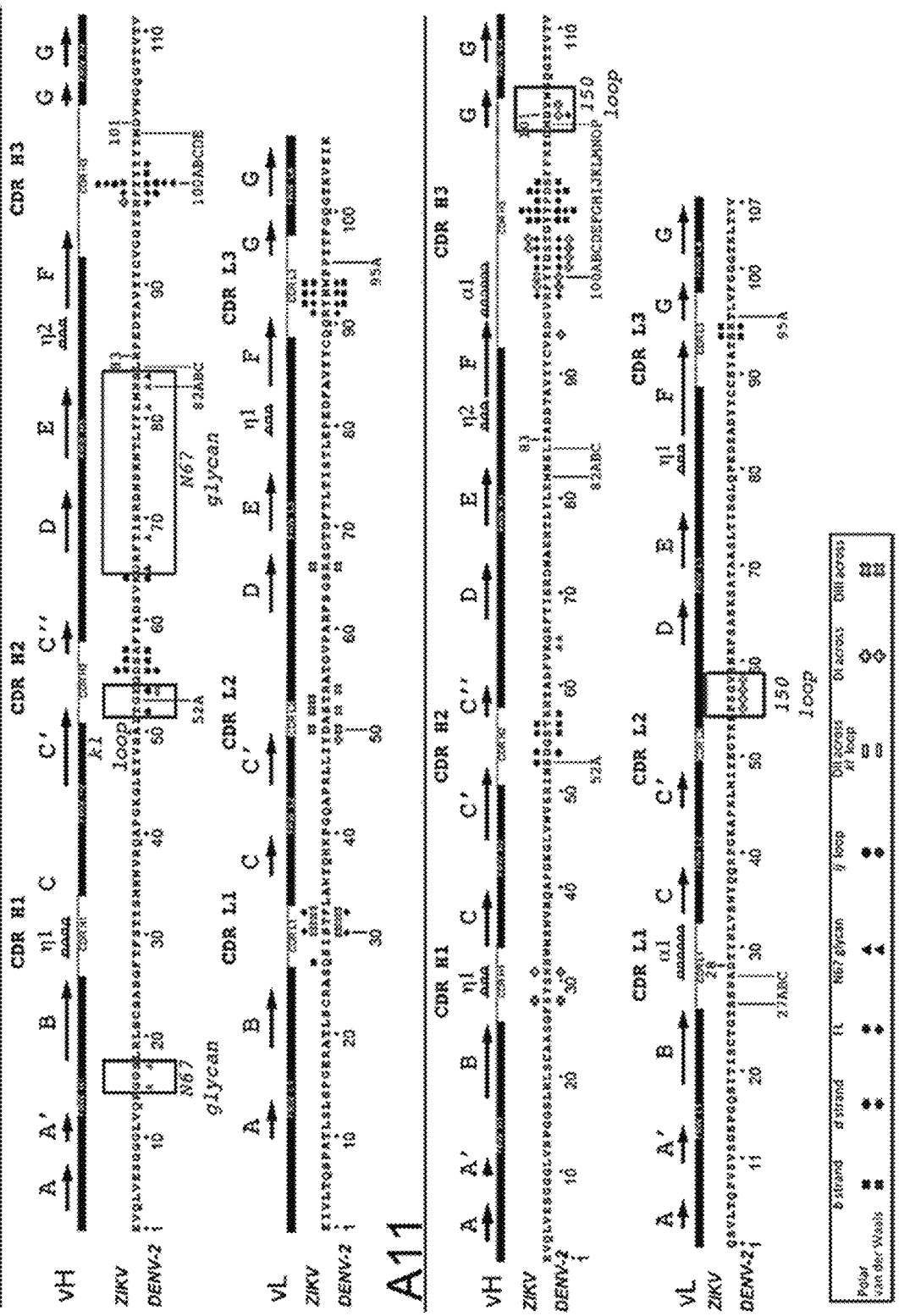

Unless otherwise specified, the amino acid residue position is numbered according to sE amino acid sequence alignment shown in FIG. 15 of WO 2016/012800. For DENV-2 the numbering may be as shown in SEQ ID No:3 and/or as shown in SEQ ID NO: 10 as discussed in the Sequence section below. For ZIKV the numbering may be as shown in SEQ ID No:1 as discussed in the Sequence section below and/or as shown in SEQ ID NO: 10. It is considered that if there is any doubt the identity of any residue referred to can be resolved by further reference to the Figures and Examples.

Nucleic acid sequences encoding DENV-1 sE of SEQ ID NO: 132, DENV-2 sE of SEQ ID NO: 133, DENV-3 sE of SEQ ID NO: 134, DENV-4 sE of SEQ ID NO: 135 of WO 2016/012800 are respectively represented as SEQ ID NO: 136, 137, 138 and 139 in WO 2016/012800.

As used herein, the term "recombinant" refers to the use of genetic engineering methods (cloning, amplification) to produce a flavivirus, for example zika or dengue virus envelope glycoprotein E ectodomain, an antibody or an antibody fragment for use of or in relation to the present invention.

The dimer can be a homodimer of two identical recombinant sE as defined above or a heterodimer of two different recombinant sE as defined above, the dimer being preferably a homodimer. The dimer may be a dimer of ZIKV recombinant mutated sE, for example.

By way of further example, it can be a heterodimer of DENV-1 sE and DENV-2 sE as defined above. It can also be a heterodimer of DENV-1 sE and a mutant sE of DENV-1 sE as defined above.

In one embodiment the compound, for example antibody or antigen binding fragment thereof, binds to the EDE wherein the EDE is a stabilised dimer of sE, wherein the stabilised dimer of envelope or recombinant sE is covalently stabilized with at least one, two or three disulphide interchain bonds between the two sE monomers.

Advantageously, said stabilized dimer involves single cysteine mutant sE located by the two-fold molecular axis of the dimer, which gives rise to a single inter-chain disulphide bond, or multiple (e.g., double) cysteine mutant sE that can make multiple (e.g., two) disulphide bonds away from the two-fold molecular axis. Said disulphide bonds can be synthetized under oxidative conditions, for example with a DMSO solution (O. Khakshoor et al., 2009) or with oxidative agents such as $CdCl_2$ or $CuSO_4$. Therefore, said stabilized dimer can be composed of monomers wherein one amino acid residue of each monomer by (near) the two-fold molecular axis of the dimer is substituted with a cysteine. Said stabilized dimer can also be composed of monomers wherein two amino acid residues of each monomer away from the two-fold molecular axis of the dimer are substituted with a cysteine. Said stabilized dimer can also be composed of monomers wherein three amino acid residues of each monomer away from the two-fold molecular axis of the dimer are substituted with a cysteine.

It may be desirable for there to be more than one inter-chain disulphide bond, as such an arrangement may limit access to the FLE region and therefore reduce the ability of the molecule to raise anti-FLE responses, as discussed further in Example 17 of WO 2016/012800; and in the Mutations section below.

In another embodiment, the compound, for example antibody or antigen binding fragment thereof, binds to the EDE wherein the EDE is a stabilised dimer of sE, wherein the stabilised dimer of envelope or recombinant sE is a homodimer of mutants sE having each the mutation A259C or S255C as defined above, and wherein the residues 259C or 255C are linked together through a disulphide inter-chain bond.

In another embodiment, wherein the EDE comprises a stabilised dimer of recombinant sE, the stabilized recombinant sE dimer is a heterodimer of a mutant sE having the mutation A259C as defined above and a mutant sE having the mutation S255C as defined above, wherein the residues 259C and 255C are linked together through a disulphide inter-chain bond.

In another embodiment, wherein the EDE comprises a stabilised dimer of recombinant sE, the stabilized recombinant sE dimer is a homodimer of mutant sE having each the mutations F108C and T315C as defined above, or a homodimer of mutants sE having each the mutations L107C and A313C as defined above, wherein the residues 108C and 315C or the residues 107C and 313C are linked together through a disulphide inter-chain bond.

In one embodiment the compound, for example antibody or antigen binding fragment thereof, binds to the EDE wherein the EDE is a stabilised dimer of sE, wherein the stabilised dimer of envelope or recombinant sE is a heterodimer of a mutant sE having the mutations F108C and A313C as defined above and a mutant sE having the mutations L107C and T315C as defined above, wherein the residues 108C and 313C are linked respectively to the residues 315C and 107C through a disulphide inter-chain bond between the two sE monomers.

In another embodiment, wherein the EDE comprises a stabilised dimer of recombinant sE, the stabilized recombinant sE dimer is selected from the group consisting of a homodimer of mutants sE having each the mutations A259C, F108C and T315C, a homodimer of mutants sE having each the mutations S255C, F108C and T315C, a homodimer of mutants sE having each the mutations A259C, L107C and A313C, and a homodimer of mutants sE having each the mutations A255C, L107C and A313C as defined above, wherein the residues 259C, 255C, 108C, 315C, 107C and 313C are linked respectively to the residues 259C, 255C, 315C, 108C, 313C and 107C through disulphide inter-chain bonds.

In another embodiment, the compound, for example antibody or antigen binding fragment thereof, binds to the EDE wherein the EDE comprises a stabilised dimer of recombinant sE, the stabilized recombinant sE dimer is a heterodimer of a mutant sE having the mutations A259C, F108C and T315C as defined above and a mutant sE having the mutations S255C, F108C and T315C as defined above, wherein the residues 259C, 108C and 315C are linked respectively to the residues 255C, 315C and 108C through disulphide inter-chain bonds.

In another embodiment, wherein the EDE comprises a stabilised dimer of recombinant sE, the stabilized recombinant sE dimer is a heterodimer of a mutant sE having the mutations S255C, L107C and A313C as defined above and a mutant sE having the mutations A259C, L107C and A313C as defined above, wherein the residues 255C, 107C and 313C are linked respectively to the residues 259C, 313C and 107C through disulphide inter-chain bonds.

For further examples of embodiments in relation to stabilised recombinant sE dimers, for example where the mutant sE is based on a Zika virus sE sequence, see the Mutations section below and claims relating to the EDE for use as set out in the claims.

As well as stabilisation via disulphide bonds, it will be appreciated that stabilisation may also be achieved via sulfhydryl-reactive crosslinkers. Thus, in one embodiment, wherein the EDE comprises a stabilised dimer of recombinant sE, the stabilized recombinant sE dimer is covalently stabilized with at least one, two or three, sulfhydryl-reactive crosslinkers (also called thiol-reactive crosslinkers) between the sE monomers.

Chemical crosslinking of proteins is well-known in the art (see for review Hemaprabha, (2012) *Journal of Pharmaceutical and Scientific Innovation* 1, 22-26).

Naturally, the sE dimer has two different faces, one exposed to the extracellular medium, where the antibodies bind, and the one exposed to the viral membrane.

Advantageously, said stabilized recombinant sE dimer involves candidate amino acid residues present in the face of sE exposed to the viral membrane and thus are not part of the epitope. One of each candidate amino acid residue of each monomer is mutated (substituted) to cysteine, producing a free sulfhydryl group that is the target of sulfhydryl-reactive crosslinkers of appropriate lengths.

Thr/Ser262 and Thr/Ala265 are candidate residues. The distance between them in the context of the dimer is 12 and 22 Å respectively. Further, these residues (Thr/Ser262, Thr/Ala265) are not fully conserved. Hence, they can tolerate point mutations.

In a preferred embodiment, the compound binds to the EDE wherein the EDE comprises a stabilised dimer of recombinant sE, the stabilized recombinant sE dimer is a homodimer of mutant sE having each the mutation T/S262C or T/A265C as defined above, wherein the residues 262C or 265C are linked together through a sulfhydryl-reactive crosslinker.

In another preferred embodiment wherein the EDE comprises a stabilised dimer of recombinant sE, the stabilized recombinant sE dimer is a heterodimer of a mutant sE having the mutation T/S262C as defined above and a mutant sE having the mutation T/A265C as defined above, wherein the residues 262C and 265C are linked together through a sulfhydryl-reactive crosslinker.

Regions of the recombinant sE which are not considered to be part of the epitope and which can be crosslinked are region A consisting of residues 1-9 of sE, region B consisting of residues 25-30 of sE, region C consisting of residues 238-282 of sE, region D consisting of residues 96-111 of sE and region E consisting of residues 311-318 of sE. Any of the residues of these five regions (A to E) of a monomer is at less than 25-30 Å of other residue of the other monomer in the recombinant sE dimer, and thus these residues can be crosslinked.

Advantageously, one or several of the candidate amino acid residues in these five regions of each monomer is mutated (substituted) to cysteine, producing a free sulfhydryl group that is the target of sulfhydryl-reactive crosslinkers of appropriate lengths as defined above.

In another embodiment, the compound, for example antibody or antigen-binding fragment thereof, binds to the EDE wherein the EDE comprises a stabilised dimer of recombinant sE, the stabilized recombinant sE dimer is a homodimer or a heterodimer of a mutant sE wherein at least one of the amino acid residues 1-9, 25-30, 238-282, 96-111 311-318 of sE is mutated (substituted) to cysteine and a mutant sE wherein at least one of the amino acid residues 1-9, 25-30, 238-282, 96-111 311-318 of sE is mutated (substituted) to cysteine, and wherein the mutated cysteine residues are linked together through a sulfhydryl-reactive crosslinker.

The sulfhydryl-reactive crosslinkers are preferably homobifunctional reagents with identical or non-identical reactive groups, permitting the establishment of inter-molecular crosslinkages between the two monomers. Homobifunctional crosslinkers have identical reactive groups at either end of a spacer arm, and generally they can be used in one-step reaction procedures. The sulfhydryl-reactive crosslinkers of the invention can be a maleimide, a haloacetyl (preferably a bromo- or iodo-acetyl), a pyridyl disulfide, a vinylsulfone, an alkyl halide or an aziridine compound, an acryloyl derivative, an arylating agent, or a thiol-disulfide exchange reagent (Hermanson G. T., Bioconjugate Techniques, 3rd Edition. Academic Press (2013); Hemaprabha, 2012), such as the bis(methanethiosulfonate) (Haberz P. et al., Organic Letters, 2006, 8, 1275-1278).

Examples of maleimide homo-bifunctional sulfhydryl-reactive crosslinkers according to the invention, with spacer of different lengths, include BMOE (1,2-bis-maleimidoethane), BMB (1,4-bis-maleimidobutane), BMH (1,6-bis-maleimidohexane), TMEA (tris-(2-maleimidoethyl)amine), BM(PEG)$_2$ (1,8-bismaleimidodiethyleneglycol), BM(PEG)$_3$ (1,11-bismaleimidotriethyleneglycol), BMDB (1,4-bismaleimidyl-2,3-dihydroxybutane), DTME (dithio-bis-maleimidoethane), and preferably BMH, BM(PEG)$_2$ and BM(PEG)$_3$.

BMH
Bismaleimidohexane
MW 276.29
Spacer Arm 13.0 Å

BM(PEG)$_2$
1,8-Bismaleimidodiethyleneglycol
MW 308.29
Spacer Arm 14.7 Å

BM(PEG)$_3$
1,11-Bismaleimidotriethyleneglycol
MW 352.34
Spacer Arm 17.8 Å

The maleimide group reacts specifically with the sulfhydryl groups is performed under mild buffer and pH conditions, in order to minimize the degree of structural shift due to crosslinking reactions. Preferably, the pH of the reaction mixture is between 6.5 and 7.5 leading to the formation of a stable thio-ether linkage that is not reversible (the bond cannot be cleaved with reducing agents).

In addition to stabilisation via disulphide bonds and sulfhydryl-reactive crosslinkers, it will be appreciated that stabilisation may be obtained through the linking of the two monomers through modified sugars. To this end, glycosylation sites are inserted on them and are reacted with modified sugars, in order to join them by click-chemistry.

According to this embodiment, the compound binds to the EDE wherein the EDE comprises a stabilised dimer of recombinant sE, the stabilized recombinant sE dimer is a homodimer or heterodimer of mutants sE, wherein:
  one sE monomer has at least one mutation which introduces a glycosylation site, and wherein the mutated amino acid residue is glycosylated with a modified sugar bearing an X functional group, and
  the other sE monomer has at least one mutation which introduces a glycosylation site, and wherein the mutated amino acid residue is glycosylated with a modified sugar bearing a Y functional group,
  and wherein both mutated residues are joined together through the modified sugars by reacting, specifically by click chemistry, the X functional group of the sugar of the first sE monomer with the Y functional group of the sugar of the other sE monomer.

By X functional group, it is meant a chemical group beared by a sugar which is able to react and form a covalent linking by click chemistry with a Y functional group, said Y functional group being preferably an azide functional group.

By Y functional group, it is meant a chemical group beared by a sugar which is able to react and form a covalent linking by click chemistry with a X functional group, said X functional group being preferably a terminal alkyne functional group.

The modified sugars can be synthesized and introduced in the sE monomers as described by Laughlin et al., 2007, and joined together as described by Speer et al., 2003.

In addition to the abovementioned covalent methods of stabilising the dimer, non-covalent means may also be used. Thus, in another embodiment wherein the EDE comprises a stabilised dimer of recombinant sE, the dimer is non-covalently stabilized by filling the cavities of said dimer at the dimer interface by substituting at least one amino acid in the amino acid sequence of one or the two monomers, preferably the two monomers, with bulky side chain amino acids. According to this embodiment, cavities unique to the quaternary conformation of the recombinant sE dimer are identified and filled by engineered hydrophobic substitutions in the monomers.

According to this embodiment, the stabilized recombinant sE dimer is non-covalently stabilized by substituting at least one amino acid residue in the amino acid sequence of at least one sE monomer with at least one bulky side chain amino acid within regions forming cavities at the dimer interface or in domain 1 (D1)/domain 3 (D3) linker of each monomer. Such substitutions allow increasing hydrophobic interactions between the two sE monomers.

In an embodiment wherein the EDE comprises a stabilised dimer of recombinant sE, the stabilized recombinant sE dimer is a homodimer or heterodimer, preferably homodimer, of two recombinant sE as defined above, wherein one of the recombinant sE or the two recombinant sE have at least one mutation (substitution) selected from the group consisting of H27F, H27W, H244F, H244W, and L278F. The mutations H27F, H27W, H244F, H244W and L278F allow stabilizing the cavity around F279 of the recombinant sE dimer, strengthening the dimer interface and mimicking the F279 conformation in the virion. Other means of non-covalently stabilising the dimer include, for example non-covalent stabilisation in domain 1 (D1)/domain 3 (D3) linker of each monomer, by substituting amino acids in the amino acid sequence of one or the two, preferably the two, monomers with at least one bulky side chain amino acid.

In a preferred embodiment the compound binds the EDE wherein the EDE comprises a stabilised dimer of recombinant sE, the stabilized recombinant sE dimer is a homodimer or heterodimer, preferably homodimer, of two recombinant sE as defined above, wherein one of the recombinant sE or the two recombinant sE have at least one mutation (substitution) selected from the group consisting of L292F and L294N. The mutations L292F, L294N are considered to allow stabilizing the D1-D3 linker in sE dimeric conformation.

Further embodiments, particularly in relation to Zika sE dimer stabilisation, are set out in the claims and in the Mutations section below.

In a preferred embodiment where the EDE is stabilised in the dimer configuration through engineering, the engineering, such as that described above, does not result in a change in the overall 3D structure of the dimer, or does not substantially change the overall 3D structure and the residues in the native dimer spatially correspond to the engineered dimer. If the native dimer spatially corresponds to the engineered dimer, this means that when a 3D model of the engineered dimer (or part thereof, for example reflecting residues of particular importance in defining the EDE, for example the residues indicated in Table 2 of WO 2016/012800 and/or discussed further below) is superimposed on the 3D model of the native dimer, coordinates defining the spatial location of the backbone atoms in the native dimer vary from the coordinates defining the analogous backbone atoms in the engineered dimer by less than about 10 angstroms. Backbone atoms are those atoms in an amino acid that form the peptide backbone, or 3D folding pattern, i.e. does not include the side chain atoms, though the position of some or all of the side chain atoms may similarly not vary significantly. The 3D structure is key to the immunogenicity of the VDE or EDE, and therefore, in a preferred embodiment, the engineering does not result in a dimer with decreased immunogenicity. In one embodiment the engineering does result in a dimer with a different 3D conformation. Preferably the engineering results in a dimer with increased immunogenicity. Such approaches have been used in Bommakanti et al 2010 PNAS 13701-13706. Thus in one embodiment, the compound binds to an engineered EDE, such as those described above.

A 3D model of the native dimer may be formed making use of the information on crystal structures for envelope glycoprotein ectodomain from dengue virus serotypes, for example serotypes 2, 3, and 4, available in the Protein Data Bank, for example under accession numbers 1OAN, 1OK8, 1UZG and 3UAJ, as noted above.

Whether or not a particular mutation or modification alters or substantially alters the 3D structure could be assessed by different techniques, including monitoring whether the antibodies described herein, which are known to bind to the VDE, can still bind to the engineered version of the VDE.

The skilled person is able to use computer programs to aid in the identification of potential stabilising modifications, for example.

The effect of the engineering on the immunogenicity of the EDE can be assessed by comparing the antibody response in a subject when administered an engineered and non-engineered EDE or by comparing binding to known anti-EDE antibodies.

Alternatively, the modified envelope protein could be expressed in a dengue virus or zika virus or other flavivirus and the ability of the compound to neutralise the virus assessed.

In order to present a stabilised EDE, non-EDE heterologous proteins that have a similar three-dimensional structure to the respective EDE (referred to as scaffold proteins), can be modified to contain the appropriate residues that enable the modified protein to hold the EDE. Thus in one embodiment the compound binds the EDE wherein the EDE is presented as part of an epitope-scaffold protein. An epitope-scaffold protein is a chimeric protein that includes an epitope sequence fused to a heterologous "acceptor" scaffold protein. Design of the epitope-scaffold is performed, for example, computationally in a manner that preserves the native structure and conformation of the epitope when it is fused onto the heterologous scaffold protein. The use of such scaffold proteins is well known in the art and such methods and techniques are described in WO 2011/050168 and WO 2016/012800 and refs McLellan, J. S. et al. Structure-based design of a fusion glycoprotein vaccine for respiratory syncytial virus. Science 342, 592-598, doi:10.1126/science.1f67283 (2013); Ofek et al 2010 PNAS 107: 17880-17887; Burton 2010 PNAS 107:17859-17860; and the skilled person can follow methods described therein and apply them to the present invention.

Accordingly, in one embodiment, the EDE comprises part of an epitope-scaffold protein, wherein the scaffold protein comprises a heterologous scaffold protein covalently linked to the Envelope Dimer Epitope. Scaffold proteins are useful for creating the EDE of the present invention in that they hold contact residues of the EDE in the proper spatial orientation to facilitate interaction between such residues and the compound, for example between contact residues of the compound when the compound is a protein, optionally an antibody or antigen binding portion thereof. A contact residue is any amino acid present in a molecule that interacts directly or indirectly (e.g. forms an ionic bond either directly, or indirectly through a salt bridge) with an amino acid in another molecule. Residues of the envelope protein which are considered to be potentially important for compound binding to the EDE, at least for DENV-1, are detailed in Table 2 of WO 2016/012800.

The scaffold protein may present the entire dimer or may present only the selected residues above. A 3D model of the native dimer or parts thereof may be formed making use of the information on crystal structures for envelope glycoprotein ectodomain from dengue virus serotypes, for example serotypes 2, 3, and 4, available in the Protein Data Bank, for example under accession numbers 1OAN, 1OK8, 1UZG and 3UAJ, as noted above.

Mutational analysis revealed particular residues of DENV1 and DENV2 which are important for binding to the antibodies identified for use of the present invention. These residues are:

DENV1: E49,K64,Q77,W101,V122,N134,N153,T155, I161,A162,P169, T200,K202,E203,L308,K310,Q323, W391,F392;

DENV2: Q77,W101,N153,T155,K310.

All of these residues are considered to be important for binding, and the Q77,W101,N153,T155,K310

Accordingly, in one embodiment, compound binds the EDE wherein the EDE is part of a scaffold protein, wherein the scaffold protein holds at least residues corresponding to one or more of E49,K64,Q77,W101,V122,N134,N153, T155,I161,A162,P169,T200, K202,E203,L308,K310,Q323, W391,F392, of the DENV-2 envelope protein or equivalent residue of a flavivirus, for example Zika or Dengue virus envelope protein, particularly for DENV-1 and DENV-2. Certain residues are considered to be more important, and a further embodiment of the EDE comprises a scaffold protein which holds at least one or more of residues corresponding to Q77,W101,N153,T155,K310 of the envelope protein or equivalent residue of a flavivirus, for example Zika or a Dengue virus envelope protein, particularly DENV-1 and DENV-2.

Residues of the envelope protein considered to be important for contacting the epitope in Dengue virus are given in FIG. 31 of WO 2016/012800 and discussed in WO 2016/012800. For example:

the C10 antibody is considered to contact the DENV2 EDE at residues R2,H27,G28,E44,L45,I46,K47,N67,T68, T69,T70,E71,S72,R73,C74,Q77,S81,L82,N83,E 84,V97, R99,W101,G102,N103,G104,C105,G106,L113,T115, K246,K247,Q248,Q271,V3 09,K310,R323,Q325,D362;

the C10 antibody is considered to contact the DENV4 EDE at residues R2,H27,G28,G29,E44,L45,T46,N67,T69, T70,A71,T72,R73,C74,Q77,V97,R99,W101,G1 02,N103, G104,C105,G106,V113,R247,Q248,D249,D271,M278, D309,K310,V324,K323, K325,T361,N362;

the C8 antibody is considered to contact the DENV2 EDE at residues N67,T68,T69,T70,E71,S72,R73,C74,Q77,N83, E84,V97,D98,R99,W101,G102,N103, G104,C105,G106, L113,E148,H158,K246,K247,Q248,D249,I308,K310,E311, R323,D362,G374.

Thus residues of the envelope protein that are considered to be important for binding to the compound, particularly for DENV2 and DENV4 are: K47,T68,S81,L82,N83,E84, T115,K246,K,V309, R2,H27,G28,G29,E44,L45,T46,N67, T69,T70,A71,T72,R73,C74,Q77,V97,R99,W101,G1 02,N103,G104,C105,G106,V113,R247,Q248,D249,D271, M278,D309,K310,V324,K323, K325,T361,N362,D98, E148,H158,K246, 1308, E311, G374.

or equivalent residue of a flavivirus, for example Zika or Dengue virus envelope protein.

Figure 14:
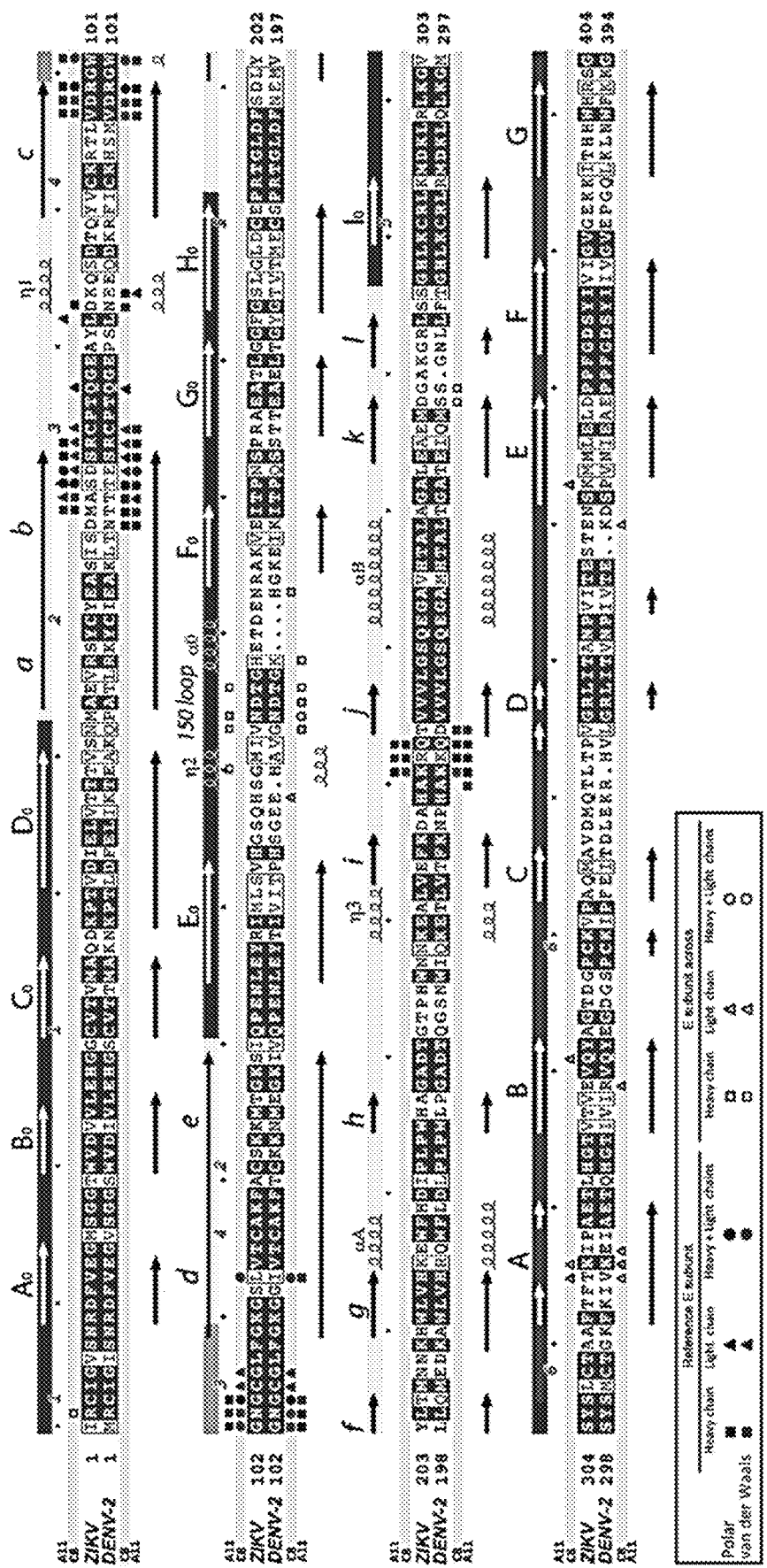

Residues that are considered to be important for binding to the compound, particularly for DENV-1 or 2 or Zika virus are: E49, K64, Q77, W101, V122 (DENV-1; K122 DENV-2), N134, N153, T155, 1161, A162 (DENV-1; 1162 DENV-2), P169 (DENY-1; S169 DENV-2), T200 (DENV-1; Q200 DENV-2), K202 (DENV-1; E202 DENV-2), E203, L308 (DENV-1; V308 or 1308 DENV-2_, K310, Q323 (DENV-1; R323 DENV-2), W391, F392, of the DENV-1 or DENV-2 polypeptide sequence; T49, S64, Q77, W101, S122, N134, N154, T156, K166 T205, N207, N208, F314, K316, E319, W400, H401 of Zika PF13; or equivalent residue of a flavivirus, optionally Zika or Dengue virus envelope protein, and/or one or more of positions corresponding to R2, M68, A69, S70, D71, S72, R73, C74, Q77, D83, V97, D98, R99, W101, G102, N103, G104, C105, G106, L113, K251, R252, Q253, T315, K316, Q331, K373 of Zika PF13 for example one or more positions corresponding to T315, K373, S70, S72, Q77, R99, G104, M68, R252, D83, Q253 of Zika PF13. These (up to and including K373) are considered to be the residues that are indicated in FIG. 14 as making contact with the EDE1 C8 antibody. The further residues (starting with T315) are considered to be those mentioned in Example 2 ED Tables 4 and 5 (FIGS. 19 and 20).

The scaffold protein may present one or more residues selected from these sets of residues, for example may present at least one or more, for example, at least 1, 2, 3, 4, 5, 6, 7, 8, 9, or 10 or all of:

E49,K64,Q77,W101,V122,N134,N153,T155,I161,A162, P169, T200,K202,E203,L308,K310,Q323,W391,F392, A71,C105,C74,D154,D249,D271,D309,D362,D98,E148, E311,E44,E71,E84,G102,G104 G106,G152,G156,G28, G29,G374,H158,H27,I113,I308,I46,K246,K247,K323, K325 K47,L113,L45,L82,M278,N103,N362,N67,N83, Q248,Q271,Q325,R2,R247, R323,R73,R99,S72,S81,T115, T361,T46,T68,T69,T70,T72,V113,V114,V250,V309 V324, V97 of DENV-2; R2, M68, A69, S70, D71, S72, R73, C74, Q77, D83, V97, D98, R99, W101, G102, N103, G104, C105, G106, L113, K251, R252, Q253, T315, K316, Q331, K373 of Zika PF13 for example one or more positions corresponding to T315, K373, S70, S72, Q77, R99, G104, M68, R252, D83, Q253 of Zika PF13, or equivalent residue of a flavivirus, for example Zika or Dengue virus envelope protein.

In addition, the scaffold protein may present any one or more or all of the following sets of residues, which as described earlier are considered to increase stability of the dimer configuration: H27F, H27W, L107C, F108C, H244F, H244W, S255C, A259C, T/S262C, T/A265C, L278F, L292F, L294N, A313C and T315C (or equivalent residues of a flavivirus, for example Zika or Dengue virus envelope protein.

The scaffold protein may hold the dimer, or fragment of dimer, and may comprise any of the described modifications above which are considered essential for immunogenicity, and/or result in increased dimer stability, for example increased disulphide bonds.

Moreover, the scaffold can be such that an improved EDE is presented. In one embodiment, the compound therefore binds an improved EDE. For example, as described below and in Examples 2 and 5 of WO 2016/012800, patients with Dengue infection and Zika infection tend to have either antibodies directed towards the VDE, which are considered useful antibodies, or antibodies directed towards the Fusion Loop (anti-FL antibodies) which are not considered to be useful. Thus a scaffold may be engineered such that only the EDE is presented, and is presented in such a way as to exclude the possibility of a compound, for example an antibody or antigen binding portion thereof, being raised to the FL. Therefore, in one preferred embodiment the EDE is capable of raising antibodies to the EDE and not to the FL, optionally by being incorporated into a scaffold protein.

Independently of a scaffold protein, the envelope protein may be engineered such that an improved EDE is generated. As detailed above, an EDE which is incapable of being recognised by the anti-FL antibodies, and incapable of raising such antibodies, is considered to be an improved EDE. This may be accomplished by one or more mutations, deletions or insertions in the envelope protein, or by generating a hybrid protein wherein the specific epitope, without any antigens which would raise anti-FL antibodies, fused to a scaffold protein. It is considered, for example, that stabilisation of the dimer, for example stabilisation that reduces "breathing" of the dimer as discussed in Example 3, for example, may reduce raising of anti-FL antibodies and may therefore represent an improved EDE.

In one embodiment, the envelope protein is engineered by modifying the internal surface of the dimer (projecting to the inside of the virus) with sugars to make it less immunogenic by adding N or O linked glycan sequences.

Extensive mutagenic resurfacing of the dimer may be useful to further reduce the generation of non-ED suboptimal responses by mutation of residues and/or addition of glycan.

As an example, the L278F mutation is considered to re-shape the kl-loop and to mimic the virion-like conformation.

See, for example, the Mutation section below and Example 3 herein for further discussion; as well as, for example, discussion in WO 2016/012800, for example in Examples 17 and 18.

Modelling an optimisation of the core EDE epitopes may also be useful to produce an optimal sequence to induce the desired EDE response to provide binding and neutralising antibodies.

It will be appreciated that the EDE may be the naturally occurring envelope protein held within a scaffold to effect increased dimer stability. The EDE may also be engineered independently of any scaffold to increase dimer stability. The two may be combined such that in one embodiment the EDE comprises a dimer wherein the envelope protein is engineered to have improved stability in the dimer configuration, which is held within a heterologous scaffold protein. Alternatively, the envelope protein may be engineered such that only the relevant portions of the protein are present, and this may then be held in a heterologous scaffold protein.

A dimer conformation may be stabilised by, for example, creating a long linker, for example a glycine-serine-rich liner between two envelope monomers to express as a single polypeptide chain comprising two envelope polypeptide domains. Alternatively or in addition, a dimeric structure may be stabilised by any antibody (for example) which binds to the inner facing surfaces of the dimer or to tags associated with the dimer.

Any reference to the envelope protein, sE, sE dimer or envelope protein dimer also includes within its scope a scaffold protein, or a structure, which comprises the particular residues that make up the EDE, held in a particular conformation so as to present a suitable EDE.

The envelope nucleotide sequence may be engineered such that the envelope protein has any one or more of mutations, insertions or deletions. The nucleotide sequence may be such that it has at least 70%, 80%, 85%, 90%, 95%, 98% or 99% homology to the native sequence of the particular envelope protein (or part thereof).

In a further embodiment the envelope protein may be engineered such that it has at least 70%, 80%, 85%, 90%, 95%, 98% or 99% homology to an envelope protein (or part or parts thereof, for example one or more portions of at least 8, 9 or 10 consecutive amino acids) from another serotype of flavivirus, for example zika virus or dengue virus. In a preferred embodiment, the envelope protein is engineered such that it has at least 70%, 80%, 85%, 90%, 95%, 98% or 99% homology to two different envelope proteins (or part or parts thereof, for example one or more portions of at least 8, 9 or 10 consecutive amino acids), more preferably to four different envelope proteins (or part or parts thereof, for example one or more portions of at least 8, 9 or 10 consecutive amino acids), most preferably to all envelope proteins (or part or parts thereof, for example one or more portions of at least 8, 9 or 10 consecutive amino acids) from all serotypes of dengue virus and/or Zika virus.

As described above, the envelope protein may be engineered such that it actually has very low homology to the native envelope protein, but wherein the integrity and conformation of the EDE is maintained, or is altered in such a way that the EDE is improved, for example, is incapable of raising the anti-FL antibodies. Thus, the level of sequence homology is not necessarily an indication of the 3D structure homology, or functional homology. For example, a particular sequence encoding a structure comprising an EDE may actually have a very low level of homology to the native envelope protein, but may nevertheless be considered a useful compound in relation to the invention. For example, the protein may have 10%, 20%, 30%, 40%, 50% or 60% homology to the native envelope protein, and the nucleotide sequence which encodes this structure may have a correspondingly low sequence identity to the native envelope sequence.

It is considered, for example, that the backbone conformation that forms an EDE may potentially be recognised broadly by anti-EDE antibodies even if there are differences in the amino acid side chains between the residues forming the EDE in different envelope proteins, for example if there are differences between the amino acids that make up the Zika and Dengue envelope protein EDEs.

In a preferred embodiment, where the envelope protein, or structure comprising the EDE has at least 70%, 80%, 85%, 90%, 95%, 98% or 99% homology to an envelope protein (or part or parts thereof, for example one or more portions of at least 8, 9 or 10 consecutive amino acids) of a flavivirus, for example zika virus or dengue virus, or at least 70%, 80%, 85%, 90%, 95%, 98% or 99% homology to two different envelope proteins (or part or parts thereof, for example one or more portions of at least 8, 9 or 10 consecutive amino acids), more preferably to four different envelope proteins, most preferably to all envelope proteins from all serotypes of flavivirus, for example zika virus or dengue virus, or wherein the protein or structure comprising the EDE has at least 10%, 20%, 30%, 40%, 50% or 60% homology to the native envelope protein of one or more serotypes of zika or dengue virus, the protein comprises one or more of, or optionally all of: E49,K64,Q77,W101,V122,N134,N153, T155,I161,A162,P169, T200,K202,E203,L308,K310,Q323, W391,F392 and/or

R2, M68, A69, S70, D71, S72, R73, C74, Q77, D83, V97, D98, R99, W101, G102, N103, G104, C105, G106, L113, K251, R252, Q253, T315, K316, Q331, K373 of Zika PF13 for example one or more positions corresponding to T315, K373, S70, S72, Q77, R99, G104, M68, R252, D83, Q253 of Zika PF13, or equivalent residue of a flavivirus, for example zika virus or dengue virus envelope protein.

Some of these residues are considered to be more important than others, as such in a further embodiment of the EDE, the envelope protein, or structure comprising the EDE comprises one or more of, or optionally all of: Q77,W101, N153,T155,K310 of DENV-2, or T315, K373, S70, S72, Q77, R99, G104, M68, R252, D83, Q253 of Zika PF13, or equivalent residue of a flavivirus, for example zika virus or dengue virus envelope protein.

It is considered that one or more of envelope protein residues E49,K64,Q77,W101,V122,N134,N153,T155,I161, A162,P169, T200,K202,E203,L308,K310,Q323,W391, F392(DENV-2); or T315, K373, S70, S72, Q77, R99, G104, M68, R252, D83, Q253 of Zika PF13, or equivalent residues of a flavivirus, for example zika virus or dengue virus protein are required for binding of the compound to the EDE. Thus in one embodiment, the envelope protein or structure comprising the EDE comprises one or more or all of these residues.

Whilst the anti-FL antibodies appear, in most cases, to require only residue W101 out of the residues mutated in the alanine scanning analysis (Example 2 of WO 2016/012800) and are not affected by mutation of any of the other residues, the anti-EDE antibodies require a much larger epitope, which requires the presence of residue W101, as does the anti-FL antibodies, but which are also affected by mutations at many of the other residues. Accordingly, in one embodiment the EDE is defined as an epitope in which residues W101 and at least one or more of positions E49,K64,Q77, W101,V122,N134,N153,T155,I161,A162,P169, T200, K202,E203,L308,K310,Q323,W391,F392 (DENV-2); or T315, K373, S70, S72, Q77, R99, G104, M68, R252, D83, Q253 of Zika PF13, or equivalent residue in the Envelope Dimer Epitope, are required for binding of the compound.

In a particular embodiment, the Envelope Dimer Epitope comprises the domain III residue K310 (DENV-2) or T315, K373, S70, S72, Q77, R99, G104, M68, R252, D83, Q253 of Zika PF13, or equivalent residues of a flavivirus, for example zika virus or dengue virus protein.

In an embodiment, the EDE is glycosylated at position 67 (Asn67 glycan) and/or at position 153 (Asn153 glycan; position 154 for Zika), for example of each envelope, for example sE, monomer, preferably at least at position 67 (Asn67 glycan) of each monomer. Asn67 is not considered to be present in Zika Envelope protein.

The compound of the invention, according to one embodiment, contacts the N67 glycan chain of the envelope protein dimer, or the N153/N154(Zika) glycan chain of the envelope protein dimer. It will be appreciated that the compound can contact both the N67 (where present) and N153 glycan chains of the envelope protein dimer.

In a particular example, the compound is an antibody wherein the CDR H2 interacts with the N67 glycan chain of the envelope protein.

In one embodiment, the compound contacts the EDE at any one or more of A71,C105,C74,D154,D249,D271,D309, D362,D98,E148,E311,E44,E71,E84,G102,G104 G106, G152,G156,G28,G29,G374,H158,H27,I113,I308,I46,K246, K247,K310,K323,K325 K47,L113,L45,L82,M278,N103, N153,N362,N67,N83,Q248,Q271,Q325,Q77,R2,R247, R323,R73,R99,S72,S81,T115,T155,T361,T46,T68,T69, T70,T72,V113,V114,V250,V309 V324,V97,W101 in the envelope protein, for example DENV-2 or DENV-4, of one or more serotypes of Dengue virus, where present, preferably all serotypes of dengue virus.

In an embodiment, the Envelope Dimer Epitope comprises a region centred in a valley lined by the b strand on the domain II side, and the "150 loop" (see, for example, 24C) on the domain I side (across from the dimer interface), wherein the 150 loop spans residues 148-159, connecting b-strands E0 and F0 of domain I, and carries the N153 residue or N153 glycan, which covers the fusion loop of the partner subunit in the dimer. The 150 loop is considered to comprise WO 2016/012800 SEQ ID NO: 148 150 loop of Denv-1 QHQVGNETTEHG; SEQ ID NO: 1149 150 loop of Denv 2 EHAVGNDTGKHG; SEQ ID NO: 150 150 loop of Denv 3 QHQVGNETQG; SEQ ID NO: 151 150 loop of Denv 4 THAVGNDIPNHG.

In some cases, the Envelope Dimer Epitope comprises domain II of the envelope protein, optionally further comprising any one or more of the following features of domain II; the b strain (residues 67-74), the fusion loop and residues immediately upstream (residues 97-106) and the ij loop (residues 246-249), and residues 243-251 and residues 307-314.

In one embodiment the EDE comprises the five polypeptide segments of the flavivirus, for example zika or dengue virus glycoprotein E ectodomain (sE) consisting of the residues 67-74, residues 97-106, residues 148-159, residues 243-251 and residues 307-314.

Thus in one embodiment the invention also provides a compound for use as indicated above, for example an isolated neutralizing antibody or antigen binding fragment thereof for use as indicated above, directed against the stabilized recombinant sE dimer as defined above, wherein said antibody or fragment thereof binds the five polypeptide segments of the flavivirus, for example zika or dengue virus glycoprotein E ectodomain (sE) consisting of the residues 67-74, residues 97-106, residues 148-159, residues 243-251 and residues 307-314.

The EDE to which the compound binds may comprise the Zika PF13 beta strand b of domain II, bcd beta-sheet edge, fusion loop main chain, fusion loop R99 side chain, Q77 side chain, disulphide bond between C74 and C105; beta strand E, K373, charged residues in domain I, kl loop of domain II, or regions corresponding thereto;

and/or may consist of Zika PF13 residues 67-77, residues 97-106, residues 313-315, residues 243-253, residue K373 or corresponding residues of the flavivirus glycoprotein E ectodomain, optionally wherein binding is unaffected by presence or absence of dengue N153 (Zika N154) glycan or corresponding residue.

The characterization of the binding of an antibody fragment, for example, for use according to the present invention to a polypeptide segment or amino acid residue can be performed by, for example, crystallization trials as describes in the Examples below and/or in WO 2016/012800.

Preferably, in addition to binding to the EDE the compound is capable of neutralising the virus. In a preferred embodiment the compound is capable of neutralising all serotypes of flavivirus, or, for example, all serotypes of zika and/or Dengue virus, preferably to at least 90% or at least 98%, for example 100%, and preferably neutralises all serotypes of zika and/or Dengue virus made in both insect and human cells to at least 90% or at least 98%, for example 100%. Preferences for the neutralisation and neutralisation assay techniques are as described earlier.

In one embodiment the EDE comprises a dimer of full length envelope protein. In another embodiment, the EDE comprises a dimer of the envelope ectodomain (sE). In a further embodiment the envelope protein comprises the (approximately, as discussed above) 400 amino terminal residues of the ectodomain of Envelope protein. See, for example, FIG. 28 of WO 2016/012800. The preferences for the stability of a dimer of the full length envelope protein described above also apply to the truncated ectodomain of envelope protein. Therefore, the dimer of ectodomain of envelope protein may be stabilised through engineering or stabilised by being incorporated into a scaffold protein, or may comprise a hybrid dimer.

In a further embodiment, the compound for use of the present invention is one which will not bind to dengue virus or virion or sub-viral particle or virus-like particle incubated at acid pH. Acidic pH causes the envelope protein to irreversibly adopt a trimer configuration. The inventors found that the compounds for use of the present invention do not bind to viral particles incubated at a low pH (see Example 4 of WO 2016/012800). Therefore, in one embodiment, the compound, for example and antibody or antigen binding portion thereof, does not bind to dengue virus or virion or sub-viral particle or virus-like particle, incubated at an acidic pH. By an acidic pH we mean any pH below 7, preferably pH 5.5.

Accordingly, the skilled person can readily identify whether a particular compound is a compound for use of the invention according to this embodiment of the invention, simply by identifying whether the compound cannot bind to one or more than one of: a) a virion or sub-viral particle or a virus-like particle made in cells lacking furin activity; b) a virion or sub-viral particle or a virus-like particle having a high percentage of prM protein, and/or c) a virion or sub-viral particle or a virus-like particle incubated under acidic conditions.

Methods to assay the binding ability of the compound to the virion, sub-viral particle or virus-like particle detailed above are provided earlier in relation to assaying the ability of the compound to bind to the EDE and is detailed in Example 4 of WO 2016/012800 and generally simply involves an ELISA against the particular virion or virus like particle to assay whether or not the compound can bind. The compound is considered useful if it binds to, or significantly binds to, the native EDE or virion or virus like particle, and does not bind to a virion or sub-viral particle or a virus-like particle that: a) is made in cells lacking furin activity; b) have a high percentage of prM protein, and/or c) are incubated under acidic conditions.

The invention further comprises specific compounds for use as indicated above. For example, in one embodiment, the compound is an antibody comprising the sequence heavy chain SEQ ID No: 11 and light chain SEQ ID No: 13; or heavy chain SEQ ID No:12 and light chain SEQ ID No: 14. Further examples of light chain, heavy chain and CRD sequences that the antibody may comprise are given in the Antibody section below. It will be appreciated that the invention also relates to truncations and mutations of these antibodies, such that the compound for use is an antigen binding portion thereof. Antibodies with a sequence homology of at least 80, 90% or at least 95% homology to the above sequences in at least one, two, three, four, five or six CDR sequences or in the whole variable region sequence, or in the whole antibody sequence, are included for the use of the invention. Particular sequences of antibodies, light and heavy chains are given in SEQ ID No's: 1-4, 37-141, 141-147 and, for example, FIG. 29 of WO 2016/012800.

It is considered that antibodies characterised as group "EDE1" in WO 2016/012800; Rouvinski et al (2015) Nature 520, 109-113; Dejnirattisai et al (2015) Nature Immunol 16, 170-177; may be of particular value, particularly in relation to use related to zika virus. EDE Group 1 antibodies are considered to be characterised by binding not being affected by presence or absence of N153 (or equivalent residue) glycosylation.

An antibody which may be particularly useful as a broad neutralising antibody in relation to Zika and Dengue viruses may be 752-2 C8 or EDE1 C8 (terminology as in WO 2016/012800; Rouvinski et al (2015) Nature 520, 109-113; Dejnirattisai et al (2015) Nature Immunol 16, 170-177); or 753(3) C10 EDE C10 (terminology as in WO 2016/012800; Rouvinski et al (2015) Nature 520, 109-113; Dejnirattisai et al (2015) Nature Immunol 16, 170-177), as also discussed further in the Antibody section below.

An antibody which may have high affinity for Zika envelope protein dimer but which may be less useful for neutralisation and which may promote antibody dependent enhancement (ADE) may be EDE2 A11 (terminology as in WO 2016/012800; Rouvinski et al (2015) Nature 520, 109-113; Dejnirattisai et al (2015) Nature Immunol 16, 170-177), which is considered to require the glycosylation site at position 153 for DENV binding, but does not make the same interaction with the 154 glycan (when present) on Zika Envelope dimer. See Example 2.

As discussed further in Example 2 below, Zika strains may differ in relation to glycosylation at position 154. The African Zika strain HD78788 has over the years been cell-culture adapted and passaged in suckling mice brain and is considered to lack E glycosylation. The PF13 strain isolated in French Polynesia in 2013 has the E protein glycosylated in the 150 loop, at position 154. EDE1 group antibodies, for example EDE1 C8, may neutralise better the non-glycosylated African strain HD78788 than the glycosylated PF13 strain, but EDE1 group antibodies may neutralise both of these Zika strains comparably or better than DENV strains.

EDE2 antibodies, for example EDE2 A11 may not show a difference between these Zika strains, but may not be as potent at neutralising either strain as EDE1 antibodies.

Particular residues of the specific heavy and light chains are considered to be important for binding to the EDE as discussed further in the Examples, particularly Example 2 and FIG. 15. Thus, the skilled person will be able to determine which residues are likely to tolerate modification and in what ways. Modifications may be tested by testing for effects on EDE binding ability or virus neutralisation ability, as will be apparent to the skilled person and as described herein.

An antibody is composed of a light chain and a heavy chain, and within each light chain and heavy chain are three variable regions. The most variable part of each of these regions is the complementary determining region and is considered to be the most crucial for antigen binding and recognition. Therefore, in one embodiment, the compound comprises one or more of the following amino acid sequences, having no, one or two amino acid substitutions, insertions or deletions:

CDR sequences identified in Table A in Antibody section below;

Or CRD sequences from WO 2016/012800 for the antibodies identified in the Antibody section below, for example identified as EDE1 antibodies.

As described above in relation to the presentation of the antigenic EDE in a protein scaffold, the compound, for example a protein, for example an antibody, may also be part of a larger structure, for example held within a protein scaffold. Preferences for the scaffold are as described earlier. For example, in one embodiment, the antibody or antigen binding portion thereof is within a larger polypeptide.

In a preferred embodiment the compound is an antibody or antigen binding portion thereof. The antigen binding portion may be a Fv portion; a Fab-like fragment (e.g. a Fab fragment, a Fab' fragment or a F(ab)$_2$ fragment); or a domain antibody.

In one embodiment the antibody or antigen binding portion thereof is, or is derived from, a monoclonal antibody. In another embodiment the antibody or antigen binding portion thereof is, or is derived from a polyclonal antibody. In a further embodiment, the compound is a composition comprising a mixture of antibodies or antigen binding portions thereof, comprising:

a) a mixture of monoclonal antibodies or antigen binding portion thereof, or b) a mixture of polyclonal antibodies or antigen binding portion thereof, or c) a mixture or monoclonal and polyclonal antibodies or antigen binding portion thereof, for example wherein the ratio of monoclonal to polyclonal antibodies or antigen binding portions thereof is 10:1, 8:1, 6:1, 4:1, 2:1, 1:1, 1:2, 1:4, 1:6, 1:8 or 1:10

It will be appreciated that the compound may be a recombinant protein, for example a recombinant antibody or antigen binding portion thereof. The compound may also be made synthetically. The compound may be a combination of recombinantly and synthetically produced.

We provide means of making such a compound, for example a protein, for example an antibody or antigen binding portion thereof.

The compound may be produced by recombinant means, for example the compound, for example a polypeptide, for example an antibody or antigen binding portion thereof may be produced and isolated or purified from various organisms, including:

a) a human cell line, optionally CHO cells, or
b) a mammal, optionally a human, or
c) a microorganism, or
d) an insect cell line.

By isolated or purified we mean that the agent has been removed from its natural environment, and does not reflect the extent to which the agent has been purified.

Therefore we provide the isolation or purification of a compound for use of the present invention from various organisms, including from a human cell line, optionally CHO cells, or from a mammal, optionally a human, or from a microorganism, or from an insect cell line.

Where the compound is a polypeptide, for example an antibody or antigen binding portion thereof, or for example included in a protein scaffold, the compound may be encoded by a nucleic acid. By nucleic acid we include the meaning of both DNA and RNA, single or double stranded and in all their various forms. We provide a nucleic acid encoding any of the proteinaceous compound for use of or in relation to the invention. In particular, SEQ ID No: 41-48 of WO 2016/012800 may be useful in relation to the present invention. Other sequences of WO 2016/012800 may also be useful, as will be apparent from the discussion herein. Any sequence derived from or comprising SEQ ID No: 41-48, for example, of WO 2016/012800, for example; or other sequences disclosed herein, which comprises mutations which would result in a silent mutation are included, as are sequences which cover any of the earlier mentioned possibilities, for example a nucleic acid sequence comprising a portion which encodes any of the antibody sequences or a sequence with at least 80, 90, 95 or 95% homology thereto.

The nucleic acid may or may not contain introns. The nucleic acid may also be modified to enable purification of the subsequently translated polypeptide, for example the open reading frame of the intended polypeptide may be modified to incorporate a tag, for example a myc tag or a his tag, to enable subsequent purification.

The nucleic acid may also be modified, for example codon optimised, to be better translated by the organism which it is to be translated in, without affecting final polypeptide sequence.

Nucleic acids of the present disclosure can be produced or modified using a number of methods known to those skilled in the art for example, classic mutagenesis, chemical treatment, restriction digestion, ligation and PCR.

An aspect of the invention provides a nucleic acid encoding the antibody or fragment thereof as defined in relation to the preceding aspects of the invention for use in vaccinating an individual against one or more flaviviruses, or for use in a method for prevention and/or treatment of infection by one or more flaviviruses, wherein the one or more flaviviruses is selected from zika virus; zika virus and dengue virus; zika virus and other flaviviruses; flaviviruses other than dengue.

An aspect of the invention provides the antibody or fragment thereof for use according to the first aspect of the invention or nucleic acid for use of the preceding aspect of the invenion wherein the antibody or fragment thereof or nucleic acid is for use in a method for treatment of infection by one or more flaviviruses as defined, wherein the treatment is to reduce antibody dependent enhancement (ADE).

The nucleic acid useful in relation to the invention, for example in a use of the invention or in relation to preparing a compound for use of the invention may be incorporated into a vector. Thus the invention, for example, may relate to use of a vector comprising the nucleic acid. By vector we mean vehicle for cloning of amplification of the nucleic acid, or for insertion into a target organism, for example the vector may be a plasmid or may be a nucleic acid used to target the nucleic acid of the invention into a target organism, for example into the genome of a target organism. The vector may further comprise nucleotide sequences required for expression of the polypeptide encoded by the nucleic acid of the invention, for example promoter sequences or termination sequences may be operably linked to the nucleic acid for use of the invention or useful in relation to the invention, and may also include reporter genes, for example antibiotic resistance cassettes. The vector may be single stranded or double stranded, and may be linear or circular. In one embodiment the vector is a plasmid.

In addition to providing a compound which can bind to an EDE as indicated above, the invention also provides an EDE compound for use as defined below. We provide a nucleic acid, or a vector, which encodes the EDE compound for use of the invention, in addition to a host cell comprising the nucleic acid or vector. Preferences for a nucleic acid and vector, for example, indicated above may also be relevant to the present aspect of the invention, as will be apparent to the skilled person. Thus the invention provides an EDE compound for use as defined below, or a nucleic acid encoding such an EDE compound for use as defined below, or a vector comprising said nucleic acid, or a host cell comprising said nucleic acid or vector for use as described below.

Thus, an aspect of the invention provides a flavivirus Envelope Dimer Epitope (EDE) for use in vaccinating an individual against one or more flaviviruses wherein the EDE is a stabilized recombinant flavivirus, optionally dengue virus and/or zika, envelope glycoprotein E ectodomain (sE) dimer, wherein the dimer is:

covalently stabilized with at least one disulphide interchain bond between the two sE monomers, and/or non-covalently stabilized by substituting at least one amino acid residue in the amino acid sequence of at least one sE monomer with at least one bulky side chain amino acid, at the dimer interface or in domain I (DI)/domain III (DIII) linker of each monomer, covalently stabilized with at least one sulfhydryl-reactive crosslinker between the two sE monomers, and/or covalently stabilised by being formed as a single polypeptide chain, optionally with a linker region, optionally a Glycine Serine rich linker region, separating the sE sequences, and/or covalently stabilized by linking the two sE monomers through modified sugars; and/or, wherein the dimer is a homodimer or heterodimer of native and/or mutant envelope polypeptides, from any one or two of DENV-1, DENV-2, DENV-3, DENV-4, Zika or other flavivirus; and wherein the one or more flaviviruses is selected from zika virus; zika virus and dengue virus; zika virus and other flaviviruses; flaviviruses other than dengue.

A further aspect of the invention provides a method for vaccinating an individual against one or more flaviviruses, wherein the one or more flaviviruses is selected from zika virus; zika virus and dengue virus; zika virus and other flaviviruses; flaviviruses other than dengue; the method comprising administering an EDE as defined in relation to the preceding aspect of the invention.

A further aspect of the invention also provides the use of an EDE as defined in relation to the preceding aspect of the invention in the manufacture of a medicament for vaccinating an individual against one or more flaviviruses, wherein the one or more flaviviruses is selected from zika virus; zika virus and dengue virus; zika virus and other flaviviruses; flaviviruses other than dengue.

Embodiments are as set out in the claims and further preferences are as set out elsewhere in relation to the EDE and in relation to the individuals to be treated. Typically the individual to be vaccinated may be one who has not yet been determined to have or be likely to have a flaviviral infection, or a Zika virus infection.

The EDE compound is intended to provide an epitope as described above as an Envelope Dependent Epitope. The EDE compound may bind specifically to one or more EDE-specific antibodies for use of the invention, for example to a preferred neutralising antibody as discussed above, or as exemplified in the Examples or the Examples of WO 2016/012800. The EDE compound typically is or comprises a polypeptide. In one embodiment, the EDE compound is a dimer of envelope protein, or envelope ectodomain or the 400 amino terminal residues of the ectodomain of Envelope protein. By "400 amino terminal residues" as used herein is included approximately 400 amino terminal residues, for example between 350 and 450 residues, 320 and 470 residues, or 330 and 480 residues (or combinations thereof), for example between 380 and 420 residues, for example between 390 and 410 residues, for example 395 or 393 residues, as noted above and as will be apparent to those skilled in the art. The envelope protein may be any of the envelope proteins from a flavivirus, for example zika, DENV-1, DENV-2, DENV-3 and DENV-3, and DENV-4, (SEQ ID No's: 29, 31, 33 or 35 of WO 2016/012800; or sequences as set out in the Sequences section below), or a protein with at least 90% homology to the sequences in SEQ ID No's: 29, 31, 33 or 35 of WO 2016/012800. The dimer may be a homodimer or a heterodimer. In a preferred embodiment the dimer is not incorporated into an intact viral particle, or a sub-viral particle, or a virus-like particle, but may typically be in the form of a free dimer for example with a molecular weight of twice that of the monomeric envelope polypeptide or in the form of a nanoparticle, for example a self-assembling nanoparticle. It will be appreciated that any form of EDE or EDE compound described herein, for example, an engineered envelope protein, for example, as part of a protein scaffold, may potentially be presented as part of a virus, virus-like particle, or sub-viral particle.

In another embodiment, the EDE compound comprises a dimer of envelope protein, or envelope ectodomain or the (approximately) 400 amino terminal residues of the ectodomain of envelope protein which has been engineered to have increased stability in the dimer configuration, for example has been engineered to have increased levels of covalent and/or non-covalent bonds between the dimers;

In a preferred embodiment, the EDE compound is a stabilised recombinant flavivirus, for example zika and/or dengue virus envelope glycoprotein E ectodomain (recombinant sE) dimer as described in relation to the earlier aspect of the invention, for example, is a stabilised recombinant zika and/or dengue virus envelope glycoprotein E ectodomain (recombinant sE) dimer wherein the dimer is:

covalently stabilized with at least one disulphide interchain bond between the two sE monomers and/or, covalently stabilized with at least one sulfhydryl-reactive crosslinker between the two sE monomers and/or, covalently stabilized by linking the two sE monomers through modified sugars; and/or, non-covalently stabilized by substituting at least one amino acid residue in the amino acid sequence of at least one sE monomer with at least one bulky side chain amino acid, at the dimer interface or in domain 1 (D1)/domain 3 (D3) linker of each monomer.

Figure 21:
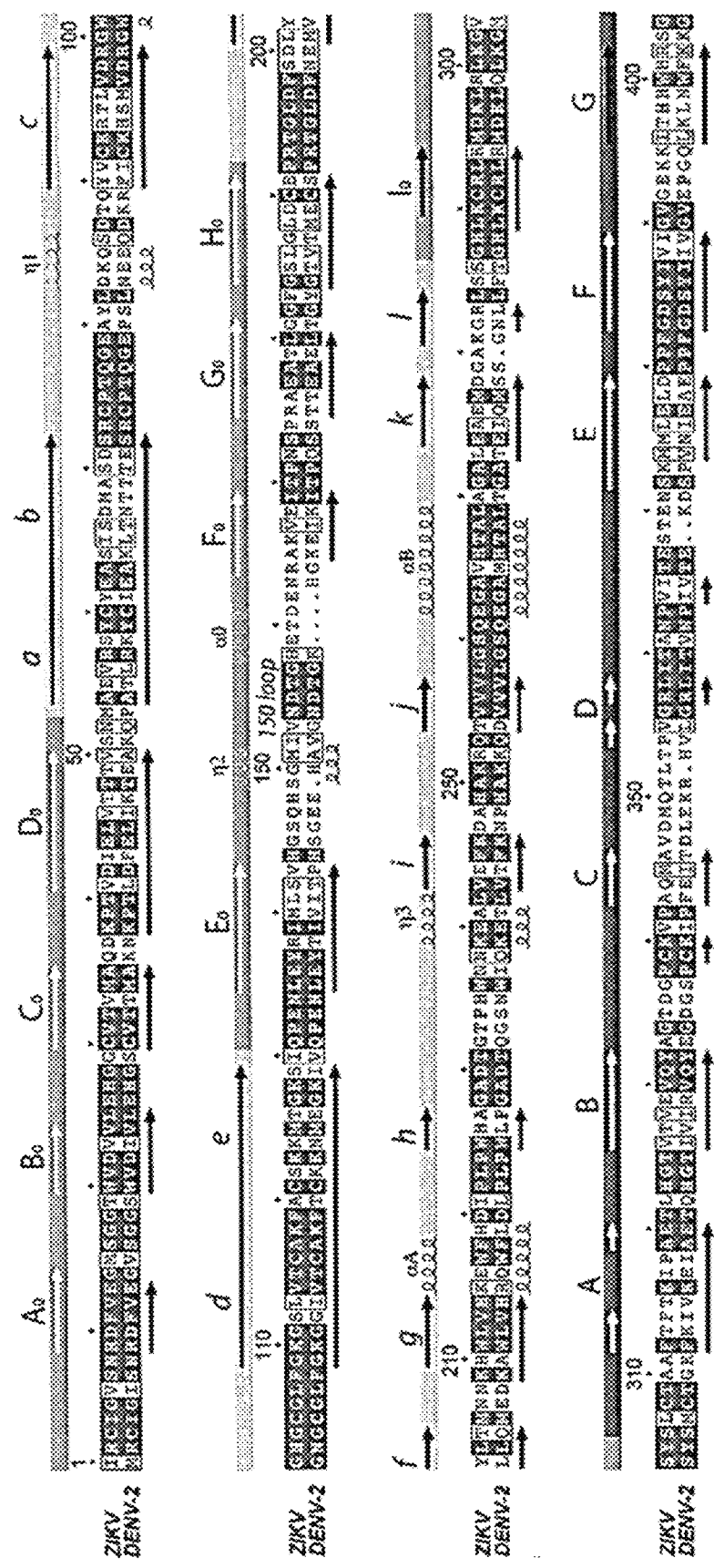

A flavivirus, zika or dengue virus envelope glycoprotein E ectodomain (sE) refers to the 1-395 amino acid fragment of the envelope glycoprotein E of the dengue virus serotypes 1, 2 and 4, to the 1-393 amino acid fragment of the envelope glycoprotein E of the dengue virus serotype 3, and to the 1-404 amino acid fragment of the envelope glycoprotein E of the Zika virus, for example as set out in Example 2, FIG. 21.

Preferences for the EDE compound are as set out earlier and in the claims relating to the stabilised dimer.

In an embodiment, the EDE compound presents an improved epitope over the naturally occurring envelope dimer within a virus, virus-like particle or sub-viral particle. By improved epitope we include the meaning of improved over any epitope naturally displayed on an intact viral particle. By improved we include the meaning of being capable of eliciting a more beneficial immune response than the native intact dengue virus particle. An EDE compound which has increased stability in the dimer configuration, for example via the modifications described above and in the claims, is considered to be an improved epitope. The EDE compound may be an EDE which has been engineered, or inserted into a scaffold, such that the FL is incapable of being recognised by a compound, for example a polypeptide, for example an antibody or antigenic portion thereof, on its own, for example where the EDE is engineered such that the FL cannot be recognised by an antibody in isolation from the immediate neighbours of the fusion loop, i.e. the fusion loop cannot be recognised (or, for example be capable of raising a response recognising the fusion loop) in a context independent of the quaternary organisation.

In an embodiment, the EDE compound comprises residues that are conserved in both amino acid and spatial position across more than one serotype of flavivirus, for example zika and/or dengue virus, preferably residues that are conserved in both amino acid and spatial position across all serotypes of flavivirus, for example zika and/or dengue virus, that is, across zika virus and four serotypes of dengue virus.

The EDE compound may comprise the dimer of envelope protein, or envelope ectodomain or the (approximately) 400 amino terminal residues of the ectodomain of the envelope protein which has been engineered to have increased stability in the dimer configuration, and also be held within a protein scaffold as described above.

In a preferred embodiment, the EDE compound is such that it may raise antibodies once administered to a subject, preferably a human, wherein the antibodies are preferably capable of binding to all flaviviruses, or to zika and/or dengue virus, for example to zika and four serotypes of dengue virus, and optionally are capable of neutralising at least zika and all four serotypes of dengue virus, preferably capable of neutralising zika and all four serotypes of dengue virus to 100%, and optionally are capable of neutralising virus made in both human and insect cells, preferably capable of neutralising zika and all four serotypes of dengue virus made in both human and insect cells to 100%.

The EDE/VDE compound may be an anti-idiotypic antibody (or fragment thereof or molecule sharing the binding specificity, as discussed above), as well known to those skilled in the art, developed against one or more of the high affinity/neutralising antibodies provided herein, for example as indicated in the Examples of WO 2016/012800.

We also provide a method for the synthesis of the EDE wherein the EDE is a stabilized recombinant sE dimer for use of the present invention, comprising at least one of the following steps:
  a) contacting two single or multiple cysteine mutant sE as defined above, under oxidative conditions, and/or,
  b) contacting two sE monomers with at least one, two or three, sulfhydryl-reactive crosslinkers as defined above, and/or,
  c) contacting two sE monomers having glycosylation sites as defined above, by click chemistry and/or
  d) contacting two sE monomers wherein at least one amino acid residue in the amino acid sequence of at least one sE monomer is substituted with a bulky side chain amino acid as defined above.

The present invention may make use of a stabilized recombinant sE dimer obtainable by the method as defined above.

To ensure the proper formation of the stabilized recombinant sE dimer for use according to the present invention the affinity for the antibodies as described below can be measured by ELISA (for the covalently and non-covalently stabilized dimer) or by Surface Plasmon Resonance (for the covalently stabilized dimer).

We also provide a host cell comprising any of the nucleic acids for use of the invention or useful in relation to the invention; or a vector for use of the invention, for example a nucleic acid or vector comprising a portion of nucleic acid that encodes the EDE compound or the compound for use of the invention. For example we provide any host cell known to be useful for the expression of heterologous proteins, for example a C6/36 insect cell, human dendritic cell, CHO cell, or a microorganism, for example a *Pichia pastoris* cell, which comprises the vector, for example a plasmid. The host cell may also comprise a nucleic acid for use or useful in relation to the invention which has been incorporated into the genome of the host cell, optionally by the use of a viral vector to target the nucleic acid to the genome, for example adenovirus, adeno-associated virus, cytomegalovirus, herpes virus, poliovirus, retrovirus, sindbis virus, vaccinia virus, or any other DNA or RNA virus vector.

We also provie a non-human transgenic animal comprising at least one cell transformed by a nucleic acid for use of the invention or the vector for use of the invention, or the host cell for use of the invention, for example by a nucleic acid or vector comprising a portion of nucleic acid that encodes the EDE compound or the compound for use of the invention.

A process for the production of the compound for use of the invention, preferably a polypeptide, preferably an antibody or antigen binding portion thereof, or the EDE compound for use of the invention, is provided herein. The process may comprise the following stages:
  i) Culture in the appropriate medium of a host cell as described above,
  ii) Recovery of said compound, preferably an antibody or antigen binding portion thereof produced, or said EDE compound, wherein said recovery is either from the culture medium or said cultured cells.

It will be appreciated that for the purification or isolation of polypeptides, for example wherein the compound is a polypeptide, or the EDE compound is a polypeptide, the skilled person would readily engineer the nucleotide coding sequence to include nucleotides which aid in purification, for example the inclusion of affinity tags, of epitope tags. Thus in one embodiment, the process for the production of the compound for use of the invention, or the EDE compound, involves culture of a host cell which comprises the nucleotide sequence encoding the compound or the EDE compound, and further comprising nucleotides that encode a portion useful in the purification of the compound or EDE compound, or vector comprising the nucleotide sequence encoding the compound or the EDE compound, and further comprising nucleotides that encode a portion useful in the purification of the compound or EDE compound.

It will be appreciated that where the compound is a polypeptide, for example an antibody or antigen binding portion thereof, as well as being made by recombinant means, polypeptide production can be triggered by the administration of a EDE as defined in any of the above embodiments, optionally an EDE compound as defined above, to a subject. Following EDE (optionally EDE compound) administration, the natural host response would produce the antibodies which can be recovered from the subject's blood. Preferably the EDE is not presented as part of an intact virus, or virus like particle or sub-viral particle.

Preferably the EDE is an envelope polypeptide dimer, as discussed above, or other EDE compound as discussed above or below.

For example, we provide a method of producing a compound for use of the present invention, where the compound is an antibody for use of the present invention, comprising the steps of:
  a) contacting a mammal with a stabilized recombinant sE dimer as defined in relation to the use of the present invention, which may be in the form of an immunogenic composition,
  b) detecting the presence of an antibody directed to said sE dimer in one or more serum samples derived from said mammal,
  c) harvesting spleen cells from said mammal,
  d) fusing said spleen cells with myeloma cells to produce hybridoma cells,
  e) identifying hybridoma cells capable of producing said antibody,
  f) culturing said hybridoma cells capable of producing said antibody, and
  g) optionally, isolating said antibody.

The present invention may make use of an antibody obtainable by any of the methods defined above.

We also provide a hybridoma cell obtainable by the method defined above.

We also provide the use of a stabilized recombinant sE dimer as defined in relation to the use of the present invention for the preparation of hybridoma cells capable of producing a neutralizing antibody directed to said dimer as defined above.

In a preferred embodiment the EDE or EDE compound is such that it is has already been determined to be capable of raising highly cross reactive and potently neutralising antibodies. The antibodies identified in the Examples (Examples 1-6) of WO 2016/012800 were raised to the intact virus in a natural infection of dengue virus. It is considered that more specific and improved antibodies can be raised by the administration of a specific EDE antigen, which may be a EDE compound as defined in relation to the pesent invention. For example, in the natural infection, some patients did not raise anti-EDE antibodies, and instead produced anti-FL antibodies which are considered to be less useful and are less cross-reactive and are less neutralising. It is considered that administration of a EDE antigen is more likely to raise the anti-EDE useful antibodies. As described earlier, in some embodiments the EDE or EDE compound is engineered to have increased stability in the dimer formation, which is considered to increase the chances of anti-VDE antibodies being made within the subject. In addition, the EDE or EDE compound in some embodiments is engineered, for example mutations within the envelope protein itself, or by the use of a scaffold protein, to present an improved epitope, for example by hiding the fusion loop so that anti-FL antibodies are less likely to be made. Administration of an EDE or EDE compound which is common to all serotypes of flavivirus, or to zika and all serotpyes of dengue virus, is likely to raise highly cross-reactive and potently neutralising antibodies. These antibodies can be recovered from the subject and used for further analysis or used in treatment of zika and/or dengue fever, or in zika and/or dengue fever clinical trials, for example.

Therefore one embodiment provides a process for the production of a compound for use according to the invention wherein the compound is a polypeptide, or an antibody or antigen binding portion thereof, wherein said process comprises the following stages:
   a. administration to a subject a Envelope Dimer Epitope or EDE compound as defined in any of the preceding embodiments,
   b. recovery and isolation of said antibody or antigen binding portion thereof from the subject's blood.

It will be appreciated that the above method of producing compounds, for example antibodies or antigen binding portions thereof, for use of the invention, comprising administering to a subject an EDE or EDE compound, can also be used as part of a method of selecting a suitable antigen for a vaccine. Current vaccines utilise attenuated versions of all four serotypes of dengue, and are not particularly effective. Such a vaccine would also be capable of triggering the production of the non-useful anti-FL antibodies. A preferred vaccine would comprise, for example, a single antigen capable of eliciting an immune response to all serotypes of dengue virus and also zika virus, wherein the immune response is capable of neutralising zika virus and all serotypes of dengue virus ie considered to be four serotypes of dengue virus.

The inventors of the present invention have, for the first time, identified highly cross-reactive and potently neutralising antibodies as recognising also zika virus, for example, and the particular epitope (EDE) to which they bind. Thus, the use of this epitope in a vaccine for zika, or zika and other flaviviruses, for example zika and dengue virus, for example, is likely to be preferable to the current vaccine strategies.

In an aspect the invention provides a method for aiding in selecting a suitable antigen for a vaccine against Zika virus wherein said method comprises characterisation of one or more antibodies made in a subject in response to a candidate antigen, optionally wherein said candidate antigen has previously been found to bind to a panel of antibodies known to bind the EDE as defined in relation to preceding aspects of the invention.

The identification of highly cross-reactive and potently neutralising antibodies in a subject which has been administered a flavivirus, for example zika or dengue antigen is indicative of that antigens likelihood of being useful in a vaccine. The present inventors have found that dengue antigen, for example, may be useful in raising antibodies that are potently neutralising for zika. In one embodiment, the antigen is not presented as part of an intact virus. In a preferred embodiment the antigen is an EDE compound as described in any of the earlier embodiments, preferably a dimer of envelope protein, preferably a stabilised dimer, optionally as part of a scaffold protein. In a preferred embodiment, the antigen is such that it has already been determined to be able to bind to highly cross-reactive and potently neutralising antibodies that can bind the EDE, for example the antibodies for use of this present invention, for example as identified in the Examples and Examples of WO 2016/012800. The antigen may be a dimer of Zika envelope protein, stabilised and optionally otherwise mutated as described herein.

By administering such an antigen, known to be able to bind to highly useful antibodies, the antibodies made in response to the antigen in the subject can be characterised. It is likely that such an antigen will cause the production of such useful antibodies within the subject and therefore be a suitable candidate antigen for use in vaccine composition. By characterisation we include the meaning of determining whether the antibodies are considered to bind the fusion loop, by, for example, determining the ability of the antibody to bind to linear or denatured or recombinant envelope protein, for example the ability to bind to the envelope protein on a western blot or ELISA, and the ability of the antibody to bind to a dimer of envelope protein, or an EDE or EDE compound as described earlier in previous embodiments. The ability of the antibody to bind to zika and/or all four serotypes of dengue virus may also be assessed, as may the ability of the antibody to neutralise zika and/or all four types of dengue virus. Methods for determining the neutralising ability of an antibody are detailed earlier. The ability of the antibody to neutralise zika and/or dengue virus made in both human and insect cells may also be determined, as described earlier and in the Examples and Examples of WO 2016/012800.

In one embodiment, an antigen is not considered to be useful as a vaccine if it raises predominantly anti-FL antibodies. For example, the antigen is considered useful if the ratio of antibodies raised against the FL and antibodies raised against the EDE is no more than 1:2, 1:4, 1:5, 1:10, 1:50, 1:100, 1:500, 1:1000. The relative amount of anti-FL antibodies and anti-EDE antibodies can be determined by methods well known to those skilled in the art, for example using ELISA based techniques. The antigen is considered to be useful if it raises antibodies capable of binding to the EDE of more than one type of flavivirus, for example zika virus and at least one serotype of dengue virus, preferably all 4 types of dengue virus. The antigen is considered to be useful if it raises antibodies capable of neutralising more than one type of flavivirus, for example zika virus and at least one serotype of dengue virus, preferably more than one serotype of dengue virus, preferably capable of neutralising all 4 types of dengue virus, preferably to 100%. The antigen is also considered useful if it raises antibodies that are capable of neutralising zika virus and dengue virus made in both human and insect cells, preferably to the same level (as discussed above), preferably neutralises the virus to at least 95% or at least 98%, for example 100%. The antigen is considered most useful if it:

a) Does not raise, or does not significantly raise anti-FL antibodies, and
b) Binds, to some significant degree, to zika virus and preferably all 4 serotypes of dengue virus, and
c) Neutralises, to some significant degree, zika virus and preferably all 4 serotypes of dengue virus made in both human and insect cells to 100%.

Further, in another embodiment, the antigen is considered to be suitable for use in a vaccination if the antibodies raised are capable of binding to the EDE as defined in the earlier embodiments.

In a further embodiment, the antigen administered to the subject may comprise an additional agent to help prevent antibodies being raised to the fusion loop.

The antibodies produced by a subject exposed to the antigen may be obtained from sorted single plasma cells of a subject.

It will be appreciated that the identification, for the first time, or highly cross-reactive and potently neutralising antibodies against flavivirus, particularly zika virus and dengue virus presents a unique opportunity to be able to treat or prevent flaviviral disease, particularly zika viral disease and dengue viral disease. In addition, it will allow clinical trials comprising live zika or dengue virus to be performed, as until the present invention, there was no reliable way to treat the infection caused during the trial. Therefore a further aspect of the present invention provides a method of treating or preventing flavivirus, for example zika Dengue virus infection in a subject.

Thus, the invention provides, for example, a method for treatment of infection by one or more flaviviruses, wherein the one or more flaviviruses is selected from zika virus; zika virus and dengue virus; zika virus and other flaviviruses; flaviviruses other than dengue. The method may comprise the steps of administering to the individual an isolated neutralizing antibody or antigen binding fragment thereof directed against the EDE as defined in relation to preceding aspecst of the invention.

The method may comprise the administration of one or more compounds for use according to the present invention, for example EDE-binding compound as defined in relation to preceding aspects of the invention, preferably a polypeptide, preferably an antibody or fragment thereof as defined in relation to preceding aspects of the invention. The invention also provides the use of a compound as defined in relation to the preceding aspect of the invention, preferably a polypeptide, preferably an antibody or fragment thereof as defined in relation to preceding aspects of the invention, in the manufacture of a medicament for treatment of infection by one or more flaviviruses, wherein the one or more flaviviruses is selected from zika virus; zika virus and dengue virus; zika virus and other flaviviruses; flaviviruses other than dengue. Preferences and embodiments are as set out for the first aspect of the invention, relating to the EDE-binding compound for use in treatment of infection.

It will be appreciated that for administration, the compound may be part of a composition, for example a pharmaceutical composition. The composition may further comprise one or more other therapeutic agents deemed to be useful in either treating the infection itself, for example further anti-viral agents, or one or more agents deemed to be useful in treating a symptom of flavivirus, for example zika or dengue, infection, for example.

The term "treating" includes the administration of any of the compounds for use of the invention, for example compound for use of the invention, EDE compound for use of the invention, vaccine composition, antibody, a stabilized recombinant sE dimer or an immunogenic composition of the present invention to a patient who has a flavivirus infection or a symptom or pattern of symtoms of flavivirus infection, for example zika virus infection or a symptom or pattern of symtoms of zika virus infection, or dengue virus infection or a symptom or pattern of symtoms of dengue virus infection, with the purpose to cure, heal, alleviate, relieve, alter, remedy, ameliorate, improve, or affect the flavivirus, for example zika or dengue virus infection and/or the symptoms of the flavivirus, for example zika or dengue infection. We include the meaning of treating of alleviating any one or more of symptoms of flavivirus, for example zika or dengue infection. Treating also includes the meaning of preventing new cells from being infected. Whether or not a patient has been successfully treated will be apparent to one skilled in the art. For example, viral load may be reduced. Signs of antibody dependent enhancement (ADE), as discussed elsewhere herein, may be reduced.

The term "preventing" means that the progression of a flavivirus, for example zika or dengue virus infection is reduced and/or eliminated, or that the onset of a flavivirus, for example zika or dengue virus infection is delayed or eliminated.

Symptoms of dengue virus infection and Dengue fever are set out in WHO Fact sheet no 117, for example. As noted therein, Dengue fever is a severe, flu-like illness that affects infants, young children and adults, but seldom causes death. Dengue should be suspected when a high fever (40° C./104° F.) is accompanied by two of the following symptoms: severe headache, pain behind the eyes, muscle and joint pains, nausea, vomiting, swollen glands or rash. Symptoms usually last for 27 days, after an incubation period of 4-10 days after the bite from an infected mosquito. Severe dengue is a potentially deadly complication due to plasma leaking, fluid accumulation, respiratory distress, severe bleeding, or organ impairment. Warning signs occur 37 days after the first symptoms in conjunction with a decrease in temperature (below 38° C./100° F.) and include: severe abdominal pain, persistent vomiting, rapid breathing, bleeding gums, fatigue, restlessness, blood in vomit. The next 24-48 hours of the critical stage can be lethal; proper medical care is needed to avoid complications and risk of death.

Signs and symptoms of Zika virus infection will also be known to those skilled in the art and are also discussed elsewhere herein.

Administration of the compound, or a composition comprising the compound is of an amount, for example a therapeutically effective amount, which causes the inhibition of infection of cells, when the compound is used prophylactically, or inhibition of further infection of cells and/or reduces signs and/or symptoms of the disease when used for therapeutic purposes.

A therapeutically effective amount is that which provides subjective relief of a symptom(s) or an objectively identifiable improvement as noted by a clinician or other qualified observer.

By preventing flavivirus, for example zika or dengue infection we include the meaning of reducing the level of infection by any significant degree. In one embodiment the compound of the present invention prevents infection by a flavivirus, for example by zika virus or one serotype of dengue virus to 30%, 50%, 70%, 80%, 90%, 95%, preferably 100%. In a preferred embodiment the compound of the present invention prevents infection by zika and by one serotype of dengue virus, by two serotypes of dengue virus, by three serotypes of dengue virus, by all four serotypes of dengue virus, to 30%, 50%, 70%, 80%, 90%, 95%, preferably 100%. In the most preferred embodiment the compound of the present invention totally prevents infection by all found serotypes of zika and dengue virus. This may be assessed by techniques well known to those skilled in the art, for example by measuring viral load.

The present invention provides the use of an EDE, preferably of a stabilized recombinant sE dimer, or an immunogenic composition as defined for use according to the present invention for immunizing an animal (non human), preferably a mammal, such as a monkey, a rabbit, a mouse or a camelid (e.g., *Llama pacos*).

A further embodiment provides one or more compounds as defined for use according to the present invention, preferably a polypeptide, preferably an antibody or fragment thereof for use in live flavivirus, for example zika or Dengue vaccine trials, for example with the intention of terminating infection.

Preferably the compound of the invention is one that is capable of neutralising zika and all four serotypes of dengue virus to at least 95% or at least 98%, for example 100%, made in both insect and human cells. It is considered that prior administration of the compound before exposure to the virus will prevent viral infection.

The compound according to the present invention, for example an antibody or fragment thereof, for example that is capable of neutralising zika and all four serotypes of dengue virus as noted above may be administered before exposure to the virus, as noted above, for example may be used as a prophylactic either in travellers or in outbreaks or in close contacts of one more infected people, for example in the neighbourbood or home, who are likely also to be bitten; or may be used in pregnant women at risk of contacting Zika infection. Alternatively or in addition, the compound may be administered when a patient first presents with fever; or when symptoms become severe.

Thus, for example, the EDE, nucleic acid or composition for use of the invention may be for use wherein the individual is a pregnant woman, optionally a pregnant woman considered at risk of contacting Zika infection, for example through being known or suspected to have been infected with Dengue virus; being in close contact with one or more individuals known to be infected with Zika virus or Dengue virus; being in a location considered to have a high rate or risk of Zika virus or Dengue virus infection; or a woman of childbearing age, optionally a woman of childbearing age considered at risk of contacting Zika infection, for example through being known or suspected to have been infected with Dengue virus; being in close contact with one or more individuals known to be infected with Zika virus or Dengue virus; being in a location considered to have a high rate or risk of Zika virus or Dengue virus infection.

All preferences for the compound are as described earlier in the embodiments of the invention.

It will be appreciated that the compound of the invention, for example an antibody or antigen binding portion thereof may be administered with further therapeutic agents, for example one or more T cell vaccines, or other anti-viral agents. These may be administered as part of the same composition as the compound of the invention, or may be administered separately. For example, T cell vaccines are proposed for protection against influenza[85].

The compound of the invention may be administered once, twice or several times. Administration may occur over 1 day, 2 days, 1 week, 2 weeks, 1 month, 6 months, 1 year or more. For treatment after infection, a shorter period, for example up to one month, may be appropriate. For prophylaxis, a longer period, for example 6 months of 1 year or more may be appropriate.

The compound, for example an antibody or antigen binding portion thereof for use in the prevention or treatment of infection by one or more flaviviruses, wherein the one or more flaviviruses is selected from zika virus; zika virus and dengue virus; zika virus and other flaviviruses; flaviviruses other than dengue, may be selected using methods of the invention. Thus the invention provides a method of selecting a suitable antibody or fragment thereof for use in the prevention or treatment of infection by one or more flaviviruses, wherein the one or more flaviviruses is selected from zika virus; zika virus and dengue virus; zika virus and other flaviviruses; flaviviruses other than dengue wherein said method comprises characterisation of an antibody or fragment thereof made in a subject in response to an antigen comprising a Envelope dimer Epitope as defined in any earlier embodiment.

The EDE compound as defined in any of the earlier embodiments is likely to be capable of raising suitable antibodies following administration of the EDE to a subject. Thus, antibodies made in such a subject are likely to be useful in the treatment or prevention of flavivirus, for example zika or dengue, infection.

In a preferred embodiment the EDE is an EDE compound for use of the invention, for example a dimer of envelope protein, preferably a stabilised dimer, optionally as part of a scaffold protein. In a preferred embodiment, the antigen/EDE compound is such that it is already known to be able to bind to highly cross-reactive and potently neutralising antibodies that can bind the EDE, for example the antibodies for use of this present invention. In a preferred embodiment the antigen is deemed to be improved over the natural envelope dimer, for example by comprising residues in a particular conformation required to raise anti-EDE antibodies that are cross-reacting and potently neutralising, but not comprising residues, or particular conformations of residues, which raise anti-FL antibodies.

In another embodiment, as well as administration of the EDE, optionally EDE compound, the subject is administered a compound or agent which blocks the formation of anti-FL antibodies, for example. A stabilised sE dimer may be useful, for example.

By characterisation we include the meaning of determining whether the antibodies are considered to bind the fusion loop, by, for example, determining the ability of the antibody to bind to linear or denatured or recombinant envelope protein, for example the ability to bind to the envelope protein on a western blot or ELISA, and the ability of the antibody to bind to a dimer of envelope protein, or an EDE or EDE compound as described earlier in previous embodiments. The ability of the antibody to bind to zika and/or all four serotypes of dengue virus may also be assessed, as may the ability of the antibody to neutralise zika and/or all four types of dengue virus. Methods for determining the neutralising ability of an antibody are detailed earlier and in the examples and in WO 2016/012800. The ability of the antibody to neutralise zika and/or dengue virus made in both human and insect cells may also be determined.

In one embodiment, an antibody is not considered to be useful if it binds to the FL. The antibody is considered to be useful if it is capable of binding to more than one serotype of flavivirus, for example zika or dengue virus, preferably zika and all 4 types of dengue virus, or of binding to more than one serotype of EDE as defined in any of the earlier embodiments. The antibody is considered to be useful if it is capable of neutralising more than one serotype of flavivirus, for example zika and dengue virus, optionally two serotypes of dengue virus, optionally three serotypes of dengue virus, preferably capable of neutralising all 4 types of dengue virus, preferably to at least 95% or at least 98%, for example 100%. The antibody is also considered useful if it is capable of neutralising zika or dengue virus made in both human cells, optionally dendritic cells, and insect cells, optionally C6/36 cells, preferably to the same level, preferably neutralises the virus to at least 95% or at least 98%, for example 100%. The antibody is considered most useful if it:
  a) Does not raise, or does not significantly raise anti-FL antibodies, and
  b) Binds, to some significant degree, to zika and all 4 serotypes of dengue virus, and
  c) Neutralises, to some significant degree, zika and all 4 serotypes of dengue virus made in both human and insect cells to 100%.

As the present inventors found that patients with dengue infection, for example, either produce the useful anti-EDE antibodies, or the non-useful anti-FL antibodies, a further method of identifying antibodies that would be useful to treat or prevent flavivirus, for example zika or dengue infection is to simply identify those antibodies which cannot bind to the envelope protein in its denatured or linear form. Any antibodies which cannot do this are likely to be useful compounds for use of the invention.

It should be appreciated that the patient may also be treated with a nucleic acid, vector, or host cell expressing the polypeptide, preferably an antibody or antigen binding portion thereof. For example, a nucleic acid encoding the polypeptide may be inserted into a suitable delivery system, for example a viral vector, for example adenovirus, adeno-associated virus, cytomegalovirus, herpes virus, poliovirus, retrovirus, sindbis virus, vaccinia virus, or any other DNA or RNA virus vector, such that the compound is expressed endogenously within the patient to be treated.

The present invention also provides a method for stratifying patients according to their likely need to receive treatment or prophylactic treatment with one or more compounds of the present invention. Therefore, herein is provided a method for identifying patients suffering from infection by one or more flaviviruses as likely to require treatment with, or an elevated dose of, compound or composition according to any one of the preceding embodiments, for example an antibody or fragment thereof as defined according to any one of the preceding embodiments, or a nucleic acid as defined in relation to preceding embodiments, wherein the method involves the determination of the levels of anti-EDE antibodies and anti-Fusion Loop antibodies in the subject, wherein the EDE is as defined in relation to preceding embodiments and wherein the one or more flaviviruses is selected from zika virus; zika virus and dengue virus; zika virus and other flaviviruses; flaviviruses other than dengue.

As identified by the present inventors, patients with dengue infection, for example, produce predominantly anti-EDE antibodies or anti-FL antibodies. The anti-FL antibodies are not considered to be useful, whilst the anti-EDE antibodies are considered to be useful. If a subject has anti-EDE antibodies, whilst it may still require some additional therapy with the compounds of the present invention, a subject with mainly anti-FL antibodies is likely to require a higher dose as they have no innate useful antibodies. Thus, a patient with only anti-FL antibodies is deemed to be one which is likely to require treatment with the compound of the invention. A patient who is already producing the anti-EDE antibodies may not require treatment. In addition a patient who does not produce anti-EDE antibodies and only produces anti-FL antibodies is likely to require a higher dose of the treatment than patients with anti-EDE antibodies. Also, a patient may make anti-EDE antibodies but only to a low level, and may thus require a higher dose of compound.

By a higher dose we mean the patient requires 2, 3, 4, 5, 10, 20, 50 times the dose of the compound of the present invention than a patient who produces anti-EDE antibodies requires.

By "make anti-VDE antibodies to a low level" we mean that the patient, in comparison to other patients which make anti-EDE antibodies, has a lower than average level of anti-EDE antibodies.

Means to identify whether or not the antibodies bind to the EDE are as described earlier and in the Examples or in WO 2016/012800, for example determine whether the antibody binds to an intact dengue or zika virus, or the EDE, and not to the denatured or linear envelope protein. Where the envelope protein has been engineered to have increased dimer stability, or where the envelope protein, or residues thereof, are presented as part of a scaffold, the ability of the antibodies to bind to that protein can be assessed.

The level of anti-FL and anti-EDE antibodies within a subject can also be used to assess the need of that subject for a flavivirus, for example zika or dengue virus vaccination. Thus in a further embodiment is provided a method for assessing the need of a patient for a Dengue virus vaccination, said method comprising the identification of the levels of anti-Envelope Dimer Epitope antibodies and anti-Fusion Loop antibodies in the subject, wherein the Envelope Dimer Epitope is as defined in any of the preceding embodiments. Similar to the criteria for a patient requiring treatment with a compound of the invention, or a higher dose of the compound, if a patient is determined to have anti-Envelope Dimer Epitope antibodies, vaccination is likely unnecessary.

Further, if the patient is determined to have anti-Envelope Dimer Epitope antibodies the patient may subjected to a boost dose.

In another embodiment, if the patient does not have anti-Envelope Dimer Epitope antibodies, full vaccination is required.

The present invention also provides the use of a stabilized recombinant sE dimer (used as an antigen) as defined above, for preparing a preventive or therapeutic immunogenic (or vaccine) composition intended for the prevention and/or the treatment of infection by one or more flaviviruses in a sensitive mammal subject, such as in human, wherein the one or more flaviviruses is selected from zika virus; zika virus and dengue virus; zika virus and other flaviviruses; flaviviruses other than dengue.

Significantly, the inventors, as described above, have identified a specific epitope that is recognised by previously unknown highly cross-reactive and potently neutralising antibodies in zika virus as well as other flaviviruses. This epitope is considered to provide a particularly effective antigen for vaccination against flaviviruses, particularly zika virus and also dengue virus, for example wherein the one or more flaviviruses is selected from zika virus; zika virus and dengue virus; zika virus and other flaviviruses; flaviviruses other than dengue. Methods to select a suitable antigen for use in a vaccination against flavivirus, for example zika virus or zika and dengue virus are described in earlier embodiments. The invention therefore provides a composition presenting a Envelope Dimer Epitope of flavivirus, optionally EDE compound for use in for preparing a preventive or therapeutic immunogenic (or vaccine) composition intended for the prevention and/or the treatment of infection by one or more flaviviruses, wherein the one or more flaviviruses is selected from zika virus; zika virus and dengue virus; zika virus and other flaviviruses; flaviviruses other than dengue, in a sensitive mammal subject, such as in human, wherein the Envelope Dimer Epitope and EDE compound are as defined in any of the preceding embodiments or identified according to the preceding methods, for example the EDE or EDE compound could be identified in the earlier embodiment setting out a method of selecting a suitable antigen for use in a vaccine, for example by characterising the antibodies made following administration of the potential vaccine candidate EDE/EDE compound to a subject. This would be well within the skilled person's remit. Alternatively, the EDE or EDE compound may be as set out in the earlier embodiments, for example in one embodiment, the EDE or EDE compound is a dimer of envelope protein, or envelope ectodomain or the (approximately) 400 amino terminal residues of the ectodomain of Envelope protein. The envelope protein may be any of the envelope proteins from zika, DENV-1, DENV-2, DENV-3 and DENV-3, and DENV-4, or a protein with at least 90% homology to the sequences (for example as set out in the Sequences section below). The dimer may be a homodimer or a heterodimer. In a preferred embodiment the dimer is not incorporated into an intact viral particle, or a sub-viral particle, or a virus-like particle, but rather is a free dimer or in the form of a nanoparticle, for example a self-assembling nanoparticle as described elsewhere herein. It will be appreciated that any form of EDE or EDE compound described herein, for example, an engineered envelope protein, for example, as part of a protein scaffold, may be presented as part of a virus, virus-like particle, or sub-viral particle, or a nanoparticle. In a preferred embodiment the EDE compound is a stabilized recombinant sE dimer as described in the earlier embodiments. Earlier embodiments and preferences apply.

In a preferred embodiment, the EDE/EDE compound is such that it may raise antibodies once administered to a subject, preferably a human, wherein the antibodies are preferably capable of binding to zika and all four serotypes of dengue virus, and optionally are capable of neutralising zika and all four serotypes of dengue virus, preferably capable of neutralising zika and all four serotypes of dengue virus to 100%, and optionally are capable of neutralising virus made in both human and insect cells, preferably capable of neutralising zika and all four serotypes of dengue virus made in both human and insect cells to 100%.

An immunogenic composition comprising an EDE wherein the EDE comprises the stabilized recombinant sE dimer as described above is particularly suitable for eliciting in said subject neutralizing antibodies:

which recognize exclusively envelope dimer epitopes (EDE) (which show no binding to recombinant E protein monomer in ELISA tests),
are cross-reactive, and
neutralize zika and dengue viruses from the four serotypes (DENV1-4).

The present invention also provides a flavivirus immunogenic composition comprising a therapeutically effective amount of a stabilized recombinant sE dimer (used as an antigen) as defined above, wherein the one or more flaviviruses is selected from zika virus; zika virus and dengue virus; zika virus and other flaviviruses; flaviviruses other than dengue.

It will be appreciated that the composition may include the EDE/EDE compound itself, or it may include the means to express the EDE/EDE compound within the subject to be vaccinated. For example, the invention includes a nucleic acid encoding the Envelope Dimer Epitope or EDE compound, for use in vaccination against infections by one or more flaviviruses wherein the one or more flaviviruses is selected from zika virus; zika virus and dengue virus; zika virus and other flaviviruses; flaviviruses other than dengue, wherein the Envelope Dimer Epitope or EDE compound is as defined in any of the preceding embodiments. Additionally, the nucleic acid may be part of a vector. Preferences for the vector and vector components are as detailed above.

For example it is well known in the art that vaccination can be carried out using a nucleic acid encoding a particular antigen, for example via direct immunisation with plasmid DNA. Such nucleic acids can be delivered via liposomes and immune-stimulating constructs. Alternatively, attenuated viral hosts or vectors or bacterial vectors can be used, for example adenovirus, adeno-associated virus, cytomegalovirus, herpes virus, poliovirus, retrovirus, sindbis virus, vaccinia virus, or any other DNA or RNA virus vector.

Where the composition for use in vaccination against infection by one or more flaviviruses is a nucleic acid, the nucleic acid can be delivered to the patient in a viral vector for example adenovirus, adeno-associated virus, cytomegalovirus, herpes virus, poliovirus, retrovirus, sindbis virus, vaccinia virus, or any other DNA or RNA virus vector.

A composition comprising any one or more of the:
a) Envelope Dimer Epitope or EDE compound,
b) nucleic acid encoding the EDE or EDE compound,
c) vector comprising the nucleic acid,
for use in vaccination against infection by one or more flaviviruses, wherein the one or more flaviviruses is selected from zika virus; zika virus and dengue virus; zika virus and other flaviviruses; flaviviruses other than dengue, wherein the Envelope Dimer Epitope or EDE compound is as defined in any of the preceding embodiments is also part of the invention.

In one embodiment, the:
a) Envelope Dimer Epitope or EDE compound,
b) nucleic acid encoding the EDE or EDE compound,
c) vector comprising the nucleic acid,
are, or encode, more than one, optionally 2, optionally 3, optionally 4 serotypes of zika and/or Dengue virus.

In a preferred embodiment, the:
a) Envelope Dimer Epitope or EDE compound,
b) nucleic acid encoding the EDE or EDE compound,
c) vector comprising the nucleic acid,
are, or result in the production of a single epitope which can raise antibodies capable of neutralising zika and all four serotypes of dengue virus, preferably neutralise zika and all four serotypes to 100%.

The use of the composition of the present invention in a vaccination against flavivirus virus is intended to reduce or prevent infection with flavivirus, for example zika and dengue virus.

By reducing or preventing flavivirus, for example zika and/or dengue infection we include the meaning of reducing the level of infection by any degree. In one embodiment the compound of the present invention reduces infection by one serotype of flavivirus, for example zika or dengue virus by 30%, 50%, 70%, 80%, 90%, 95%, preferably 100%. In a preferred embodiment the compound of the present invention reduces infection by two serotypes of zika and dengue virus, by three serotypes of dengue virus, by all four serotypes of dengue virus, by 30%, 50%, 70%, 80%, 90%, 95%, preferably 100%. In the most preferred embodiment the compound of the present invention totally prevents infection by all found serotypes of zika and dengue virus.

The EDE or EDE compound, for example stabilized recombinant sE dimer of the present invention, which induces neutralizing antibodies against zika and dengue virus infection, for example, is administered to a mammal subject, preferably a human, in an amount sufficient to prevent or attenuate the severity, extent of duration of the infection by flavivirus, for example zika and dengue virus.

The therapeutically effective amount varies depending on the subject being treated, the age and general condition of the subject being treated, the capacity of the subject's immune response to synthesize antibodies, the degree of protection desired, the severity of the condition to be treated, the particular EDE compound, for example the particular stabilized recombinant sE dimer selected and its mode of administration, among other factors. An appropriate effective amount can be readily determined by one of skill in the art. A therapeutically effective amount will fall in a relatively broad range that can be determined through routine trials.

More particularly the EDE compound, for example stabilized recombinant sE dimer of the invention is administered in a therapeutically effective amount that comprises from 1 to 1000 μg of dimer, preferably 1 to 50 μg.

An optimal amount for a particular vaccine can be ascertained by standard studies involving measuring the anti-sE dimer antibody titers in subjects.

The immunogenic composition of the invention may be administered with or without adjuvant. Adjuvants can be added directly to the immunogenic composition or can be administered separately, either concurrently with or shortly after, administration of the vaccine. Such adjuvants include but are not limited to aluminium salts (aluminium hydroxide), oil-in-water emulsion formulations with or without specific stimulating agents such as muramyl peptides, saponin adjuvants, cytokines, detoxified mutants of bacteria toxins such as the cholera toxin, the pertussis toxin, or the *E. coli* heat-labile toxin.

The immunogenic composition of the invention may be administered with other immunogens or immunoregulatory agents, for example, immunoglobulins, cytokines, lymphokines and chemokines.

Vaccination programmes often include a boost strategy. Following an initial vaccination, subjects may receive one or two booster injections at an appropriate interval determined by one of skill in the art. In one embodiment, the vaccination can comprise a prime followed by one or more boosts. The antigen, composition, nucleic acid or vector which result in the expression of an antigen are included in the present invention for use in a boost strategy for vaccination against flavivirus, for example zika and Dengue virus infection, optionally wherein the antigen, compound, nucleic acid, vector or composition is for administration before (prime) or after (boost) administration of zika or Dengue virus, optionally attenuated zika or Dengue virus, and/or zika or Dengue virus like particle, wherein the zika or Dengue virus or zika or Dengue virus like particle can be a collection of one or more serotypes of zika and Dengue virus, and may comprise or present a EDE, for example a non-native EDE or EDE compound, as described above. As a further example, heterologous flavivirus such as the chimerivax with yellow fever may be used, for example followed by one or more of dimer, DNA, vaccinia, adeno virus, Different orders and timings of administration of different antigen and/or antigen-encoding nucleic acid may be possible, as will be apparent to those skilled in the art, and the present invention is not limited to any particular combination or order of administration.

The invention also comprises a vaccination strategy to provide protection against one or more flaviviruses, wherein the one or more flaviviruses is selected from zika virus; zika virus and dengue virus; zika virus and other flaviviruses; flaviviruses other than dengue, wherein the vaccination strategy comprises, for example:

a) A single time administration of a Envelope Dimer Epitope or EDE compound as defined in any of the preceding embodiments, capable of raising antibodies to zika and all four dengue serotypes, or the vaccine composition according to the preceding embodiments, or the nucleic acid for use in vaccination, or the vector for use in vaccination, optionally followed by administration of the attenuated Zika or Dengue virus, or
b) Administration of two Envelope Dimer Epitopes or EDE compounds from two serotypes, as defined in any of the preceding embodiments, followed by administration of Envelope Dimer Epitopes or EDE compounds from the other two serotypes, optionally followed by administration of the attenuated Zika or Dengue virus, or
c) Administration of the attenuated Zika or Dengue virus followed by administration of an Envelope Dimer Epitope as defined in any of the preceding embodiments, capable of raising antibodies to Zika and all four Dengue serotypes, or
d) Administration of the attenuated Zika or Dengue virus followed by administration of two Envelope Dimer Epitopes or EDE compounds from two serotypes, as defined in any of the preceding embodiments, followed by administration of Envelope Dimer Epitopes or EDE compounds from the other two serotypes.

It is also envisaged that a patient which has received a vaccination according to the present invention may still require subsequent treatment with a compound or composition according to the present invention for use in treating or preventing zika or dengue, for example, infection.

Thus the compound of the present invention is for use in treating or preventing flavivirus, for example zika infection in a patient which has previously received a flavivirus, for example zika or dengue vaccination, or in a patient which has not previously received a flavivirus, for example zika or dengue vaccination.

The vaccine is preferably administered prior to symptoms of flavivirus, for example zika or dengue infection, or before the patient is known to have flavivirus, for example zika or dengue infection, though the vaccination is still considered to be useful if the patient already has flavivirus, for example zika or dengue infection, as the vaccination is considered to offer protection to more than one serotype of flavivirus, for example zika or dengue virus, preferably offer protection to zika and all four serotypes of dengue virus. It will be appreciated that infection with more than one flavivirus type may be present or likely simultaneously and may often be undetected/unrecognised.

Thus the vaccination is for use in a patient who has not been previously infected with flavivirus, for example zika or dengue, and is not currently, at the time of the administration of the vaccine, infected with flavivirus, for example zika or dengue. Alternatively, the vaccination is for use in a patient who has previously been infected with one or more serotypes of flavirirus, for example zika or dengue infection, but is not considered to be infected at the time of administration of the vaccine, or the vaccination is for use in a patient who has previously been infected with one or more serotypes of flavivirus, for example zika or dengue virus, and is currently, at the time of administration, considered to be infected with one or more serotypes of flavivirus, for example zika or dengue virus.

The vaccination is also for use in a patient which has previously been treated with a compound of the invention but is not currently being treated with a compound of the invention, and is also for use in a patient which has previously been treated with a compound of the invention and is currently being treated with a compound of the invention. The vaccination is also for use in a patient which is being treated with a compound of the invention for the first time.

The present invention also provides an EDE compound, for example a stabilized recombinant sE dimer or an immunogenic composition as defined above for use as a medicament, preferably for preventing and/or treating infection with one or more flaviviruses, wherein the one or more flaviviruses is selected from zika virus; zika virus and dengue virus; zika virus and other flaviviruses; flaviviruses other than dengue.

The present invention also provides the use of an EDE compound, for example a stabilized recombinant sE dimer or an immunogenic composition as defined above for the manufacturing of a medicament, preferably of a preventive or therapeutic vaccine against infection with one or more flaviviruses, wherein the one or more flaviviruses is selected from zika virus; zika virus and dengue virus; zika virus and other flaviviruses; flaviviruses other than dengue.

The present invention also provides a method for preventing and/or treating infection with one or more flaviviruses, wherein the one or more flaviviruses is selected from zika virus; zika virus and dengue virus; zika virus and other flaviviruses; flaviviruses other than dengue, comprising administering to a subject in need thereof an EDE compound, for example a stabilized recombinant sE dimer or an immunogenic composition as defined above, in an amount effective to inhibit flavivirus virus infection of susceptible cells so as to thereby prevent or treat the infection.

The present invention also provides a diagnostic agent comprising or consisting of an EDE compound of the invention, for example a stabilized recombinant sE dimer, or a compound of the invention, for example an antibody or fragment thereof according to the present invention.

In an embodiment of said diagnostic agent, the compound, for example antibody or fragment thereof according to the present invention is linked, directly or indirectly, covalently or non-covalently to a detectable marker.

The detectable marker can be directly and covalently linked to the compound, for example antibody or fragment thereof, either to one of the terminal ends (N or C terminus) of said antibody or fragment thereof, or to the side chain of one of the amino acids of said antibody or fragment thereof. The detectable marker can also be indirectly and covalently linked to said antibody or fragment thereof through a connecting arm (i.e., a cross-linking reagent) either to one of the terminal ends of said antibody or fragment thereof, or to a side chain of one of the amino acids of said antibody or fragment thereof. Linking methods of a compound of interest to a peptide or antibody are well-known in the art.

Advantageously, said detectable marker is selected from the group consisting of:
  enzymes such as horseradish peroxidase, alkaline phosphatase, glucose-6-phosphatase or beta-galactosidase;
  fluorophores such as green fluorescent protein (GFP), blue fluorescent dyes excited at wavelengths in the ultraviolet (UV) part of the spectrum (e.g. AMCA (7-amino-4-methylcoumarin-3-acetic acid); Alexa Fluor 350), green fluorescent dyes excited by blue light (e.g. FITC, Cy2, Alexa Fluor 488), red fluorescent dyes excited by green light (e.g. rhodamines, Texas Red, Cy3, Alexa Fluor dyes 546, 564 and 594), or dyes excited with far-red light (e.g. Cy5) to be visualized with electronic detectors (CCD cameras, photomultipliers);
  heavy metal chelates such as europium, lanthanum or yttrium;
  radioisotopes such as [$^{18}$F]fluorodeoxyglucose, $^{11}$C-, $^{125}$I-, $^{3}$H-, $^{14}$C-, $^{35}$S, or $^{99}$Tc-labelled compounds.

The present invention also provides the use of an EDE compound, for example a stabilized recombinant sE dimer, an antibody or fragment thereof, or a diagnostic agent according to the present invention for diagnosing or monitoring a infection with one or more flaviviruses, wherein the one or more flaviviruses is selected from zika virus; zika virus and dengue virus; zika virus and other flaviviruses; flaviviruses other than dengue.

The present invention also provides an in vitro method for diagnosing infection with one or more flaviviruses, wherein the one or more flaviviruses is selected from zika virus; zika virus and dengue virus; zika virus and other flaviviruses; flaviviruses other than dengue, comprising the steps of:
  a) contacting in vitro an appropriate biological sample from said subject with an antibody or fragment thereof, or a diagnostic agent comprising or consisting of an antibody or fragment thereof according to the present invention, and
  b) determining the presence or the absence of a flavivirus virus envelope glycoprotein E in said biological sample,
  the presence of said flavivirus virus envelope glycoprotein E indicating that said subject has flavivirus infection.

Step b) can be carried out by determining the presence or the absence of the antibody-antigen complex (i.e., antibody directed to the flavivirus virus envelope glycoprotein E-flavivirus virus envelope glycoprotein E complex).

The present invention also provides an in vitro method for determining the presence of one or more flavivirus virus envelope glycoprotein E in an appropriate biological sample from a subject, comprising the steps of
  a) contacting in vitro said appropriate biological sample from said subject with an antibody or fragment thereof, or a diagnostic agent comprising or consisting of an antibody or fragment thereof according to the present invention, and flavivirus virus envelope glycoprotein E in said biological sample.

The present invention also provides an in vitro method for diagnosing one or more flavivirus virus infection in a subject, comprising the steps of:

a) contacting in vitro an appropriate biological sample from said subject with a stabilized recombinant sE dimer according to the present invention, and b) determining the presence or the absence of antibodies directed to said dimer in said biological sample, the presence of said antibodies indicating that said subject has flavivirus virus infection.

The present invention also provides an in vitro method for determining the presence of antibodies directed to one or more flavivirus virus envelope glycoprotein E in an appropriate biological sample from a subject, comprising the steps of:

a) contacting in vitro said appropriate biological sample from said subject with a stabilized recombinant sE dimer according to the present invention, and b) determining the presence or the absence of antibodies directed to said dimer in said biological sample.

As in other aspects of the invention, in the above aspects the one or more flaviviruses is selected from zika virus; zika virus and dengue virus; zika virus and other flaviviruses; flaviviruses other than dengue.

The present invention also provides an in vitro method for monitoring the progression or regression of infection with one ore more flaviviruses in a subject, comprising the steps of:

a) contacting in vitro an appropriate biological sample from said subject with an antibody or fragment thereof, a diagnostic agent comprising or consisting of an antibody or fragment thereof according to the present invention, b) determining the amount of flavivirus virus envelope glycoprotein E in said biological sample, and c) comparing the amount determined in step (b) with the amount of flavivirus virus envelope glycoprotein E previously obtained for said subject, a significant increase in amount of flavivirus virus envelope glycoprotein E constituting a marker of the progression of said flavivirus virus infection and a significant decrease of flavivirus virus envelope glycoprotein E constituting a marker of the regression of said flavivirus virus infection, wherein the one or more flaviviruses is selected from zika virus; zika virus and dengue virus; zika virus and other flaviviruses; flaviviruses other than dengue.

As used herein the terms "significant increase" and "significant decrease" refer to a higher amount or lower amount respectively of flavivirus virus envelope glycoprotein E in an appropriate biological sample with respect to the amount of flavivirus virus envelope glycoprotein E in an appropriate biological sample from said subject, that was previously determined and used as a reference amount.

Step b) can be carried out by determining the presence or the absence of the antibody-antigen complex (i.e., antibody directed to the flavivirus virus envelope glycoprotein E-flavivirus virus envelope glycoprotein E complex).

The present invention also provides an in vitro method for predicting a favourable prognosis of the evolution of infection by one or more flaviviruses in a subject, comprising the steps of:

a) contacting in vitro an appropriate biological sample from said subject with a stabilized recombinant sE dimer according to the present invention, b) determining the amount of neutralizing antibodies directed to said dimer in said biological sample, and c) comparing the amount determined in step (b) with the amount of antibodies directed to said dimer previously obtained for said subject, a significant increase in amount of neutralizing antibodies directed to said dimer constituting a marker of favourable prognosis of the evolution of said flavivirus virus infection, wherein the one or more flaviviruses is selected from zika virus; zika virus and dengue virus; zika virus and other flaviviruses; flaviviruses other than dengue.

The present invention also provides an in vitro method for monitoring the success of a vaccination protocol against one or more flavivirus infection in a subject vaccinated against one or more flaviviruses, comprising the steps of:

a) contacting in vitro an appropriate biological sample from said subject with a stabilized recombinant sE dimer according to the present invention, b) determining the amount of neutralizing antibodies directed to said dimer in said biological sample, and c) comparing the amount determined in step (b) with the amount of antibodies directed to said dimer previously obtained for said subject, a significant increase in amount of neutralizing antibodies directed to said dimer constituting a marker of success of said vaccination protocol, wherein the one or more flaviviruses is selected from zika virus; zika virus and dengue virus; zika virus and other flaviviruses; flaviviruses other than dengue.

Said appropriate biological sample can be blood, serum, urine or a liver biopsy, preferably blood.

Immunological methods for detecting and determining the amount of proteins or antibodies are well known in the art. By way of examples, EIA, ELISA, RIA or immunofluorescence tests can be used.

Polynucleotides useful in relation to the present invention may be obtained by well-known methods of recombinant DNA technology and/or of chemical DNA synthesis.

We provide several kits of parts useful in relation to the present invention. One embodiment provides a kit for diagnosing or monitoring, in a subject, a flavivirus infection, comprising a stabilized recombinant sE dimer, or an antibody or fragment thereof according to the present invention and an appropriate diagnostic reagent.

The appropriate diagnostic reagent is necessary for performing an assay for diagnosing or monitoring, in a subject, a dengue virus infection. The appropriate diagnostic reagent can be a solvent, a buffer, a dye, an anticoagulant.

The kit can also comprise a micro-titre plate.

In one embodiment the kit of parts comprises the means to identify patients requiring treatment with the compound of the invention, or requiring a higher dose of the compound of the invention, according to the preceding embodiments. The kit may provide means to identify the presence or absence of anti-EDE and anti-FL antibodies, for example the kit may comprise a micro-titre plate, optionally wherein the micro-titre plate is coated with linear or denatured envelope protein, and separately coated with the EDE epitope according to any of the preceding embodiments, and/or may also include reagents to carry out an ELISA test, optionally a colourimetric test on a stick. Preferably the kit contains means to simply identify the presence or absence of the antibodies, preferably on a solid support. The kit may also further comprise a compound or composition of the present invention for use in treating or preventing flavivirus infection.

A further kit of parts comprising means to identify patients requiring vaccination is also provided. A patient is deemed to require vaccination based on the presence and absence, and level of, anti-EDE antibodies and anti-FL antibodies. The kit may therefore provide means to identify the presence or absence of anti-EDE and anti-FL antibodies, for example the kit may comprise a micro-titre plate, optionally wherein the micro-titre plate is coated with linear or denatured envelope protein, and separately coated with the EDE epitope according to any of the preceding embodiments, and/or may also include reagents to carry out an ELISA test, optionally a colourimetric test on a stick. Preferably the kit contains means to simply identify the presence or absence of the antibodies, preferably on a solid support. The kit may also further comprise a composition for use in vaccination, as described in the preceding embodiments.

A further kit comprises the means to treat or prevent dengue infection, and includes one or more compounds of the invention that bind to the EDE, or the composition comprising a compound of the invention that binds to the EDE, and optionally includes a further therapeutic agent, for example a further anti-viral agent.

It will be appreciated that any compound or composition or antigen or antibody mentioned herein may be part of a composition. The composition may comprise stabilising agents, such a PEG. It will be appreciated that a polypeptide component, for example, may be covalently modified or conjugated, for example PEGylated, as will be well known in the art Thus, for example, any compound or antibody for use in treating or preventing dengue infection, or any polypeptide or antigen, or nucleic acid or vector encoding the antigen or antibody, may be conjugated to one or more further entities, for example may be conjugated to a reporter moiety, or may be conjugated to one or more further therapeutic agents.

One such further therapeutic agent is an agent to prevent Fc receptor binding. It is well known that flavivirus, for example dengue virus causes antibody dependent enhancement, and this is thought to be due to the production of certain antibodies that can bind to, but not neutralise the virus. This leads to internalisation of the antigen via the Fc receptor, leading to a heightened response upon reinfection. It is believed that agents which can block Fc receptor binding may prevent antibody dependent enhancement. Examples of such agents are and such agents are considered to be useful when administered along with (or separately to) the compounds of the invention for use in treating or preventing dengue infection, and the antigen for use in vaccination. It may also be useful to modify or select the antibody molecule such that interaction with Fc receptor is lessened, as will be known to those skilled in the art.

It will be appreciated that administration of any agent described herein is typically administered as part of a pharmaceutical composition together with a pharmaceutically acceptable excipient, diluent, adjuvant, or carrier. Thus, any mention of a compound, polypeptide, antibody, antigen binding portion thereof, composition, nucleic acid, vector, antigen, host cell, and any mention of a further therapeutic agent, equally applies to a pharmaceutically acceptable composition comprising that compound, composition, nucleic acid, vector, antigen, host cell, and/or further therapeutic agent (e.g. a formulation).

The compound, polypeptide, antibody, antigen binding portion thereof, composition, nucleic acid, can be part of a nanoparticle.

Routes of administration will be known to those skilled in the art. For example, the agents of the invention (compound, polypeptide, antibody, antigen binding portion thereof, composition, nucleic acid, vector, antigen, host cell, further therapeutic agent) can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection. The compound polypeptide, antibody, antigen binding portion thereof, composition, nucleic acid, vector, antigen, host cell, further therapeutic agent according to the present invention can be orally administered to a mammal subject, preferably a human. They can also be administered to said subject by injection, such as intravenous, intraperitoneal, intramuscular, intradermal or subcutaneous injection.

The agents may be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the subject to be treated, as well as the route of administration, the agents may be administered at varying doses.

Preferably, the formulation is a unit dosage containing a daily dose or unit, daily sub-dose or an appropriate fraction thereof, a weekly dose, a monthly dose, or a 6 monthly dose of the agent or active ingredient.

In human therapy, the agents (compound, polypeptide, antibody, antigen binding portion thereof, composition, nucleic acid, vector, antigen, host cell, further therapeutic agent) can be administered alone but will generally be administered in admixture with a suitable pharmaceutical excipient diluent or carrier selected with regard to the intended route of administration and standard pharmaceutical practice.

Tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included. Capsules or tablets may also be enteric coated to enhance gastric stability.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The agents (compound, polypeptide, antibody, antigen binding portion thereof, composition, nucleic acid, vector, antigen, host cell, further therapeutic agent, vaccine) can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral Formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the Formulation isotonic with the blood of the intended recipient; and aqueous and non-aqueous sterile suspensions which may include suspending agents and thickening agents. The Formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human subjects, the daily dosage level of the agents (compound, polypeptide, antibody, antigen binding portion thereof, composition, nucleic acid, vector, antigen, host cell, further therapeutic agent, vaccine) will usually be from 1 to 5000 mg per adult, administered in single or divided doses.

Thus, for example, the tablets or capsules comprising the compound, polypeptide, antibody, antigen binding portion thereof, composition, nucleic acid, vector, antigen, host cell, further therapeutic agent, vaccine of the invention may contain from 1 mg to 1000 mg (i.e. from about 60-120 mg/m$^2$) of active compound for administration singly or two or more at a time, as appropriate. The physician in any event will determine the actual dosage which will be most suitable for any individual subject and it will vary with the age, weight and response of the particular subject. The above dosages are exemplary of the average case. There can, of course, be individual instances where higher or lower dosage ranges are merited and such are within the scope of this invention.

The agents (compound, polypeptide, antibody, antigen binding portion thereof, composition, nucleic acid, vector, antigen, host cell, further therapeutic agent, vaccine) can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the compound, polypeptide, antibody, antigen binding portion thereof, composition, nucleic acid, vector, antigen, host cell, further therapeutic agent, vaccine, e.g. using a mixture of ethanol and the propellant as the solvent, which may additionally contain a lubricant, e.g. sorbitan trioleate.

Capsules and cartridges (made, for example, from gelatin) for use in an inhaler or insufflator may be Formulated to contain a powder mix of a compound of the invention and a suitable powder base such as lactose or starch.

Aerosol or dry powder formulations are preferably arranged so that each metered dose or "puff" contains at least 1 mg of an agent (compound, polypeptide, antibody, antigen binding portion thereof, composition, nucleic acid, vector, antigen, host cell, further therapeutic agent, vaccine) for delivery to the subject. It will be appreciated that he overall daily dose with an aerosol will vary from subject to subject, and may be administered in a single dose or, more usually, in divided doses throughout the day.

Alternatively, the agents (compound, polypeptide, antibody, antigen binding portion thereof, composition, nucleic acid, vector, antigen, host cell, further therapeutic agent, vaccine) can be administered in the form of a suppository or pessary, or they may be applied topically in the form of a lotion, solution, cream, ointment or dusting powder. The compound, polypeptide, antibody, antigen binding portion thereof, composition, nucleic acid, vector, antigen, host cell, further therapeutic agent, vaccine of the invention may also be transdermally administered, for example, by the use of a skin patch. They may also be administered by the ocular route, particularly for treating diseases of the eye.

For ophthalmic use, the agents (compound, polypeptide, antibody, antigen binding portion thereof, composition, nucleic acid, vector, antigen, host cell, further therapeutic agent, vaccine), can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agents (compound, polypeptide, antibody, antigen binding portion thereof, composition, nucleic acid, vector, antigen, host cell, further therapeutic agent, vaccine), can be formulated as a suitable ointment containing the active compound, polypeptide, antibody, antigen binding portion thereof, composition, nucleic acid, vector, antigen, host cell, further therapeutic agent, vaccine suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or topical administration of the agents (compound, polypeptide, antibody, antigen binding portion thereof, composition, nucleic acid, vector, antigen, host cell, further therapeutic agent, vaccine) is the preferred route, being the most convenient. In circumstances where the recipient suffers from a swallowing disorder or from impairment of drug absorption after oral administration, the drug may be administered parenterally, e.g. sublingually or buccally.

For veterinary use, the agent (compound, polypeptide, antibody, antigen binding portion thereof, composition, nucleic acid, vector, antigen, host cell, further therapeutic agent, vaccine) is administered as a suitably acceptable formulation in accordance with normal veterinary practice and the veterinary surgeon will determine the dosing regimen and route of administration which will be most appropriate for a particular animal.

Conveniently, the formulation is a pharmaceutical formulation. The formulation may be a veterinary formulation.

It will be appreciated that for a composition comprising one or more antibodies or fragments thereof, an intravenous administration route may be appropriate, for example.

It will be appreciated that the term administration is not restricted to a one time administration. The term administration is taken to cover all of, but not limited to, a single dose administration, multiple administrations over a period of time, variable dosage administrations over a period of time, variable means of administration over a period of time, administration in conjunction with one or more further therapeutic agents.

Administration can be by any means known in the art and includes, but is not limited to, oral, intravenous, topically direct to a tumour, sublingually or suppository.

The listing or discussion of an apparently prior-published document in this specification should not necessarily be taken as an acknowledgement that the document is part of the state of the art or is common general knowledge.

Preferences and options for a given aspect, feature or parameter of the invention should, unless the context indicates otherwise, be regarded as having been disclosed in combination with any and all preferences and options for all other aspects, features and parameters of the invention. For example, the various definitions for the EDE are relevant to all aspects of the invention, for example an epitope comprising the EDE for use in vaccination against infection by the one or more flaviviruses could comprise any one or more of: an epitope-scaffold protein, wherein the scaffold protein comprises a heterologous scaffold protein covalently linked to the Envelope Dependent Epitope; at least Q77,W101, N153,T155,K310 of the envelope protein; or domain II of the envelope protein, optionally further comprising any one or more of the following features of domain II; the b strain (residues 67-74), the fusion loop and residues immediately upstream (residues 97-106) and the ij loop (residues 246-249), for example.

Sequences

Exemplary wild-type flavivirus envelope ectodomain sequences include the following. Numbering used herein is considered to relate to these exemplary wild-type flavivirus sequences. Further flavivirus sequences will be known to those skilled in the art. Flavivirus sequences, mutated flavivirus sequences and antibody sequences relevant to the present invention are also set out in WO 2016/012800.

```
Zika virus (ZIKV, KJ776791, strain H-PF-
2013_French_Polynesia) Envelope portion of
polyprotein sequence;
                                      SEQ ID No: 1
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSG

MIVNDTGHETDENRAKVEITPNSPRAEATLGGFGSLGLDCEPRTGLDFSD

LYYLTMNNKHWLVHKEWFHDIPLPWHAGADTGTPHWNNKEALVEFKDAHA

KRQTVVVLGSQEGAVHTALAGALEAEMDGAKGRLSSGHLKCRLKMDKLRL

KGVSYSLCTAAFTFTKIPAETLHGTVTVEVQYAGTDGPCKVPAQMAVDMQ

TLTPVGRLITANPVITESTENSKMMLELDPPFGDSYIVIGVGEKKITHHW

HRSG;

dengue virus serotype 1 (DENV-1, NC_001477)
Envelope portion of polyprotein sequence;
                                      SEQ ID No: 2
MRCVGIGNRDFVEGLSGATWVDVVLEHGSCVTTMAKDKPTLDIELLKTEV

TNPAVLRKLCIEAKISNTTTDSRCPTQGEATLVEEQDTNFVCRRTFVDRG

WGNGCGLFGKGSLITCAKFKCVTKLEGKIVQYENLKYSVIVTVHTGDQHQ

VGNETTEHGTTATITPQAPTSEIQLTDYGALTLDCSPRTGLDFNEMVLLT

MKKKSWLVHKQWFLDLPLPWTSGASTSQETWNRQDLLVTFKTAHAKKQEV

VVLGSQEGAMHTALTGATEIQTSGTTTIFAGHLKCRLKMDKLILKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKKG;

dengue virus serotype 2 (DENV-2, NC_001474)
Envelope portion of polyprotein sequence;
                                      SEQ ID No: 3
MRCIGMSNRDFVEGVSGGSWVDIVLEHGSCVTTMAKNKPTLDFELIKTEA

KQPATLRKYCIEAKLTNTTTESRCPTQGEPSLNEEQDKRFVCKHSMVDRG

WGNGCGLFGKGGIVTCAMFRCKKNMEGKVVQPENLEYTIVITPHSGEEHA

VGNDTGKHGKEIKITPQSSITEAELTGYGTVTMECSPRTGLDFNEMVLLQ

MENKAWLVHRQWFLDLPLPWLPGADTQGSNWIQKETLVTFKNPHAKKQDV

VVLGSQEGAMHTALTGATEIQMSSGNLLFTGHLKCRLRMDKLQLKGMSYS

MCTGKFKVVKEIAETQHGTIVIRVQYEGDGSPCKIPFEIMDLEKRHVLGR

LITVNPIVTEKDSPVNIEAEPPFGDSYIIIGVEPGQLKLNWFKKG;

dengue virus serotype 3 (DENV-3, NC_001475)
Envelope portion of polyprotein sequence;
                                      SEQ ID No: 4
MRCVGVGNRDFVEGLSGATWVDVVLEHGGCVTTMAKNKPTLDIELQKTEA

TQLATLRKLCIEGKITNITTDSRCPTQGEAVLPEEQDQNYVCKHTYVDRG

WGNGCGLFGKGSLVTCAKFQCLEPIEGKVVQYENLKYTVIITVHTGDQHQ

VGNETQGVTAEITPQASTTEAILPEYGTLGLECSPRTGLDFNEMILLTMK

NKAWMVHRQWFFDLPLPWASGATTETPTWNRKELLVTFKNAHAKKQEVVV

LGSQEGAMHTALTGATEIQNSGGTSIFAGHLKCRLKMDKLELKGMSYAMC

TNTFVLKKEVSETQHGTILIKVEYKGEDAPCKIPFSTEDGQGKAHNGRLI

TANPVVTKKEEPVNIEAEPPFGESNIVIGIGDNALKINWYKKG;

dengue virus serotype 4 (DENV-4, NC_002640)
Envelope portion of polyprotein sequence;
                                      SEQ ID No: 5
MRCVGVGNRDFVEGVSGGAWVDLVLEHGGCVTTMAQGKPTLDFELTKTTA

KEVALLRTYCIEASISNITTATRCPTQGEPYLKEEQDQQYICRRDVVDRG

WGNGCGLFGKGGVVTCAKFSCSGKITGNLVQIENLEYTVVVTVHNGDTHA

VGNDTSNHGVTAMITPRSPSVEVKLPDYGELTLDCEPRSGIDFNEMILMK

MKKKTWLVHKQWFLDLPLPWTAGADTSEVHWNYKERMVTFKVPHAKRQDV

TVLGSQEGAMHSALAGATEVDSGDGNHMFAGHLKCKVRMEKLRIKGMSYT

MCSGKFSIDKEMAETQHGTTVVKVKYEGAGAPCKVPIEIRDVNKEKVVGR

IISSTPLAENTNSVTNIELEPPFGDSYIVIGVGNSALTLHWFRKG;
```

Other Flavivirus:

Saint Louis encephalitis virus (SLEV, NC_007580)
Envelope portion of polyprotein sequence;
SEQ ID No: 6
FNCLGTSNRDFVEGASGATWIDLVLEGGSCVTVMAPEKPTLDFKVMKMEAT

ELATVREYCYEATLDTLSTVARCPTTGEAHNTKRSDPTFVCKRDVVDRGWG

NGCGLFGKGSIDTCAKFTCKNKATGKTILRENIKYEVAIFVHGSTDSTSHG

NYSEQIGKNQAARFTISPQAPSFTANMGEYGTVTIDCEARSGINTEDYYVF

TVKEKSWLVNRDWFHDLNLPWTSPATTDWRNRETLVEFEEPHATKQTVVAL

GSQEGALHTALAGAIPATVSSSTLTLQSGHLKCRAKLDKVKIKGTTYGMCD

SAFTFSKNPTDTGHGTVIVELQYTGSNGPCRVPISVTANLMDLTPVGRLVT

VNPFISTGGANNKVMIEVEPPFGDSYIVVGRGTTQINYHWHKEG;

Japanese encephalitis virus (JEV, NC_001437)
Envelope portion of polyprotein sequence;
SEQ ID No: 7
FNCLGMGNRDFIEGASGATWVDLVLEGDSCLTIMANDKPTLDVRMINIEA

SQLAEVRSYCYHASVTDISTVARCPTTGEAHNEKRADSSYVCKQGFTDRG

WGNGCGLFGKGSIDTCAKFSCTSKAIGRTIQPENIKYEVGIFVHGTTTSE

NHGNYSAQVGASQAAKFTITPNAPSITLKLGDYGEVTLDCEPRSGLNTEA

FYVMTVGSKSFLVHREWFHDLALPWTSPSSTAWRNRELLMEFEEAHATKQ

SVVALGSQEGGLHQALAGAIVVEYSSSVKLTSGHLKCRLKMDKLALKGTT

YGMCTEKFSFAKNPADTGHGTVVIELSYSGSDGPCKIPIVSVASLNDMTP

VGRLVTVNPFVATSSANSKVLVEMEPPFGDSYIVVGRGDKQINHHWHKAG;

Murray Valley encephalitis virus (MVEV, NC_000943)
Envelope portion of polyprotein sequence;
SEQ ID No: 8
FNCLGMSSRDFIEGASGATWVDLVLEGDSCITIMAADKPTLDIRMMNIEA

TNLALVRNYCYAATVSDVSTVSNCPTTGESHNTKRADHNYLCKRGVTDRG

WGNGCGLFGKGSIDTCAKFTCSNSAAGRLILPEDIKYEVGVFVHGSTDST

SHGNYSTQIGANQAVRFTISPNAPAITAKMGDYGEVTVECEPRSGLNTEA

YYVMTIGTKHFLVHREWFNDLLLPWTSPASTEWRNREILVEFEEPHATKQ

SVVALGSQEGALHQALAGAIPVEFSSSTLKLTSGHLKCRVKMEKLKLKGT

TYGMCTEKFTFSKNPADTGHGTVVLELQYTGSDGPCKIPISSVASLNDMT

PVGRMVTANPYVASSTANAKVLVEIEPPFGDSYIVVGRGDKQINHHWHKE

G;

West Nile virus (WNV, NC_001563) Envelope portion
of polyprotein sequence;
SEQ ID No: 9
FNCLGMSNRDFLEGVSGATWVDLVLEGDSCVTIMSKDKPTIDVKMMNMEA

ANLADVRSYCYLASVSDLSTRAACPTMGEAHNEKRADPAFVCKQGVVDRG

WGNGCGLFGKGSIDTCAKFACTTKATGWIIQKENIKYEVAIFVHGPTTVE

SHGKIGATQAGRFSITPSAPSYTLKLGEYGEVTVDCEPRSGIDTSAYYVM

SVGEKSFLVHREWFMDLNLPWSSAGSTTWRNRETLMEFEEPHATKQSVVA

LGSQEGALHQALAGAIPVEFSSNTVKLTSGHLKCRVKMEKLQLKGTTYGV

CSKAFKFARTPADTGHGTVVLELQYTGTDGPCKVPISSVASLNDLTPVGR

LVTVNPFVSVATANSKVLIELEPPFGDSYIVVGRGEQQINHHWHKSG;

It will be appreciated that there will be variants to these sequences. For example, the sequence of the envelope ectodomain of the DENV-2 strain used in the structural studies described in Example 2 herein is shown in SEQ ID NO: 10, for example, and is considered to differ slightly from that of dengue virus serotype 2 (DENV-2, NC_001474) SEQ ID No: 3 indicated above. For example, the residue at position 308 is I in the sequence shown in SEQ ID No: 10 and is V in DENV-2, NC_001474 SEQ ID No: 3. It is considered that the variations do not have a significant effect on the EDE epitope. Structurally, for example, it is considered that whether residue 308 is V or I is not expected to make much differences in contacts made between the envelope dimer and interacting antibodies.

Other strains that may be used, for example, in preparing mutated polypeptides as described herein may also differ slightly from the sequence of SEQ ID No: 3 or from that of SEQ ID No: 10. For example, differences between different DENV-2 sequences, or within other Dengue serogroups, for example, either as obtained from the wild or following periods of laboratory culture, may typically be up to about 15%.

Mutations

Examples of E protein mutations considered useful are shown in the context of DENV and ZIKV E sequences. Corresponding mutations are also considered to be potentially useful in other flavivirus E protein backgrounds, for example other ZIKV or DENV sequences, or other flavivirus E protein sequences, for example sequences as set out in the Sequence section above.

TABLE M

| Suggested Mutations for DENV and ZIKV E protein based on structural alignment | | | | |
|---|---|---|---|---|
| # | DENV | ZIKV | Rationale | Notes |
| Dimer stabilization | | | | |
| #1 | S255C | S260C | Covalent stabilization of the dimer using a single SS in the loop j-αB | This mutation stabilizes the DENV dimer in solution. Although ZIKA virus sE is already a dimer in solution, it binds efficiently to FLE antibodies. It is therefore useful to stabilize the ZIKA dimer too with this mutation |
| #2 | A259C | A264C | Covalent stabilization of the dimer using a single SS in the helix αB | This mutation stabilizes the DENV dimer in solution. Same as above |

TABLE M-continued

Suggested Mutations for DENV and ZIKV E protein based on structural alignment

| | | | | |
|---|---|---|---|---|
| #3 | L107C/ A313C | L107C/ A319C | Covalent stabilization of the dimer using a double SS between the loop cd and loop AB. To prevent the formation of FL induced Abs Can be tried in the two disulfide combination with mutation #1 or #2 | |
| #4 | F108C/ T315C | F108C/ T321C | Covalent stabilization of the dimer using a double SS between the loop cd and loop AB. To prevent the formation of FL induced Abs Can be tried in the two disulfide combination with mutation #1 or #2 | |
| #5 | I312P/G | P318G | Only for DENV: To break the A strand of DIII and increase flexibility to facilitate the dimerization induced by the cysteine mutations To be combined with mutations #1, #2, #3 or #4 or combination of them | ZIKA has already a P in the corresponding position (P318). Still it might be useful to program to put a glycine there, if the P leads to aggregates |

Fusion loop

| | | | |
|---|---|---|---|
| #6 | L107F | L107F | Either alone or in conjunction with mutation #1 or #2 To stabilize FL/DIII interface in the dimer To hide FL and promote formation of conformational EDE Abs To mutate linear epitope of FL and avoid formation of adverse FLE antibodies |
| #7 | Insertion G107A | Insertion G107A | Insertion in conjunction either with mutation #3, #4 or #5 or two disulfide combination (#3 + #1 or #3 + #2) (#4 + #1 or #4 + #2) (#3 − #1 or #3 − #2) + #5 (#4 − #1 or #4 − #2) + #5 To add flexibility to the FL for compatibility with disulphide formation. To change linear FL epitope and avoid formation of adverse FLE antibodies |

Virion-like conformation

| | | | |
|---|---|---|---|
| #8 | L278F | NA | For DENV: To fill cavity around F279. The new F278 can take the place of F279 recapitulating a virion-like conformation in sE dimer |

TABLE M-continued

Suggested Mutations for DENV and ZIKV E protein based on structural alignment

| #  | DENV | ZIKV | Rationality | Notes |
|----|------|------|-------------|-------|
| #9 | A245C/ D98C or K246C/ V97C | A250C/ D98C | To recapitulate the virion-like conformation | This mutation will also change the sequence of FL linear epitopes and help avoid some adverse FLE antibodies |

| # | DENV | ZIKV | Rationality | Notes |
|---|------|------|-------------|-------|

Cavity filling

| # | DENV | ZIKV | Rationality | Notes |
|---|------|------|-------------|-------|
| #10 | H27F/W | H27F/W | | |
| #11 | H244F/W | H249F/W | | |
| #12 | L292F | L298F | To stabilize the DI-DIII linker in the dimer conformation | |
| #13 | L292F/ L294N | L298F/ L300N | To stabilize the DI-DIII linker in the dimer conformation To destabilize the DI-DII linker in the trimer conformation | |

Masking serotype specific epitopes by glycan shield

| # | DENV | ZIKV | Rationality | Notes |
|---|------|------|-------------|-------|
| #14 | Q227N | NA | Introducing glycan shield at antigenic regions that elicit dengue serotype-specific antibodies To mask epitopes that are cross reactive but not cross neutralizing (ADE-inducing) DI-DII hinge | As the conservation between ZIKA virus and DENV is essentially within the EDE, there is no point to resurface ZIKA virus (as there are no ZIKA serotypes either). Using the ZIKA virus sE protein to vaccinate against DENV would amount to an already re-surfaced sE protein. |
| #15 | E174N | NA | To mask epitopes that are cross reactive but not cross neutralizing (ADE-inducing) G0 strand DI | Same as above |
| #16 | D329N | NA | To mask epitopes that are cross reactive but not cross neutralizing (ADE-inducing) B strand DIII | |
| #17 | Q227N E174N D329N | NA | Any combination of #14-#16 This can be used in combination with the dimer stabilizing mutants (#1-#7) and/or with cavity filling mutants (#10-#13) | |

KO of glycosylation site in 150 loop

| # | DENV | ZIKV | Rationality | Notes |
|---|------|------|-------------|-------|
| #18 | N153D N153Q T155N T155A D154P | N154D N154Q T156N T156A D155P | To prevent the generation of EDE2 Abs | This may skew the response towards only EDE1 Abs. The rationale here is that EDE1 antibodies bind better when there is no glycan present on E protein. In addition EDE2 antibodies, which require the glycan, appear to cause ADE in ZIKA. |

Antibody Sequences

EDE1 antibodies identified in WO 2016/012800; Rouvinski et al (2015) Nature 520, 109-113; Dejnirattisai et al (2015) Nature Immunol 16, 170-177 are considered generally to be useful for neutralising flaviviruses, for example Zika virus. For example, antibodies EDE 1 752-2 C8 (also termed EDE1 C8) and EDE 1 753(3) C10 (also termed EDE1 C10) as identified in WO 2016/012800, Rouvinski et al (2015) and/or Dejnirattisai et al (2015), are considered to be useful for neutralising flaviviruses, for example Zika virus.

Sequences for EDE1 C8 and EDE1 C10 are shown in Table A below. CRD amino acid sequences are indicated as SEQ ID NO: 15 to 26.

| Name | SEQ ID NO: | Sequence AA (H chain) | SEQ ID NO: | Sequence AA (L chain) |
|---|---|---|---|---|
| 752-2 C8 | 11 | EVQLVESGGGLVQPGGSLRLSCSAS GFTFSTYSMHWVRQAPGKGLEYVS AITGEGDSAFYADSVKGRFTISRDNS KNTLYFEMNSLRPEDTAVYYCVGG YSNFYYYYTMDVWGQGTTVTV | 13 | EIVLTQSPATLSLS PGERATLSCRASQ SISTFLAWYQHKP GQAPRLLIYDAST RATGVPARFSGSR SGTDFTLTISTLEP EDFAVYYCQQRY NWPPYTFGQGTK VEIK |
| 753(3) C10 | 12 | EVQLVESGAEVKKPGASVKVSCKAS GYTFTSYAMHWVRQAPGQRLEWM GWINAGNGNTKYSQKFQDRVTITRD TSASTAYMELSSLRSEDTAIYYCARD KVDDYGDYWFPTLWYFDYWGQGT LVTV | 14 | QSALTQPASVSGS PGQSITISCTGTSS DVGGFNYVSWFQ QHPGKAPKLMLY DVTSRPSGVSSRF SGSKSGNTASLTIS GLQAEDEADYYC SSHTSRGTWVFG GGTKLTVL |
| C8 CDR H1 | 15 | TYSMH | | |
| C8 CDR H2 | 16 | AITGEGDSAFYADSVKG | | |
| C8 CDR H3 | 17 | GYSNFYYY | | |
| C10 CDR H1 | 18 | SYAMH | | |
| C10 CDR H2 | 19 | WINAGNGNTKYSQKFQD | | |
| C10 CDR H3 | 20 | DKVDDYGDYWFPTLW | | |
| C8- CDR L1 | | | 21 | RASQSISTFLA |
| C8 CDR L2 | | | 22 | DASTRAT |
| C8 CDR L3 | | | 23 | QQRYNWPPYT |
| C10 CDR L1 | | | 24 | TGTSSDVGGFNY VS |
| C10 CDR L2 | | | 25 | DVTSRPS |
| C10 CDR L3 | | | 26 | SSHTSRGTWVF |

Figure 7:
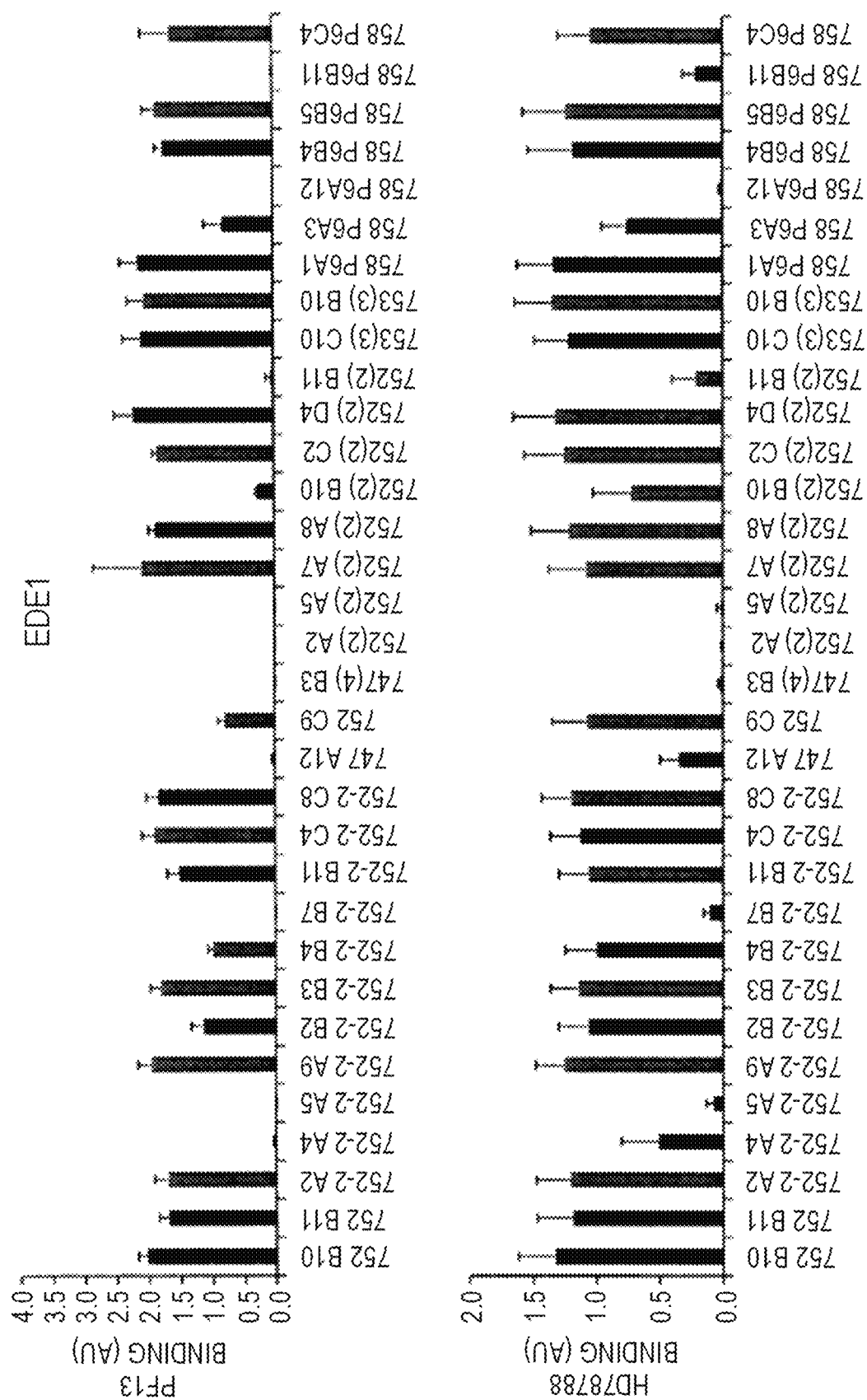

Other EDE1 antibodies that are considered to be useful are those indicated in Example 1 FIG. 7 as binding, and variants thereof. The antibodies are designated using the terminology used in WO 2016/012800.

Thus, EDE1 antibodies considered to be useful include:
752 B10
752 B11
752-2 A2
752-2 A9
752-2 B2
752-2 B3
752-2 B4
752-2 B11
752-2 C4
752-2 C8
752 C9
752(2) A7
752(2) A8
752(20 C2
752(2) D4
753(3) C10
753(3) B10
758 P6A1
758 P6A3
758 P6B4
758 P6B5
758 P6C4

Sequences are shown in WO 2016/012800 and the relevant portion of the table is inserted below. Variants may also be useful, as discussed in WO 2016/012800

| Sequence ID | epitope | SEQ ID NO: | Sequence AA (H chain) | SEQ ID NO: | Sequence AA (L chain) |
|---|---|---|---|---|---|
| 752 B10 | EDE1 | 42 | EVQLVESGGGLVQPGGSLRLSCSASGFTFSTYSMHWVRQAPGKGLEYVSAITTDGNSAFYADSVKGRFTISRDNSKNTMYFHMNSLRPEDTAVYYCVGGYSSFYYYYTMDVWGQGTTVTVSS | 88 | EIVLTQSPATLSLSAGDRATLSCRASQDISSFLAWYQQKPGQAPRLLMYDTSNRATGVPARFSGSRSGTDFTLTISTLEPEDVAVYYCQHRYNWPPYTFGQGTKVEIK |
| 752 B11 | EDE1 | 43 | QVQLVESGGGLVQPGGSLRLSCSASGFTFSTYSMHWVRQAPGKGLEYVSAITTDGDSAFYADSVKGRFTISRDNSKNTMFFHMSNLRPEDTAVYYCVGGYSSFYYYYTLDVWGQGTTVTVSS | 89 | EIVLTQSPATLSLSPGERATLSCRASQSISSFLAWYQQKPGQAPRLLIYDASNRVTGVPARFSGSRSGTDFTLTISTLEPEDFAVYYCQHRYNWPPYTFGQGTKVEIK |
| 752 C9 | EDE1 | 44 | EVQLVESEGGLVQPGGSLRLSCSASGFTFSTYSMHWVRQAPGKGLEYVSAITTNGDSTFYADSVKGRFTISRDNSKNTLYFQMSSLRAEDTGVYYCVGGYSSFYYYYTMDVWGQGTTVTVSS | 90 | EIVLTQSPATLSLSPGERATLSCRASQSISTYLAWYQQKPGQAPRLLIYDASNRATGVPARFSGSRSGTDFTLTISTLEPEDFAVYYCQQRYNWPPYTFGQGTKVEIK |
| 752 (22) A7 | EDE1 | 47 | QVQLQESGPGLVKPSQTLSLTCTVSGDSISSNNYQWNWIRQPAGKGLEWLGRIDTTGSTNYNPSLKSRISISIDTSKKQFSLRLNSVTAADTAVYYCARSLWSGELWGGPLGYWGQGTLVTVSS | 93 | EIVMTQSPATLSASPGERATLSCRASQDVSTFVAWFQQNPGQAPRLLIYDASTRAPGIPARFSGSRSGTEFTLTINSLQSEDFAVYYCQQYYNWPPWTFGQGTKVEIK |
| 752 (22) A8 | EDE1 | 48 | EVQLVESGAEVKNPGASVKVSCKASGYTFIGYYIHWVRQAPGQGLEWMGWINPNSGATYSAQKFQGRVTLTGDASPSTVYMELSSLRSDDTAIYYCAGRSYNWNDVFYYYYMDVWGQGTTVTVSS | 94 | DIQMTQSPSSVSASVGDRVTISCRASQDISASLGWYQQKPGKAPKLLIYRASNLEGGVPSRFRGSGSGTDFTLTISSLQPEDFATYYCLQANSFPLTFGGGTKVEIK |

-continued

| Sequence ID | epitope | SEQ ID NO: | Sequence AA (H chain) | SEQ ID NO: | Sequence AA (L chain) |
|---|---|---|---|---|---|
| 752 (22) B10 | EDE1 | 49 | EVQLVESGPGLVKPSETLSLTCTISGVSIS DYYWTWIRQPPGKGLEWIGNIYNTGST NYNPSLKSRVAIWMDTSKNKFSLRLTSV TSADTAVYYCARVEGGPKYYFGSGDFY NLWGRGSLVTVSS | 95 | DIQMTQSPSSLSA SVGDSVTVACRA SQPIYRNLNWYQ QKPGKAPKLLIYD ASTLQSGVPARFS GSGSGTDFTLTISS LQAEDFATYYCQ QSYSSPRTFGQGT KVEIK |
| 752 (22) C2 | EDE1 | 50 | SQVQLVQSGAELKKPGASVKVSCKTSG YTFSYYIHWVRQAPGQGLEWMAMINPT SGSTSYAQRFQGRVTMTRDTPTNTVYM EVRSLRSDDTAVYFCASRGYNWNDVQY YYTMDVWGQGTTVTVSS | 96 | DIQMTQSPSTLSA SVGDRVTITCRAS QSISTYLAWYQQK PGKAPKLLIYKAS SLEIGVPSRFSGSG SGTEFTLTISSLQP DDDFAIYYCQQYN NYSPPVTFGGGTK VEIK |
| 752 (22) D4 | EDE1 | 51 | SEVQLVQSGAELKKPGASVKVSCKASG YTFSYYIHWVRQAPGQGLEWMAIINPTS GSTSYAQRFQGRVTMTRDTSTNTVYME LSSLISEDTAVYYCASRGYNWNDVHYY YTMDVWGQGTTVTVSS | 97 | DIQMTQSPSTLSA SVGDRVTITCRAS QSISTYLAWYQQK PGKAPKLLIYKAS TLESGVPLRFSGS GSGTEFTLTISSLQ PDDFAIYYCQQYN NYSPPVTFGGGTK VEIK |
| 752-2 A2 | EDE1 | 53 | QVQLVESGGGLVQPGGSLRLSCSASGFT FSTYSMHWVRQAPGKGLEYISAITTDGD SAFYADSVKGRFTISRDNSKNTMYFHM NSLRPEDTAVYYCVGGYSSFYYYYTMD VWGQGTTVTVSS | 99 | EIVLTQSPATLSLS AGERATLSCRASQ SISSYLAWYQQKP GQAPRLLIYDASN RATGVPARFSGSQ SGTDFTLTISTLEP EDFAVYYCQLRY NWPPYTFGQGTK VEIK |
| 752-2 A9 | EDE1 | 56 | EVQLVESGGGLVQPGGSLRLSCSASGFT FSTYSMHWVRQAPGKGLEYVSAITTDG DSAFYADSVKGRFTISRDNSKNTMYFH MNSVRPEDTAVYYCVGGYSSFYYYYTM DVWGQGTTVTVSS | 102 | EIVLTQSPATLSLS AGERATLSCRASQ DISTFLAWYQQKP GQAPRLLIYDTST RATGVPARFSGSR SGTDFTLTITTLEP EDFAVYYCQHRY NWPPYTFGQGTK VEIK |
| 752-2 B2 | EDE1 | 57 | EVQLVESGGGLVQPGGSLRLSCSASGFT FSTYSMHWVRQAPGKGLEYVSAITTDG DSAFYADSVKGRFTISRDNSKNTMYFH MNSLRPEDTAVYYCVGGYSSFYYYYTM DVWGQGTTVTVSS | 103 | EIVLTQSPATLSLS AGERATLSCRASQ SISSYLAWYQQKP GQAPRLLIYDASN RATGVPARFSGSR SGTDFTLTISTLEP EDFAVYYCQHRY NWPPYTFGQGTK VEIK |
| 752-2 B3 | EDE1 | 58 | EVQLLESGGGLVQPGGSLRLSCSASGFT FSTYSMHWVRQAPGKGLEYVSAISTDG DSAFYADSVKGRFTISRDNSKNTLYFHM SSLRAEDTAVYYCLGGYSTFYYYYTMD VWGQGTTVTVSS | 104 | EIVLTQSPATLSLS PGERATLSCRASH SISTFLAWYQQKP GQAPRLLIYDTST RATGVPARFSGSR SGTDFTLTINTLEP EDFAVYYCQQRY NWPPYTFGQGTK VEIK |
| 752-2 B4 | EDE1 | 59 | QVQLVESGGGLVQPGGSLRLSCSASGFP FSTYSMHWVRQAPGKGLEYVSAITTNG DSTFYADSVKGRFTISRDNSKNTVYFQL SSLRAEDTAVYYCVGGYSSFYFYYTMD VW | 105 | EIVLTQSPATLSLS PGERATLSCRASQ SISSFLAWYQQKP GQAPRLLIYDTSN RATGVPARFSGSR SGTDFTLTISTLEP |

-continued

| Sequence ID | epitope | SEQ ID NO: | Sequence AA (H chain) | SEQ ID NO: | Sequence AA (L chain) |
|---|---|---|---|---|---|
| | | | | | EDFAIYYCQHRYN WPPYTFGQGTKV EIK |
| 752-2 B11 | EDE1 | 61 | EVQLVESGGGLVQPGGSLRLSCSASGFT FTTYSLHWVRQTPGKGLEYVSAITTDGD SAFYADSVKGRFTISRDNSKNTMYFHMS SLRPEDTAVYYCVGGYSSFYYFYTVDV WGQGTTVTVSF | 107 | EIVLTQSPATLSLS PGERATLSCRASQ SISTYLVWYQQKP GQAPRLLIYDAST RATGVPARFSGSR SGTDFTLTISTLEP EDFAVYYCQHRY NWPPYTFGRGTK VEIK |
| 752-2 C4 | EDE1 | 62 | SQVQLVESGAELKKPGASVKVSCKASG YTFSYYMHWVRQAPGQGLEWMAIINPT SGSTTYAQRFQGRVTMTRDTSTSTVYM ELSSLRSEDTAVYYCASRGYNWNDVHY YYTMDVWGQGTTVTVSS | 108 | DIQMTQSPSTLSA SVGDRVTITCRAS QSISTYLAWYQQK VGKAPKLLIYKAS TLEGGVPSRFSGS GSGTEFTLTISSLQ PEDFAIYYCQQYN NYSPPVTFGGGTK VEIK |
| 752-2 C8 | EDE1 | 1 | EVQLVESGGGLVQPGGSLRLSCSASGFT FSTYSMHWVRQAPGKGLEYVSAITGEG DSAFYADSVKGRFTISRDNSKNTLYFEM NSLRPEDTAVYYCVGGYSNFYYYYTMD VWGQGTTVTVSS | 37 | EIVLTQSPATLSLS PGERATLSCRASQ SISTFLAWYQHKP GQAPRLLIYDAST RATGVPARFSGSR SGTDFTLTISTLEP EDFAVYYCQQRY NWPPYTFGQGTK VEIK |
| 753 (3) C10 | EDE1 | 2 | EVQLVESGAEVKKPGASVKVSCKASGY TFTSYAMHWVRQAPGQRLEWMGWINA GNGNTKYSQKFQDRVTITRDTSASTAY MELSSLRSEDTAIYYCARDKVDDYGDY WFPTLWYFDYWGQGTLVTVSS | 38 | QSALTQPASVSGS PGQSITISCTGTSS DVGGFNYVSWFQ QHPGKAPKLMLY DVTSRPGVSSRF SGSKSGNTASLTIS GLQAEDEADYYC SSHTSRGTWVFG GGTKLTVL |
| 753 (3) B10 | EDE1 | 63 | EVQLVESGPEVKKPGASVKVSCKTSGYT FINYYIHWVRQAPGQGLEWLGLINPRGG NTNYAEKFEDRVTMTRDTSTSTVNMEL SSLTSEDTAVYYCARPLAHTYDFWSGY HRATGYGMDVWGQGTTVTVSS | 109 | DIVMTQSPLSLSV TPGEPASISCRSSQ SLVYSDGNKYLD WYVQKPGQSPQL LIYLTSTRASGVP DRFSGSASGTDFT LKISRVEAEDVGL YYCMQALQTPFT FGPGTKVDIK |
| 758 P6A1 | EDE1 | 64 | EVQLVESGGGLVQPGGSLRLSCAAFGFT FVNYAMNWVRQAPGKGPEWVAVIYAA GDGANYGDSVKGRFTISRDNSRNTLYLQ MNSLRAEDTAIYYCAKPAHYDDSGYPY MAYFDSWGQGTLVTVSS | 110 | EIVMTQSPATLSV SPGERATLTCRAS QTISTFLAWYQQK PGQPPRLLIYDTST RATGIPGRFSGSRS GTEFTLTISSLQSE DVAVYYCQHYYN WPPWTFGQGTKV EIK |
| 758 P6A3 | EDE1 | 65 | QVQLVQSGAEVKKPGSSVKVSCKASGG FFSSYAITWVRQAPGQGLEWMGGIIPDY DSAKYAQKFQGRVTITADESTSTAYLEL RSLRSEDTAVYYCARRHCSSTSCSDPWT FFPSWGQGTLVTSPQ | 111 | QSALTQPPSASGS PGQSVTISCTGSSS DIGGNEYVSWYQ LQPGKAPKLMIYE VTKRPSGVPNRFS GSKSGNTASLTVS GLQSEDEGDYYC SSYADNSVLFGGG TTLTVL |
| 758 P6B4 | EDE1 | 67 | EVQLVQSGATVRKPGASVTISCKTSGYT FTDYALHWVRQAPGQRLEWMGWLIPG | 113 | EIVLTQSPVTLSLS PGERATLSCRASQ |

| Sequence ID | epitope | SEQ ID NO: | Sequence AA (H chain) | SEQ ID NO: | Sequence AA (L chain) |
|---|---|---|---|---|---|
| | | | SGYTKFAENFQGRVTITRATSAHTAYME LSNLRSEDTAVYYCARWGGDCNAGSCY GPYQYRGLDAWGQGTTVTVSS | | TVDSTYLAWYQQ KPGRAPRLLIYGA SNRAIGVPSRFTG SGSGTDFTLTISRL EPEDFALYYCQQS DGSLFTFGPGTKV DIK |
| 758 P6B5 | EDE1 | 68 | EVQLVQSGAEVKKPGASVKVSCKASGY SFIGYYLHWVRQAPGQGLEWMGRINPN SGGIDYGQTFQGRVTMTRDMSSSTVYLE LTRLRSDDTARYYCAGRSDNWNDVYY NYALDVWGQGTTVTVSS | 114 | DIQMTQSPASVSA SVGDRVTISCRAS QGIASWLAWYQQ KPGKAPRLLIYGA SSLQSGVPSRFRG SGSGTDFTLTISSL QPEDFATYYCQQ ANSFPFTFGPGTK VDIK |
| 758 P6C4 | EDE1 | 70 | QVQLVQSGAEVKKPGASVKVSCKASGY TFTAYYIHWVRQAPGQGLEWMGSINPN NGGTNYAQGFQGRVTMTRDTSIRTVYM ELSKLRSDDTALYYCARDLGAMGYYLC SAGNCPFDYWGQGTLVTVSS | 116 | QSALTQPPSASGS PGQSVTISCTGTSS DVGGYNYVSWY QHHPGKAPKLIIY EVSKRPSGVPHRF SGSKSGNTASLTV SGLQAEDEAEYY CSSYAGSNTFTFG GGTKLTVL |

FIGURE LEGENDS

Figure 1B:
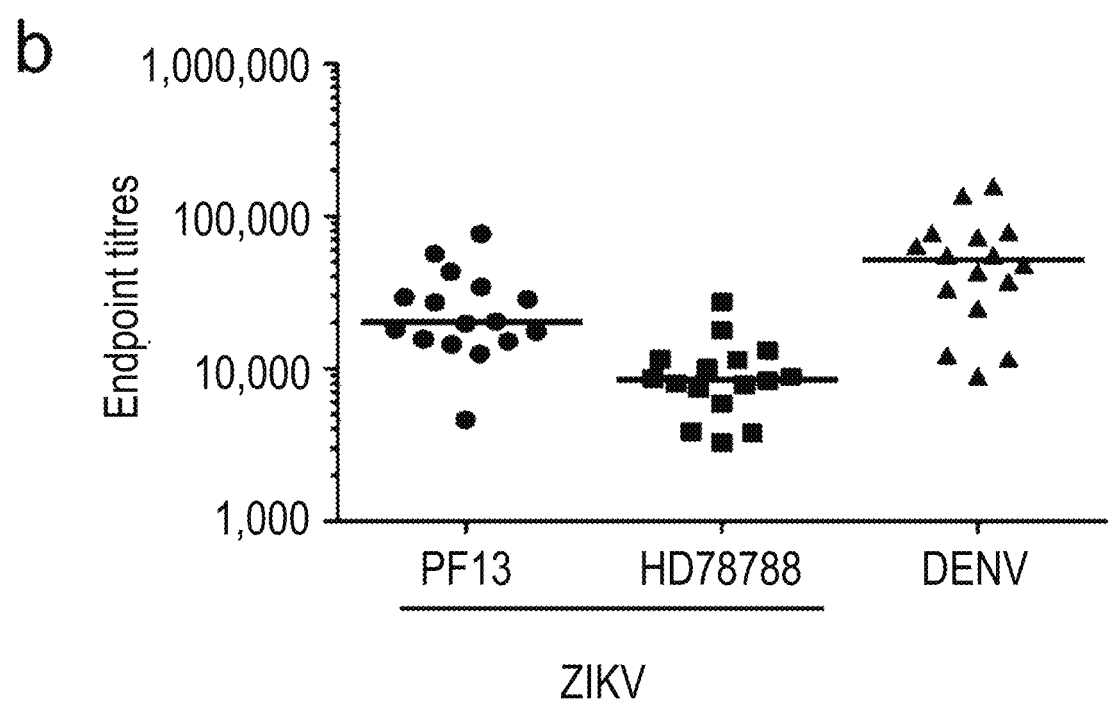

Example 1:

FIGS. 1A and 1B. DENV immune plasma crossreacts with ZIKV.

FIG. 1A Binding titration curves of 6 representative DENV sera against ZIKV strains PF13 and HD78788 and DENV measured by capture ELISA (6-month convalescent plasma using the DENV serotype corresponding to their previous acute infection). FIG. 1B End point titers of DENV plasma against ZIKV (strain PF13 and HD78788) and DENV determined by capture ELISA (n=18). Small horizontal lines indicate the median values.

Figure 2A:
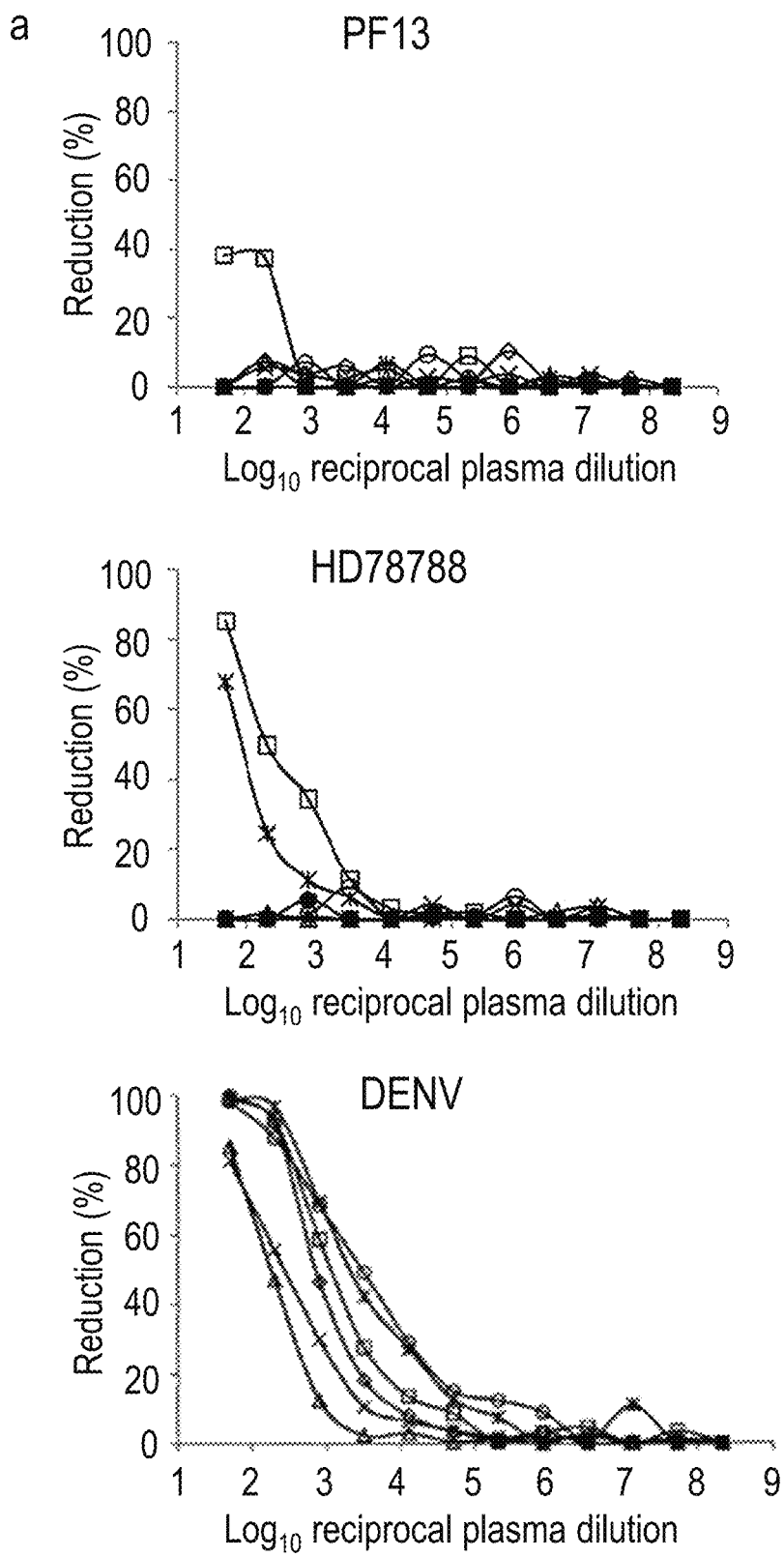
Figure 2B:
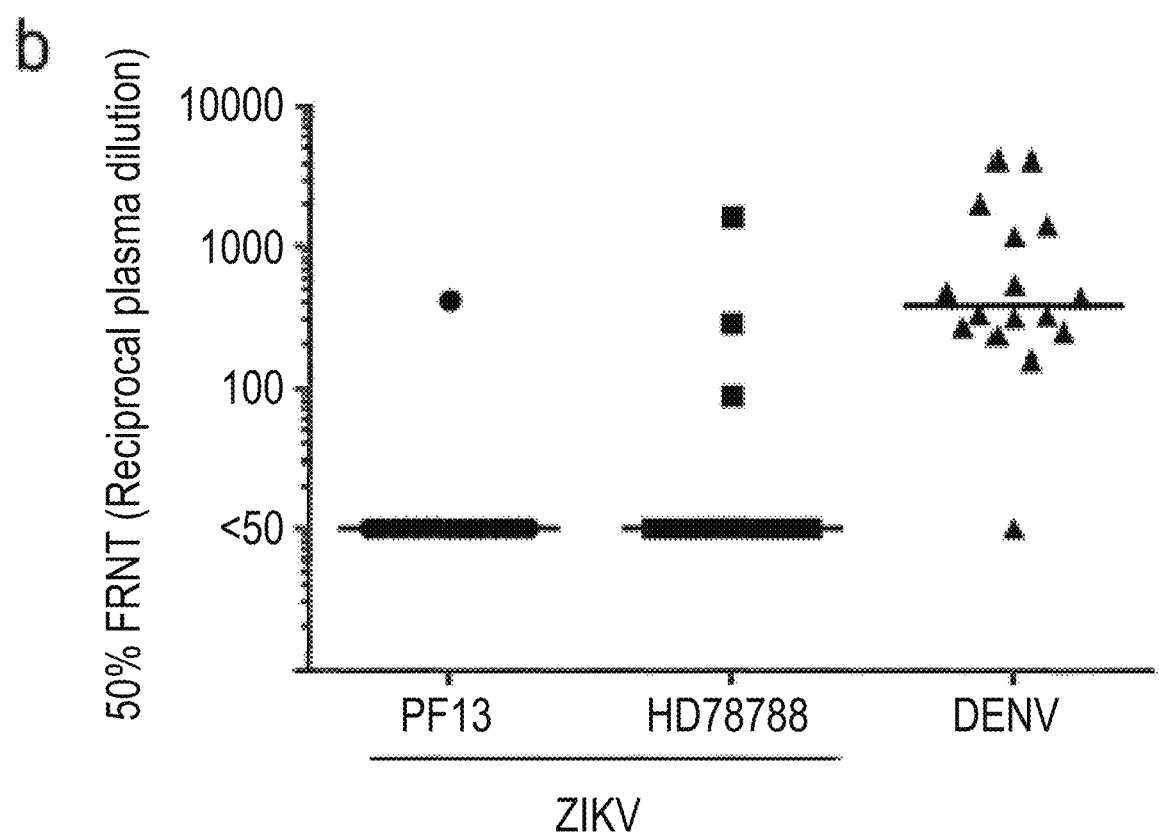

FIGS. 2A and 2B. Neutralization of ZIKV by DENV immune plasma.

FIG. 2A Neutralization of ZIKV determined on Vero cells for 6 representative DENV plasma with 2 ZIKV strains PF13 and HD78788 and DENV (6-month convalescent plasma using the DENV serotype corresponding to their recent infection). Pooled DENV negative serum (PND) was used as negative control. FIG. 2B NT50 values for DENV plasma on ZIKV and DENV infection (n=18).

Figure 3B:
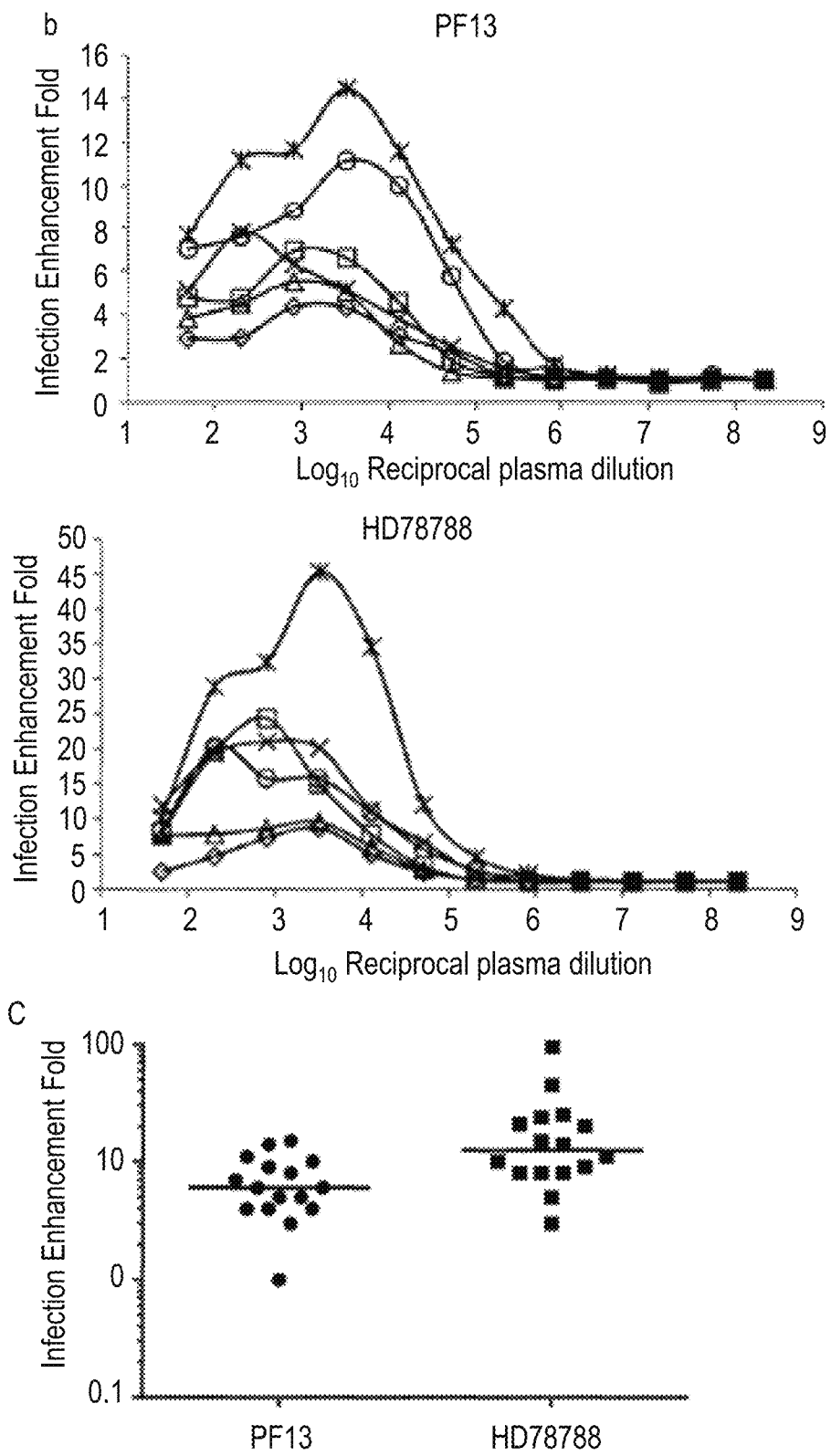

FIGS. 3A and 3B. DENV plasma enhances ZIKV infection.

FIG. 3A Six representative ADE curves of U937 cells infected with ZIKV strains PF13 and HD78788 and DENV (6-month convalescent plasma using the DENV serotype corresponding to their recent infection) in the presence of serially diluted DENV plasma. Pooled negative serum (PND) was used as negative control. FIGS. 3B Peak fold enhancement of DENV plasma on ZIKV and DENV (n=18).

Figure 4A:
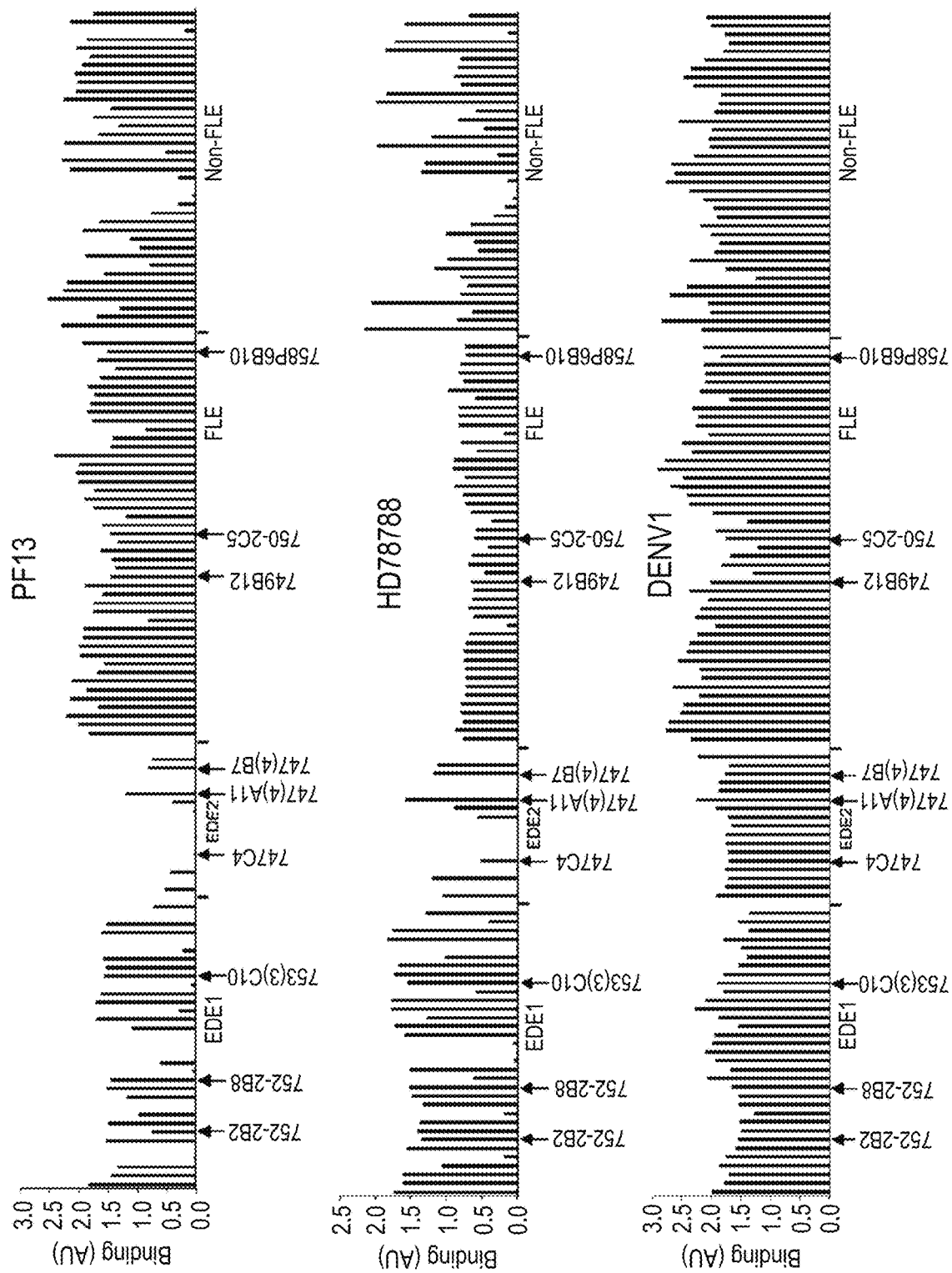
Figure 4B:
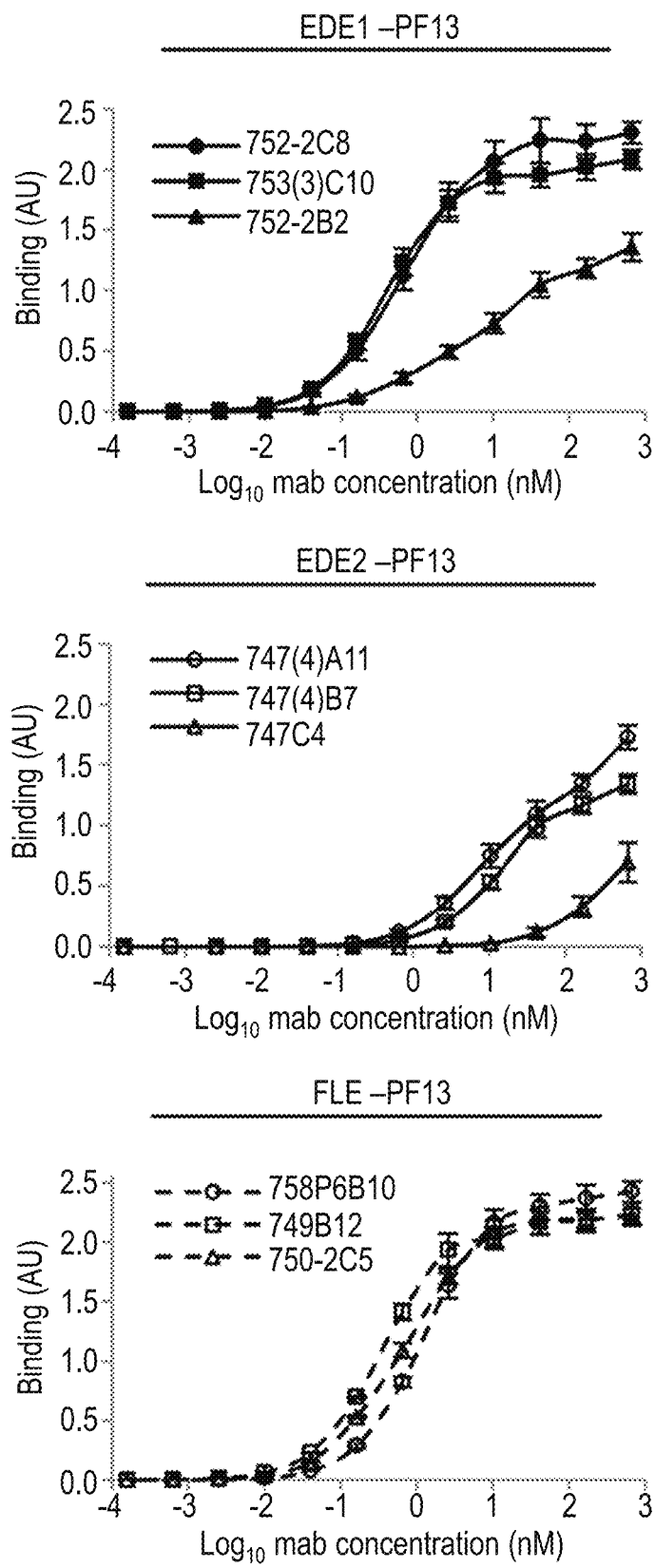
Figure 4C:
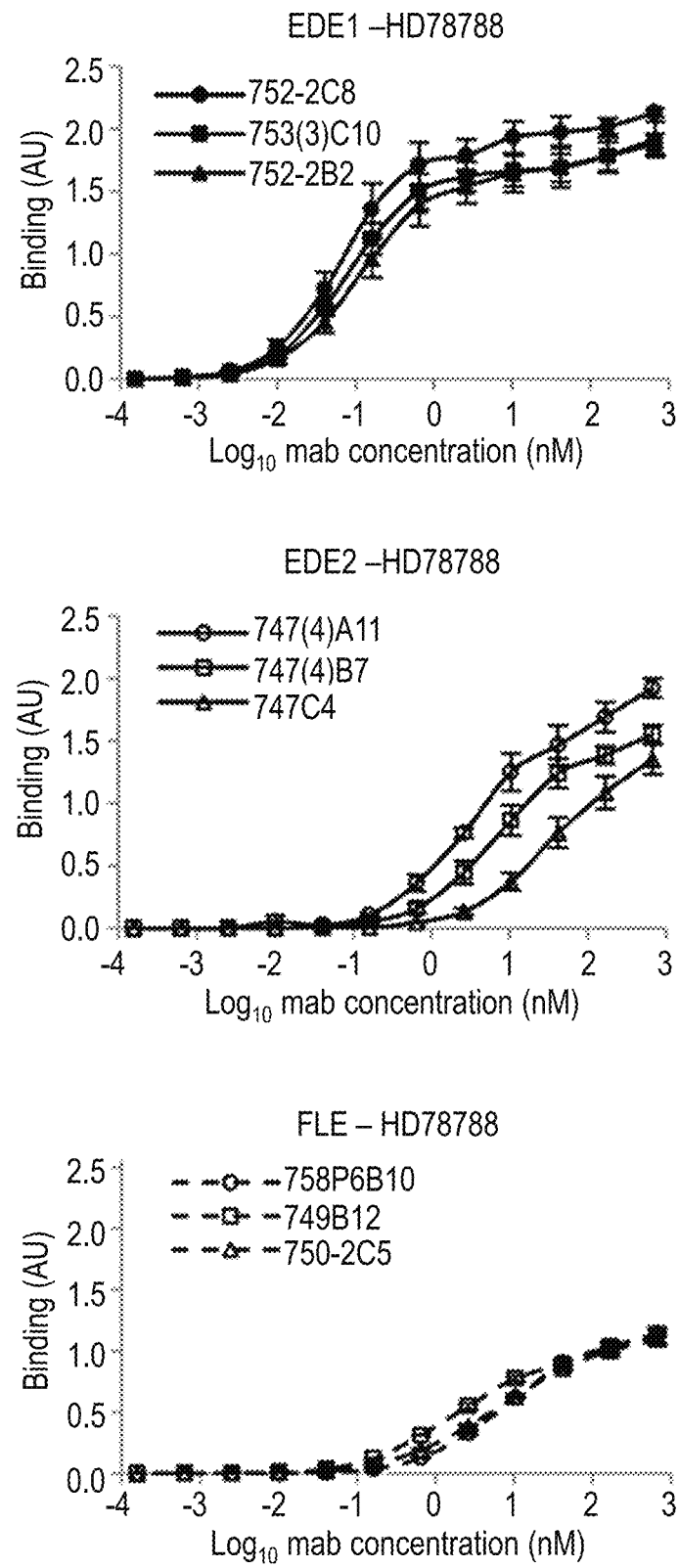

FIGS. 4A-4C. anti-DENV human monoclonal antibodies bind to ZIKV.

FIG. 4A Binding of ZIKV strains PF13 and HD78788 and DENV serotype 1 by 33, 17, 45, 37 of anti-EDE1, EDE2, FLE and non-FLE mAbs at 10 ug/ml, this is representative of three separate experiments. The arrows indicated mAbs used in FIGS. 4B, 4C, 5A-5C, and 6A-6C. FIGS. 4B and 4C Binding titration curves for 9 representative mAbs (3 each for anti-EDE1, EDE2, and FLE mAbs). The assays were done by capture ELISA and shown as mean±2SE from 3 independent experiments.

Figure 5A:
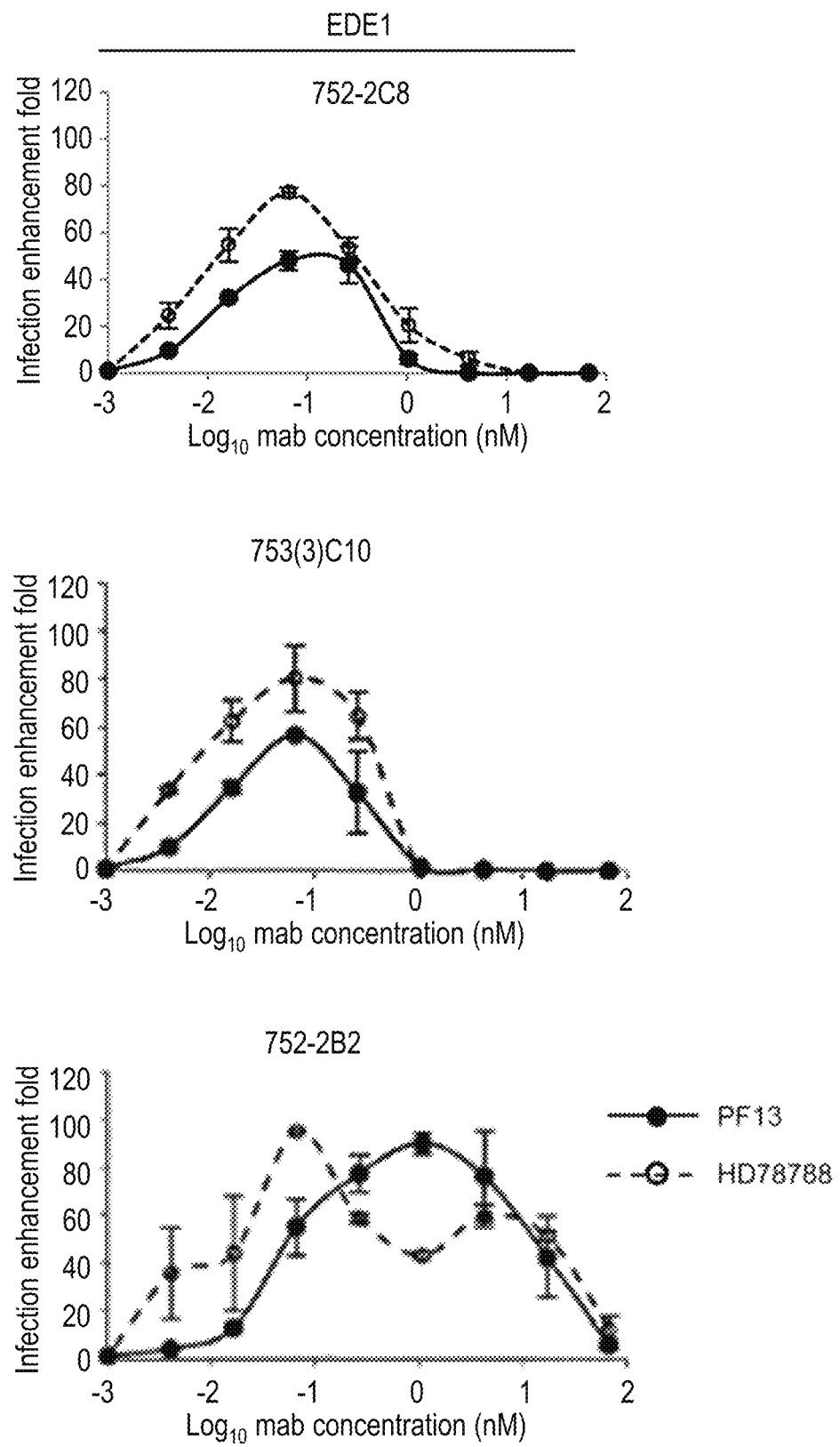
Figure 5B:
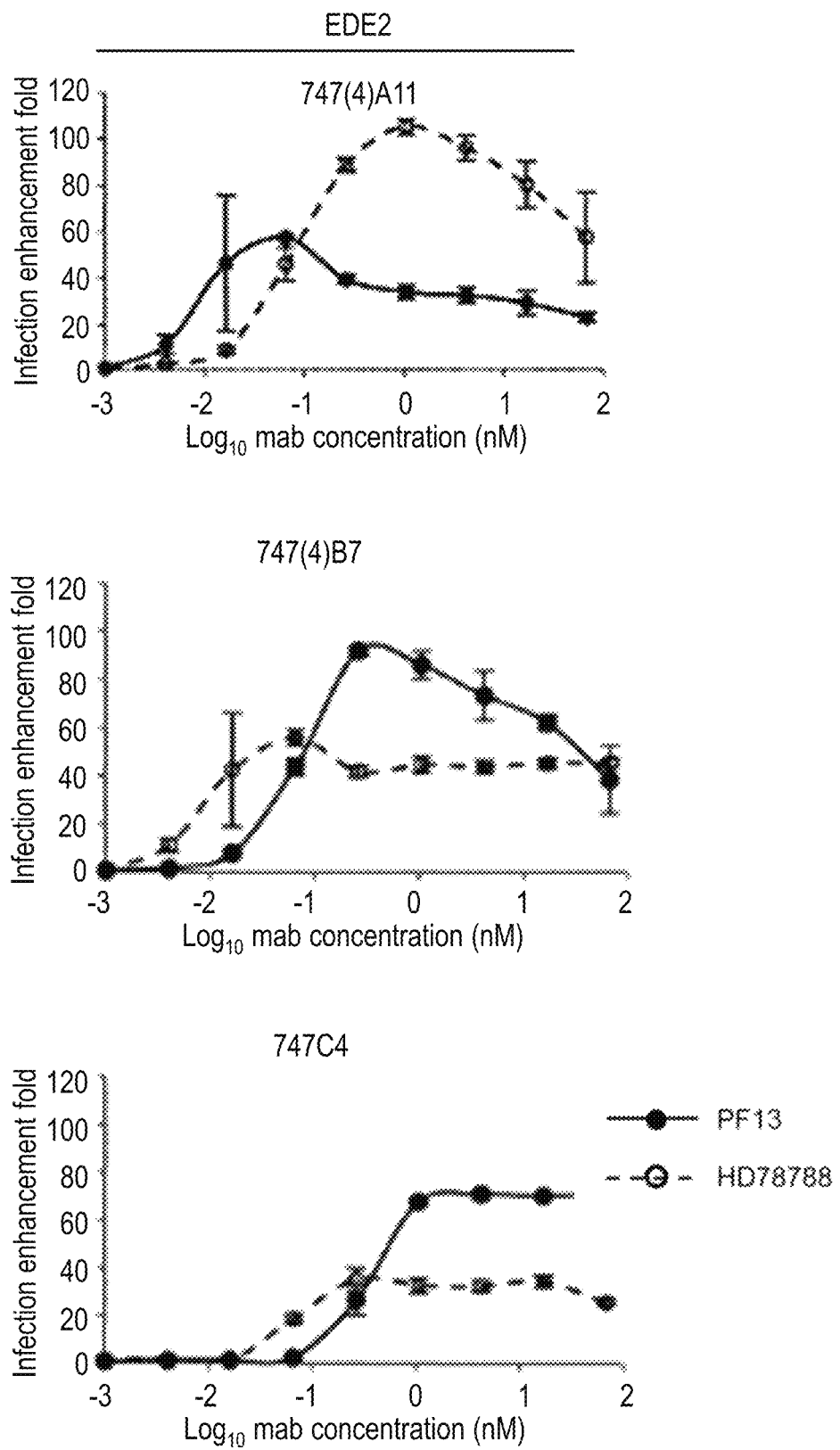
Figure 5C:
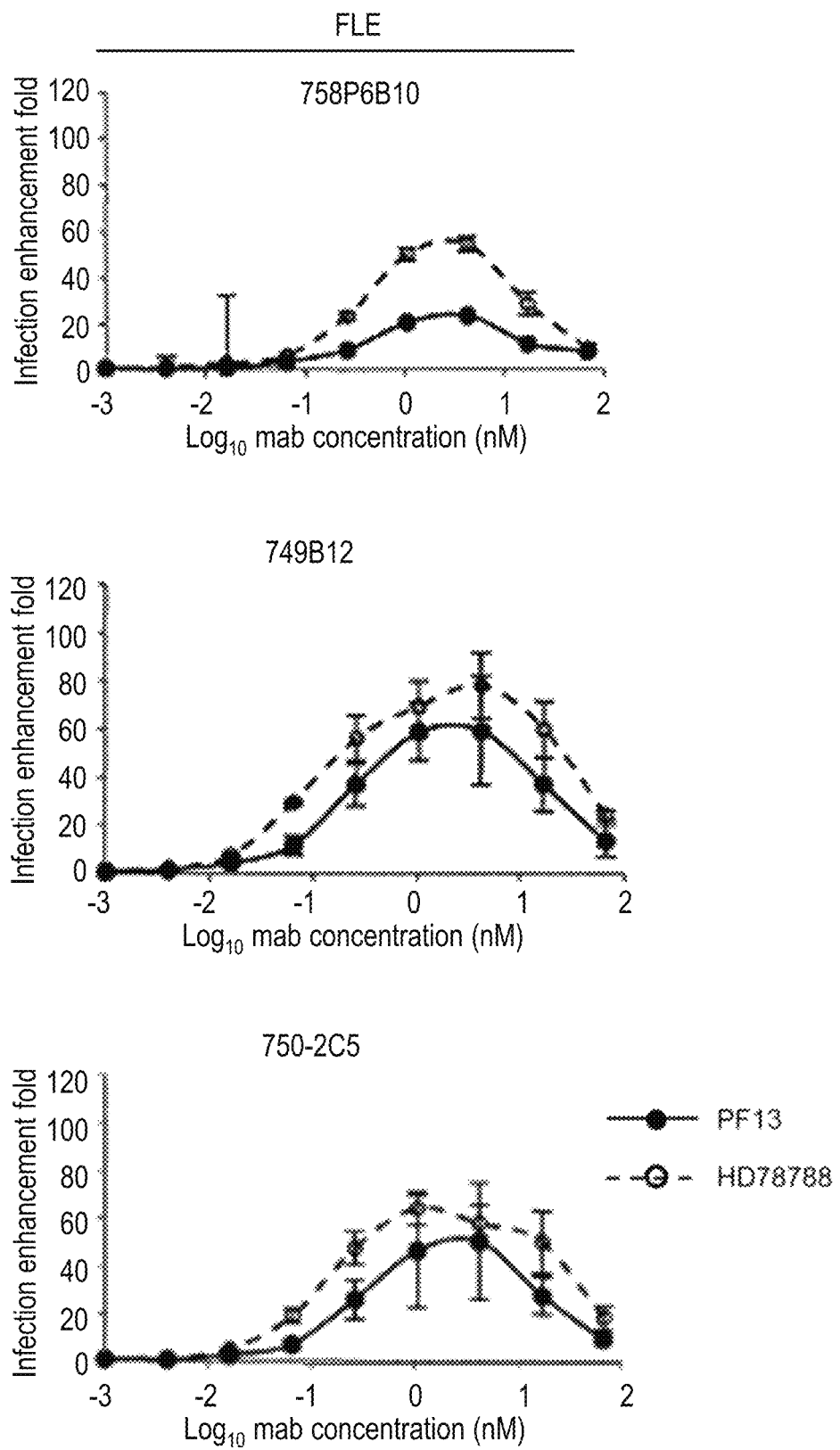

FIGS. 5A-5C. anti-DENV human monoclonal antibodies enhance ZIKV infection.

Infection enhancement curves of 9 anti-DENV mAbs (3 each for anti-EDE1, EDE2, and FLE mAbs) on ZIKV strains PF13 and HD78788. U937 cells were used as target cells. The data are shown as mean±2SE from 2 independent experiments.

Figure 6A:
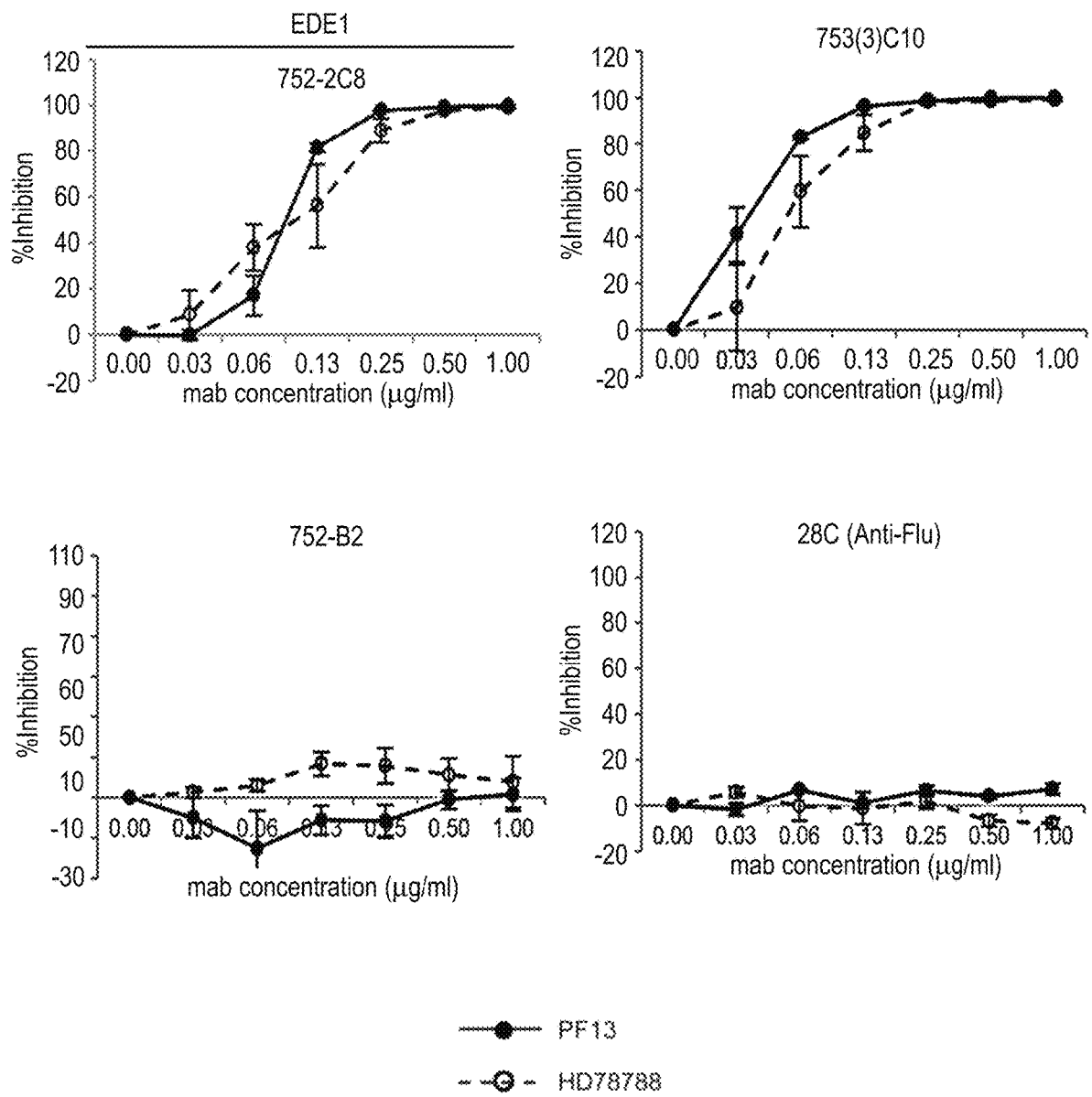
Figure 6B:
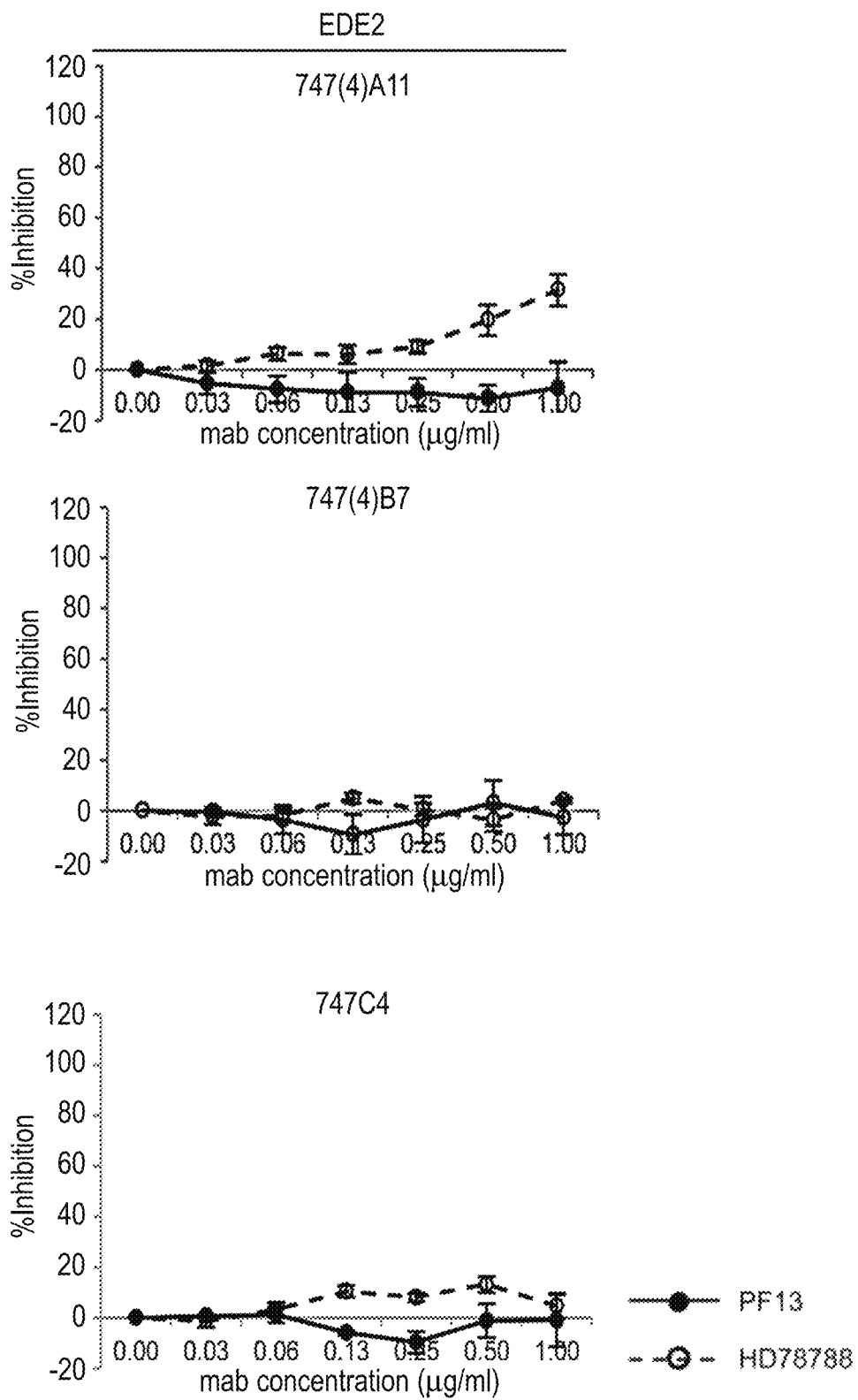
Figure 6C:
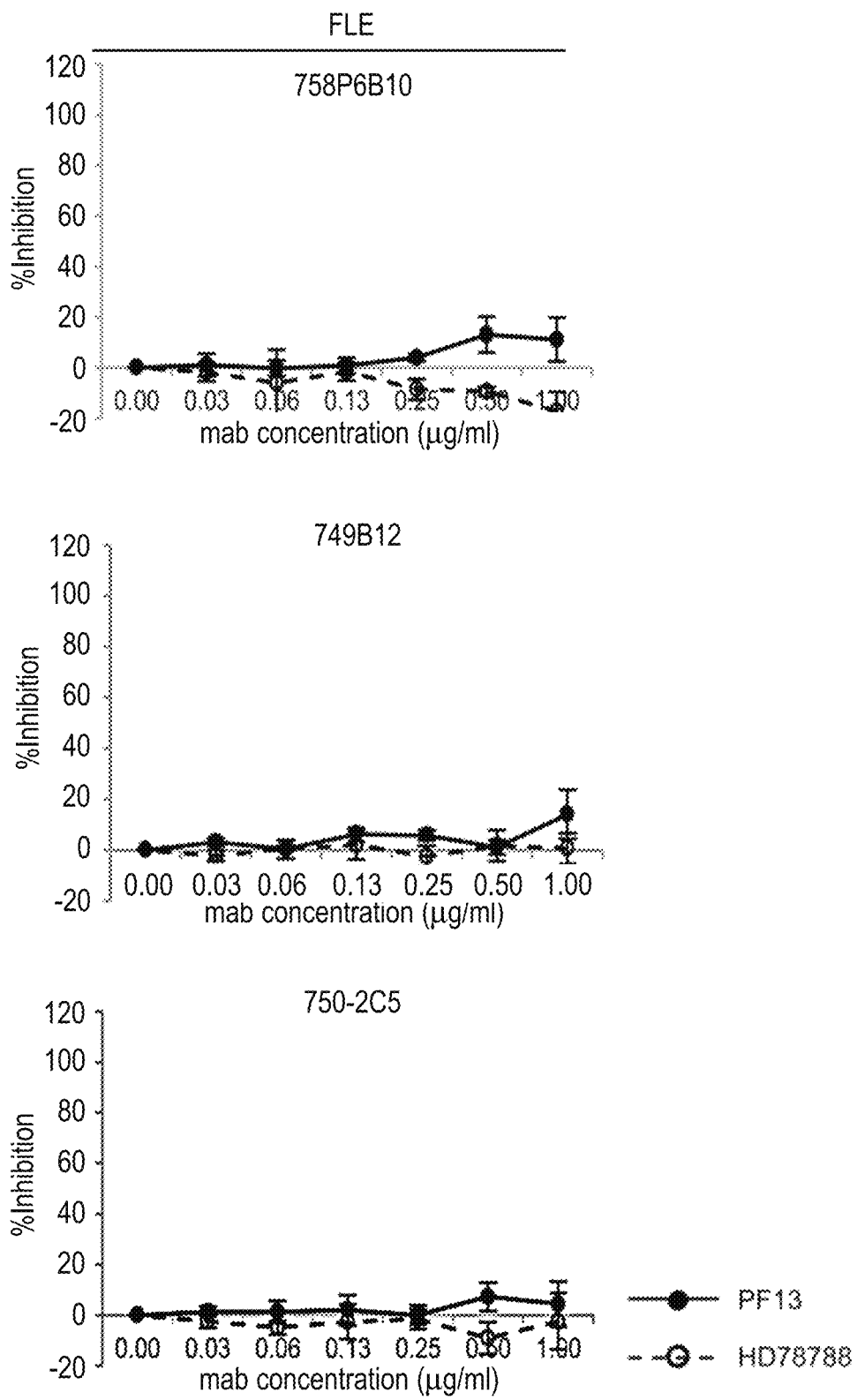

FIGS. 6A-6C. anti-EDE1 human monoclonal antibodies inhibit ADE of DENV plasma.

The inhibition curves of 9 anti-DENV mAbs 3 each for anti-EDE1, EDE2, and FLE mAbs) on ZIKV strains PF13 and HD78788. U937 cells were infected with ZIKV in the presence of 1:1000 pooled convalescent dengue serum (the dilution giving peak enhancement) together with serially diluted anti-DENV mAbs. Anti-flu mAb, 28C, was used as a negative control. The data are representative of 3 independent experiments.

FIG. 7. EDE1 antibody binding to Zika virus strains PF13 and HD78788. Antibody designations are as used in WO 2016/012800.

Example 2 Figure Legends:

FIGS. 8A and 8B: ZIKV/DENV E protein phylogeny and reactivity with DENV-elicited antibodies. FIGS. 8A, Phylogenetic trees of the main human pathogenic flaviviruses based on the amino acid sequences of the E protein (left panel) and of the polymerase NS5 protein (right panel). The arthropod vectors are differentiated by the background color. FIGS. 8B, ZIKV sE reactivity with human recombinant IgG mAbs FLE P6B10, EDE1 C8 and EDE2 A11. Left panel: Binding properties were monitored by Biolayer interferometry on Octet RED (ForteBio). Normalized response values at inferred equilibrium were deduced from individual sensograms of binding monitored at different ZIKV sE concentration (see right panel for EDE1 C8). The response values expressed as fraction of binding site occupancy are plotted against concentrations of ZIKV sE dimer shown at logarithmic scale. Lines denote global curve fits used for Kd evaluation (see FIGS. 13A and 13B for linear concentration range showing concentration dependent saturation fits). Right panel: Binding and dissociation kinetics of ZIKV sE dimer in solution to human IgG1 C8 immobilized on anti-human IgG Fc capture biosensors; shown are individual sensograms of 2-fold serial dilutions of ZIKV sE (as indicated). See also FIG. 13A.

Figure 9:
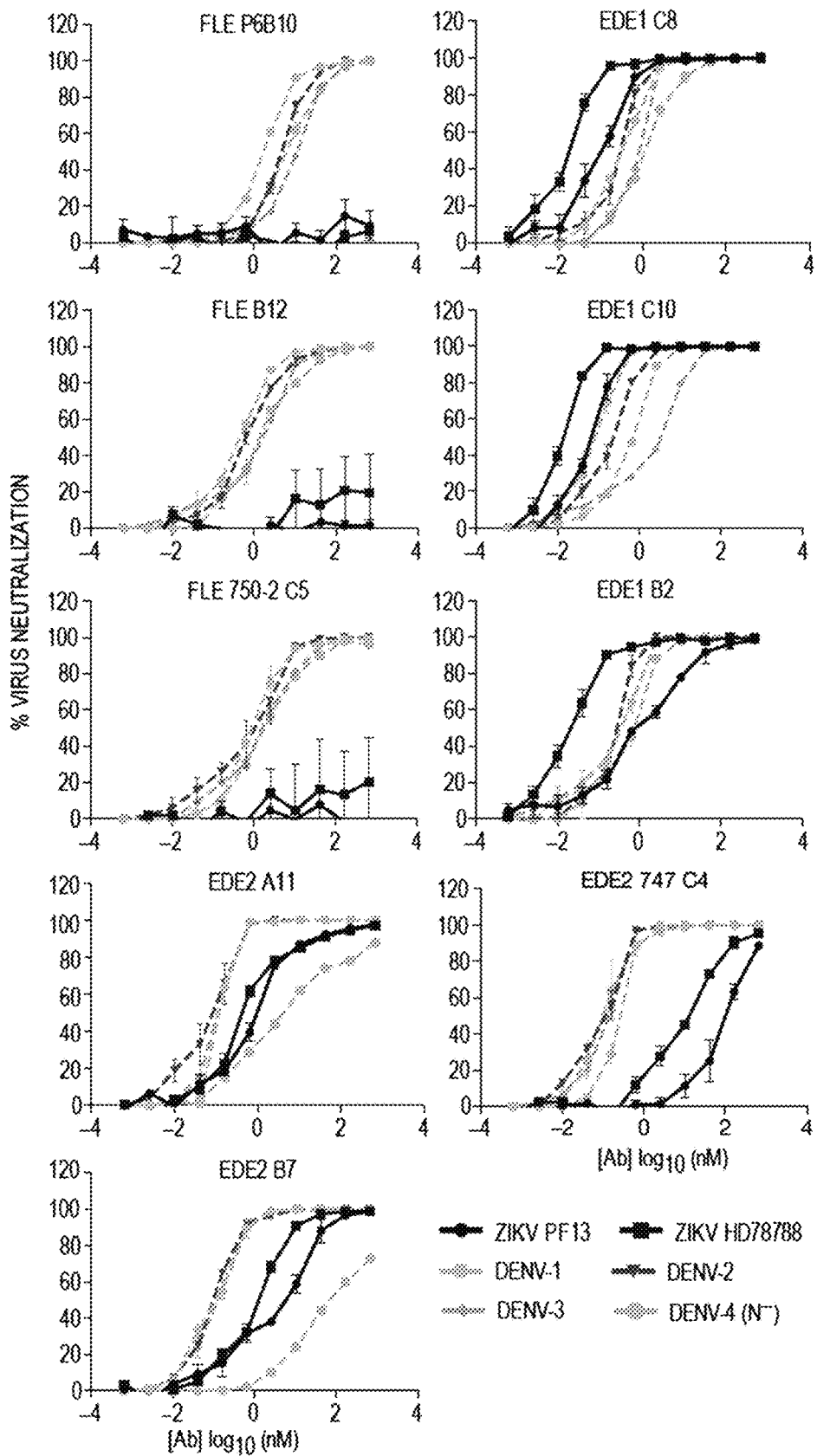

FIG. 9: Neutralization curves using three antibodies each from the three subsets FLE, EDE1 and EDE2. The results represent the mean of four independent experiments done each in triplicate for PF13 and duplicate for HD78788 strains. The two ZIKV strains are in bright colors, red and blue. The neutralization data for the 4 DENV serotypes (pale colors) were taken from ref[27], and are given here for comparison. The corresponding 50% FRNT values are provided in FIG. 12. Note that the DENV4 strain used was a natural isolate lacking the N153 glycosylation site.

FIGS. 10A-10F: EDE1 C8/ZIKV sE complex. FIG. 10A overall view of the complex, with the sE moiety colored according to domains (domains I, II and III in red, yellow and blue, respectively, and the fusion loop in orange) and the antibodies colored grey and dark green for light and heavy chains, respectively. The CDRs are distinguished by different colors labeled in b in the corresponding color (H1 light blue, H2 sand, H3 pink, L1 light gray, L2 red, L3 orange). The inset shows a comparison with the corresponding DENV-2 complex. The antibodies are in yellow and sE in grey. For clarity, the variable region of the C8 Fab fragment of the DENV2-C8 complex was superposed on the scFv in complex with ZIKV sE in order to draw the Fab axis and better show the binding angles. These angles look different because of the difference in curvature in the two crystal structures. FIG. 10B Zoom of the EDE1 C8/sE interaction to show the recognition of the b strand. Hydrogen bonds are shown as dotted lines and immobilized water molecules at the interface as red spheres. FIG. 10C Same region on the DENV-2 sE/C8 Fab complex. Note that the N67 glycan on DENV also interacts with the antibody. FIG. 10D The footprint of EDE1 C8 is outlined on ZIKV sE dimer shown in surface representation (looking from outside the virion) colored according to conservation of surface exposed amino acids. Main chain atoms and atoms from conserved side chains are colored orange, highly similar side chains are yellow and all the other atoms are white. FIGS. 10E and 10F Footprints of EDE1 C8 on a surface representation of ZIKV sE FIG. 10E and DENV2 sE FIG. 10F shown in pink. The two protomers of sE in the dimer are in light and dark gray for clarity. Relevant antigenic sE regions are labeled. Note the more confined interacting surface in ZIKV sE dimer than DENV2, eg N67 glycan is absent in ZIKV sE.

FIGS. 11A-11E: EDE2 A11/ZIKV sE complex. Color coding is as in FIGS. 10A-10F. FIG. 11A Overall view of the complex, with only one Fab bound per sE dimer, due to crystal packing. The dashed ellipse represents the position of the missing A11 Fab. The inset compares the angle of binding to the sE dimer in ZIKV and in DENV-2. FIG. 11B Interactions at the b strand in ZIKV (left panel) and FIG. 11C in DENV-2 (right panel). Note the different angle of the b strand with respect to the antibody (the antibody is exactly in the same orientation in both panels) FIGS. 11D and 11E Zoom of the glycan on the 150 loop for ZIKV sE (FIG. 11D) and for DENV-2 sE (FIG. 11E), with sugar residue numbers described in the key. The CDR H3 helix is too far to make interactions with the glycan, as is the case in the DENV-2 structure (see FIGS. 15 and 18B).

FIGS. 13A and 13B: Antibody binding to recombinant ZIKV protein. FIG. 13A Biolayer interferometry experiments plotted on a linear scale. The antibodies were immobilized on the biosensor tip, and the ZIKV sE protein was in solution at the indicated concentrations. The antibody used is indicated in each plot. Note that the horizontal scale is different for the three antibodies. The estimated dissociation constant (Kd) and the estimated dissociation rate (Koff) are indicated. FIG. 13B Size exclusion chromatography results for isolated sE, isolated Fab fragments, and ZIKV sE+Fab fragments, as indicated.

FIG. 14. Residues involved in bnAB/antigen interactions. Antibody contacts on the amino acid sequence alignment of ZIKV and DENV-2 sE. A red background highlights identical residues. Secondary structure elements are indicated together with their labels above (ZIKV) and below (DENV-2) the sequences. The domain organization of ZIKV and DENV-2 sE is symbolized by a colored bar above the sequences (domain I red, domain II yellow, domain III blue and the fusion loop orange). Residues involved in polar and van der Waals protein-protein contacts are marked using blue and green symbols, respectively, as indicated in the inset key, displayed above and below the alignment for ZIKV and DENV-2 sE, respectively. Full and empty symbols correspond to antibody contacts on the reference subunit of sE (defined as the one contributing the fusion loop to the epitope) and the opposite subunit of sE, respectively. Residues contacted only by the heavy or light chain are marked with squares or triangles, respectively, and those contacted by both antibody chains with circles. The details of the amino acid contacts are listed in the ED Tables 4 and 5. Dots above the sequences mark every 10 residues on the ZIKV sE sequence. Disulfide bridges are numbered in green above the sequences.

FIG. 15. Amino acid sequence of the heavy and light chains variable domains (vH and vL) of bnAbs EDE1 C8 (top) and EDE2 A11 (bottom) with the framework (FRW) indicated by black bars and IMGT CDR regions by thin dashed lines. The secondary structure elements of the Ig vH and vL β-barrels are indicated above the sequences. Somatic mutations are in red and residues arising from recombination at the V-D-J junction are in green. Symbols above and below the sequences mark residues involved in contacts with ZIKV and DENV-2 sE, respectively, coded for the contacted site in sE as indicated in the key (inset at the bottom). Polar and van der Waals contacts are shown in blue and green, respectively. The antibody residues contacting the reference sE subunit (defined as the one contributing the fusion loop to the epitope) are marked by plain color symbols while those making contact across the dimer interface by empty colored symbols. Red boxes highlight the contacts found in the DENV-2 sE complex and absent in the ZIKV sE complex, involving N67 glycan, kl and 150 loops. The details of the polar contacts are listed in FIGS. 19 and 20 (see also FIGS. 10E and 10F). The predicted vH and vL germline alleles are indicated with the corresponding CDR lengths (see Table 1 in ref[30]).

Figure 16A:
Figure 16B:
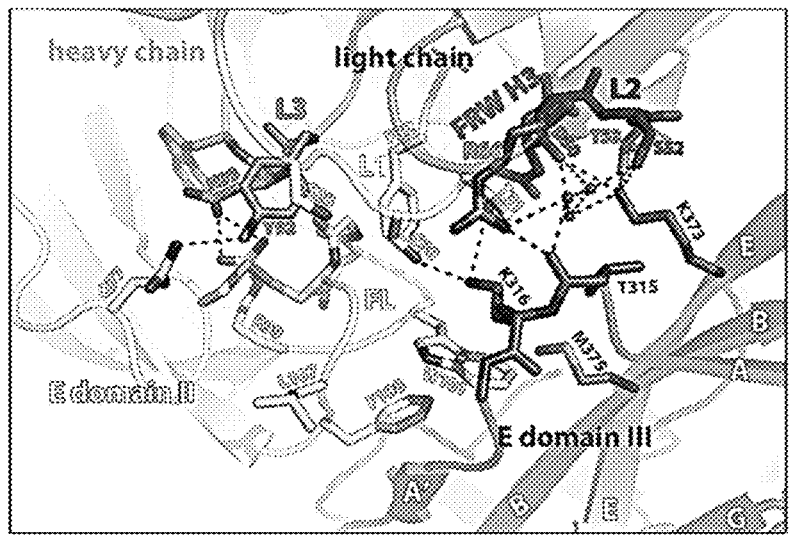
Figure 16C:
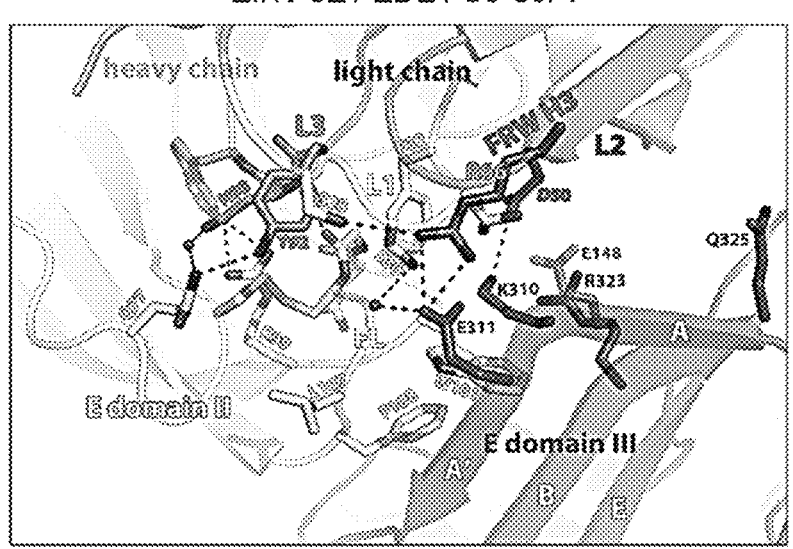
Figure 16D:
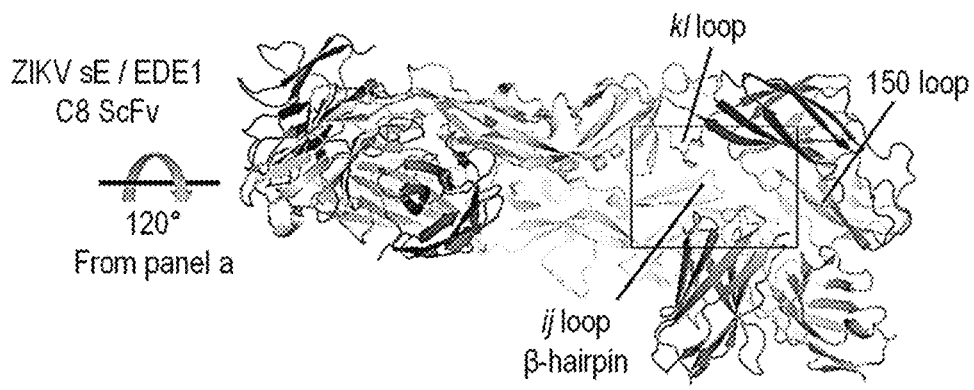
Figure 16E:
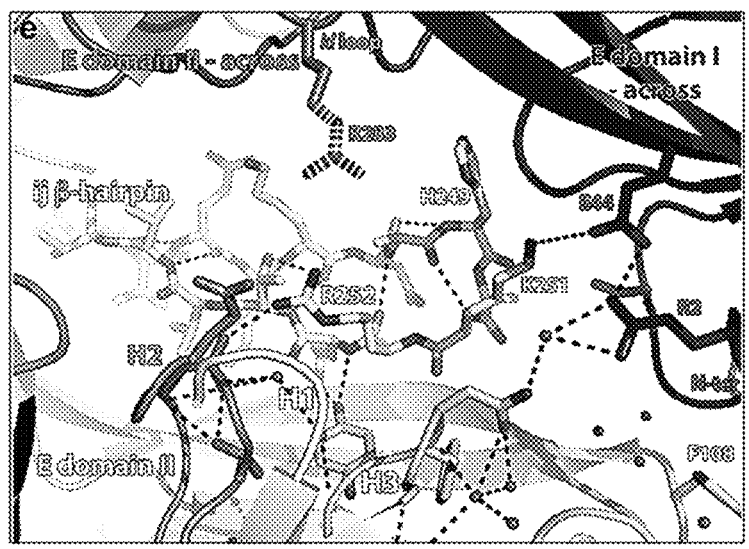
Figure 16F:
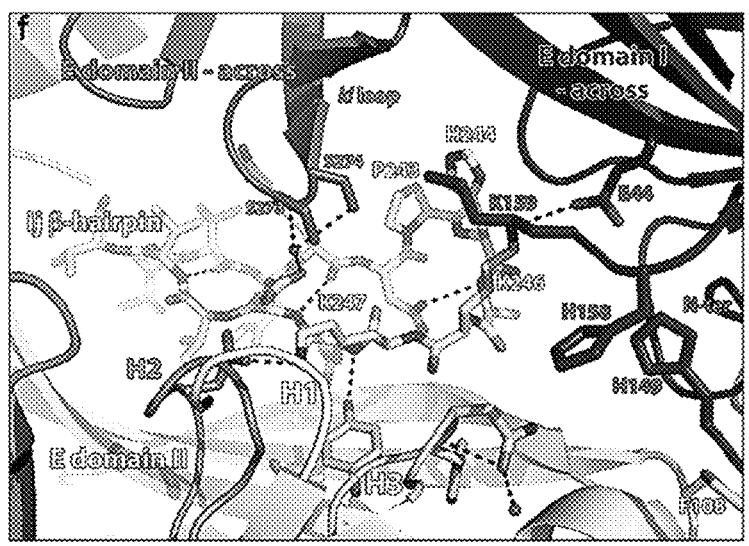

FIGS. 16A-16F. Details of EDE1 C8 bnAb contact across the dimer interface. FIG. 16A Overall view of the ZIKV sE/EDE1 C8 scFv complex. The box indicates the region zoomed in b. FIG. 16B Details of the interactions of the C8 light chain with domain III across the dimer interface. FIG. 16C Same region for the EDE1 C8/DENV-2 complex. Note that the sE residues involved are different. FIG. 16D The complex rotated by 120 degrees (as indicated by the arrow)

to show the interaction in the ij loop, enlarged in e. FIG. 16E The ij loop is displayed in sticks, in order to show the interaction of its main chain with the antibody. Domain II from the subunit across is colored green to distinguish from domain II of the reference subunit; the dashed sticks for the Arginine shown is to indicate that it has poor electron density in the crystal. FIG. 16F Same view of the complex with DENV-2. Note that the residues from across the dimer interface that contact the antibody are different. The residues in the various CDRs are colored coded, matching their label color (as in FIGS. 10A-10F and 11A-11E).

Figure 17:
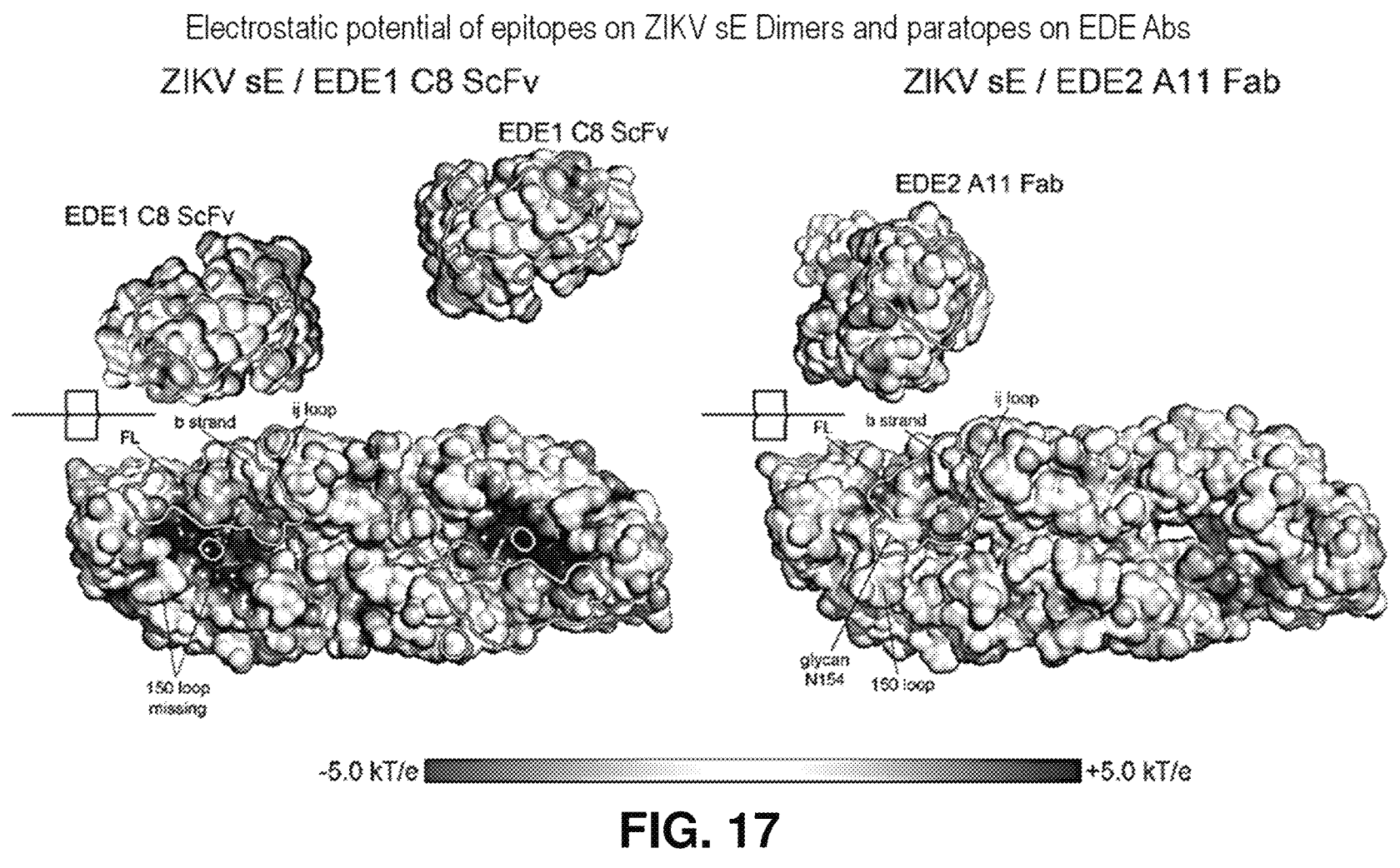

FIG. 17. Surface electrostatic potential on an open-book representation of the immmunocomplexes. The electrostatic potential is colored according to the bar underneath. The antibody footprints are outlined in green. The disordered 150 loop in the complex with C8 (left panels) results in a positive surface patch at one edge of the epitope, which is counteracted by the residues in the 150 loop, as shown on the right hand panel, in the complex with A11 where this loop is ordered.

Figure 18A:
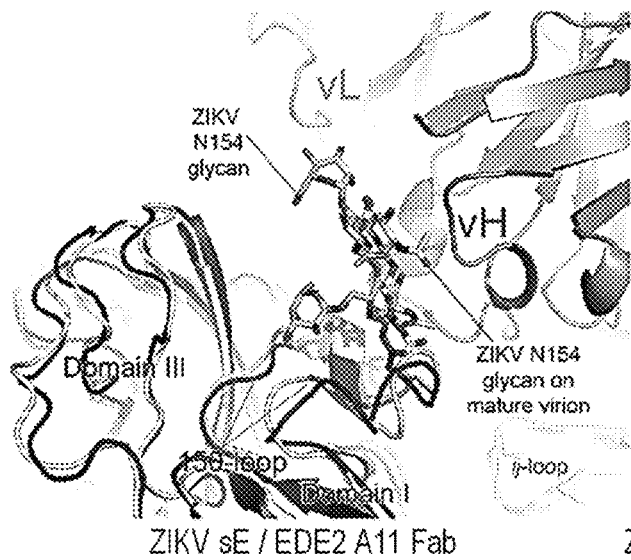
Figure 18B:
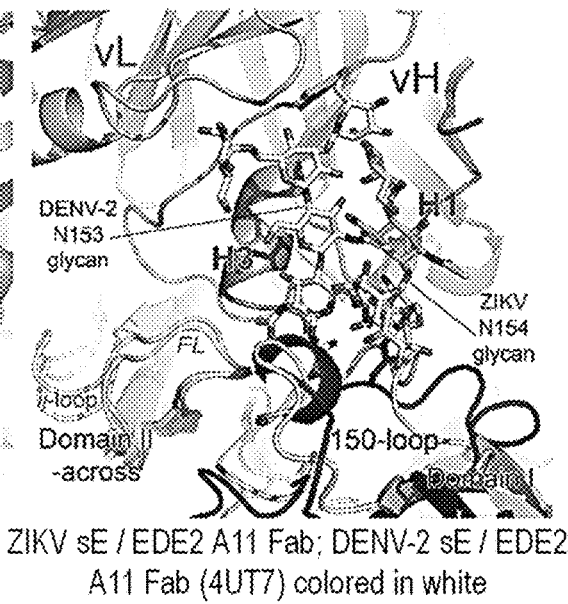
Figure 18C:
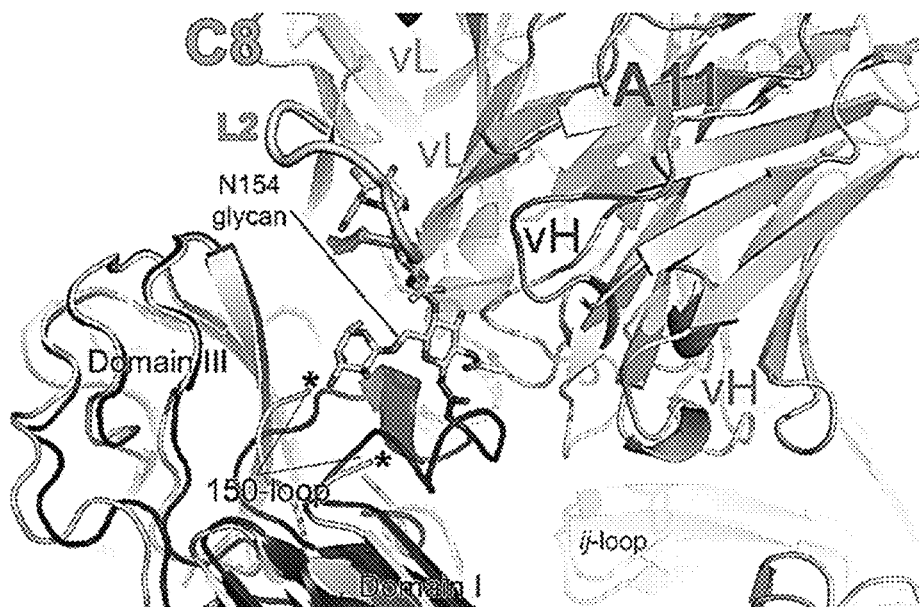

FIGS. 18A-18C. Details of the A11 interaction with the glycan on the 150 loop. FIG. 18A superposition of the ZIKV sE/A11 complex (in colors) on the E protein from the cryo-EM structure of the mature virion[18] (PDB code SIRE) in white. The E-protein was superimposed on the tip of domain II of the reference subunit together with domain III from the opposite subunit. It shows that the 150 loop adopts essentially the same conformation, although fewer sugar residues are visible in the absence of the antibody. FIG. 18B Superposition of the A11/ZIKV complex (in colors) on the A11/DENV sE complex (in white). The variable domains of the antibody from the two structures were superimposed on each other. Note that in DENV-2 the glycan packs against the α-helix of the CDR H3, whereas in ZIKV sE the glycan is too far to make the same interaction. FIG. 18C The C8/ZIKV sE complex (in pink) was superimposed on the ZIKV/A11 complex (in colors), to show the clash of the C8 light chain with the glycan, forcing it to move out of the way and be disordered. The superposition also shows that EDE1 C8 reaches further in to contact the ij loop and the kl loop of the adjacent subunit, as well as domain III. As in FIG. 18A, the superposition was done using the tip of domain II of the reference subunit and domain III of the adjacent subunit in the dimer as anchors. The two black asterisks mark the places where the electron density of the 150 loop is lost, resulting in no density in the C8/sE crystal for the short helix, nor for the glycan; FIG. 18D Crystallization conditions, data collection and refinement statistics; FIG. 18E Root mean square deviations between sE dimers in the various structures of ZIKV and DENV-2; FIG. 18F Buried Surface area of SE protein by Fabs or ScFv.

FIG. 21. Sequence alignment sE ZIKV-DENV-2

Example 3 Figure Legends:

FIG. 22A Homology of E protein sequences between different flaviviruses showing the close similarity between Zika and Dengue; Zika-DV3—58%, DV1—57%, DV4—56%, DV2—54%. FIG. 22B Schematic of the dengue genome translated into a single polyprotein which is cleaved into 3 structural and 7 non-structural proteins by host proteases, Furin and signalase, and viral protease, NS3/2B.

FIGS. 23A and 23B. Dengue virus structure at neutral pH FIG. 23A the structure of the immature dengue particle shows the arrangement of E and prM into sirmerc (heterohexameric spikes). Mackenzie et al *Nat. Med.* 2004 10:S98 FIG. 23B the mature dengue virus shows 90 head to tail dimers of E arranged into a smooth virus particle following cleavage of prM. Kuhn et al *Cell* 2002 108: 717.

FIGS. 24A-24C. The structures of DENV-2 in complex with anti-EDE-mAB showing the epitope of anti-EDE antibody lies across 2 E within a dimer. FIG. 24A side view and FIG. 24B top view. Domain I, II and III of E protein are indicated in red, yellow and blue. On the top view, grey and green ovals show the binding areas of heavy and light chains of the anti-EDE mAb. FIG. 24C Exposed main-chain atoms in the epitope. Surface representative of DENV-2 sE as viewed from outside the virion with exposed main-chain atoms orange (top) or with main-chain atoms plus conserved side chains in orange, and highly similar side chains in yellow (bottom). The epitopes of two EDE mAbs are indicated.

Figure 25A:
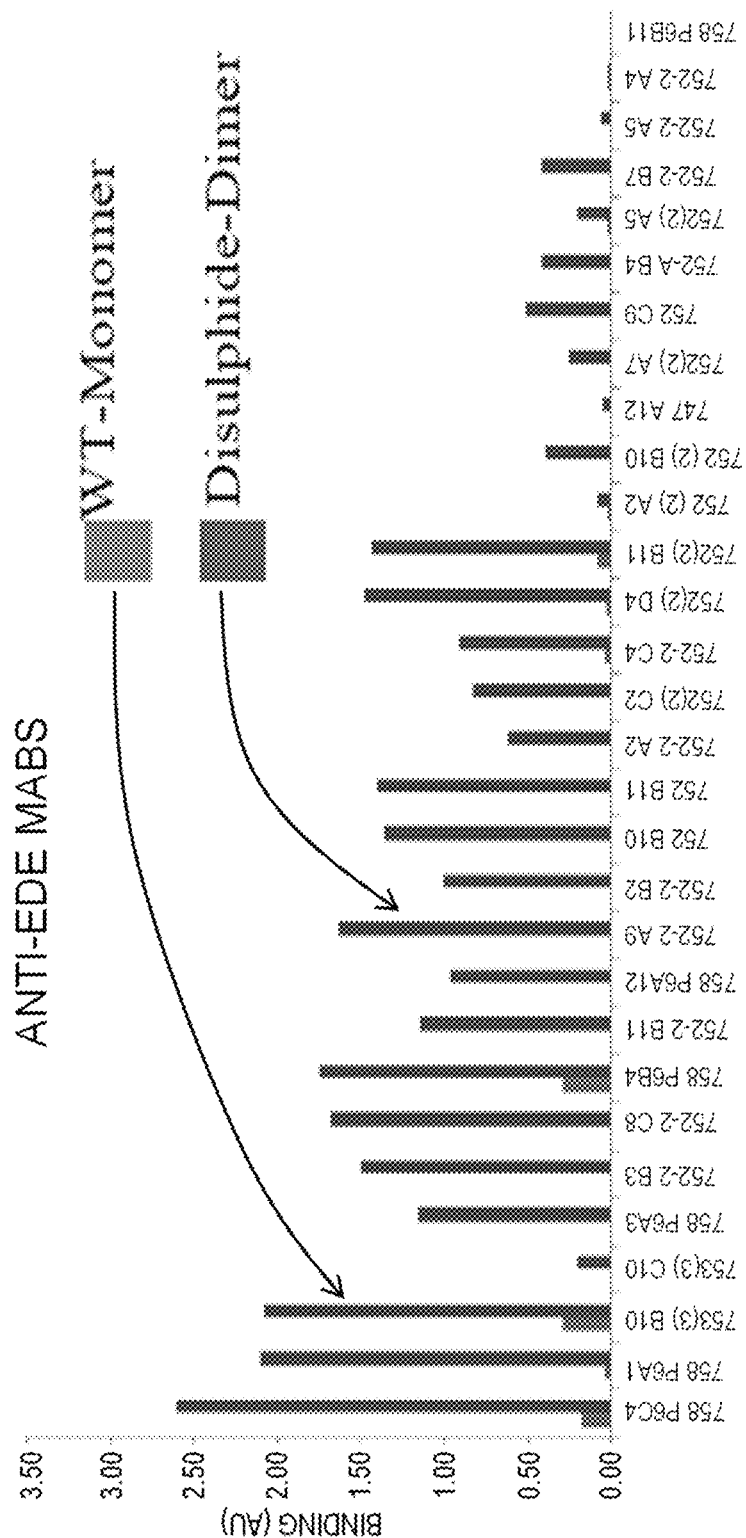
Figure 25B:
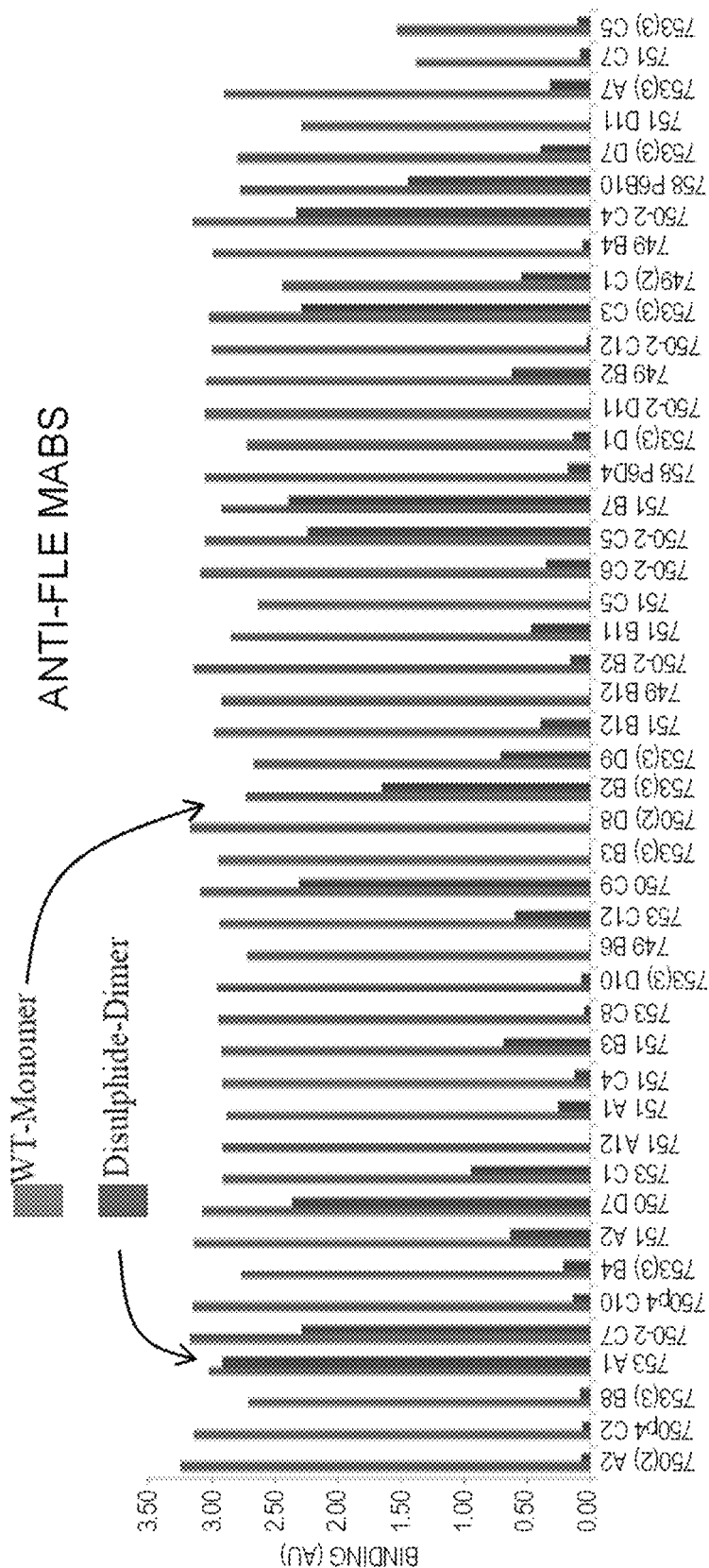

FIGS. 25A and 25B. Binding of a panel of EDE and FLE mb to engineered disulphide stabilised dimer (red) versus wild type E which is predominantly in the monomer form (blue) by ELISA. FIG. 25A Anti-EDE mAbs bind to the dimer but not monomer FIG. 25B Most anti-FLE binding mAb show reduced binding to dimer compared to monomer.

Figure 26:
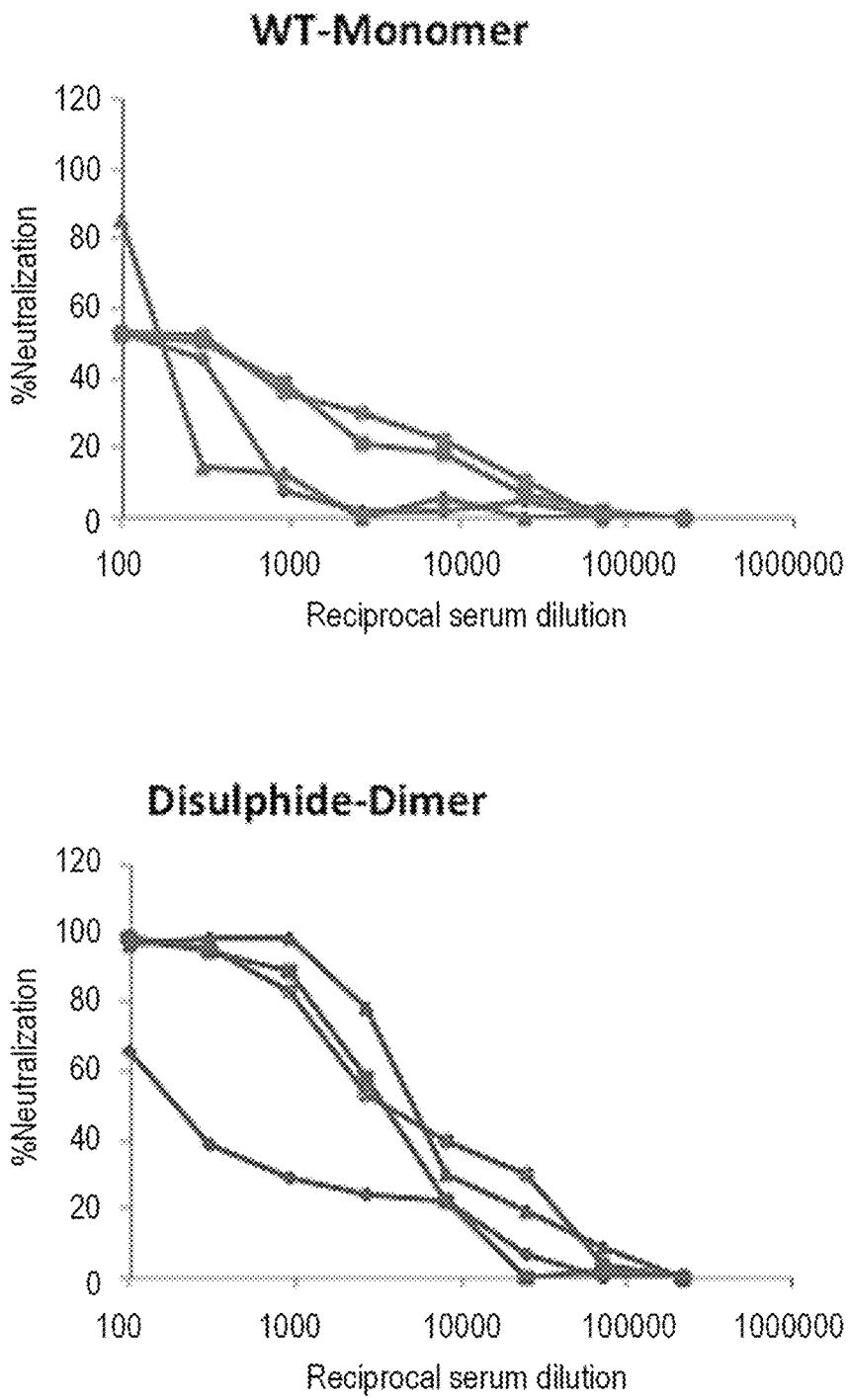

FIG. 26. Neutralization assays from 4 mice primed and boosted with either wild type monomeric DENV2 or mutant disulphide bond linked E-dimers shwing increased neutralisation titres with the dimeric-E.

FIG. 27. Flowchart for resurfacing strategy.

FIG. 28. The E dimer is shown in surface representation one subunit in white and the other in grey, with the fusion loop region in yellow. The outline of the EDE is in black. Candidate residues for resurfacing are displayed in bright colours: green and red for serotype variable and conserved residues, respectively.

Figure 29A:
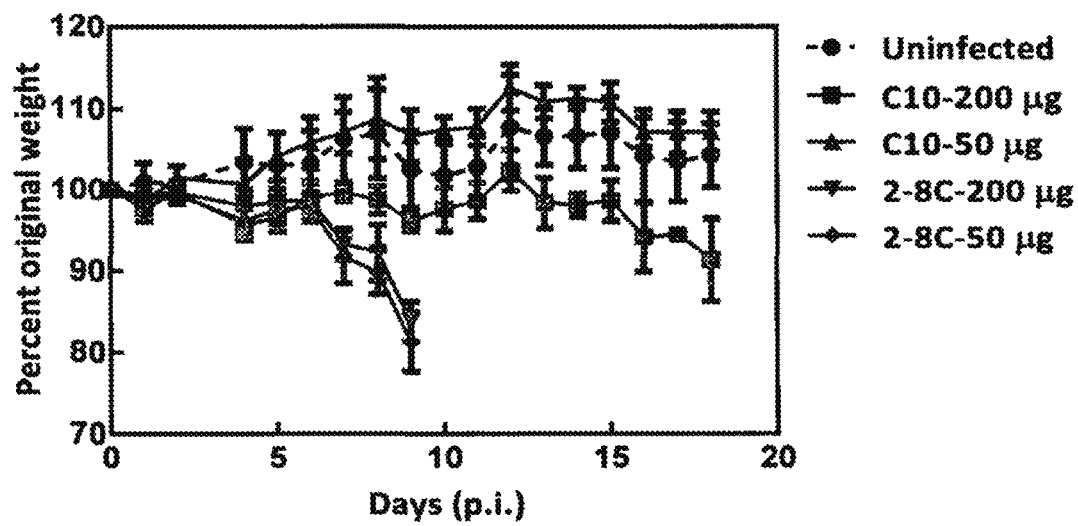
Figure 29B:
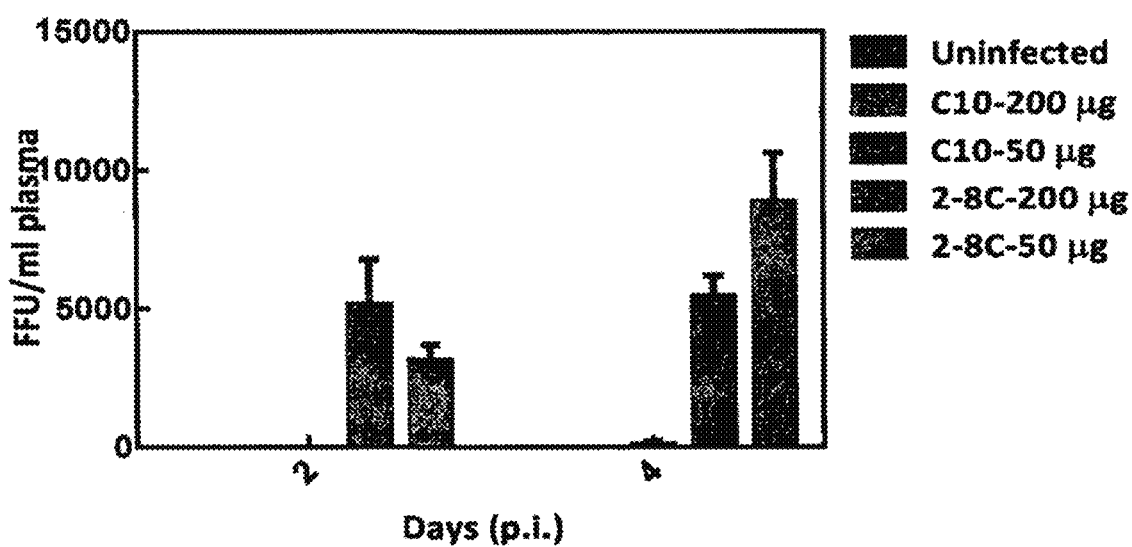

FIGS. 29A and 29B. In vivo efficacy of C10 in the AG129 mouse model. AG129 mice (female, 8-10 weeks of age; n=3) were treated with 50 or 200 µg purified C10 or 2-8C intraperitoneally as described in the Methods section. Mice were infected intraperitoneally with 200 µL of a $1.2 \times 10^2$ FFU/mouse with ZIKV PE243; 24 h post antibody treatment. FIG. 29A Percentage original body weight curves of ZIKV-infected mice treated with C10 antibody (red and blue symbols) or 2-8C isotype control (green and purple symbols) were plotted compared to PBS treated uninfected mice (black symbols). Data represent results from one experiment and are plotted as average+/− weight measurements from 3 mice per infected group. FIG. 29B Viral titres were determined from plasma samples isolated from individual mice at day 2 and day 4 post infection. Viral titres calculated as foci forming units per ml plasma have been represented as mean+/− SEM of plasma viral titres in individual mice.

EXAMPLE 1

Dengue Serocrossreactivity Drives Antibody Dependent Enhancement of Zika virus Infection Zika virus was discovered in 1947 and was thought to lead to relatively mild disease. The recent explosive outbreak of Zika in South America has led to widespread concern with reports of neurological sequelae ranging from Guillain Bane syndrome to microcephaly. Zika has followed in the path of dengue a flavivirus closely related to Zika. Here we investigate the serological crossreaction between the two viruses. Dengue immune plasma substantially crossreacts with Zika and can drive antibody dependent enhancement of Zika infection. Using a panel of human anti-dengue monoclonal antibodies we show that most antibodies reacting to dengue envelope protein also react to Zika and antibodies to linear epitopes including the immunodominant fusion loop epitope whilst binding to Zika cannot neutralize the virus but promote ADE. These data indicate that dengue immunity may drive higher Zika replication and have implications for disease pathogenesis and future Zika and dengue vaccine programmes.

Zika virus (ZIKV) is an arbovirus belonging to the family flaviviridae and is transmitted to man by *Aedes* mosquitos'. ZIKV was first isolated from a sentinel rhesus monkey in the Zika forest of Uganda in 1947 and has subsequently been found in mosquitos and humans[2,3]. Until recently ZIKV has not been viewed as a particularly important pathogen as the majority of infections are asymptomatic[4]. Symptomatic cases of ZIKV resemble mild cases of dengue fever with fever, myalgia, arthralgia, headache, conjunctivitis and rash[1, 7, 12, 13, 14].

Until recently cases were sporadic largely in Africa and South East Asia and epidemic activity had not been observed[1, 8, 9, 10, 11]. A large outbreak of ZIKV occurred on Yap island in the Western Pacific in 2007 and spread through Oceania and reached Brazil in 2015 where it rapidly spread to involve other South American countries[1, 7, 12, 13, 14].

It is now apparent that ZIKV infection can case significant neurological complications; increased cases of Guillain Bane syndrome were first reported following the outbreak in French Polynesia in 2013[15]. Dramatic increases in the incidence of microcephaly originating in North Eastern Brazil were reported in late 2015 coincident with a large increase in ZIKV infection 16, 17. These increases in Guillain Barre syndrome and microcephaly led the World Health Organization to declare ZIKV a public health emergency in February 2016[18].

ZIKV can be carried by a variety of *Aedes* mosquitos but the principal species responsible for the current outbreaks is thought to be *Aedes aegypti*[1, 5]. In parts of Brazil *Aedes aegypti* is also spreading DENV and chikungunya viruses concurrently with ZIKV[19, 20, 21, 22, 23, 24]. In the last 20 years DENV has spread through areas of South America and the seroprevalence of DENV in some areas affected by ZIKV exceeds 90%[25, 26, 27].

DENV exists as four serotypes which differ in amino acid sequence by 30-35% and the DENV serocomplex in turn differs from ZIKV by 41-46% (E protein)[28]. Recent reports have shown difficulty in distinguishing DENV and ZIKV infections serologically implying a degree of antigenic similarity between the viruses[7, 29, 30].

Following a primary DENV infection an individual develops life long immunity to the infecting serotype but not to the other serotypes[31, 32]. In DENV endemic areas all four viruses frequently co-circulate or cyclically replace each other meaning that multiple sequential infections are common[33]. One of the interesting features of DENV infection is that the life threatening complications, leading to dengue haemorrhagic fever, are more common following secondary rather than primary infections[28]. One theory to explain this is antibody dependent enhancement (ADE)[28]. The ADE hypothesis suggests that antibodies generated to a primary infection will not be of sufficient concentration or avidity to neutralize a secondary infecting DENV, which differs in amino acid sequence by 30-35%. However, they may still opsonize the secondary virus and target it for Fc receptor mediated endocytosis into myeloid cells, such as monocytes and macrophages, which are the principal site for DENV replication, thus driving higher virus loads. ADE can be readily demonstrated in vitro and has also be shown to drive higher dengue virus loads in animal models[34, 35, 36, 37].

Here we take advantage of panel of 132 human monoclonal antibodies generated from DENV infected individuals to demonstrate substantial crossreactivity between DENV and ZIKV. Most anti-DENV monoclonal antibodies also bind to ZIKV but those recognizing the major linear fusion loop epitope (FLE) are non-neutralizing. DENV plasma and mAb can potently enhance ZIKV infection suggesting the possibility that preexisting DENV immunity may increase ZIKV replication.

Results

DENV Plasma Crossreacts with ZIKV

Plasma from individuals taken 6 months following secondary DENV infection with serotypes 1-4 was tested for binding to ZIKV and DENVs by capture ELISA. In all cases DENV immune plasma bound to both DENV and ZIKV (FIG. 1A). There were no appreciable differences in binding to viral strains originating in Africa (HD78788) or French Polynesia (PF13) (FIG. 1B).

Next we tested neutralization of ZIKV by convalescent DENV plasma. All convalescent DENV plasma could neutralize DENV infection to nearly 100% at the lowest dilution used of 1:50 (FIG. 2A). However, neutralization of ZIKV was considerably less efficient with most sera showing no appreciable neutralization (FIGS. 2A and 2B). The finding that anti-DENV plasma substantially crossreacts with ZIKV prompted us to determine whether it could promote ADE.

DENV Plasma Potently Induces ADE

One of the hallmarks of DENV infection is the increase in severity of illness during secondary infections. One of the explanations of this is antibody dependent enhancement, whereby preexisting antibodies directed to a previous DENV infection, opsonize but do not neutralize a secondary infection. Opsonized virus is targeted for uptake by Fc receptor expressing myeloid cells such as monocytes and macrophages driving higher virus replication.

We tested the ability of DENV plasma to promote ADE in the myeloid cell line U937 which is relatively resistant to infection by DENV in the absence of ADE and here we show U937 is also poorly permissive to ZIKV infection in the absence of ADE. ZIKV was preincubated with a titration of pooled convalescent anti-dengue plasma obtained at 2 weeks and then used to infect U937 cells. Pooled convalescent plasma led to substantial enhancement of infection >100 fold to both Zika viruses and as expected pooled control non-dengue serum did not enhance infection (FIG. 3A). Next we tested a panel of convalescent plasma obtained 6 months following acute secondary dengue infection. In all but one case DENV plasma increased ZIKV infection with a median 12-fold increase of HD78788 infection (FIG. 3B). In summary these results demonstrate that crossreacting anti-DENV antibodies can promote ADE of ZIKV but are poorly neutralizing.

Cross Reaction of Anti DENV Monoclonal Antibodies

We have previously created a pool of 145 human monoclonal antibodies reacting to the DENV envelope protein, generated from plasmablasts isolated from DENV infected patients[34]. Detailed epitope mapping of these antibodies demonstrated three broad reactivities. Around ⅓ of the antibodies reacted to the well described fusion loop epitope (FLE), ⅓ were not definitively mapped, but like the fusion loop antibodies they reacted to envelope protein by Western Blot (these are termed non-FLE as they were not sensitive to mutation of envelope residue W101). Finally, a group of around 40 antibodies did not react to envelope protein by western blot and only bound to intact virus particles. These antibodies were shown by cryo electron microscopy and X-ray crystallography to bind to a conformational quaternary epitope formed at the interface of two envelope protein monomers making up the basic head to tail dimer, 90 of which are arranged in icosahedral symmetry into the DENV glycoprotein shell[34, 38]. We termed this new epitope the E dimer epitope (EDE), which were subdivided into two groups EDE1 and EDE2 based on the sensitivity to the removal of the N-linked glycan N153 in E (EDE2 binding was reduced by removal of N153, EDE1 not). Some EDE antibodies were fully crossreactive to all four DENV serotypes and could neutralize infection in the picomolar range.

Binding of the panel of anti-DENV monoclonal antibodies to ZIKV was tested by capture ELISA and compared to binding to DENV (FIG. 4A). The profile of binding between the African (HD78788) and French Polynesian (PF13) strains was highly similar, all of the fusion loop antibodies cross reacted with ZIKV, 36/37 of the non fusion loop antibodies crossreacted whereas the crossreaction of the EDE antibodies was variable with 27/33 EDE1 and 8/17 EDE2. Binding curves showed a lower avidity of binding of EDE2 antibodies versus EDE1 and lower avidity of the EDE1 mAb 752-2B2 (FIGS. 4B AND 4C).

It has previously been demonstrated that almost all mAb generated against DENV promote ADE, which includes all of the 145 human monoclonal antibodies we generated in our previous studies'. Because of the crossreactivity of the DENV mAb to ZIKV we next tested the ability of anti-DENV monoclonal antibodies to promote ADE of ZIKV virus infection (FIGS. 5A-5C). Firstly, we tested 3 fusion loop antibodies which showed no neutralization activity against ZIKV. All of these antibodies promoted ADE enhancing infection of HD78788 54-78 fold compared to ZIKV incubated with no antibody or irrelevant control mAb. As expected, the ZIKV neutralizing EDE mAb also promoted ADE of ZIKV when added in subneutralizing concentrations, although peak enhancement was seen with lower concentrations than with the fusion loop mAb. This demonstrates that monoclonal antibodies isolated from dengue infected patients, with a number of different specificities, have broad crossreactivities to ZIKV.

EDE mAb can Inhibit ADE of DENV Plasma

Fusion loop and EDE mAb have overlapping epitopes as the footprint of the EDE also covers the fusion loop region. To test whether EDE antibodies could overcome ADE induced by polyclonal anti-DENV plasma we added a titration of anti-DENV EDE1 mAb to ZIKV incubated with an enhancing concentration of anti-DENV plasma (FIGS. 6A-6C). Fusion loop antibodies had no effect, whereas the EDE1 mAb, except 752-2B2 which has lower avidity for ZIKV, were able to potently inhibit ADE of PF13 infection with 50% inhibition occurring at titers of 0.091±0.007 and 0.034±0.006 ug/ml of 752-2C8 and 753(3)C10, respectively. EDE2 mAb which are of lower avidity for ZIKV than the EDE1 mAb were not able to inhibit ADE in this assay. These studies demonstrate that EDE1 antibodies can potently inhibit ZIKV ADE and if present at sufficient levels could be protective in vivo.

Discussion

The recent explosion of ZIKV virus infection in South America with associated Guillain Barre syndrome and microcephaly are of great concern[15, 16, 17]. Guillain Bane Syndrome, is a relatively rare complication, estimated to affect 0.024% of ZIKV infected individuals, but owing to the scale of the ZIKV epidemic this still translates to large number of cases[15]. Much work still needs to be performed to understand the exact causes of microcephaly, however, it is becoming increasingly clear that this is caused by intra-uterine infection of the developing brain[17, 39, 40, 41, 42.] Zika has been shown in animal models to infect the placenta and stunt growth and also to be able to cross the placenta and infect the brain[43, 44, 45]. Furthermore in vitro ZIKV can infect neural cell cultures and disrupt development in neurospheres[46, 47]. The exact risk of neurological damage following maternal infection remains to be determined, but early studies suggest that this may be up to 22% in the first trimester although other reports from French Polynesia put the risk at around 1%[48, 49].

ZIKV is spread by *Aedes* mosquitos and currently in South America these mosquitos are also promoting epidemic spread of DENV and Chikungunya viruses[19]. In many areas affected by ZIKV the seropositivity to DENV is very high and in such areas there is great difficulty in distinguishing ZIKV and DENV infection serologically[26, 27, 30]. In this paper we have demonstrated substantial crossreactivity of the anti-DENV serological response towards ZIKV. Most anti-DENV plasma poorly neutralizes ZIKV yet can potently induce ADE.

In a related Example we have studied neutralization of ZIKV by anti-DENV human monoclonal antibodies. Interestingly, anti-fusion loop antibodies, which form a major part of the antibody response in DENV infection[28] and which we show here promote ADE, fail to neutralize infection. Antibodies reacting to the fusion loop are known to be broadly reactive across a number of flaviviruses but despite often strong crossreaction by ELISA methods rarely show crossneutralizing activity perhaps because their epitopes are poorly exposed on native virus particles[50]. In addition we show that EDE1 mAb showed potent neutralization in a similar picomolar range to their neutralization of DENV whilst EDE2 mAb also neutralize ZIKV but not as potently as EDE1 mAb. These results are presented together with X-ray crystallographic structures of EDE1 and EDE2 Fab in complex with the ZIKV envelope.

Antibody dependent enhancement was first recognized nearly 50 years ago in DENV infection and is believed to be one of the factors driving increased severity of secondary infections which is a hallmark of DENV[36]. The risk of ADE has made the development of DENV vaccines particularly difficult. The most advanced DENV vaccine Dengvaxia (CYD-TDV) produced by Sanofi Pasteur has just been licensed in several countries and gives some protection from infection; it is estimated that it will reduce the burden of disease by 10-30% over a 30 year period if deployed in endemic countries[51].

Dengvaxia is a tetravalent live attenuated vaccine where the sequences encoding the precursor membrane protein and envelope proteins that make up the glycoprotein shell of the DENV are combined with the non-structural sequences from the attenuated 17D yellow fever vaccine strain[28]. Dengvaxia seems to give protection to individuals who have been previously infected with DENV but efficacy when given to DENV naïve vaccinees is less[28, 51].

A recent longer term analysis of the vaccine trials of Dengvaxia has raised some safety concerns[28]. In the under 9 age groups hospitalization from DENV infection was higher in vaccinated children than in the non-vaccinated control group. This may represent antibody dependent enhancement in children who at entry to the study trial were DENV naïve and have been primed but not protected by the vaccine. For this reason the vaccine is not licensed for use in children <9 years and furthermore it is recommended to be used only in populations where the seroprevalence of prior DENV exposure in the age group to be vaccinated is 70% or greater[51].

There is now great pressure to produce a vaccine against ZIKV, the extensive crossreaction between DENV and ZIKV serologically must be considered in this regard. It is likely that the vaccine will need to be deployed in areas with high DENV seroprevalence and raising de novo ZIKV neutralizing responses in such a setting may be challenging. There is also the possibility that ZIKV vaccination in DENV naïve subjects may promote ADE of DENV and conversely that DENV vaccination may promote ADE of ZIKV infection.

The results described here show a complex serological interaction between DENV and ZIKV. The precise reason for the explosion of ZIKV infection and its complications in Brazil will need to be fully determined but it is possible that the preexisting DENV immunity is driving higher virus replication in infected individuals which may in turn may drive higher mosquito infection and spread and greater risk of complications. The possibility that ADE may aid transplacental transfer of ZIKV also needs to be investigated. The timings of DENV versus ZIKV infection may also be important as cross reacting protective and enhancing immunity may change over time following DENV infection.

In summary, although ZIKV differs in sequence by around 41-46% (E protein) from DENVs the similarities are sufficient to allow crossreaction of anti-DENV antibodies with the ZIKV and to drive antibody dependent enhancement. In this respect ZIKV could be considered as a fifth member of the DENV serocomplex, a factor which must be considered in vaccine approaches to these two viruses.

Methods

Samples

Blood samples were collected after written informed consent and the approval of the ethical committee of the Khon Kaen and Siriraj Hospitals in Thailand and the Riverside Ethics Committee in UK. The serotypes of DENV infection was determined by RT-PCR detection of the viral genome. Samples were collected 6 months after recovery from dengue illness.

Cells, Reagents and Antibodies Vero cells (a gift from AFRIMS), 293T, and U937 cells were cultured at 37° C. in MEM, DMEM and RPMI-1640, respectively. C6/36 cells (a gift from AFRIMS) were grown in Leibovitz L-15 at 28° C. All media contained 10% heat-inactivated foetal bovine serum, 100 units/ml penicillin and 100 ug/ml streptomycin. All cell lines were free from mycoplasma contamination.

Alkaline phosphatase (ALP)-conjugated anti-human IgG (A9544) and horseradish peroxidase-conjugated anti-human IgG (P0214) were purchased from Sigma and Dako, respectively. Mouse monoclonal anti-DENV E, 4G2, was a gift from AFRIMS. RPMI-1640 (R8758), DMEM (D5046), p-nitrophenylphosphate (PNPP, N2770-50), Bovine serum albumin (BSA, A7030), diaminobenzidine (D5905), and polyethylenimine (408727; Sigma) were from Sigma. MEM (31095) and Leibovitz L-15 (11415) were from Gibco and UltraDOMA-PF (12-727F) was from Lonza.

Viral stocks.

All viruses were grown in C6/36 cells. ZIKV strain HD78788 (African strain) was provided by Anavaj Sakuntabhai. ZIKV strain PF13/251013-18 (PF13) was isolated from a patient during ZIKV outbreak in French Polynesia 2013. DENV-1 (Hawaii), DENV-2 (16681), DENV-3 (H87) and DENV-4 (1-0093) were gifts from AFRIMS. Virus containing supernatants were clarified by centrifugation at 2000 rpm at 4° C. before being stored at −80° C. Viral titres were determined by a focus-forming assay on Vero cells[34]. All virus stocks were free from mycoplasma contamination.

Expression of Human Monoclonal Anti-DENV E Antibodies

A pair of plasmids containing heavy and light chains of immunoglobulin G1 were co-transfected into 293T cells by a polyethylenimine method and cultured in protein-free media. Culture supernatant containing antibodies was harvested after 5 days.

Determination of ZIKV Crossreactivity of anti-DENV Antibodies by ELISA

A MAXISORP immunoplate (442404; NUNC) was coated with mouse anti-E protein, 4G2 (a fusion loop murine Ab which crossreacts to ZIKV). Plates were blocked with 3% BSA for one hour followed by incubation with viral supernatant. After one hour, 10 ug/ml anti-DENV humAbs or serially diluted plasma was added. The reaction was visualized by ALP-conjugated anti-human IgG antibody (A9544; Sigma) and PNPP substrate. Reactions were stopped with NaOH and the absorbance measured at 405 nm. Endpoint titers (EPTs) were defined as reciprocal plasma dilutions that corresponded to 2 times the average OD values obtained with mock antigen.

Neutralization Assay

The focus reduction neutralization assay (FRNT) was employed to determine the neutralizing potential of antibodies. Virus was incubated with serial dilutions of antibodies or plasma samples for an hour at 37° c. The mixtures were then added to Vero cells and incubated for 2 (for ZIKV) or 3 days (for DENV). Focus forming assays were then performed as described[34]. Briefly, Vero cells were stained with anti-E mAb 4G2 followed by peroxidase-conjugated goat anti-mouse Ig (P0047; Sigma). The foci (infected cells) were visualized by adding peroxidase substrate, DAB. The percentage focus reduction was calculated and 50% FRNT was calculated using the probit program from the SPSS package.

Antibody-Dependent Enhancement Assay

Serially diluted antibody or plasma samples were incubated with virus for one hour at 37° C. before adding to U937 cells. After incubation 2 (for ZIKV) or 3 days (for DENV), supernatants were harvested and viral titres determined by focus forming assay. Fold enhancement was calculated by comparison to viral titres in the presence/absence of antibody.

The ADE inhibition by human mAbs was performed by premixing pooled convalescent dengue hyper immune serum at 1:10,000 dilution (a peak enhancing dilution) with serially diluted antibody before performing the ADE assay as described above.

REFERENCES

1. Musso, D., Gubler D. J. Zika Virus. *Clin Microbiol Rev* 29, 487-524 (2016).
2. Dick, G. W., Kitchen S. F., Haddow A. J. Zika virus. I. Isolations and serological specificity. *Trans R Soc Trop Med Hyg* 46, 509-520 (1952).
3. Macnamara, F. N. Zika virus: a report on three cases of human infection during an epidemic of jaundice in Nigeria. *Trans R Soc Trop Med Hyg* 48, 139-145 (1954).
4. Lazear, H. M., Diamond M. S. Zika Virus: New Clinical Syndromes and Its Emergence in the Western Hemisphere. *J Virol* 90, 4864-4875 (2016).
5. World Health Organization. Zika Virus Fact sheet: www.who.int/mediacentre/factsheets/zika/en/. (2016).
6. Bearcroft, W. G. Zika virus infection experimentally induced in a human volunteer. *Trans R Soc Trop Med Hyg* 50, 442-448 (1956).
7. Duffy, M. R. et al. Zika virus outbreak on Yap Island, Federated States of Micronesia. *N Engl J Med* 360, 2536-2543 (2009).

8. Dick, G. W. Zika virus. II. Pathogenicity and physical properties. *Trans R Soc Trop Med Hyg* 46, 521-534 (1952).
9. Fagbami, A. H. Zika virus infections in Nigeria: virological and seroepidemiological investigations in Oyo State. *J Hyg (Lond)* 83, 213-219 (1979).
10. Haddow, A. D. et al. Genetic characterization of Zika virus strains: geographic expansion of the Asian lineage. *PLoS Negl Trop Dis* 6, e1477 (2012).
11. Hayes, E. B. Zika virus outside Africa. *Emerg Infect Dis* 15, 1347-1350 (2009).
12. Cao-Lormeau, V. M. et al. Zika virus, French polynesia, South pacific, 2013. *Emerg Infect Dis* 20, 1085-1086 (2014).
13. Zanluca, C. et al. First report of autochthonous transmission of Zika virus in Brazil. *Mem Inst Oswaldo Cruz* 110, 569-572 (2015).
14. Campos, G. S., Bandeira A. C., Sardi S. I. Zika Virus Outbreak, Bahia, Brazil. *Emerg Infect Dis* 21, 1885-1886 (2015).
15. Cao-Lormeau, V. M. et al. Guillain-Barre Syndrome outbreak associated with Zika virus infection in French Polynesia: a case-control study. *Lancet* 387, 1531-1539 (2016).
16. Teixeira, M. G., da Conceicao N. C. M., de Oliveira W. K., Nunes M. L., Rodrigues L. C. The Epidemic of Zika Virus-Related Microcephaly in Brazil: Detection, Control, Etiology, and Future Scenarios. *Am J Public Health* 106, 601-605 (2016).
17. Mlakar, J. et al. Zika Virus Associated with Microcephaly. *N Engl J Med* 374, 951-958 (2016).
18. World Health Organization. Zika emergency: www.who.int/mediacentre/news/statements/2016/1st-emergency-committee-zika/en/. (2016).
19. Musso, D., Cao-Lormeau V. M., Gubler D. J. Zika virus: following the path of dengue and chikungunya? *Lancet* 386, 243-244 (2015).
20. Cardoso, C. W. et al. Outbreak of Exanthematous Illness Associated with Zika, Chikungunya, and Dengue Viruses, Salvador, Brazil. *Emerg Infect Dis* 21, 2274-2276 (2015).
21. Teixeira, M. G. et al. East/Central/South African genotype chikungunya virus, Brazil, 2014. *Emerg Infect Dis* 21, 906-907 (2015).
22. Weaver, S. C., Lecuit M. Chikungunya virus and the global spread of a mosquito-borne disease. *N Engl J Med* 372, 1231-1239 (2015).
23. Guzman, M. G., Harris E. Dengue. *Lancet* 385, 453-465 (2015).
24. Morrison, T. E. Reemergence of chikungunya virus. *J Virol* 88, 11644-11647 (2014).
25. Brathwaite Dick, O. et al. The history of dengue outbreaks in the Americas. *Am J Trop Med Hyg* 87, 584-593 (2012).
26. Castanha, P. M. et al. Force of infection of dengue serotypes in a population-based study in the northeast of Brazil. *Epidemiol Infect* 141, 1080-1088 (2013).
27. Braga, C. et al. Seroprevalence and risk factors for dengue infection in socio-economically distinct areas of Recife, Brazil. *Acta Trop* 113, 234-240 (2010).
28. Screaton, G., Mongkolsapaya J., Yacoub S., Roberts C. New insights into the immunopathology and control of dengue virus infection. *Nat Rev Immunol* 15, 745-759 (2015).
29. Buathong, R. et al. Detection of Zika Virus Infection in Thailand, 2012-2014. *Am J Trop Med Hyg* 93, 380-383 (2015).
30. Lanciotti, R. S. et al. Genetic and serologic properties of Zika virus associated with an epidemic, Yap State, Micronesia, 2007. *Emerg Infect Dis* 14, 1232-1239 (2008).
31. Guzman, M. G. et al. Neutralizing antibodies after infection with dengue 1 virus. *Emerg Infect Dis* 13, 282-286 (2007).
32. Sabin, A. B. Research on dengue during World War II. *Am J Trop Med Hyg* 1, 30-50 (1952).
33. Guzman, M. G. et al. Dengue: a continuing global threat. *Nat Rev Microbiol* 8, S7-16 (2010).
34. Dejnirattisai, W. et al. A new class of highly potent, broadly neutralizing antibodies isolated from viremic patients infected with dengue virus. *Nat Immunol* 16, 170-177 (2015).
35. Halstead, S. B., O'Rourke E. J. Dengue viruses and mononuclear phagocytes. I. Infection enhancement by non-neutralizing antibody. *J Exp Med* 146, 201-217. (1977).
36. Halstead, S. B., O'Rourke E. J. Antibody-enhanced dengue virus infection in primate leukocytes. *Nature* 265, 739-741 (1977).
37. Zompi, S., Harris E. Animal models of dengue virus infection. *Viruses* 4, 62-82 (2012).
38. Rouvinski, A. et al. Recognition determinants of broadly neutralizing human antibodies against dengue viruses. *Nature*, (2015).
39. Calvet, G. et al. Detection and sequencing of Zika virus from amniotic fluid of fetuses with microcephaly in Brazil: a case study. *Lancet Infect Dis*, (2016).
40. Martines, R. B. et al. Notes from the Field: Evidence of Zika Virus Infection in Brain and Placental Tissues from Two Congenitally Infected Newborns and Two Fetal Losses—Brazil, 2015. *MMWR Morb Mortal Wkly Rep* 65, 159-160 (2016).
41. Meaney-Delman, D. et al. Zika Virus Infection Among U.S. Pregnant Travelers—August 2015-February 2016. *MMWR Morb Mortal Wkly Rep* 65, 211-214 (2016).
42. Sarno, M. et al. Zika Virus Infection and Stillbirths: A Case of Hydrops Fetalis, Hydranencephaly and Fetal Demise. *PLoS Negl Trop Dis* 10, e0004517 (2016).
43. Cugola, F. R., Fernandes I. R., Russo F. B., Freitas B. C. The Brazilian Zika virus strain causes birth defects in experimental models. *Nature*, (2016).
44. Miner, J. J. et al. Zika Virus Infection during Pregnancy in Mice Causes Placental Damage and Fetal Demise. *Cell* 165, 1-11 (2016).
45. Li, C., Xu D., Ye Q., Hong S., Jiang Y. Zika Virus Disrupts Neural Progenitor Development and Leads to Microcephaly in Mice. *Cell Stem Cell* 19, 1-7 (2016).
46. Dang, J. et al. Zika Virus Depletes Neural Progenitors in Human Cerebral Organoids through Activation of the Innate Immune Receptor TLR3. *Cell Stem Cell*, (2016).
47. Garcez, P. P. et al. Zika virus impairs growth in human neurospheres and brain organoids. *Science*, (2016).
48. Brasil, P. et al. Zika Virus Infection in Pregnant Women in Rio de Janeiro-Preliminary Report. *N Engl J Med*, (2016).
49. Cauchemez, S. et al. Association between Zika virus and microcephaly in French Polynesia, 2013-15: a retrospective study. *Lancet*, (2016).
50. Stiasny, K., Kiermayr S., Holzmann H., Heinz F. X. Cryptic properties of a cluster of dominant flavivirus cross-reactive antigenic sites. *J Virol* 80, 9557-9568 (2006).

51. World Health Organization (WHO) Strategic Advisory Group of Experts. Dengue vaccine: http://www.who.int/immunization/sage/meetings/2016/april/SAGE_April_2016_Meeting_Web_Summary.pdf?ua=1. (2016)

EXAMPLE 2

Structural Basis of Potent Cross-Neutralization between Zika and Dengue Viruses

Zika virus is a member of the flavivirus genus that had not been associated with severe disease in humans until the recent outbreaks, when it was linked to microcephaly in newborns in Brazil and to Guillain-Barré Syndrome in adults in French Polynesia. Zika virus is related to dengue virus, and we report here that a category of antibodies isolated from dengue patients and targeting a conformational epitope potently neutralize Zika virus. The crystal structure of two of these antibodies in complex with the envelope protein of Zika virus reveals the details of a conserved epitope, which is also the site of interaction of the envelope protein dimer with the precursor prM protein during virus maturation. Comparison of the Zika and dengue virus immunocomplexes lays the foundation for a rational, epitope-focused design of a universal vaccine capable of eliciting potently neutralizing antibodies to protect against Zika and dengue viruses simultaneously.

The explosive spread of Zika Virus (ZIKV) in Brazil and other South and Central American countries upon its recent introduction was linked with increasing numbers of microcephaly cases[1-4]. There have also been cases of Guillain Barré syndrome linked to ZIKV infections in the 2013-2014 French Polynesian outbreak[5], leading the World Health Organization to declare these neurological disorders a Public Health Emergency of International Concern on Feb. 1, 2016[6]. Prior to the epidemics of recent years, ZIKV was thought to cause only mild or self-limiting disease[7]. The physiological processes leading to fetal infections and neurological complications are unresolved and specific therapeutic or prophylactic interventions are currently not available. In order to obtain insight into ZIKV pathogenesis and especially for developing safe and protective vaccines it is essential to understand the structural basis of virus neutralization and cross-reactivity with other flaviviruses. ZIKV transmission among humans and epidemic spread is primarily maintained by *Aedes* mosquitoes, but there are reports of sexual transmission as well[8-10]. ZIKV is an arthropod-borne enveloped virus belonging to the flavivirus genus in the family Flaviviridae, which also includes the human pathogenic yellow fever, dengue, West Nile and tick-borne encephalitis viruses[11]. Flaviviruses have two structural glycoproteins, prM and E (for precursor Membrane and Envelope proteins, respectively), which form a heterodimer in the endoplasmic reticulum (ER) of the infected cell and drive the budding of spiky immature virions into the ER lumen. The budded particles are subsequently transported across the secretory pathway of the cell, a process during which prM undergoes proteolytic maturation by the trans-Golgi resident furin protease[12-14]. This maturation process is required for infectivity and results in the reorganization on E at the virion surface. The mature particles released from the infected cell have a smooth aspect, with 90 E dimers coating the external surface of the virion, organized with icosahedral symmetry in a "herringbone" pattern[15,16]. Three-dimensional cryo-EM structures of the mature ZIKV particles have recently been reported to near atomic resolution (3.8 Å)[17,18], showing that it has essentially the same organization as the other flaviviruses of known structure, such as dengue virus (DENV), for which a 3.5 Å cryo-EM reconstruction was reported previously[16] and also West Nile virus[19,20]. The E protein is about 500 amino acids long, with the 400 N-terminal residues forming the ectodomain, essentially folded as β-sheet with three domains named I, II and III, aligned in a row with domain I at the center. The highly conserved fusion loop is at the distal end of the rod in domain II, buried at the E dimer interface. At the C-terminus, the E ectodomain is followed by the so-called "stem", featuring two α-helices lying flat on the viral membrane (the "stem" helices), which link to two C-terminal trans-membrane α-helices. The main distinguishing feature of the ZIKV virion is an insertion in a glycosylated loop of E (the "150" loop), which protrudes from the virion surface[17,18].

Flaviviruses have been grouped into serocomplexes based on cross-neutralization studies with polyclonal immune sera[21]. The E protein is the main target of neutralizing antibodies. Because E is responsible for membrane fusion during virus entry, it is maintained in a metastable conformation such that it can be triggered to undergo a conformational change to induce fusion of the viral envelope with an endosomal membrane, thereby releasing the viral genetic material into the cytoplasm. One consequence of this metastability of the E dimer is that it displays a dynamic behavior, termed "breathing"[22], such that it exposes regions normally buried within the dimer interface. One such region is the fusion loop epitope (FLE), which is a dominant cross-reactive antigenic site[23]. Although antibodies to this site can be protective by complement-mediated mechanisms, as shown for West Nile virus in a mouse model[24], they are poorly neutralizing and have been shown to lead to antibody-dependent enhancement (ADE)[25-29], thereby aggravating flavivirus pathogenesis and complicating the development of safe and effective vaccines.

We recently reported the isolation and structural characterization of a panel of antibodies isolated from dengue patients[27,30]. A majority of these antibodies targeted the FLE, but others targeted a quaternary site readily accessible at the exposed surface of the E protein on the virion, at the interface between the two E subunits in the dimer. These broadly neutralizing antibodies (bnAbs), termed EDE for "E-dimer epitope", potently neutralize all four serotypes of DENV. Their binding site is conserved across serotypes because it is also the interaction site of prM with E dimers during transport of the immature virus particles through the Golgi apparatus of the cell. There were two subsets of EDE Mabs, characterized by a differential requirement for glycosylation on the 150 loop for binding. The EDE1 bnAbs bind better in the absence of glycan, whereas EDE2 bnAbs bind better when the glycan is present.

In this Example we identified that the EDE Mabs neutralize ZIKV as potently as they neutralize DENY. We also found that the FLE antibodies, which neutralize DENV—although not as potently as the EDE Mabs—do not neutralize ZIKV at concentrations up to 1 µM in spite of a very high affinity for the recombinant ZIKV E protein. We further describe the crystal structure of the ZIKV E protein dimer in complex with EDE1 C8 and EDE2 A11, identifying their binding determinants. We show that EDE2 A11, which requires the glycosylation site at position 153 in DENV for binding, cannot make the same interactions with the 154 gly can on ZIKV sE, which strongly reduces its binding potential such that despite its nM IC50, it displays increased ADE as described in Example 1.

A ZIKV-DENV super serogroup

Phylogenetic analyses of the main human pathogenic flaviviruses using the amino acid sequences of the viral RNA polymerase NS5 indicate a clustering of ZIKV with the group of mosquito-borne encephalitic viruses (FIG. 8A). Interestingly, this clustering is different when the amino acid sequences of the E protein are considered, with ZIKV branching with the DENV group. To see if this clustering could be reflected in the interaction with the antibodies, we used bio-layer interferometry (BLI) with an Octet instrument to measure the affinity of the poorly neutralizing, cross-reactive FLE and the potently neutralizing EDE MAbs for the recombinant soluble ZIKV E ectodomain (ZIKV sE) produced in insect cells (see Online Methods). In contrast to DENV sE, which was essentially monomeric in solution as monitored by size exclusion chromatography (SEC) and was converted to dimer upon binding by the EDE antibody fragments[30], ZIKV sE behaved as a dimer in SEC (ED. FIG. 13B).

The BLI experiments were done using three antibodies, EDE1 C8, EDE2 A11 and a representative FLE antibody, P6B10. The FLE Mab bound with almost one log higher affinity with respect to EDE1 C8 (1.5 nM vs 9 nM), and about 3 logs higher than EDE2 A11, which had a dissociation constant close to the µM range (FIG. 8B and FIG. 13A). Consistent with their binding affinities, we were able to isolate a ZIKV sE/C8 Fab complex by SEC, whereas no such complex was observed for A11 (FIG. 13B). Neutralization assays in African green monkey (VERO) cells using these and other members of the three antibody subsets, showed that the EDE1 antibodies strongly neutralized ZIKV, whereas the EDE2 were at least one log less potent. In spite of its strong binding affinity, P6B10 did not neutralize in the concentration range used, nor did any of the two other FLE antibodies tested (FIG. 9). The EDE1 Mabs neutralized better the African strain HD78788, which has over the years been cell-culture adapted and passaged in suckling mice brain, and lacks E glycosylation. But the PF13 strain isolated in French Polynesia in 2013 and in which the E protein is glycosylated in the 150 loop, at position 154, was neutralized by EDE1 Mabs with an IC50 comparable (and often lower) than that of the four serotypes of DENV (see summary in FIG. 12). The EDE2 Mabs showed no difference in neutralization of the two strains, suggesting that the presence of the N154 glycan in the ZIKV E protein did not enhance the interaction, contrary to DENV.

The immune complexes of ZIKV with EDE bnAbs

The crystallization conditions, the crystals obtained and the structure determination are described in the Online Methods section and are summarized in FIG. 18D. The crystals of the complexes of ZIKV sE with EDE1 C8 and EDE2 A11 were obtained with scFv and Fab fragments, respectively. The average resolution of the structures are 2.7 Å and 2.9 Å (respectively) and 3.1 Å for the structure of unliganded ZIKV sE dimer. The diffraction pattern was anisotropic in the three crystals; the resolution limits in the three orthogonal directions are quoted in FIG. 18D. In the structure of unliganded ZIKV, the 150 loop is ordered, contrary to the recently determined structure of ZIKV sE produced in bacteria and in vitro re-folded, which behaved as a monomer in solution[31], indicating that the glycan helps structure the loop and also promotes sE dimerization, as we observed a dimer in SEC.

As expected, the antibodies recognize a quaternary epitope in the ZIKV sE dimer in the same way they recognize the DENY serotype 2 (DENV-2) sE dimer described earlier[30].

The antibody contacts per E amino acid on the ZIKV and DENV-2 sE alignment are displayed in FIG. 14, while the E protein contacts on the sequence of the antibodies are shown in FIG. 15. The pattern is, as expected, very similar, with the few regions in which it is different highlighted in red frames in the Figure. Both epitopes in the sE dimer are occupied in the case of the complex with C8 (FIGS. 10A-10F) whereas in the case of A11, only one site was found occupied (FIGs. 11A-11E), although the conformations of occupied and unoccupied epitopes are similar. Inspection of the crystal environment showed that a second Fab could not be docked at this position without clashing with neighboring complexes in the crystal. This observation indicates that crystal growth selected for incorporation of sE dimers with a single Fab bound, which is facilitated by the low affinity of A11.

The binding angles of the MAbs to ZIKV sE are different compared to DENV-2 sE (see insets in FIGS. 10A-10F and FIGS. 11A-11E). In the case of the C8 complex, the difference in angle results mainly from an altered curvature of the sE dimer. We note that the conformation of ZIKV sE in complex with the antibodies is very similar to the one it adopts on the virus particle, with roughly 1.5 Å root mean square deviation (RMSD) for 790 Cα atoms (see FIG. 18E). The unbound ZIKV sE crystallized here displays a more distant conformation (2.5 Å RMSD when comparing to both virion ZIKV E and either sE antibody complex), suggesting that the antibodies stabilize a conformation more close to that in the viral particle. In contrast, the same comparisons done for DENV-2 sE, alone or in complex with the antibodies result in RMSD values of 5-7 Å with respect to its conformation on the virion observed by cryo-EM. In those structures, the curvature of the sE dimer is strikingly different to that on the virion (FIGS. 10A and FIG. 11A), a feature that is likely related to the absence of the interactions with the underlying stem α-helices and with the M protein (the membrane-anchored remnant of prM after furin cleavage) on the virion.

For comparison, superposition of the ectodomain of virion E from ZIKV and DENV-2 results in a similar 1.5 Å RMSD, indicating that they are presented roughly in the same way, but that DENV sE is more deformable in solution. This malleability may reflect the high conformational breathing reported for DENV E[22]. In contrast, the conformation of the E ectodomain in ZIKV seems to be more stable, remaining the same in the absence of additional interactions on the virion. This feature may be linked to the higher stability of the ZIKV virion described recentlyl[17].

EDE1 C8 Complex

The total buried surface area (BSA) of EDE1 in the complex with ZIKV sE is about 900 Å$^2$, compared to about 1300 Å$^2$ in the DENV-2 sE complex FIG. 18F. The conservation of the epitope area is shown in FIG. 10D, and FIGS. 10E and 10F compare the C8 footprint on ZIKV and DENV sE. The glycan at position N67, which was ordered in the DENV-2 sE structure (FIG. 10C), accounts for around two-thirds of the overall difference in footprint area. The N67 glycan interacts with the framework region 2 of the heavy chain (FRH2), and its absence in ZIKV sE shows that these contacts are not essential for binding. The key cluster of interactions that is maintained is centered on β-strand b of domain II, with side chains from CDRs H2, H3 and L3 recognizing all the available hydrogen bond donors (NH atoms) and acceptors (main chain carbonyls) of the bdc β-sheet edge (FIGS. 10B and 10C). In addition, the fusion loop main chain (which contains several glycine residues) and the disulfide bond between Cys74 and Cys105, are framed by aromatic side chains of the CDRs L1 and L3 (see also FIGS. 13A and 13B). Residues from these two CDRs also recognize strictly conserved side chains of the fusion loop (Arg 99) or nearby (Gln 77).

Across the dimer interface, and similar to the complex with DENV2, the 150 loop is partially disordered, with no detectable density for the N154 glycan. As shown in FIGS. 16A-16F, the interactions with domains I, II and III across the dimer interface are different, because of the difference in sequence: in the DENV-2 sE complex, these contacts were made with β-strands A and B of domain III, but in ZIKV they mainly involve Lys 373 from β-strand E interacting with CDRs L1 and L2, with a network of direct or water-mediated hydrogen bonds (FIGS. 16B AND 16C). Similarly, a number of charged residues in domain I and from the nearby kl loop of domain II across the interface, contribute to the binding and interact with the heavy chain CDRs H2 and H3 (FIGS. 16E and 16F). All the polar interactions between C8 and ZIKV sE are listed in FIGS. 19 and 20, and the electrostatic surface of the epitope is displayed in FIG. 17, left panel. In summary, these observations place the conserved cluster of contacts with the b strand and the fusion loop in domain II as the main binding determinants of C8, with additional contacts from across the dimer interface—or from the N67 glycan in DENV—further stabilizing but not determining the interaction.

EDE2 A11 Complex

The A11 antibody binds at a very different angle than seen with DENV-2 sE, even accounting for the difference in sE dimer curvature. The contacts along the b-strand are preserved, but the antibody makes a different angle the strand (FIG. 11B). Compared to C8, the b strand is recognized only at its end (residues 71 and 73), whereas C8 recognizes it all along, from residue 68 (or from 67 in DENV). Because the contacts with the glycan on the 150 loop are also important for binding, the observed tilted binding of A11 is likely related to the shifted position of the 154 glycan compared to the 153 glycan in DENY. The details of the hydrogen bond interactions are less well defined in the complex with DENV-2 sE, because of the more limited resolution of 3.8 Å. Yet it is clear that there is a different set of contacts with the glycan (FIGS. 11C and 18B). In the DENV2 sE/A11 complex, the glycan is recognized by an α-helix in the long CDR3 loop. In the case of ZIKV sE, there is an insertion preceding the glycan site, which results in a shift of about 6-7 Å, such that it cannot make the same interactions with the CDR H3 α-helix. Importantly, comparison with the structure of ZIKV on the virion or with unbound glycosylated ZIKV sE shows that the 150 loop is well ordered (FIG. 18A), and that it is induced into disorder by the EDE1 antibodies, as was the case for the DENV2 virus. FIG. 18C shows the clash with C8 would the glycan chain had remained in place.

Discussion

Our results identify the structural details of a quaternary epitope that provides a previously unrecognized link of potent cross-neutralization between Zika and dengue viruses, and thus identifies an antigenic flavivirus cluster beyond the traditional serocomplexes. This relationship defines a super serogroup on the basis of strong cross-neutralization through a conserved epitope that had not been recognized using polyclonal sera[21]. This work thus lays the foundation for the rational design of a universal vaccine that can protect against all the viruses from this group.

Vaccine design against dengue virus has been hampered by the heterogeneity of DENV particles and the need to use polyvalent formulas to immunize against all four serotypes[32,33]. One feature of DENV is that it undergoes incomplete furin maturation cleavage of prM in many cell types, giving rise to heterogeneous mosaic particles with an immature-like spiky patch on one side and a smooth mature-like region on the opposite side[34]. These particles are infectious, as they can fuse with the cellular membrane through the smooth, mature side. Because the FLE is exposed in immature regions[35], an overwhelming antibody response in DENV infected patients is directed against it[36]. These highly cross-reactive antibodies coat the particles essentially on the "immature side"[35], and therefore are weakly neutralizing, relying on the "breathing" effect of the E dimers to bind and neutralize on the mature, infectious side[37-39]. The high avidity of the FLE antibody for the E protein, as exemplified by Mab P6B10 (FIGS. 8A AND 8B), and the fact that it is non- or very poorly neutralizing (FIG. 9), suggest that it is likely to bind only to immature patches on ZIKV particles. A recently published structure of monomeric Zika sE in complex with a FLE-specific Mab of low neutralizing activity indeed shows that its binding site would be occluded in the dimeric E protein on mature infectious virions[31]. The observation that Mab P6B10 and other FLE antibodies still neutralize DENV[27] suggests that the mature patches may have different "breathing" kinetics, fast in DENV and slow in ZIKV, as suggested by the high thermal stability of ZIKV reported recently[17], allowing it to more rapidly coat the mature patches in DENV but not in ZIKV to neutralize.

Our data suggest that developing an epitope-focused vaccine against the ZIKV/DENV super-serogroup is a viable approach. It is clear from our results that the epitope targeted by the EDE1 bnAbs is best suited for this purpose, in stark contrast with the FLE, which induces poorly neutralizing and strong infection enhancing antibodies[26-28]. The EDE2 antibodies were also shown to induce ADE[26], in line with their poor avidity for the sE dimer (FIGS. 8A and 8B). The EDE1 is more extended on the E surface than the EDE2 (see comparison in FIG. 17) and does not rely on the presence of glycan, with the shift in the 154 glycan in ZIKV being the likely reason why it binds so poorly. In contrast, although EDE1 Mabs require a dimer to bind, the contact points in the adjacent subunit in the dimer do not appear to be important determinants of the interaction, provided that they are not incompatible with Mab binding, with the actual determinants centered on the b strand and on the highly conserved E dimer exposed elements of the fusion loop only. As the main chain is strictly conserved, with no amino acid insertions nor deletions observed in the polypeptide chain in the region of the b strand in any flavivirus, the potential to extend this approach to other flaviviruses is high. Such an approach would be a powerful alternative to the multi-immunogen approaches against the DENV cluster that have had limited success in clinical trials[40]. Finally, our study also suggests that the EDE1 antibodies carrying the "LALA" mutation in the effector site to eliminate all remaining ADE effect could be useful for immune prophylaxis for pregnant women at risk of contracting ZIKV infection.

REFERENCES

1 Brasil, P. et al. Zika Virus Infection in Pregnant Women in Rio de Janeiro—Preliminary Report. *N Engl J Med*, doi:10.1056/NEJMoa1602412 (2016).

2 Faria, N. R. et al. Zika virus in the Americas: Early epidemiological and genetic findings. *Science* 352, 345-349, doi:10.1126/science.aaf5036 (2016).

3 Zanluca, C. et al. First report of autochthonous transmission of Zika virus in Brazil. *Mem Inst Oswaldo Cruz* 110, 569-572, doi:10.1590/0074-02760150192 (2015).

4 Broutet, N. et al. Zika Virus as a Cause of Neurologic Disorders. *N Engl J Med* 374, 1506-1509, doi:10.1056/NEJMp1602708 (2016).

Cao-Lormeau, V. M. et al. Guillain-Barre Syndrome outbreak associated with Zika virus infection in French Polynesia: a case-control study. *Lancet* 387, 1531-1539, doi:10.1016/S0140-6736(16)00562-6 (2016).

6 WHO. WHO *Director-General summarizes the outcome of the Emergency Committee regarding clusters of microcephaly and Guillain-Barré syndrome*, 2016).

7 Paixao, E. S., Barreto, F., da Gloria Teixeira, M., da Conceicao, N. C. M. & Rodrigues, L. C. History, Epidemiology, and Clinical Manifestations of Zika: A Systematic Review. *Am J Public Health* 106, 606-612, doi:10.2105/AJPH.2016.303112 (2016).

8 D'Ortenzio, E. et al. Evidence of Sexual Transmission of Zika Virus. *N Engl J Med*, doi:10.1056/NEJMc1604449 (2016).

9 Foy, B. D. et al. Probable non-vector-borne transmission of Zika virus, Colorado, USA. *Emerg Infect Dis* 17, 880-882, doi:10.3201/eid1705.101939 (2011).

10 WHO. *Situation Report: Zika virus microcephaly Guillain-Barré syndrome* 5 May 2016, (2016).

11 Lindenbach, B., Murray, C., Thiel, H. & Rice, C. *Flaviviridae: the viruses and their replication*. 6th edn, Vol. 1 1101-1152 (Lippincott Williams & Wilkins, 2013).

12 Li, L. et al. The flavivirus precursor membrane-envelope protein complex: structure and maturation. *Science* 319, 1830-1834, doi:10.1126/science.1153263 (2008).

13 Stadler, K., Allison, S. L., Schalich, J. & Heinz, F. X. Proteolytic activation of tick-borne encephalitis virus by furin. *J Virol* 71, 8475-8481 (1997).

14 Yu, I. M. et al. Structure of the immature dengue virus at low pH primes proteolytic maturation. *Science* 319, 1834-1837, doi:10.1126/science.1153264 (2008).

15 Kuhn, R. J. et al. Structure of dengue virus: implications for flavivirus organization, maturation, and fusion. *Cell* 108, 717-725 (2002).

16 Zhang, X. et al. Cryo-EM structure of the mature dengue virus at 3.5-A resolution. *Nat Struct Mol Biol* 20, 105-110, doi:10.1038/nsmb.2463 (2013).

17 Kostyuchenko, V. A. et al. Structure of the thermally stable Zika virus. *Nature*, doi:10.1038/nature17994 (2016).

18 Sirohi, D. et al. The 3.8 A resolution cryo-EM structure of Zika virus. *Science* 352, 467-470, doi:10.1126/science.aaf5316 (2016).

19 Mukhopadhyay, S., Kim, B. S., Chipman, P. R., Rossmann, M. G. & Kuhn, R. J. Structure of West Nile virus. *Science* 302, 248, doi:10.1126/science.1089316 (2003).

20 Zhang, W., Kaufmann, B., Chipman, P. R., Kuhn, R. J. & Rossmann, M. G. Membrane curvature in flaviviruses. *J Struct Biol* 183, 86-94, doi:10.1016/j.jsb.2013.04.005 (2013).

21 Calisher, C. H. et al. Antigenic relationships between flaviviruses as determined by cross-neutralization tests with polyclonal antisera. *J Gen Virol* 70 (Pt 1), 37-43, doi:10.1099/0022-1317-70-1-37 (1989).

22 Kuhn, R. J., Dowd, K. A., Beth Post, C. & Pierson, T. C. Shake, rattle, and roll: Impact of the dynamics of flavivirus particles on their interactions with the host. *Virology* 479-480, 508-517, doi:10.1016/j.virol.2015.03.025 (2015).

23 Stiasny, K., Kiermayr, S., Holzmann, H. & Heinz, F. X. Cryptic properties of a cluster of dominant flavivirus cross-reactive antigenic sites. *J Virol* 80, 9557-9568, doi:10.1128/JVI.00080-06 (2006).

24 Vogt, M. R. et al. Poorly neutralizing cross-reactive antibodies against the fusion loop of West Nile virus envelope protein protect in vivo via Fcgamma receptor and complement-dependent effector mechanisms. *J Virol* 85, 11567-11580, doi:10.1128/JVI.05859-11 (2011).

25 Balsitis, S. J. et al. Lethal antibody enhancement of dengue disease in mice is prevented by Fc modification. *PLoS Pathog* 6, e1000790, doi:10.1371/journal.ppat.1000790 (2010).

26 Dejnirattisai, W. et al. Dengue serocrossreactivity drives antibody dependent enhancement of Zika virus infection. (Submitted, related manuscript) (2016).

27 Dejnirattisai, W. et al. A new class of highly potent, broadly neutralizing antibodies isolated from viremic patients infected with dengue virus. *Nat Immunol* 16, 170-177, doi:10.1038/ni.3058 (2015).

28 Goncalvez, A. P., Engle, R. E., St Claire, M., Purcell, R. H. & Lai, C. J. Monoclonal antibody-mediated enhancement of dengue virus infection in vitro and in vivo and strategies for prevention. *Proc Natl Acad Sci USA* 104, 9422-9427, doi:10.1073/pnas.0703498104 (2007).

29 Halstead, S. B. In vivo enhancement of dengue virus infection in rhesus monkeys by passively transferred antibody. *J Infect Dis* 140, 527-533 (1979).

30 Rouvinski, A. et al. Recognition determinants of broadly neutralizing human antibodies against dengue viruses. *Nature* 520, 109-113, doi:10.1038/nature14130 (2015).

31 Dai, L. et al. Structures of the Zika Virus Envelope Protein and Its Complex with a Flavivirus Broadly Protective Antibody. *Cell Host Microbe*, doi:10.1016/j.chom.2016.04.013 (2016).

32 Sabchareon, A., Wallace, D., Lang, J., Bouckenooghe, A. & Moureau, A. Efficacy of tetravalent dengue vaccine in Thai schoolchildren—Authors' reply. *Lancet* 381, 1094-1095, doi:10.1016/50140-6736(13)60755-2 (2013).

33 Vannice, K. S., Durbin, A. & Hombach, J. Status of vaccine research and development of vaccines for dengue. *Vaccine*, doi:10.1016/j.vaccine.2015.12.073 (2016).

34 Plevka, P. et al. Maturation of flaviviruses starts from one or more icosahedrally independent nucleation centres. *EMBO Rep* 12, 602-606, doi:10.1038/embor.2011.75 (2011).

35 Cherrier, M. V. et al. Structural basis for the preferential recognition of immature flaviviruses by a fusion-loop antibody. *EMBO J* 28, 3269-3276, doi:10.1038/emboj.2009.245 (2009).

36 Beltramello, M. et al. The human immune response to Dengue virus is dominated by highly cross-reactive antibodies endowed with neutralizing and enhancing activity. *Cell Host Microbe* 8, 271-283, doi:10.1016/j.chom.2010.08.007 (2010).

37 Dowd, K. A., Mukherjee, S., Kuhn, R. J. & Pierson, T. C. Combined effects of the structural heterogeneity and dynamics of flaviviruses on antibody recognition. *J Virol* 88, 11726-11737, doi:10.1128/JVI.01140-14 (2014).

38 Lee, P. D. et al. The Fc region of an antibody impacts the neutralization of West Nile viruses in different maturation states. *J Virol* 87, 13729-13740, doi: 10.1128/JVI.02340-13 (2013).

39 Mukherjee, S. et al. Mechanism and significance of cell type-dependent neutralization of flaviviruses. *J Virol* 88, 7210-7220, doi:10.1128/JVI.03690-13 (2014).

40 Capeding, M. R. et al. Clinical efficacy and safety of a novel tetravalent dengue vaccine in healthy children in Asia: a phase 3, randomised, observer-masked, placebo-controlled trial. *Lancet* 384, 1358-1365, doi: 10.1016/S0140-6736(14)61060-6 (2014).

41 Hessell, A. J. et al. Fc receptor but not complement binding is important in antibody protection against HIV. *Nature* 449, 101-104, doi:10.1038/nature06106 (2007).

Methods

Recombinant production of ZIKV sE protein. Recombinant Zika virus sE protein (strain H/PF/2013, GenBank accession no. KJ776791) was produced with a tandem strep-tag in the *Drosophila* Expression System (Invitrogen) as described previously[42,43]. A chemically synthesized DNA fragment (GeneArt) containing the Zika sE sequence (amino acid 1-408) was cloned into the expression vector pT389[44] that encodes the export signal sequence BIP, an enterokinase cleavage site and the strep-tag. *Drosophila* Schneider 2 cells were stably transfected using blasticidin for selection. Protein expression was induced by the addition of $CuSO_4$ and supernatants were harvested 7-10 days after induction. Antigens were purified via affinity chromatography with Streptactin columns (IBA) according to the manufacturer's instructions. A final purification gel filtration step used a Superdex increase 200 10/300 GL column equilibrated in 50 mM Tris pH8, 500 mM NaCl.

Production of antigen-binding (Fab) and single-chain Fv (scFv) fragments of the bnAbs. The bnAb fragments were cloned into plasmids for expression as Fab[45] and scFv[46] in *Drosophila* S2 cells. The constructs contain a tandem strep tag fused at the C terminus (only of the heavy chain in the case of the Fab) for affinity purification. The purification protocol included a Streptactin affinity column followed by gel filtration as described above.

Immune complex formation and isolation. The purified ZIKV sE protein was mixed with Fab A11 or scFv C8 (in approximately twofold molar excess) in standard buffer (500 mM NaCl, Tris 50 mM pH 8.0). The volume was brought to 0.5 ml by centrifugation in a Vivaspin 10 kDa cutoff; after 30 min incubation at 4° C., the complex was separated from excess Fab or scFv by size-exclusion chromatography (SEC) for ZIKV sE and scFv C8. For ZIKV sE and Fab A11 no apparent complex formation could be seen in SEC; therefore a solution containing sE at a concentration of 1.5 mg/ml and Fab A11 at a concentration of 3 mg/ml (corresponding to a molar ratio ~1:2 antigen:antibody) was directly used for crystallization. In all cases, the buffer was exchanged to 150 mM NaCl, 15 mM Tris, pH 8 for crystallization trials. The protein concentrations used for crystallization, determined by measuring the absorbance at 280 nm and using an extinction coefficient estimated from the amino-acid sequences, are listed in Extended Data Table 1 (FIG. 18D).

Real-time biolayer interferometry binding assays. The interactions of purified ZIKV E protein with Mabs IgG FLE P6B10, IgG EDE1 C8, IgG EDE2 A11, and control Mabs IgG 28C (an anti-Influenza virus) and IgG K9 (an anti-Chikungunya virus) were monitored in real-time using a Bio-layer interferometry Octet-Red384 device (Pall ForteBio). Anti-human IgG Fc capture biosensors (Pall ForteBio) were loaded for 10 min at 1000 rpm shaking speed using antibodies at 5 µg/ml in assay buffer (PBS+0.2 mg/ml BSA+tween 0.01%). Unbound antibodies were washed away for 1 min in assay buffer. IgG-loaded sensors were then incubated for 15 min at 1200 rpm in the absence and presence of two fold serially diluted ZIKV sE protein concentrations in assay buffer. Molar concentrations were calculated for the sE protein in a dimeric form. For Mabs FLE P6B10, EDE1 C8 and EDE2 A11, the following ZIKV sE concentration ranges: 50-0.78 nM, 200-3.125 nM and 3200-50 nM, were respectively used. Reference binding experiments were carried out in parallel on sensors loaded with control IgGs (28C and K9). Dissociation of the complexes formed was then monitored for 10 min by dipping sensors in assay buffer alone. Operating temperature was maintained at 25° C. The real-time data was analyzed using Scrubber 2.0 (Biologic Software) and Biaevaluation 4.1 (GE Healthcare). Specific signals were obtained by double-referencing, ie subtracting non-specific signals measured on non-specific IgG-loaded sensors and buffer signals on specific IgG-loaded sensors. Association and dissociation profiles, as well as steady-state signal vs concentration curves, were fitted assuming a 1:1 binding model.

Crystallization and X-ray structure determinations. The crystallization and cryo-cooling conditions for diffraction data collection are listed in Extended Data Table 1(FIG. 18D). Crystallization trials were performed in sitting drops of 400 nl. Drops were formed by mixing equal volumes of the protein and reservoir solution in 96 wells Greiner plates, using a Mosquito robot and monitored by a Rock-Imager. Crystals were optimized using a robotized Matrix Maker and Mosquito setups on 400 nl sitting or hanging drops, or manually in 24-well plates using 2-3 µl hanging drops.

Because of the strong anisotropy of the crystals (see results for anisotropy in Extended Data Table 1(FIG. 18D)), an important number of crystals was tested at several beam lines at different synchrotrons (SOLEIL, St Aubin, France; ESRF, Grenoble, France; SLS, Villigen, Switzerland). The crystals having the less anisotropic diffraction data and used to solve the structures were collected at the beam lines PROXIMA-1 and PROXIMA-2 at the SOLEIL synchrotron and beam line ID23-2 at ESRF. The datasets were indexed, integrated, scaled and merged using XDS[47] and AIMLESS[48]. A preliminary model of ZIKV sE protein was built from the DENV-2 sE (4UTA) structure using the structure homology-modeling server SWISS-MODEL[49]. The structures of the complexes were then determined by molecular replacement with PHASER[50] using the search models listed in Extended Data Table 1. AIMLESS and PHASER programs were used within the CCP4 suite[51].

The DEBYE and STARANISO programs developed by Global Phasing Ltd. were applied to the AIMLESS scaled data without truncation of the resolution, using the STARANISO server (staraniso.globalphasing.org/). These softwares perform an anisotropic cut-off of merged intensity data with a Bayesian estimation of the structure amplitudes, and apply an anisotropic correction to the data. These corrected anisotropic amplitudes were then used for further refinement of both structures with BUSTER/TNT[52.] Please note that the Extended Data Table 1 shows the refinement statistics for the full sets of reflections truncated at the best high-resolution along h, k or l axis, values output from AIMLESS without the anisotropic corrections computed by the STARANISO server.

The models were then alternatively manually corrected and completed using COOT[53] and refined using BUSTER/TNT against the amplitudes corrected for anisotropy. Refinements were constrained using non-crystallographic symmetry (see Extended Data Table 1). The refined structures ZIKV sE/EDE2 A11 Fab, ZIKV sE/EDE1 C8 scFv and ZIKV sE have a final Rwork/Rfree (in %) of 21.8/23.8 and of 18.7/22.0 and of 22.9/27.5, respectively.

Analysis of the atomic models and illustrations. Each complex was analyzed with the CCP4 suite of programs and the polar contacts were computed with the PISA website[54].

For the intermolecular interactions shown in (FIGS. 16A-16F and FIGS. 18A-18C) and Extended Data Tables 4 and 5 (FIG. 19 and FIG. 20), the maximal cutoff distances used were 4 Å and 4.75 Å for polar and van der Waals contacts, respectively. Multiple sequence alignments were calculated using Clustal W and Clustal X version 2[55] on the EBI server[56]. All protein structure figures were prepared using ESPript[57] and the PyMOL Molecular Graphics System, version 1.5.0.4 (Schrödinger) (pymol. sourceforge.net).

Phylogenic trees. The Maximum likelihood phylogenetic trees were inferred using 12 representative amino-acid sequences of flaviviruses envelope protein E or RNA-polymerase NS5 proteins, utilizing the LG model available in PhyML[58] and a combination of SPR+NNI branch-swapping. Bootstrap values were calculated from 100 bootstrap replicates. Trees were visualized using Figtree (http://tree.bio.ed.ac.uk.software/figtree/). The accession codes of sequences used in the tree: Zika virus (ZIKV, KJ776791, strain H-PF-2013 French Polynesia); dengue virus serotype 1 (DENY-1, NC_001477); dengue virus serotype 2 (DENV-2, NC_001474); dengue virus serotype 3 (DENV-3, NC_001475); dengue virus serotype 4 (DENV-4, NC_002640); Saint Louis encephalitis virus (SLEV, NC_007580); Japanese encephalitis virus (JEV, NC_001437; Murray Valley encephalitis virus (MVEV, NC_000943); West Nile virus (WNV, NC_001563); yellow fever virus (YFV, NC_002031); tick-borne encephalitis virus (TBEV, NC_001672); Powassan virus (POWV, NC_003687).

Virus stocks. The African strain Zika HD78788 was obtained from the Institut Pasteur collection and the Asian strain Zika PF13, isolated from a patient during ZIKV outbreak in French Polynesia in 2013, was obtained through the DENFREE (FP7/2007-2013) consortium. Viral stocks were prepared from supernatant of infected C6/36 cells clarified by centrifugation at 3000 g at 4° C. and titrated on Vero cells by a focus-forming assay. Stocks were kept at −80° C. until use.

Neutralization Assays. Virus neutralization by the tested human antibodies was evaluated using a focus reduction neutralization test (FRNT). About 100 ffu (focus forming unit) from virus stocks were incubated with a serial dilution of antibody for 1 h at 37° C. The mixture was then added to Vero cells and foci were let to develop in presence of 1.5% methylcellulose for two days. Foci were then stained after fixation with 4% formaldehyde using anti-E 4G2 antibody and anti-mouse HRP-conjugated secondary antibody. The foci were visualized by DAB staining and plates were counted using the ImmunoSpot S6 Analyser (Cellular Technology Limited, CTL). Neutralization curves and 50% FRNT were calculated using GraphPad Prism software.

METHODS REFERENCES

42 Vratskikh, O. et al. Dissection of antibody specificities induced by yellow fever vaccination. *PLoS Pathog* 9, e1003458, doi: 10.1371/journal.ppat.1003458 (2013).

43 Jarmer, J. et al. Variation of the specificity of the human antibody responses after tick-borne encephalitis virus infection and vaccination. *J Virol* 88, 13845-13857, doi:10.1128/JVI.02086-14 (2014).

44 DuBois, R. M. et al. Functional and evolutionary insight from the crystal structure of rubella virus protein E1. *Nature* 493, 552-556, doi:10.1038/nature11741 (2013).

45 Backovic, M. et al. Efficient method for production of high yields of Fab fragments in *Drosophila* S2 cells. *Protein Eng Des Sel* 23, 169-174, doi:10.1093/protein/gzp088 (2010).

46 Gilmartin, A. A. et al. High-level secretion of recombinant monomeric murine and human single-chain Fv antibodies from *Drosophila* S2 cells. *Protein Eng Des Sel* 25, 59-66, doi:10.1093/protein/gzr058 (2012).

47 Kabsch, W. Xds. *Acta Crystallogr D Biol Crystallogr* 66, 125-132, doi:10.1107/S0907444909047337 (2010).

48 Evans, P. R. & Murshudov, G. N. How good are my data and what is the resolution? *Acta Crystallogr D Biol Crystallogr* 69, 1204-1214, doi:10.1107/S0907444913000061 (2013).

49 Biasini, M. et al. SWISS-MODEL: modelling protein tertiary and quaternary structure using evolutionary information. *Nucleic Acids Res* 42, W252-258, doi: 10.1093/nar/gku340 (2014).

50 McCoy, A. J. et al. Phaser crystallographic software. *Journal of applied crystallography* 40, 658-674, doi: 10.1107/S0021889807021206 (2007).

51 Winn, M. D. et al. Overview of the CCP4 suite and current developments. *Acta Crystallogr D Biol Crystallogr* 67, 235-242, doi:10.1107/50907444910045749 (2011).

52 Blanc, E. et al. Refinement of severely incomplete structures with maximum likelihood in BUSTER-TNT. *Acta Crystallogr D Biol Crystallogr* 60, 2210-2221, doi:10.1107/S0907444904016427 (2004).

53 Emsley, P., Lohkamp, B., Scott, W. G. & Cowtan, K. Features and development of Coot. *Acta Crystallogr D Biol Crystallogr* 66, 486-501, doi:10.1107/S0907444910007493 (2010).

54 Krissinel, E. & Henrick, K. Inference of macromolecular assemblies from crystalline state. *J Mol Biol* 372, 774-797, doi:10.1016/j.jmb.2007.05.022 (2007).

55 Larkin, M. A. et al. Clustal W and Clustal X version 2.0. *Bioinformatics* 23, 2947-2948, doi:10.1093/bioinformatics/btm404 (2007).

56 Goujon, M. et al. A new bioinformatics analysis tools framework at EMBL-EBI. *Nucleic Acids Res* 38, W695-699, doi:10.1093/nar/gkq313 (2010).

57 Gouet, P., Courcelle, E., Stuart, D. I. & Metoz, F. ESPript: analysis of multiple sequence alignments in PostScript. *Bioinformatics* 15, 305-308 (1999).

58 Guindon, S. et al. New algorithms and methods to estimate maximum-likelihood phylogenies: assessing the performance of PhyML 3.0. *Systematic biology* 59, 307-321, doi:10.1093/sysbio/syq010 (2010).

EXAMPLE 3

Increasing the Flavivirus Envelope Glycoprotein Dimer Stability to Elicit Potent and Broadly Neutralizing Antibody Responses Potently cross-neutralizing human antibodies against the four serotypes of dengue virus (DENV) have recently been isolated and structurally characterised. See, for example, WO 2016/012800; Rouvinski et al (2015) Nature 520, 109-113; Dejnirattisai et al (2015) Nature Immunol 16, 170-177. These antibodies bind to a highly conserved epitope termed the E-dimer-epitope (EDE), which we have now discovered is also conserved in Zika virus (ZikaV), leading also to potent neutralization of ZikaV. The mature DENV particle is an assembly of metastable E dimers with a strong "breathing" behaviour, meaning that it promotes the generation of many poorly neutralizing, yet disease enhancing antibodies. We describe a reverse vaccinology approach to develop antigens capable of eliciting a protective immune response against flaviviruses, for example zika-dengue group of flaviviruses, based upon the production of stabilized E-protein dimers whilst minimising the production of poorly neutralizing antibody responses.

The present inventors have studied the immune response to DENV infection to both understand immunopathogenesis and to inform vaccine design. This has included studying the human antibody response to infection.

These studies have included consideration of antibodies to precursor membrane protein. PrM-specific antibodies are a major component of the memory B cell response to dengue; these antibodies show poor neutralization (maximum 30-50%) even at high concentration[16,34-37]. prM-specific antibodies do not bind to fully mature virions which do not contain prM, whereas many partially mature particles do not contain a high enough density of prM to allow neutralization but yet may be sufficient to promote ADE[16,38]. We have speculated that the inefficient cleavage of prM may be an immune evasion/enhancement strategy, leading to the generation of poorly neutralizing antibodies directed to prM. The high frequency, low potency and high ADE potential of antibodies directed to prM has implications for vaccine design; all attenuated vaccines at an advanced stage of development contain prM, the ideal vaccine would focus responses to the E and the prM component of the response be minimized if the potential for ADE in vaccines is to be reduced.

In a second series of experiments we have recently described the cloning of a large panel of anti-E mAb from dengue infected patients[17]. One third of the antibodies do not bind to recombinant E protein, suggesting a conformationally sensitive quaternary epitope and many of these antibodies showed broad neutralization of all four dengue serotypes. The bnAb anti-dengue mAb (bnAb) are amongst the most potent described to date and bind to the basic repeating envelope dimers making up the virion surface lattice, to a site that we termed the E-dimer epitope EDE (FIGS. 24 and 24B)[17,39]. In addition, we have identified (Example 1) that the epitope recognized by some EDE antibodies is also conserved in at least the ZikaV E-dimer, leading to equally potent neutralization making the EDE also a potential target in flaviviruses other than Dengue, for example Zika.

Structural characterization of these antibodies has shown they bind in a valley formed between the two E subunits of the head to tail dimers present at the surface of the virion[39]. The antibodies make contact with a conserved surface patch at the dimer surface, including atoms of the fusion loop main chain but not its side chains (FIG. 24C). This conformational site is also responsible for the interaction of the E-dimer with prM during virus maturation, explaining its conservation within the flavivirus, for example dengue-Zika, group. In addition to their broad neutralizing potential the anti-EDE mAb also efficiently neutralize virus produced in insect as well as in primary human cells[17]. The latter are a probable surrogate of viruses produced in the infected human host, contain low levels of prM and are the most difficult to neutralize.

The discovery of the EDE opens up a number of interesting future possibilities in dengue vaccine research. Current vaccination strategies use tetravalent formulations with the aim of raising single serotype specific responses against all four serotypes. The demonstration that potent bnAb are produced in dengue infection, which can also potently neutralize at least ZikaV, means that the generation of such antibodies should be a goal for the next generation vaccines. Importantly, as the response is limited to the E-dimer it opens the way for subunit vaccines consisting of E-dimers alone and furthermore, it may be possible to design a single universal immunogen, rather than a multivalent formulation to achieve this response. Alternatively, heterologous prime boost strategies may be used to focus the response to the EDE, potentially following LATV priming.

Dengue vaccines are now at an important juncture; a large scale Phase III trial has underperformed expectations and given a concerning safety signal of enhanced infection. We consider the E-dimer can be stabilised, removing prM from the immunogen and further reducing the generation of poorly neutralising antibodies such as the immunodominant response to the fusion loop epitope (FLE). We consider a subunit flavivirus (for example Dengue or Zika) vaccine aimed at driving a potent bnAb response to the EDE also has utility against flavivirus infection beyond Dengue, for example against ZikaV infection; or against both Dengue and ZikaV infection; or against Dengue, ZikaV and other flavivirus infection.

Possible Experimental Plan

A reverse vaccinology approach may be taken to design a subunit vaccine to dengue and/or other flaviviruses. This may make use of the generation and structural characterization of the bnAb EDE epitope based on a panel of recombinant antibodies targeting conformational epitopes such as the EDE as well as linear epitopes such as the FLE and prM, for example as described in WO 2016/012800; Rouvinski et al (2015) Nature 520, 109-113; Dejnirattisai et al (2015) Nature Immunol 16, 170-177. The general aim of this plan is to generate a stable version of the E-dimer and then through an iterative structural/modelling informed design process to develop immunogens to specifically target the generation of an anti-EDE response whilst resurfacing non-EDE related areas of the dimer to reduce the generation of less protective but infection enhancing antibodies. Immunogenicity can be tested in human immunoglobulin transgenic mice (for example mice such as those described in Lee et al (2014) Nature Biotechnology Vol 32(4), 356-363; or mice such as those described in EP1360287 or EP2264163) and in vivo neutralization can be tested in murine models of DENV infection, for example.

1. Stabilisation of the E-dimer. The E-dimer is the pre-fusion form of E, which is presented at the virion surface in a metastable conformation[40]. This meta-stability is important to allow the glycoprotein shell encasing the viral membrane, which is formed by lateral interactions between E-dimers, to dissociate under the mildly acidic environment of the early endosomes. The resulting E-monomers can then insert the fusion loop into the endosomal membrane[7,41]. The subsequent acid-triggered irreversible conformational change of E leads to a very stable "post-fusion" E-trimer, which is the ground state of the molecule[41]. The energy released in this transition between a high energy, dimeric state of E and its lowest energy conformation—the post-fusion trimer—is used to drive lipid merger and allow the release of the viral genome into the cytosol of the cell. Because of its meta-stability, E has been shown to display considerable "breathing" at the virion surface under standard conditions (neutral pH), exposing to the immune system regions that are not relevant for antibody neutralization[42-44].

Recombinant DENV sE (i.e., Dengue "soluble-E", lacking stem and trans-membrane segments) is predominantly monomeric in solution having a dissociation constant in the micromolar range. For immunogen design, the aim is to make the sE-dimer as stable as possible, rendering it inert and not exhibiting the dynamic breathing observed at the virion surface. In addition, the aim is to alter (resurface) the E-dimer surface on regions outside the EDE, to limit the extent of elicitation of serotype specific antibodies. We have now identified that the ZikaV-sE is stable as a dimer in solution, providing us with an important number of mutations that preserve the EDE, yet in a quite different context, since the rest of the glycoprotein is different enough to those of the DENVs such that the cross-reactivity may be limited to the EDE.

For other viral diseases, capture and stabilization of quaternary structures in the meta-stable, prefusion conformation (i.e., the active form of the virion) is indeed now a key objective of several subunit anti-viral vaccine approaches. In respiratory syncytial virus, potent neutralizing antibodies to the trimeric pre-fusion conformation of the F-protein have led to the design of novel immunogens stabilizing the F-protein pre-fusion trimer[45,46]. In HIV, the recent structural determination of mAb bound to the pre-fusion conformation of Env will drive efforts to stabilise pre-fusion viral intermediates for potential HIV subunit vaccines[47]. Similar approaches for influenza-HA have shown that a recombinant stabilized trimeric stalk fragment was able to elicit cross-reactive antibodies against the virus[48,49].

Two main classes of mutants can be developed to stabilize the dimer:

A. Disulphide stabilized mutants: We used a structure-based approach[50] for triaging possible pairs of mutations for disulphide bond formation to improve sE-dimer stability. Analysis of the crystal structure of the sE-dimer from DENV revealed a number of pairs of residues facing each other with $C_\beta$-$C_\beta$ distances under 4.5 Å across the dimer interface. We have thus identified six locations where substitution by a pair of cysteines (two of which are residues facing each other across the molecular 2-fold axis of the sE-dimer, requiring only a single substitution to cysteine). 3 of the mutants have already led to successful covalent DENV sE-dimer expression, recapitulating the EDE and binding to our panel of EDE-mAbs (FIGS. 25A and 25B) and in preliminary experiments induce higher neutralizing antibody titres compared to monomeric-E in immunized mice (FIG. 25). Although the ZikaV sE-dimer is more stable than E-dimers of the four DENVs, FLE (fusion loop epitope)-antibodies still bind to ZikaV, suggesting that such antibodies resulting from a previous dengue infection could enhance Zika disease. It is thus important to further stabilize the ZikaV sE-dimer such that the FLE is not exposed. We have now transferred the same cysteine mutations to the ZikaV protein, and, for example, immunization tests can be conducted in parallel, with ZikaV-sE and DENV-sE disulfide-stabilized mutants.

Rouvinski et al (2017) NATURE COMMUNICATIONS|8:15411|DOI: 10.1038/ncomms15411

"Covalently linked dengue virus envelope glycoprotein dimers reduce exposure of the immunodominant fusion loop epitope" also reports the inventors' engineering of E dimers locked by inter-subunit disulfide bonds, and shows by X-ray crystallography and by binding to a panel of human antibodies that these engineered dimers do not expose the FLE, while retaining the EDE exposure.

B. Cavity filling and resurfacing mutants: Using Rosetta software[51] we have identified hydrophobic cavities in the structure of the sE-dimer, and residues that could be substituted in order to fill these cavities to stabilize the dimer. These mutations will be designed manually using the prevalent rotamers looking to minimize clashes or with Rosetta software. Of particular relevance will be the domain I/III interface, which creates a binding pocket for the fusion loop of the partner subunit in the dimer. Release of domain III from the interaction with domain I is key to expose the fusion loop so freezing the domain I/III interaction is therefore an important goal. Alternatively or in parallel, de novo computational resurfacing, for example as described in[52,53] can be used. This de novo approach may allow a greater variety of potential solutions to be tested. Alternatively or in addition, for example if computational approaches are insufficient, mammalian display directed evolution may be used to carry out resurfacing. For a review relating to resurfacing approaches, see, for example, Chapman & McNaughton (2016) Cell Chemical Biology 23, 543-553.

Further mutagenesis of the selected re-surfaced genes is considered to allow determination of viable substitutions within the area of the EDE that do not interfere with binding to EDE-antibodies. We have information from previous alanine scanning mutagenesis (see for example WO 2016/012800; Rouvinski et al (2015) Nature 520, 109-113; Dejnirattisai et al (2015) Nature Immunol 16, 170-177), and residues that are not binding determinants can be substituted, as long as they do not introduce a bulky side chain that may cause steric clashes with the antibody. Similarly, additional N-linked glycosylation sites can be introduced strategically positioned to mask serotype specific epitopes while not interfering with binding of EDE-mAbs. In total, we estimate that the process of dimer stabilization and resurfacing may entail screening around 100 mutations on the best performing initial resurfaced genes.

In total, we have identified ~100 initial individual mutations of sE, which can, for example, be tested both in a DENV2 (for example) serotype and in a ZikaV-sE background (see for example the Mutation section above). Preliminary data suggest that DENV2 has the least stable sE-dimer, and is the most prone to breathing, whereas the ZikaV sE-protein is the most stable. All mutants can be tested for expression, dimerization and antibody reactivity. The mutants performing best can be used as combinations of pairs of mutants, which can be tested iteratively.

Analytical ultracentrifugation can be used to determine dimerization constants in solution. Thermofluorimetry along with differential scanning calorimetry can be used to determine the denaturation profile of stabilized mutants upon heating or destabilizing chaotropes+/− EDE/Abs. Surface plasmon resonance, Biolayer interferometry as well as isothermal calorimetry can be used to determine Kon and Koff values between a subset of selected mutants and a panel of EDE/FLE-mAbs in different pH conditions. Stabilized sE-mutants can also be tested by flotation assay in presence of liposomes in comparison with wild type sE. We consider that stabilized dimers may be impaired in flotation upon acidification as the fusion loop should not be available to interact with liposomes. Finally, a subset of stabilized dimer mutants showing high thermal chemical stabilities, high affinities to broadly cross-reactive EDE-Abs, low affinities to FLE-mAbs and low affinities to serotype specific EDE-Abs and to other serotype specific Abs may be selected for further structural studies by X-ray crystallography.

High throughput expression strategy. Recombinant sE can be produced in a *Drosophila* expression system; this may be useful particularly in characterizing multiple E-mutants. We have previously used 293T to produce virus like particles (VLP) through transient transfection of vectors encoding prM/E. A large panel of >100 alanine substitutions to surface residues on envelope allowed us to produce mutant VLP, which we used to epitope map anti-dengue mAb[17]. In addition, we have developed a mammalian system to produce sE or E-dimers in 293T by transient transfection. This, for example, can be used to produce strep-tagged sE-mutants, promising candidates can then be expressed at high levels by transient transfection in Expi293F cells for further characterization.

We have generated a considerable resource useful in such a plan, namely the panel of around 150 human anti-dengue mAb (see, for example, WO 2016/012800; Rouvinski et al (2015) Nature 520, 109-113; Dejnirattisai et al (2015) Nature Immunol 16, 170-177). Around ⅓ bind to the EDE, ⅓ to the FLE and ⅓ to as yet undetermined epitopes[17]. To understand the structural determinants governing the binding of poorly neutralizing anti-dengue mAb, cryo-EM and crystallography can be used to determine the binding determinants of antibodies taken from such a mAb panel. These results can inform further modelling and mutagenesis to engineer out these unwanted epitopes whilst preserving the EDE. Interestingly, our preliminary results with one of our stabilised dimers shows much reduced reactivity to anti-FLE mAb underscoring the feasibility of manipulating recognition of the EDE vs. FLE, which have overlapping epitopes (FIGS. 25A AND 25B).

3. A universal dengue/zika immunogen. Structural characterization can be used to gain insight into the determinants of the bnAbs and their interactions with E from each of the four-dengue serotypes and of ZikaV. X-ray crystallography and cryo-EM can be used to analyse a selected broadly neutralizing anti-EDE mAb in complex with stabilized sE-mutants. Within the repertoire of anti-EDE mAb we have generated, some show restricted serotype cross-reactivity or even mono-specificity and these can be characterized to understand what determines broad specificity. A cryo-EM structure of mAb-2D22 in complex with a Denv2 virion reported by She-Mei Lok[54] is informative in this respect; 2D22 requires an E-dimer to bind, is specific for serotype 2 viruses (i.e. does not show broad specificity) and has a footprint similar to that of the EDE-1 bnAbs that we have reported, except that it appears to contact more residues on domain III of E.

In summary, the results of this section can guide further mutagenesis for resurfacing the sE-dimer, helping to develop a single immunogen incorporating the identified cross-reactive elements of the EDE and eliminating those that can result in serotype specific reactivity. These resurfaced immunogens are considered to be useful for heterologous prime boost strategies that may be required to focus responses towards the EDE.

Finally, once an or most appropriate stabilized, resurfaced sE-dimer has been identified, this sequence may be used in attempts to produce VLPs lacking prM but presenting multiple copies of the corresponding E-dimer at the surface, to increase its immunogenicity. As an alternative to the development of E-only VLPs, self-assembling nanoparticles presenting stabilized sE-dimers on their surfaces may be developed, analogous to, for example, nanoparticles developed for HIV and influenza vaccine development[53,55-58,66]. Nanoparticles may be produced by either genetic fusion or chemical conjugation of sE-dimers to pre-existing particles, for example. The particles may comprise ferritin, for example. In the case of genetic fusion, a single chain dimer may be created to allow fusion to a wide variety of nanoparticles or fusion could be restricted to particles with suitable 2-fold symmetry axes, for example. In sum, there are numerous options for how to present stable sE-dimers on nanoparticles for improved immunogenicity and epitope-focusing; different potential avenues may be explored.

5. Test immunogens in transgenic mice, for example fully human Ig mice. Transgenic mice useful in vaccine assessment have been developed, for example as described in Lee et al (2014) Nature Biotechnology Vol 32(4), 356-363. Such mice may, for example, have a completely normal immune system except the variable regions of the antibodies are human.

Using such a mouse model system is considered to be useful for a number of reasons: 1) Most importantly, such models, for example as described in Lee et al supra are probably the closest we can get to a preclinical model of human immunization in terms of the antibody response. 2) Primary immunoglobulin repertoires have diverged significantly between species, thus specific antibody responses in one species differ in both variable region usage therefore epitope selection, consequently extrapolating function from one species to another is unreliable. There is already evidence that murine antibody response to dengue differ from human, in particular antibodies to E domain III are quite dominant in the mouse but less so in humans. 3) Repertoires and fully human mAbs can be rapidly generated from immunized mice by deep sequencing, paired single cell cloning, network analysis and high-through-put expression respectively. 4) There is also the potential to generate further potent broadly neutralizing human anti-EDE mAb in the process, which may outperform those currently available.

Antigen can be delivered in a variety of different formats, which allows a throughput antigen testing far greater than could be justified in humans. The work may proceed via the following three phases:

a) High Throughput Polyclonal Analysis

This can involve the analysis of a large number of antigens (for example n=50, batched for operational efficiency) from which a subset can be selected and iterated further. For example, 5 disulphide stabilized mutants, 5 cavity filling mutants and 20 resurfaced mutant sE-dimers and 20 heterologous prime boost combinations can be examined. Since the number of different antigens is large the number of immunized mice may be limited to five per antigen. Antigen priming and two boosts with appropriate serial and terminal bleeds may be performed, for example. For maximum efficiency tissues can be banked from each animal in a form that it can be recovered and examined later, if required. A down-selection process can be followed based on polyclonal serum as follows:

Polyclonal ELISA positive responses in 4/5 or 5/5 mice with titres $>10^{-4}$ using native antigen.

In vitro neutralization 50% titres of $>10^{-3}$

Cross-reactivity of the responses between the 4 virus serotypes and Zika, for example Binding site analysis using mutant antigen VLP's and antibody competition assays.

b) Deep sequencing of antibody repertoire, mAb expression and functional screening. The 10 most effective immunization conditions may be selected for deep immune repertoire sequencing and mAb production from antigen sorted B-cells. A total Ig-heavy chain immune repertoire may be produced using NGS and high throughput methods may be used to produce approximately 500 mAb per immunogen, which may be tested for binding to sE-dimers and in neutralization assays. Common BCR solutions to dengue EDE binding may be determined by determining Ig-H&L family frequencies in 4/5 or 5/5 animals at frequencies greater than seen in non-immunized animals. A subset of transgenic mouse-generated mAbs, that represent different BCR evolutionary solutions but bind sE-dimer EDE may be produced in larger quantities for characterization in vitro and in vivo.

6. In vivo neutralization. Mice deficient in type I and II interferon receptors (AG129) represent an in vivo model for DENV infection and pathogenesis[59-62]. Upon infection with DENV animals develop rapid viraemia in multiple organs[63]. Infection is associated with weight loss, thrombocytopenia and vascular leakag[64,65]. AG129 mice may be used to demonstrate the presence of neutralizing antibodies from the mouse immunizations described above by injecting serum or individual Kymouse mAbs (or cocktails of mAbs) shown to bind and neutralize DENY in vitro into AG129 mice prior to challenge with mouse adapted dengue-2 strain D2S10.

7. Prime boost strategies. Initial studies may inform 1) whether it is possible to attain a focused response to the EDE and 2) can bnAb responses be generated using single immunogens. We have described a number of strategies to achieve this such as the design of a single universal immunogen and the resurfacing of non-EDE related parts of the E-protein dimer to destroy the epitopes for unwanted responses such as those against the FLE. However, the difficulty of focusing a bnAb response to the EDE may mean that heterologous prime boost strategies may be required to achieve this.

Heterologous prime boost are considered to increase the focusing of responses on the EDE and drive broad reactivity. A variety of different experimental approaches can be used to achieve these objectives, for example:

Use sE dimers from different DenV serotypes and from ZikaV in prime boost combinations to drive broad reactivity Use a fully resurfaced sE-dimer only containing the EDE in prime boost combination with wild type dimers.

Prime boost strategies using recombinant sE-dimers and VLP's.

Prime boost combinations of attenuated viruses with sE-dimers.

In conclusion, we have presented an exemplar plan for exploring the feasibility of a novel subunit vaccine for dengue, which is also considered to have utility for other flavivirus disease, for example zika disease. Despite progress with LATV it is not yet clear that this approach will deliver a safe and efficacious product that can be used in all age groups. Until then, preclinical development of alternative and potentially synergistic technologies to LATV should be pursued. A successful conclusion to this program is considered to lead to production of an immunogen which is suitable for use or further evaluation, for example for primate and early phase clinical evaluation.

REFERENCES

1 Bhatt, S. et al. *Nature* 496, 504-507, (2013).
2 Simmons, C. P., Farrar, J. J., Nguyen v, V. & Wills, B. *N Engl J Med* 366, 1423-1432, (2012).
3 ECDC. European Centre for Disease Prevention and Control: ecdc.europa.eu/en/publications/Publications/zika-virus-americas-association-with-microcephaly-rapid-risk-assessment.pdf., (2015).
4 Mlakar, J. et al. *N Engl J Med* 374, 951-958, (2016).
Carteaux, G. et al. *N Engl J Med*, (2016).
6 Cao-Lormeau, V. M. et al. *Lancet*, (2016).
7 Mukhopadhyay, S., Kuhn, R. J. & Rossmann, M. G. *Nat Rev Microbiol* 3, 13-22, (2005).
8 Wengler, G. & Wengler, G. *J Virol* 63, 2521-2526, (1989).
9 Zhang, Y. et al. *EMBO J* 22, 2604-2613, (2003).
10 Stadler, K., Allison, S. L., Schalich, J. & Heinz, F. X. *J Virol* 71, 8475-8481, (1997).
11 Yu, I. M. et al. *Science* 319, 1834-1837, (2008).
12 Junjhon, J. et al. *Journal of virology* 84, 8353-8358, (2010).
13 Cherrier, M. V. et al. *EMBO J* 28, 3269-3276, (2009).
14 Dowd, K. A., Mukherjee, S., Kuhn, R. J. & Pierson, T. C. *J Virol* 88, 11726-11737, (2014).
15 Mukherjee, S. et al. *J Virol* 88, 7210-7220, (2014).
16 Dejnirattisai, W. et al. *Science* 328, 745-748, (2010).
17 Dejnirattisai, W. et al. *Nat Immunol* 16, 170-177, (2015).
18 Guzman, M. G. et al. *Emerg Infect Dis* 13, 282-286, (2007).
19 Sabin, A. B. *Am J Trop Med Hyg* 1, 30-50, (1952).
20 World Health Organization. www.who.int/mediacentre/factsheets/fs117/en/, (2015).
21 Guzman, M. G. et al. *Am J Epidemiol* 152, 793-799, (2000).
22 Sangkawibha, N. et al. *Am J Epidemiol* 120, 653-669., (1984).
23 Halstead, S. B. et al. *Yale J Biol Med* 42, 261-275, (1970).
24 Halstead, S. B., Mahalingam, S., Marovich, M. A., Ubol, S. & Mosser, D. M. *Lancet Infect Dis* 10, 712-722, (2010).
25 Halstead, S. B. & O'Rourke, E. J. *J Exp Med* 146, 201-217., (1977).
26 Halstead, S. B. & O'Rourke, E. J. *Nature* 265, 739-741, (1977).
27 Zellweger, R. M., Prestwood, T. R. & Shresta, S. *Cell Host Microbe* 7, 128-139, (2010).
28 Bhamarapravati, N. & Sutee, Y. *Vaccine* 18 Suppl 2, 44-47, (2000).
29 Guy, B. et al. *Vaccine* 29, 7229-7241, (2011).
30 Capeding, M. R. et al. *Lancet*, (2014).
31 Sabchareon, A. et al. *The Lancet* 380, 1559-1567, (2012).
32 Villar, L. et al. *N Engl J Med* 372, 113-123, (2015).
33 Hadinegoro, S. R. et al. *N Engl J Med*, (2015).
34 Beltramello, M. et al. *Cell Host Microbe* 8, 271-283, (2010).
35 de Alwis, R. et al. *PLoS Negl Trop Dis* 5, e1188, (2011).
36 Smith, S. A. et al. *J Virol* 86, 2665-2675, (2012).
37 Smith, S. A. et al. *J Infect Dis* 207, 1898-1908, (2013).

38 Rodenhuis-Zybert, I. A. et al. *PLoS Pathog* 6, e1000718, (2010).
39 Rouvinski, A. et al. *Nature*, (2015).
40 Kuhn, R. J. et al. *Cell* 108, 717-725, (2002).
41 Modis, Y., Ogata, S., Clements, D. & Harrison, S. C. *Nature* 427, 313-319, (2004).
42 Fibriansah, G. et al. *J Virol* 87, 7585-7592, (2013).
43 Lok, S. M. et al. *Nat Struct Mol Biol* 15, 312-317, (2008).
44 Zhang, X. et al. *Proc Natl Acad Sci USA* 110, 6795-6799, (2013).
45 McLellan, J. S. et al. *Science* 342, 592-598, (2013).
46 McLellan, J. S. et al. *Science* 340, 1113-1117, (2013).
47 Sanders, R. W. et al. *Science* 349, aac4223, (2015).
48 Impagliazzo, A. et al. *Science*, (2015).
49 Mallajosyula, V. V. et al. *Frontiers in immunology* 6, 329, (2015).
50 Salam, N. K., Adzhigirey, M., Sherman, W. & Pearlman, D. A. *Protein Eng Des Sel* 27, 365-374, (2014).
51 Liu, Y. & Kuhlman, B. *Nucleic acids research* 34, W235-238, (2006).
52 Correia, B. E. et al. *J Mol Biol* 405, 284-297, (2011).
53 Correia, B. E. et al. *Nature* 507, 201-206, (2014).
54 Fibriansah, G. et al. *Science* 349, 88-91, (2015).
55 Jardine, J. et al. *Science* 340, 711-716, (2013).
56 Jardine, J. G. et al. *Science* 349, 156-161, (2015).
57 Kanekiyo, M. et al. *Nature* 499, 102-106, (2013).
58 Yassine, H. M. et al. *Nat Med* 21, 1065-1070, (2015).
59 Johnson, A. J. & Roehrig, J. T. *J Virol* 73, 783-786, (1999).
60 Sarathy, V. V. et al. *J Virol* 89, 1254-1266, (2015).
61 Shresta, S., Sharar, K. L., Prigozhin, D. M., Beatty, P. R. & Harris, E. *J Virol* 80, 10208-10217, (2006).
62 Milligan, G. N. et al. *PLoS One* 10, e0125476, (2015).
63 Schoggins, J. W. et al. *Proc Natl Acad Sci USA* 109, 14610-14615, (2012).
64 Tan, G. K. et al. *Ann Acad Med Singapore* 40, 523-532, (2011).
65 Zust, R. et al. *J Virol* 88, 7276-7285, (2014).
Kanekiyo et al *Nature* 499(7456)102-106 (2013)

EXAMPLE 4

In Vivo Protection

Anti-EDE1 mAb clone 753(3)C10 (C10) was tested for its ability to confer protection from Zika infection in the AG129 mouse model. AG129 mice were obtained from B&K (Hull, UK) and were bred at the CBS facility at Imperial College. All animal experiments were performed in containment level 3 facilities as per the guidelines of the Ethical Committee of Imperial College, under the UK home office license. Virus stock was produced as described earlier and titrated on Vero cells prior to use in the mouse model. Female 129/Sv mice deficient in both interferon (IFN)-α/β and IFN-γ receptors (AG129 mice; female, 8-10 weeks of age) were administered purified human anti EDE-1 clone C10 or isotype control 2-8C at either 200 or 50 μg/mouse, intra-peritoneally (i.p; 200 μL) 24 h prior to infection with Zika virus (Brazilian strain PE243). Mice were infected intra-peritoneally with $1.2 \times 10^2$ FFU/mouse of Zika PE243. Mice administered PBS alone were used as experimental controls. Mice were monitored by daily body weight measurements and development of virus-induced disease. Blood samples were collected at days 2 and 4 post infection. Plasma samples were titrated for viral loads using focus forming assays on Vero cell monolayers. Mice were euthanized prior to body weight loss nearing 20% and/or severe illness specified under the project license as humane endpoints. Percent original body weight was calculated based on the weight at day 0 just prior to infection. The body weight measurements are represented as mean+/− SEM of 3 mice in each experimental group. The experiment was performed once and showed protection afforded by monoclonal antibody C10.

The invention claimed is:

1. A composition comprising an isolated neutralizing antibody or antigen binding fragment thereof directed against a flavivirus envelope dimer epitope (EDE) and an adjuvant,
wherein the antibody or fragment comprises six CDRs wherein each CDR comprises an amino acid sequence selected from the group consisting of:
SEQ ID Nos: 15 to 26 and sequences with no more than 30% modification from any one of said SEQ ID No. 15 to 26,
wherein:
(a) said antibody or fragment thereof binds the five polypeptide segments of the dengue virus glycoprotein E ectodomain (sE) consisting of the residues 67-74, residues 97-106, residues 307-314, residues 148-159 and residues 243-251, or corresponding residues of the flavivirus or Zika virus glycoprotein E ectodomain, or consisting of Zika PF13 residues 67-77, residues 97-106, residues 313-315, residues 243-253, residue K373 or corresponding residues of the flavivirus glycoprotein E ectodomain, or
(b) binding is unaffected by presence or absence of dengue N153 (Zika N154) glycan or corresponding residue.

2. The composition of claim 1, wherein the antibody or fragment thereof recognizes exclusively virion-dependent (including sub-viral particle or virus-like particle) epitope(s) of a flavivirus, optionally Zika or dengue virus.

3. The composition of claim 1, wherein the fragment is a Fab fragment.

4. The composition of claim 1, wherein the antibody or fragment thereof comprises an amino acid sequence selected from the group consisting of SEQ ID Nos: 15 to 26 and sequences with no more than 20, 15, or 10% modification from any one of said SEQ ID No. 15 to 26.

5. The composition of claim 1 wherein the EDE comprises a region centred in a valley lined by the h strand on the domain II side, and the "150 loop" on the domain I side (across from the dimer interface), wherein the 150 loop spans residues 148-159, connecting b-strands E0 and F0 of domain 1, and carries the N153 glycan, which covers the fusion loop of the partner subunit in the dimer, optionally wherein the region comprises the h strand (residues 67-74 which bear the N67 glycan), the fusion loop and residues immediately upstream (residues 97-106) and the ij loop (residues 246-249) of the reference subunit, wherein the reference subunit is the subunit which contributes the fusion loop,
optionally wherein the EDE further comprises the 150 loop and the N153 glycan chain of the second subunit,
optionally wherein one or both regions is in a similar spatial configuration as the native region;
or wherein the EDE comprises the Zika PF13 beta strand b of domain IL bed beta-sheet edge, fusion loop main chain, fusion loop R99 side chain, Q77 side chain, disulphide bond between C74 and C105; beta strand E, K373, charged residues in domain I, kl loop of domain II, or regions corresponding thereto.

6. The composition of claim 1, wherein the antibody or fragment thereof neutralises one or more serotypes of Dengue virus and/or Zika virus to 80%.

7. The composition of claim 1, wherein the antibody or fragment thereof neutralises all serotypes of Dengue virus and Zika virus, to 80%.

8. The composition of claim 1 wherein the antibody or fragment thereof neutralises one or more serotypes of Dengue virus and/or Zika virus to 80, 90, 98 or 100% at a concentration of 0.5-0.01 µg/ml.

9. The compositional of claim 1 wherein the antibody or fragment thereof neutralises all serotypes of Dengue virus and Zika s to 80, 90, 98 or 100% at a concentration of 0.5-0.01 µg/ml.

10. The composition of claim 1 wherein the fragment is a Fv fragment; a Fab-like fragment; or a domain antibody; or wherein the antibody is a monoclonal antibody or a recombinant antibody.

11. The composition of claim 1 wherein the antibody is a polyclonal antibody or antigen binding portion thereof.

12. The composition of claim 1 wherein the antibody or fragment thereof is part of a composition comprising a mixture of antibodies, optionally:
a) a mixture of monoclonal antibodies or antigen binding portion thereof, or
b) a mixture of polyclonal antibodies or antigen binding portion thereof, or
c) a mixture or monoclonal and polyclonal antibodies or antigen binding portion thereof.

13. The composition of claim 6, wherein the antibody or fragment thereof neutralises one or more serotypes of Dengue virus and/or Zika virus to 90% or 98% or 100%.

14. The composition of claim 13, wherein the antibody or fragment thereof neutralises one or more serotypes of Dengue virus and/or Zika virus to 98% or 100%.

15. The composition of claim 7, wherein the antibody or fragment thereof neutralises all serotypes of Dengue virus and Zika virus to 90%.

16. The composition of claim 7, wherein the antibody or fragment thereof neutralises all serotypes of Dengue virus and Zika virus, 98% or 100%.

17. The composition of claim 16, wherein the antibody or fragment thereof neutralises all serotypes of Dengue virus and Zika virus to 100% at the same concentration of antibody or fragment.

18. The composition of claim 10 wherein the Fab-like fragment is a Fab' fragment or a F(ab)2 fragment.

19. A composition comprising an adjuvant and an isolated neutralizing antibody or antigen binding fragment thereof directed against a flavivirus envelope dimer epitope (EDE), wherein the antibody or fragment comprises a heavy chain comprising SEQ ID NO: 120 and/or a light chain comprising SEQ ID NO: 121, or a sequence with at least 90% homology to the said sequences.

* * * * *